United States Patent
Merico et al.

(10) Patent No.: US 11,427,821 B2
(45) Date of Patent: Aug. 30, 2022

(54) THERAPEUTIC SPLICE-SWITCHING OLIGONUCLEOTIDES

(71) Applicant: Deep Genomics Incorporated, Toronto (CA)

(72) Inventors: Daniele Merico, Toronto (CA); Joao Antonio Lourenco Goncalves, Toronto (CA); Erno Wienholds, Toronto (CA); Mark George Ford Sun, Toronto (CA)

(73) Assignee: DEEP GENOMICS INCORPORATED, Toronto (CA)

( * ) Notice: Subject to any disclaimer, the term of this patent is extended or adjusted under 35 U.S.C. 154(b) by 0 days.

(21) Appl. No.: 16/777,214

(22) Filed: Jan. 30, 2020

(65) Prior Publication Data

US 2020/0165611 A1 May 28, 2020

Related U.S. Application Data

(63) Continuation of application No. PCT/CA2019/051141, filed on Aug. 21, 2019.

(60) Provisional application No. 62/720,684, filed on Aug. 21, 2018.

(51) Int. Cl.
*C12N 15/113* (2010.01)
*A61K 9/00* (2006.01)
*A61K 45/06* (2006.01)

(52) U.S. Cl.
CPC .......... *C12N 15/113* (2013.01); *A61K 9/0019* (2013.01); *A61K 45/06* (2013.01); *C12N 2310/11* (2013.01); *C12N 2310/314* (2013.01); *C12N 2310/321* (2013.01); *C12N 2310/346* (2013.01); *C12N 2320/33* (2013.01)

(58) Field of Classification Search
CPC .............. C12N 2320/33; C12N 15/113; C12N 2310/11; C12N 2310/314; C12N 2310/321; C12N 2310/346; C12N 2310/322; C12N 2310/315
See application file for complete search history.

(56) References Cited

U.S. PATENT DOCUMENTS

| | | | | |
|---|---|---|---|---|
| 6,344,323 | B1* | 2/2002 | Seifert | C12N 15/1137 435/325 |
| 2003/0087861 | A1* | 5/2003 | Iversen | A61K 31/337 514/44 A |
| 2003/0219770 | A1* | 11/2003 | Eshleman | C12Q 1/6869 435/6.14 |
| 2005/0108783 | A1* | 5/2005 | Koike | A01K 67/0276 800/17 |
| 2007/0105807 | A1* | 5/2007 | Sazani | A61P 29/00 514/44 A |
| 2010/0261175 | A1* | 10/2010 | Rasmussen | C12N 15/113 435/6.1 |
| 2014/0336238 | A1* | 11/2014 | Collin | A61P 27/02 514/44 A |
| 2017/0081711 | A1* | 3/2017 | Nitta | C12Q 1/6816 |

FOREIGN PATENT DOCUMENTS

| | | |
|---|---|---|
| WO | WO-2013036105 A1 | 3/2013 |
| WO | WO-2015004133 A1 | 1/2015 |
| WO | WO-2016135334 A1 | 9/2016 |
| WO | WO-2020037415 A1 | 2/2020 |

OTHER PUBLICATIONS

Littink et al (IOVS, 51(7): 3646-3652, 2010) (Year: 2010).*
Gen Bank Accession NG_008417.1 (https://www.ncbi.nlm.nih.gov/nuccore/197313679?sat=46&satkey=134002855, 2017) (Year: 2017).*
Buck et al. (Biotechniques, 1999, 27:528-536) (Year: 1999).*
Harding et al (Mo. Ther. 15(1): 157-166, 2007) (Year: 2007).*
Maruyama et al (Methods Mol Biol. 2018;1828:79-90) (Year: 2018).*
Aartsma-Rus et al (Mol. Ther. 17(3): 548-553, 2009) (Year: 2009).*
Gerard, et al. AON-mediated Exon Skipping Restores Ciliation in Fibroblasts Harboring the Common Leber Congenital Amaurosis CEP290 Mutation.Mol Ther Nucleic Acids. 2012;1(6):e29. Published Jun. 26, 2012. doi:10.1038/mtna.2012.21.
Gerard, et al. Intravitreal Injection of Splice-switching Oligonucleotides to Manipulate Splicing in Retinal Cells. Mol Ther Nucleic Acids. 2015;4(9):e250. Published Sep. 1, 2015. doi:10.1038/mtna. 2015.24.
PCT/CA2019/051141 International Search Report dated Nov. 14, 2019.

* cited by examiner

*Primary Examiner* — Richard A Schnizer
(74) *Attorney, Agent, or Firm* — Wilson Sonsini Goodrich & Rosati

(57) ABSTRACT

The present disclosure provides compositions and methods for treating a disorder associated with mutations in the CEP290 gene. The disclosure includes synthetic polynucleotides for skipping a reading-frame of a CEP290 pre-RNA, yielding a CEP290 translated product that lacks one or more exons. The disclosure also provides methods of treating patients with the synthetic polynucleotides disclosed herein.

19 Claims, 31 Drawing Sheets

Specification includes a Sequence Listing.

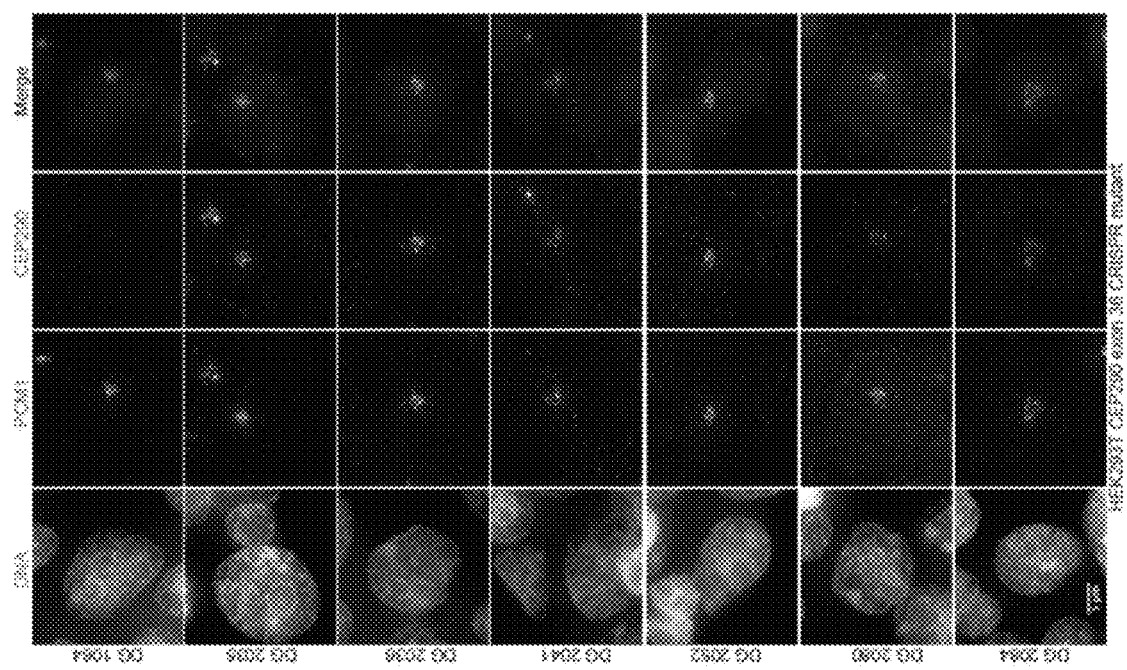

THERAPEUTIC SPLICE-SWITCHING OLIGONUCLEOTIDES

CROSS-REFERENCE

This application is a continuation of PCT/CA2019/051141, filed on Aug. 21, 2019, which claims priority to U.S. Provisional Patent Application No. 62/720,684, filed Aug. 21, 2018, both of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 30, 2020, is named 51110-710_301_SL.txt and is 200,275 bytes in size.

BACKGROUND

Despite recent advances in genome biology, computational genomics, and artificial intelligence, none or insufficient treatment options exist for rare Mendelian disorders caused by genetic variants resulting in shifted reading frame or gain of premature stop codons and thus complete protein loss-of-function. Thus, there exists a high demand for new genetic medicines that counteract such effects, restore protein functionality and thus treat, cure, and/or prevent disease formation.

SUMMARY

In some aspects, the present disclosure provides a composition comprising a therapeutically effective amount of a synthetic polynucleotide between 10 nucleotides to 200 nucleotides in length that is at least 60% complementary to a region of a pre-mRNA molecule, which pre-mRNA encodes a centrosomal protein 290. In some instances, the region of the pre-mRNA molecule corresponds to an intron of the pre-mRNA molecule. In some instances, at least 90% of the region of the pre-mRNA molecule comprises an intron of the pre-mRNA molecule. In some instances, at least 90% of the region of the pre-mRNA molecule corresponds to an exon of the pre-mRNA molecule. In some instances, the region of the pre-mRNA molecule comprises a junction between an intron and an exon of the pre-mRNA molecule. In some instances, the region of the pre-mRNA molecule is within 500 bases from an exon of the pre-mRNA molecule. In some instances, the region of the pre-mRNA molecule comprises exon 7 of the centrosomal protein 290. In some instances, the synthetic polynucleotide is any one of SEQ ID NO: 270-SEQ ID NO: 309. In some instances, the region of the pre-mRNA molecule comprises exon 31 of the centrosomal protein 290. In some instances, the synthetic polynucleotide is any one of SEQ ID NO: 110-SEQ ID NO: 269. In some instances, the region of the pre-mRNA molecule comprises exon 34 of the centrosomal protein 290. In some instances, the synthetic polynucleotide is any one of SEQ ID NO: 70-SEQ ID NO: 109. In some instances, the region of the pre-mRNA molecule comprises exon 36 of the centrosomal protein 290. In some instances, the synthetic polynucleotide is any one of SEQ ID NO: 461-SEQ ID NO: 540, or SEQ ID NO: 703-SEQ ID NO: 824. In some instances, the region of the pre-mRNA molecule comprises exon 41 of the centrosomal protein 290. In some instances, the synthetic polynucleotide is any one of SEQ ID NO: 1-SEQ ID NO: 19, SEQ ID NO: 310-SEQ ID NO: 394, or SEQ ID NO: 541-SEQ ID NO: 684. In some instances, the region of the pre-mRNA molecule comprises exon 46 of the centrosomal protein 290. In some instances, the synthetic polynucleotide is any one of SEQ ID NO: 20-SEQ ID NO: 69, SEQ ID NO: 395-SEQ ID NO: 460, or SEQ ID NO: 685-SEQ ID NO: 702. In some instances, the synthetic polynucleotide comprises a modified internucleoside linkage. In some instances, the modified internucleoside linkage is selected from the group consisting of a phosphorothioate internucleoside linkage, a phosphoroamidate internuceloside linkage, and a phosphorodiamidate internucleoside linkage. In some instances, the modified internucleoside linkage is a phosphorodiamidate Morpholino oligomer. In some instances, 100% of the synthetic polynucleotide comprises a modified internucleoside linkage. In some instances, at least the three terminal residues in either the 3' end, the 5' end, or both ends of the synthetic polynucleotide comprises the modified internucleoside linkage. In some instances, the synthetic polynucleotide comprises a modified sugar moiety. In some instances, the modified sugar moiety is selected from the group consisting of a 2' O-methyl modification, a locked nucleic acid (LNA), and a peptide nucleic acid (PNA). In some instances, 100% of the synthetic polynucleotide comprises the modified sugar moiety. In some instances, the modified sugar moiety is 2'-O-methoxyethyl (MOE). In some instances, at least the three terminal residues in either the 3' end, the 5' end, or both ends of the synthetic polynucleotide comprise the modified sugar moiety. In some instances, the composition is formulated for administration to a subject. In some instances, the composition is formulated for intravitreal administration to the subject. In some instances, the composition is formulated for systemic administration to the subject. In some instances, the subject is afflicted with any one of Leber Congenital Amaurosis (LCA), Senior-Locken Syndrome (SLS), Joubert syndrome (JS), or Meckel Syndrome (MS). In some instances, the subject is a human. In some instances, the composition is used for the treatment of a retinal condition. In some instances, the composition is used for the retinal condition is retinal degeneration, retinal dystrophy, or retinitis pigmentosa. In some instances, the composition is used for the treatment of renal disease, retinal dystrophy, coloboma, kidney nephronophthisis, ataxia, mental retardation. In some instances, the therapeutically effective amount is from 50 µg to 950 µg.

In some aspects, the present disclosure provides a method of treating a subject afflicted with a condition comprising administering to the subject a therapeutically effective amount of a composition comprising a synthetic polynucleotide between 15 nucleotides to 200 nucleotides in length that is at least 60% complementary to a region of a pre-mRNA molecule, which pre-mRNA molecule encodes a centrosomal protein 290. In some instances, the synthetic polynucleotide induces exon-skipping of one or more exons in the pre-mRNA molecule when the synthetic polynucleotide is administered to the subject. In some instances, the condition is an ocular condition. In some instances, the ocular condition is any one of retinal dystrophy, retinitis pigmentosa, or coloboma. In some instances, the condition is a renal condition. In some instances, the renal condition is a kidney nephronophthisis. In some instances, the condition is a neurological condition. In some instances, the neurological condition is an ataxia or mental retardation. In some instances, the region of the pre-mRNA molecule corresponds to an intron of the pre-mRNA molecule. In some instances, at least 90% of the region of the pre-mRNA molecule comprises an intron of the pre-mRNA molecule. In some instances, at least 90% of the region of the pre-mRNA molecule corresponds to an exon of the pre-mRNA molecule. In some instances, the region of the pre-mRNA molecule comprises a junction between an intron and an exon of the pre-mRNA molecule. In some instances, the region of the pre-mRNA molecule is within 500 bases from an exon of the pre-mRNA molecule. In some instances, the region of the pre-mRNA molecule comprises exon 7 of the centrosomal protein 290. In some instances, the synthetic polynucleotide is any one of SEQ ID NO: 270-SEQ ID NO: 309. In some instances, the region of the pre-mRNA molecule comprises exon 31 of the centrosomal protein 290. In some instances, the synthetic polynucleotide is any one of SEQ ID NO: 110-SEQ ID NO: 269. In some instances, the region of the pre-mRNA molecule comprises exon 34 of the centrosomal protein 290. In some instances, the synthetic polynucleotide is any one of SEQ ID NO: 70-SEQ ID NO: 109. In some instances, the region of the pre-mRNA molecule comprises exon 36 of the centrosomal protein 290. In some instances, the synthetic polynucleotide is any one of SEQ ID NO: 461-SEQ ID NO: 540, or SEQ ID NO: 703-SEQ ID NO: 824. In some instances, the region of the pre-mRNA molecule comprises exon 41 of the centrosomal protein 290. In some instances, the synthetic polynucleotide is any one of SEQ ID NO: 1-SEQ ID NO: 19, SEQ ID NO: 310-SEQ ID NO: 394, or SEQ ID NO: 541-SEQ ID NO: 684. In some instances, the region of the pre-mRNA molecule comprises exon 46 of the centrosomal protein 290. In some instances, the synthetic polynucleotide is any one of SEQ ID NO: 20-SEQ ID NO: 69, SEQ ID NO: 395-SEQ ID NO: 460, or SEQ ID NO: 685-SEQ ID NO: 702. In some instances, the synthetic polynucleotide comprises a modified internucleoside linkage. In some instances, the modified internucleoside linkage is selected from the group consisting of a phosphorothioate internucleoside linkage, a phosphoroamidate internuceloside linkage, and a phosphorodiamidate internucleoside linkage. In some instances, the modified internucleoside linkage is a phosphorodiamidate Morpholino oligomer. In some instances, 100% of the synthetic polynucleotide comprises a modified internucleoside linkage. In some instances, at least the three terminal residues in either the 3' end, the 5' end, or both ends of the synthetic polynucleotide comprises the modified internucleoside linkage. In some instances, the synthetic polynucleotide comprises a modified sugar moiety. In some instances, the modified sugar moiety is selected from the group consisting of a 2' O-methyl modification, a locked nucleic acid (LNA), a peptide nucleic acid (PNA), and a morpholino. In some instances, the modified sugar moiety is 2'-O-methoxyethyl (MOE). In some instances, 100% of the synthetic polynucleotide comprises the modified sugar moiety. In some instances, at least the three terminal residues in either the 3' end, the 5' end, or both ends of the synthetic polynucleotide comprises the modified sugar moiety. In some instances, the composition is formulated for intravitreal administration to the subject. In some instances, the composition is formulated for intrathecal administration to the subject. In some instances, the composition is formulated for systemic administration to the subject. In some instances, the subject is afflicted with any one of Leber Congenital Amaurosis, Senior-Locken Syndrome, Joubert syndrome, or Meckel Syndrome. In some instances, the subject is afflicted with Leber Congenital Amaurosis. In some instances, the subject is afflicted with Senior-Locken Syndrome. In some instances, the subject is afflicted with Joubert syndrome. In some instances, the subject is afflicted with Meckel Syndrome. In some instances, the subject is a human. In some instances, the therapeutically effective amount is from 50 μg to 950 μg. In some instances, the disclosure provides methods comprising monitoring the subject for a progression or regression of the condition.

Additional aspects and advantages of the present disclosure will become readily apparent to those of ordinary skill from the following detailed description, wherein illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure," "Fig.," and "FIG." herein), of which:

FIG. 8D shows the sub-cellular localization analysis of the rescued CEP290 protein. HEK293T CEP290 exon 36 CRISPR mutant cells were transfected with the indicated SPs and stained with antibodies against PCM1 (centriolar satellite marker) and CEP290. DNA was stained with Hoechst dye.

DETAILED DESCRIPTION

Figure 1A:
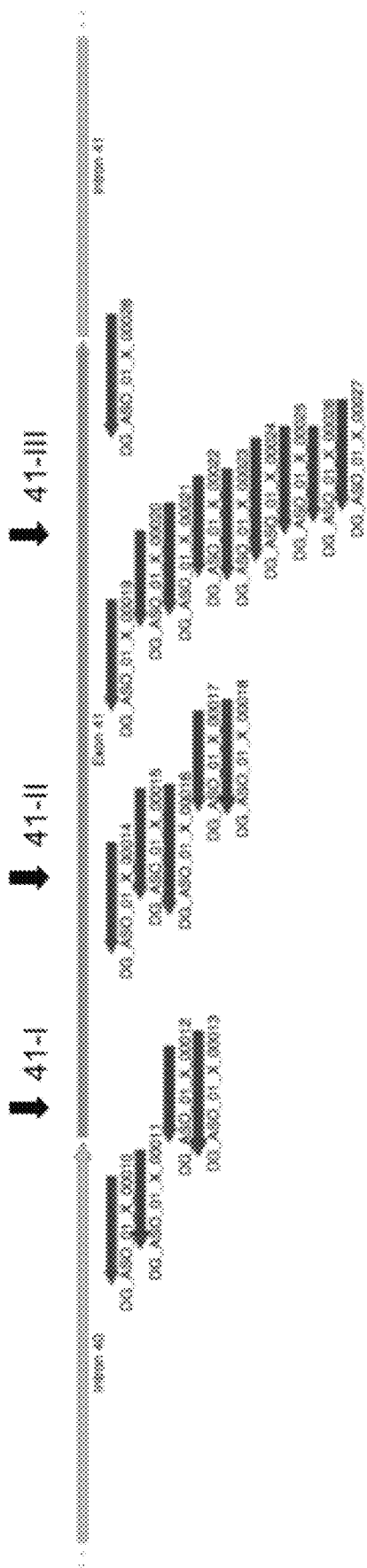
FIG. 1A is a schematic representation of a set of synthetic polynucleotides that were designed to modulate splicing of centrosomal protein 290 kDa (CEP290) exon 41 (SEQ ID NO: 1-SEQ ID NO: 19). CEP290 exon 41 hotspot region (I, II and III) center points are indicated by arrows.

While various embodiments of the disclosure have been shown and described herein, it will be obvious to those of ordinary skill that such embodiments are provided by way of example. Numerous variations, changes, and substitutions may occur to those of ordinary skill without departing from the disclosure. Moreover, various alternatives to the embodiments of the disclosure described herein may be employed.

Splicing may naturally occur at the pre-messenger RNA (pre-mRNA) stage through the removal of introns and the formation of mature mRNA consisting solely of exons. For many eukaryotic introns, splicing may be carried out in a series of reactions which are catalyzed by the spliceosome, a complex of small nuclear ribonucleoproteins (snRNPs). Self-splicing introns, or ribozymes capable of catalyzing their own excision from their parent RNA molecule, also exist. If one or more of those exons contains variants introducing premature stop codons or shifting the reading frame of the coding sequence, the resulting proteins will not be produced (thus complete loss-of-function, or LOF, variants). This can lead to severe diseases in the host organism as shown by the discovery of multiple human diseases (e.g., Duchenne muscular dystrophy (DMD) and other Mendelian disorders).

As used herein, the term "nucleic acid" or "polynucleotide," generally refers to a polymeric form of nucleotides of any length, either ribonucleotides or deoxyribonucleotides. Polynucleotides include sequences of deoxyribonucleic acid (DNA), ribonucleic acid (RNA), or DNA copies of ribonucleic acid (cDNA). The term also refers to polynucleotide polymers that comprise chemically modified nucleotides. A polynucleotide can be formed of D-ribose sugars, which can be found in nature, and L-ribose sugars, which are not found in nature. The term also refers to polynucleotide polymers that comprise chemically modified nucleotides and nucleotide analogues. "Analogues" in reference to nucleotides may include synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like. For example, a nucleotide analogue of the present disclosure may comprise a morpholino moiety that replaces the ribose moiety present in naturally occurring nucleotides. Moreover, nucleotide analogues of the present disclosure may comprise a non-phosphodiester backbone such as a peptide or a phophoramidate backbone.

As used herein, the term "subject," generally refers to a human or to another animal. An animal can be a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

As described herein, all variant coordinates of genes, including variant coordinates of centrosomal protein 290 (CEP290) may be presented with respect to the hg19/b37 genome build; all exons may be reported with respect to Ref Seq transcript NM_025114; prevalence estimates may be reported with respect to 500M industrialized country individuals regardless of ethnicity.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 may include a range from 8.5 to 11.5.

The term "pharmaceutically acceptable salt" generally refers to physiologically and pharmaceutically acceptable salt of a compound of the disclosure: e.g., salt that retains the biological activity of the parent compound and does not impart toxicological effects thereto. For oligomers, examples of pharmaceutically acceptable salts and their uses are further described in U.S. Pat. No. 6,287,860, which is hereby incorporated by reference in its entirety.

Therapeutic Splice-Switching Oligonucleotides to Skip Exons Containing Complete Loss-of-Function Variants (skipLOF)

Genetic variants with stop-gain or frameshift effect (consisting of single- or short multi-nucleotide substitutions, or short insertions/deletions) typically lead to complete loss-of-function (LOF). If the exon in which the LOF resides is not strictly required for protein function, and its skipping does not alter the reading frame, then its skipping is expected to result in modest or no loss-of-function, and thus it can be utilized to remediate the effect of LOF variant(s) (skipLOF mechanism). For the gene CEP290, spontaneous low-level skipping of non-required exons containing LOFs is believed to result in minimal levels of functional protein.

In some instances, disorder severity can be used to infer the functional requirement of an exon. For example, a study of 234 patients suggested that, among exons that do not cause frameshift upon skipping, exons 6, 9, 40 and 41 may be important for protein function. However, review of the study data reveals some inconsistencies for specific exons. In addition, molecular and cellular biology assays for subjects carrying pathogenic LOFs within non-frameshift exons 8 and 32 demonstrated that low-level spontaneous skipping of these exons lead to partial functional restoration, suggesting these exons may not be required for protein function.

The compositions and methods of the present disclosure provide synthetic polynucleotides that have sequences that are complementary to a region of a pre-mRNA molecule encoding a CEP290. The disclosure utilizes these synthetic polynucleotides to provide new information on CEP290 exon function and demonstrate that such polynucleotides can be used for the skipLOF mechanism as described herein. In some instances, systemic administration of such peptides can be used treat a Mendelian disorder.

In some cases, a synthetic polynucleotide of the disclosure can hybridize to a region that is at least 5%, 10%, 15%, 20%, 25%, 30%, 35%, 40%, 45%, 50%, 55%, 60%, 65%, 70%, 75%, 80%, 85%, 90%, or 95% homologous or complementary to a pre-mRNA sequence associated with the CEP290 gene.

In some cases, a synthetic polynucleotide of the present disclosure can be complementary to at least 60%, at least 70%, at least 80%, at least 90%, or at least 95% of the region of the pre-mRNA molecule comprising exon 7 of the centrosomal protein 290. In some cases, the synthetic polynucleotide can comprise a sequence according to any one of SEQ ID NO: 270-SEQ ID NO: 309. In some cases, a synthetic polynucleotide of the present disclosure can be complementary to at least 60%, at least 70%, at least 80%, at least 90%, or at least 95% of the region of the pre-mRNA molecule comprising exon 31 of the centrosomal protein 290. In some cases, the synthetic polynucleotide can comprise a sequence according to any one of SEQ ID NO: 110-SEQ ID NO: 269. In some cases, a synthetic polynucleotide of the present disclosure can be complementary to at least 60%, at least 70%, at least 80%, at least 90%, or at least 95% of the region of the pre-mRNA molecule comprising exon 34 of the centrosomal protein 290. In some cases, the synthetic polynucleotide can comprise a sequence according to any one of SEQ ID NO: 70-SEQ ID NO: 109. In some cases, a synthetic polynucleotide of the present disclosure can be complementary to at least 60%, at least 70%, at least 80%, at least 90%, or at least 95% of the region of the pre-mRNA molecule comprising exon 36 of the centrosomal protein 290. In some cases, the synthetic polynucleotide can comprise a sequence according to any one of SEQ ID NO: 461-SEQ ID NO: 540, or SEQ ID NO: 703-SEQ ID NO: 824. In some cases, a synthetic polynucleotide of the present disclosure can be complementary to at least 60%, at least 70%, at least 80%, at least 90%, or at least 95% of the region of the pre-mRNA molecule comprising exon 41 of the centrosomal protein 290. In some cases, the synthetic polynucleotide can comprise a sequence according to any one of SEQ ID NO: 1-SEQ ID NO: 19, SEQ ID NO: 310-SEQ ID NO: 394, or SEQ ID NO: 541-SEQ ID NO: 684. In some cases, a synthetic polynucleotide of the present disclosure can be complementary to at least 60%, at least 70%, at least 80%, at least 90%, or at least 95% of the region of the pre-mRNA molecule comprising exon 46 of the centrosomal protein 290. In some cases, the synthetic polynucleotide can comprise a sequence according to any one of SEQ ID NO: 20-SEQ ID NO: 69, SEQ ID NO: 395-SEQ ID NO: 460, or SEQ ID NO: 685-SEQ ID NO: 702.

In some aspects of the present disclosure, the region to which the synthetic polynucleotide is complementary to may correspond to an intron of the pre-mRNA molecule. In some cases, at least about 90% of the region of the pre-mRNA molecule may comprise an intron of the pre-mRNA molecule. In other aspects, at least about 90% of the region of the pre-mRNA molecule may correspond to an exon of the pre-mRNA molecule. In some cases, the region to which the synthetic polynucleotide is complementary to may correspond to a junction between an intron and an exon of the pre-mRNA molecule. In some cases, the region of the pre-mRNA molecule is within 500 bases from an exon of the pre-mRNA molecule.

In some cases, a synthetic polynucleotide of the present disclosure can be from about 10 nucleotides to about 200 nucleotides in length. In some cases, a synthetic polynucleotide can be from about 20 nucleotides to about 200 nucleotides in length. In some cases, a synthetic polynucleotide can be from about 50 nucleotides to about 150 nucleotides in length. In some cases, a synthetic polynucleotide can be from about 10 nucleotides to about 30 nucleotides in length. In some cases, a synthetic polynucleotide can be from about 15 nucleotides to about 25 nucleotides in length.

In some cases, and when administered to a subject (e.g., a human), the synthetic polynucleotides of the present disclosure can be used to treat a disease or condition by inducing exon-skipping of one or more exons in the pre-mRNA molecule that are associated with the disease or condition.

CEP290 and Associated Disorders

CEP290 encodes a centrosome, centriolar satellite and ciliary protein that is an important component of the primary cilium and of the retinal photoreceptor organ in photoreceptor cells. CEP290 is a key component of the ciliary transition zone. This ciliary domain acts as a gate that regulates in a very strict way the protein and lipid composition of the ciliary compartment. Loss-of-function of the CEP290 gene can cause several recessive Mendelian disorders. These include Leber Congenital Amaurosis (OMIM 611755), characterized by retinal dystrophy, Senior-Locken Syndrome (OMIM 610189), characterized by retinitis pigmentosa and renal disease, Joubert syndrome (OMIM 610188), characterized by retinal dystrophy, anatomical eye abnormalities such as coloboma, kidney nephronophthisis, brain anatomical abnormalities with ataxia and mental retardation, and Meckel Syndrome (OMIM 611134), characterized by multiple organ abnormalities determining prenatal or perinatal lethality.

Based on prevalence data reported in the literature, Joubert Syndrome is observed in about 1 per 80,000 Northern Europeans, and about 7.2% of the cases are caused by CEP290 pathogenic variants, resulting in a prevalence estimate of about 1 per 1,000,000 million. Leber Congenital Amaurosis is observed in about 2-3 per 100,000 individuals and about 21% of the cases are caused by CEP290 pathogenic variants, resulting in a prevalence estimate of about 5 per 1,000,000. However, these may be underestimates due to under-reporting or misclassification. The degree of CEP290 loss of function may correlate with disorder severity and syndromic phenotype, suggesting that retinal photoreceptor function may be more sensitive to reduction of functional CEP290 compared to developmental processes requiring primary cilium function.

The compositions and methods of the present disclosure can be used to remediate retinal dystrophy using splice-switching therapeutic oligonucleotides (also described herein as "synthetic polynucleotides" or "SPs" or "oligomers" or "antisense oligomer (ASO)") delivered to eye corpus vitreum and which can be designed to cause skipping of exons 7, 31, 34, 36, 41 or 46 of CEP290 in patients that carry pathogenic LOF variants in these exons. When homozygous, pathogenic LOF variants in these exons are expected to cause Joubert syndrome, whereas when compound heterozygous those variants can cause Joubert syndrome, Senior-Locken Syndrome or Leber Congenital Amaurosis depending on the amount of loss of function imparted by the other variant.

There are currently no treatment options for retinal dystrophy caused by CEP290 LOF pathogenic variants in these exons, and thus novel strategies to treat these diseases may be advantageous.

As disclosed herein, all variant coordinates are presented with respect to the hg19/b37 genome build, and all exons are reported with respect to RefSeq transcript NM_025114. Prevalence estimates are reported with respect to 500M industrialized country individuals regardless of ethnicity.

CEP290 Exon 7

Exon 7 contains the pathogenic stop-gain chr12: 88524986:G:A (NM_025114.3 effect: c.451C>T p.Arg151Ter). This variant has been reported to be present in 70 patients from industrialized countries (of which 50 are individuals of European descent); it is reported in 1 per 234 patients, who are compound heterozygous and present LCA10. The neighboring exons 6, 7, and 9 were found to be potentially required for function, whereas the neighboring exon 8 may not be required for function based on in-silico prediction. Finally, no pathogenic focal deletion is reported in ClinVar. ClinVar is a publicly available archive of relationships among sequence variation and human phenotype.

CEP290 Exon 31

Exon 31 contains the pathogenic stop-gains chr12: 88482895:C:A (NM_025114.3 effect: c.3943G>T p.Glu1315Ter), chr12:88482934:G:A (NM_025114.3 effect: c.3904C>T p.Gln1302Ter) and the likely pathogenic frameshifts chr12:88483053:T:TAA (NM_025114.3 effect: c.3784_3785insTT p.His1262Leufs), chr12:88483059: GCT:G (NM_025114.3 effect: c.3777_3778delAG p.Arg1259Serfs). In aggregate, these variants are expected to be present in 92 patients from industrialized countries (of which 65 are individuals of European descent). They were reported in 13 per 234 and always in patients with compound heterozygosity as follows: 7 patients presented LCA10, 4 patients presented JS, one presented SLS6 and one presented MS. Exon 31 is reported to be part of the RAB8A binding domain. The neighboring exon 32 was reported as potentially not required for function, whereas exon 31 was inferred as potentially required for function. However, patient severity does not clearly suggest whether exon 31 is required for function. Based on in-silico predictions, exon 31 may or may not be required for function. No pathogenic focal deletion is reported in ClinVar.

CEP290 Exon 34

Exon 34 contains the pathogenic stop-gain chr12: 88479860:G:A (NM_025114.3 effect: c.4393C>T p.Arg1465Ter) and the pathogenic frameshift chr12: 88479868:TC:T (NM_025114.3 effect: c.4384delG p.Glu1462Argfs). In aggregate, these variants are expected to be present in 106 patients from industrialized countries (of which 43 are individuals of European descent). They are reported in 4 per 234 patients, always in compound heterozygosity as follows; 2 patients present SLS, 1 JS and 1 LCA. Exon 34 was reported to be part of the RAB8 binding domain. The neighboring exon 32 is reported to be likely not required for function. Similarly, exon 34 may not be required for function, which is consistent with the observed patient phenotype. Based on in-silico prediction, the exon is also characterized as not required for function. No pathogenic focal deletion is reported in ClinVar.

CEP290 Exon 36

Exon 36 contains the pathogenic stop-gain 88477713:T:A (NM_025114.3 effect: c.4723A>T p.Lys1575Ter). This variant is expected to be present in 720 patients from industrialized countries. It is reported in 32 per 234 patients, with homozygosis in 15 patients. Exon 36 was reported to be part of the RAB8 binding domain. Exon 36 may be required for function, however since the 15 homozygous patients are reported to have JS and never MS, whereas 2 per 17 compound heterozygous patients have MS, this exon is more likely not required for function based on patient disorder severity, or at least unlikely required for function. Based on in-silico prediction, however, the exon is characterized to be likely not required for function.

CEP290 Exon 41

Exon 41 contains the pathogenic stop-gains chr12: 88471001:T:A (NM_025114.3 effect: c.5707A>T p.Glu1903Ter), chr12:88471004:C:A (NM_025114.3 effect: c.5704G>T p.Glu1902Ter), chr12:88471040:C:A (NM_025114.3 effect: c.5668G>T p.Gly1890Ter), and the pathogenic frameshift chr12:88471093:CTTTG:C (NM_025114.3 effect:c.5611_5614delCAAA p.Gln1871Valfs). In aggregate, these variants are expected to be present in 600 patients from industrialized countries (of which 400 are individuals of European descent). They are reported in 41 per 234 patients, with homozygosis in 12 patients. Exon 41 is reported to be part of the microtubule binding domain. Exon 41 may be required for function, however since the 12 homozygous patients are reported to have JS and never MS, whereas 3 per 29 compound heterozygous patients have MS, this exon is more likely not required for function based on patient disorder severity, or at least unlikely required for function. The neighboring exon 40 is inferred to be required for function. Based on in-silico prediction, however, the exon is characterized to be likely not required for function. No pathogenic focal deletion is reported in ClinVar.

CEP290 Exon 46

Exon 46 has been reported to contain the pathogenic frameshift chr12:88456548:AC:A (NM_025114.3 effect: c.6277delG p.Val2093Serfs). This variant is expected to be present in 225 patients from industrialized countries (of which 161 are individuals of European descent). It is reported in 1 per 234 patients, who is a JS compound heterozygous case. Exon 46 is reported to be part of the RPGR binding domain. Exon 46 is labelled to be not required for function according to supplementary data, which is consistent with the patient's disease phenotype. Based on in-silico prediction, the exon may or may not be required for function). No pathogenic focal deletion is reported in ClinVar.

TABLE 1 shows synthetic polynucleotide sequences (SEQ ID NO: 1-SEQ ID NO: 824) that were tested to induce skipping of exon 7, 31, 34, 36, 41 or 46 of the CEP290 mRNA (Ref. NM_025114) as described in the present disclosure.

TABLE 1

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG10 | Exon41 | AAATAAAATGTAACTTTA | 18 | 88471127 | 88471144 | 1 |
| DG11 | Exon41 | TAAAAAATAAAATGTA | 16 | 88471123 | 88471138 | 2 |
| DG12 | Exon41 | TGTCAGGGGTTTGCCC | 16 | 88471107 | 88471122 | 3 |
| DG13 | Exon41 | TCTGTCAGGGGTTTGCCCTA | 20 | 88471105 | 88471124 | 4 |
| DG14 | Exon41 | GGAGTTCTTCAATTAGAC | 18 | 88471076 | 88471093 | 5 |
| DG15 | Exon41 | TTTCCTTTGGAGTTCTTC | 18 | 88471068 | 88471085 | 6 |
| DG16 | Exon41 | CTTTCCTTTGGAGTTCTTCAA | 21 | 88471067 | 88471087 | 7 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG17 | Exon41 | TAGTTTTTTAACTTTC | 16 | 88471056 | 88471071 | 8 |
| DG18 | Exon41 | TCTAGTTTTTTAACTTTC | 18 | 88471054 | 88471071 | 9 |
| DG19 | Exon41 | CCCTCTAATTGGTTCTCT | 18 | 88471039 | 88471056 | 10 |
| DG20 | Exon41 | CCTCCACCTTTCCCTC | 16 | 88471028 | 88471043 | 11 |
| DG21 | Exon41 | ACTTCCTCCACCTTTCCC | 18 | 88471024 | 88471041 | 12 |
| DG22 | Exon41 | GTCTACTTCCTCCACC | 16 | 88471020 | 88471035 | 13 |
| DG23 | Exon41 | GGTCTACTTCCTCCACCT | 18 | 88471019 | 88471036 | 14 |
| DG24 | Exon41 | TTTTAGGTCTACTTCCTCCA | 20 | 88471014 | 88471033 | 15 |
| DG25 | Exon41 | GGTTTTAGGTCTACTTCC | 18 | 88471012 | 88471029 | 16 |
| DG26 | Exon41 | GGTTTTAGGTCTACTT | 16 | 88471012 | 88471027 | 17 |
| DG27 | Exon41 | CATAGGTTTTAGGTCTAC | 18 | 88471008 | 88471025 | 18 |
| DG28 | Exon41 | ATACCTTTTCTTTCATAGGT | 20 | 88470995 | 88471014 | 19 |
| DG29 | Exon46 | TTAACATAGCTACAGCCA | 18 | 88456586 | 88456603 | 20 |
| DG30 | Exon46 | AAGATAACAAGCAAACAT | 18 | 88456560 | 88456577 | 21 |
| DG31 | Exon46 | CAAATCTCTGACTTGATTCT | 20 | 88456538 | 88456557 | 22 |
| DG32 | Exon46 | TTTCCTTCAAATCTCTGA | 18 | 88456531 | 88456548 | 23 |
| DG33 | Exon46 | AAGAAATTCACACATTTC | 18 | 88456517 | 88456534 | 24 |
| DG34 | Exon46 | AACTTCTGCTTTTCTTT | 18 | 88456496 | 88456513 | 25 |
| DG35 | Exon46 | GAACTTCTGCTTTTCTTTCT | 21 | 88456495 | 88456515 | 26 |
| DG36 | Exon46 | TCCGCTGAACTTCTGCTT | 18 | 88456489 | 88456506 | 27 |
| DG37 | Exon46 | TCCGCTGAACTTCTGC | 16 | 88456489 | 88456504 | 28 |
| DG38 | Exon46 | GGCCAAGTTTCCGCTGAACT | 20 | 88456480 | 88456499 | 29 |
| DG39 | Exon46 | GGCCAAGTTTCCGCTGAA | 18 | 88456480 | 88456497 | 30 |
| DG40 | Exon46 | GGCCAAGTTTCCGCTG | 16 | 88456480 | 88456495 | 31 |
| DG41 | Exon46 | CTAACATGGCCAAGTTTC | 18 | 88456473 | 88456490 | 32 |
| DG42 | Exon46 | TCTAACATGGCCAAGTTTCC | 20 | 88456472 | 88456491 | 33 |
| DG43 | Exon46 | CCCTCTAACATGGCCAAG | 18 | 88456469 | 88456486 | 34 |
| DG44 | Exon46 | CCCTCTAACATGGCCA | 16 | 88456469 | 88456484 | 35 |
| DG45 | Exon46 | ACATACCCCTCTAACATG | 18 | 88456463 | 88456480 | 36 |
| DG46 | Exon46 | TCTCACATACCCCTCTAACA | 20 | 88456459 | 88456478 | 37 |
| DG180 | Exon46 | TACAGCCATTGAAAAGAAAA | 20 | 88456596 | 88456615 | 38 |
| DG181 | Exon46 | ACATAGCTACAGCCATTGAA | 20 | 88456589 | 88456608 | 39 |
| DG182 | Exon46 | AATTTAACATAGCTACAGCC | 20 | 88456583 | 88456602 | 40 |
| DG183 | Exon46 | TGTAATAATTTAACATAGCT | 20 | 88456577 | 88456596 | 41 |
| DG184 | Exon46 | CAAACATGTAATAATTTAAC | 20 | 88456571 | 88456590 | 42 |
| DG185 | Exon46 | AACAAGCAAACATGTAATAA | 20 | 88456565 | 88456584 | 43 |
| DG186 | Exon46 | AAAGATAACAAGCAAACATG | 20 | 88456559 | 88456578 | 44 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG187 | Exon46 | ATTCTGAAAGATAACAAGCA | 20 | 88456553 | 88456572 | 45 |
| DG188 | Exon46 | GACTTGATTCTGAAAGATAA | 20 | 88456547 | 88456566 | 46 |
| DG189 | Exon46 | ATCTCTGACTTGATTCTGAA | 20 | 88456541 | 88456560 | 47 |
| DG190 | Exon46 | CTTCAAATCTCTGACTTGAT | 20 | 88456535 | 88456554 | 48 |
| DG191 | Exon46 | CATTTCCTTCAAATCTCTGA | 20 | 88456529 | 88456548 | 49 |
| DG192 | Exon46 | TTCACACATTTCCTTCAAAT | 20 | 88456523 | 88456542 | 50 |
| DG193 | Exon46 | AAGAAATTCACACATTTCCT | 20 | 88456517 | 88456536 | 51 |
| DG194 | Exon46 | TTTCTTAAGAAATTCACACA | 20 | 88456511 | 88456530 | 52 |
| DG195 | Exon46 | TTTTTCTTTCTTAAGAAATT | 20 | 88456505 | 88456524 | 53 |
| DG196 | Exon46 | TTCTGCTTTTTCTTCTTAA | 20 | 88456499 | 88456518 | 54 |
| DG197 | Exon46 | CTGAACTTCTGCTTTTTCTT | 20 | 88456493 | 88456512 | 55 |
| DG198 | Exon46 | TTTCCGCTGAACTTCTGCTT | 20 | 88456487 | 88456506 | 56 |
| DG199 | Exon46 | GCCAAGTTTCCGCTGAACTT | 20 | 88456481 | 88456500 | 57 |
| DG200 | Exon46 | AACATGGCCAAGTTTCCGCT | 20 | 88456475 | 88456494 | 58 |
| DG201 | Exon46 | CCCTCTAACATGGCCAAGTT | 20 | 88456469 | 88456488 | 59 |
| DG202 | Exon46 | ACATACCCCTCTAACATGGC | 20 | 88456463 | 88456482 | 60 |
| DG203 | Exon46 | ATTCTCACATACCCCTCTAA | 20 | 88456457 | 88456476 | 61 |
| DG204 | Exon46 | TGGTAAATTCTCACATACCC | 20 | 88456451 | 88456470 | 62 |
| DG205 | Exon46 | AATGTATGGTAAATTCTCAC | 20 | 88456445 | 88456464 | 63 |
| DG206 | Exon46 | AAAACAAATGTATGGTAAAT | 20 | 88456439 | 88456458 | 64 |
| DG207 | Exon46 | GAAACCAAAACAAATGTATG | 20 | 88456433 | 88456452 | 65 |
| DG208 | Exon46 | ACTGCTGAAACCAAAACAAA | 20 | 88456427 | 88456446 | 66 |
| DG209 | Exon46 | CTTATCACTGCTGAAACCAA | 20 | 88456421 | 88456440 | 67 |
| DG210 | Exon46 | TTCTGGCTTATCACTGCTGA | 20 | 88456415 | 88456434 | 68 |
| DG211 | Exon46 | TTTCATTTCTGGCTTATCAC | 20 | 88456409 | 88456428 | 69 |
| DG212 | Exon34 | CATTGAGAGTAACTATTAAT | 20 | 88479991 | 88480010 | 70 |
| DG213 | Exon34 | GTTGCAGCATTGAGAGTAAC | 20 | 88479984 | 88480003 | 71 |
| DG214 | Exon34 | AAAGCAGTTGCAGCATTGAG | 20 | 88479978 | 88479997 | 72 |
| DG215 | Exon34 | TTTAAAAAAGCAGTTGCAGC | 20 | 88479972 | 88479991 | 73 |
| DG216 | Exon34 | ATGTTTTTAAAAAAGCAGT | 20 | 88479966 | 88479985 | 74 |
| DG217 | Exon34 | AATAGTATGTTTTTTAAAAA | 20 | 88479960 | 88479979 | 75 |
| DG218 | Exon34 | TTAAGAAATAGTATGTTTTT | 20 | 88479954 | 88479973 | 76 |
| DG219 | Exon34 | AAACTATTAAGAAATAGTAT | 20 | 88479948 | 88479967 | 77 |
| DG220 | Exon34 | TTCTTCAAACTATTAAGAAA | 20 | 88479942 | 88479961 | 78 |
| DG221 | Exon34 | TGTAGCTTCTTCAAACTATT | 20 | 88479936 | 88479955 | 79 |
| DG222 | Exon34 | TGATCCTGTAGCTTCTTCAA | 20 | 88479930 | 88479949 | 80 |
| DG223 | Exon34 | AGGGATTGATCCTGTAGCTT | 20 | 88479924 | 88479943 | 81 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG224 | Exon34 | AGGGTCAGGGATTGATCCTG | 20 | 88479918 | 88479937 | 82 |
| DG225 | Exon34 | CAAACTAGGGTCAGGGATTG | 20 | 88479912 | 88479931 | 83 |
| DG226 | Exon34 | AAGGGGCAAACTAGGGTCAG | 20 | 88479906 | 88479925 | 84 |
| DG227 | Exon34 | ATTTGGAAGGGGCAAACTAG | 20 | 88479900 | 88479919 | 85 |
| DG228 | Exon34 | AAGTTGATTTGGAAGGGGCA | 20 | 88479894 | 88479913 | 86 |
| DG229 | Exon34 | GATCTCAAGTTGATTTGGAA | 20 | 88479888 | 88479907 | 87 |
| DG230 | Exon34 | TAGAGCGATCTCAAGTTGAT | 20 | 88479882 | 88479901 | 88 |
| DG231 | Exon34 | TTTCCTTAGAGCGATCTCAA | 20 | 88479876 | 88479895 | 89 |
| DG232 | Exon34 | CTTAATTTTCCTTAGAGCGA | 20 | 88479870 | 88479889 | 90 |
| DG233 | Exon34 | GTTCTCCTTAATTTTCCTTA | 20 | 88479864 | 88479883 | 91 |
| DG234 | Exon34 | TCGAATGTTCTCCTTAATTT | 20 | 88479858 | 88479877 | 92 |
| DG235 | Exon34 | AATTATTCGAATGTTCTCCT | 20 | 88479852 | 88479871 | 93 |
| DG236 | Exon34 | TTCTAGAATTATTCGAATGT | 20 | 88479846 | 88479865 | 94 |
| DG237 | Exon34 | CCGTGTTTCTAGAATTATTC | 20 | 88479840 | 88479859 | 95 |
| DG238 | Exon34 | AGTTGCCCGTGTTTCTAGAA | 20 | 88479834 | 88479853 | 96 |
| DG239 | Exon34 | TTTGCAAGTTGCCCGTGTTT | 20 | 88479828 | 88479847 | 97 |
| DG240 | Exon34 | TAGTGATTTGCAAGTTGCCC | 20 | 88479822 | 88479841 | 98 |
| DG241 | Exon34 | CTCTTCTAGTGATTTGCAAG | 20 | 88479816 | 88479835 | 99 |
| DG242 | Exon34 | AATTACCTCTTCTAGTGATT | 20 | 88479810 | 88479829 | 100 |
| DG243 | Exon34 | TCTTCTAATTACCTCTTCTA | 20 | 88479804 | 88479823 | 101 |
| DG244 | Exon34 | GCAAATTCTTCTAATTACCT | 20 | 88479798 | 88479817 | 102 |
| DG245 | Exon34 | CAAAATGCAAATTCTTCTAA | 20 | 88479792 | 88479811 | 103 |
| DG246 | Exon34 | ACTAATCAAAATGCAAATTC | 20 | 88479786 | 88479805 | 104 |
| DG247 | Exon34 | TAATACACTAATCAAAATGC | 20 | 88479780 | 88479799 | 105 |
| DG248 | Exon34 | ACCAAATAATACACTAATCA | 20 | 88479774 | 88479793 | 106 |
| DG249 | Exon34 | AAACATACCAAATAATACAC | 20 | 88479768 | 88479787 | 107 |
| DG250 | Exon34 | CCCCCCAAACATACCAAATA | 20 | 88479762 | 88479781 | 108 |
| DG251 | Exon34 | AGAAAGCCCCCCAAACATAC | 20 | 88479756 | 88479775 | 109 |
| DG252 | Exon31 | TTTTTCCAGTGAAAGTTATC | 20 | 88483305 | 88483324 | 110 |
| DG253 | Exon31 | CAAATTTTTCCAGTGAAAGT | 20 | 88483301 | 88483320 | 111 |
| DG254 | Exon31 | TTTCAAATTTTTCCAGTGAA | 20 | 88483298 | 88483317 | 112 |
| DG255 | Exon31 | TAAGTTTCAAATTTTTCCAG | 20 | 88483294 | 88483313 | 113 |
| DG256 | Exon31 | TAGTAAGTTTCAAATTTTTC | 20 | 88483291 | 88483310 | 114 |
| DG257 | Exon31 | TTTGTAGTAAGTTTCAAATT | 20 | 88483287 | 88483306 | 115 |
| DG258 | Exon31 | ATATTTGTAGTAAGTTTCAA | 20 | 88483284 | 88483303 | 116 |
| DG259 | Exon31 | ATATATATTTGTAGTAAGTT | 20 | 88483280 | 88483299 | 117 |
| DG260 | Exon31 | AAAATATATATTTGTAGTAA | 20 | 88483277 | 88483296 | 118 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG261 | Exon31 | AAAAAAAATATATATTTGTA | 20 | 88483273 | 88483292 | 119 |
| DG262 | Exon31 | ATTAAAAAAATATATATTT | 20 | 88483270 | 88483289 | 120 |
| DG263 | Exon31 | TGATATTAAAAAAATATAT | 20 | 88483266 | 88483285 | 121 |
| DG264 | Exon31 | GCCTGATATTAAAAAAATA | 20 | 88483263 | 88483282 | 122 |
| DG265 | Exon31 | CTGTGCCTGATATTAAAAAA | 20 | 88483259 | 88483278 | 123 |
| DG266 | Exon31 | AGACTGTGCCTGATATTAAA | 20 | 88483256 | 88483275 | 124 |
| DG267 | Exon31 | CATCAGACTGTGCCTGATAT | 20 | 88483252 | 88483271 | 125 |
| DG268 | Exon31 | TTTCATCAGACTGTGCCTGA | 20 | 88483249 | 88483268 | 126 |
| DG269 | Exon31 | GACTTTTCATCAGACTGTGC | 20 | 88483245 | 88483264 | 127 |
| DG270 | Exon31 | AGCGACTTTTCATCAGACTG | 20 | 88483242 | 88483261 | 128 |
| DG271 | Exon31 | AATGAGCGACTTTTCATCAG | 20 | 88483238 | 88483257 | 129 |
| DG272 | Exon31 | GGCAATGAGCGACTTTTCAT | 20 | 88483235 | 88483254 | 130 |
| DG273 | Exon31 | ACTTGGCAATGAGCGACTTT | 20 | 88483231 | 88483250 | 131 |
| DG274 | Exon31 | GCAACTTGGCAATGAGCGAC | 20 | 88483228 | 88483247 | 132 |
| DG275 | Exon31 | TGGTGCAACTTGGCAATGAG | 20 | 88483224 | 88483243 | 133 |
| DG276 | Exon31 | TGTTGGTGCAACTTGGCAAT | 20 | 88483221 | 88483240 | 134 |
| DG277 | Exon31 | ATTATGTTGGTGCAACTTGG | 20 | 88483217 | 88483236 | 135 |
| DG278 | Exon31 | GACATTATGTTGGTGCAACT | 20 | 88483214 | 88483233 | 136 |
| DG279 | Exon31 | GAGAGACATTATGTTGGTGC | 20 | 88483210 | 88483229 | 137 |
| DG280 | Exon31 | GAAGAGAGACATTATGTTGG | 20 | 88483207 | 88483226 | 138 |
| DG281 | Exon31 | AGTTGAAGAGAGACATTATG | 20 | 88483203 | 88483222 | 139 |
| DG282 | Exon31 | CTCAGTTGAAGAGAGACATT | 20 | 88483200 | 88483219 | 140 |
| DG283 | Exon31 | CTCACTCAGTTGAAGAGAGA | 20 | 88483196 | 88483215 | 141 |
| DG284 | Exon31 | AGCCTCACTCAGTTGAAGAG | 20 | 88483193 | 88483212 | 142 |
| DG285 | Exon31 | CAGTAGCCTCACTCAGTTGA | 20 | 88483189 | 88483208 | 143 |
| DG286 | Exon31 | GAGCAGTAGCCTCACTCAGT | 20 | 88483186 | 88483205 | 144 |
| DG287 | Exon31 | CCAAGAGCAGTAGCCTCACT | 20 | 88483182 | 88483201 | 145 |
| DG288 | Exon31 | TTACCAAGAGCAGTAGCCTC | 20 | 88483179 | 88483198 | 146 |
| DG289 | Exon31 | CAACTTACCAAGAGCAGTAG | 20 | 88483175 | 88483194 | 147 |
| DG290 | Exon31 | CTCCAACTTACCAAGAGCAG | 20 | 88483172 | 88483191 | 148 |
| DG291 | Exon31 | TTGACTCCAACTTACCAAGA | 20 | 88483168 | 88483187 | 149 |
| DG292 | Exon31 | TAATTGACTCCAACTTACCA | 20 | 88483165 | 88483184 | 150 |
| DG293 | Exon31 | GATGTAATTGACTCCAACTT | 20 | 88483161 | 88483180 | 151 |
| DG294 | Exon31 | TTAGATGTAATTGACTCCAA | 20 | 88483158 | 88483177 | 152 |
| DG295 | Exon31 | CAGTTTAGATGTAATTGACT | 20 | 88483154 | 88483173 | 153 |
| DG296 | Exon31 | CTGCAGTTTAGATGTAATTG | 20 | 88483151 | 88483170 | 154 |
| DG297 | Exon31 | TCTTCTGCAGTTTAGATGTA | 20 | 88483147 | 88483166 | 155 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG298 | Exon31 | CCATCTTCTGCAGTTTAGAT | 20 | 88483144 | 88483163 | 156 |
| DG299 | Exon31 | GCCTCCATCTTCTGCAGTTT | 20 | 88483140 | 88483159 | 157 |
| DG300 | Exon31 | TAGGCCTCCATCTTCTGCAG | 20 | 88483137 | 88483156 | 158 |
| DG301 | Exon31 | GTTGTAGGCCTCCATCTTCT | 20 | 88483133 | 88483152 | 159 |
| DG302 | Exon31 | CAAGTTGTAGGCCTCCATCT | 20 | 88483130 | 88483149 | 160 |
| DG303 | Exon31 | AGCGCAAGTTGTAGGCCTCC | 20 | 88483126 | 88483145 | 161 |
| DG304 | Exon31 | CTAAGCGCAAGTTGTAGGCC | 20 | 88483123 | 88483142 | 162 |
| DG305 | Exon31 | TGCTCTAAGCGCAAGTTGTA | 20 | 88483119 | 88483138 | 163 |
| DG306 | Exon31 | TTCTGCTCTAAGCGCAAGTT | 20 | 88483116 | 88483135 | 164 |
| DG307 | Exon31 | AAGTTTCTGCTCTAAGCGCA | 20 | 88483112 | 88483131 | 165 |
| DG308 | Exon31 | ATCAAGTTTCTGCTCTAAGC | 20 | 88483109 | 88483128 | 166 |
| DG309 | Exon31 | TTTCATCAAGTTTCTGCTCT | 20 | 88483105 | 88483124 | 167 |
| DG310 | Exon31 | CTTTTTCATCAAGTTTCTGC | 20 | 88483102 | 88483121 | 168 |
| DG311 | Exon31 | TGTTCTTTTTCATCAAGTTT | 20 | 88483098 | 88483117 | 169 |
| DG312 | Exon31 | GCCTGTTCTTTTTCATCAAG | 20 | 88483095 | 88483114 | 170 |
| DG313 | Exon31 | GAGAGCCTGTTCTTTTTCAT | 20 | 88483091 | 88483110 | 171 |
| DG314 | Exon31 | ATAGAGAGCCTGTTCTTTTT | 20 | 88483088 | 88483107 | 172 |
| DG315 | Exon31 | CATAATAGAGAGCCTGTTCT | 20 | 88483084 | 88483103 | 173 |
| DG316 | Exon31 | GAGCATAATAGAGAGCCTGT | 20 | 88483081 | 88483100 | 174 |
| DG317 | Exon31 | AAACGAGCATAATAGAGAGC | 20 | 88483077 | 88483096 | 175 |
| DG318 | Exon31 | TCCAAACGAGCATAATAGAG | 20 | 88483074 | 88483093 | 176 |
| DG319 | Exon31 | TCCCTCCAAACGAGCATAAT | 20 | 88483070 | 88483089 | 177 |
| DG320 | Exon31 | TCTTCCCTCCAAACGAGCAT | 20 | 88483067 | 88483086 | 178 |
| DG321 | Exon31 | TGTTTCTTCCCTCCAAACGA | 20 | 88483063 | 88483082 | 179 |
| DG322 | Exon31 | CTCTGTTTCTTCCCTCCAAA | 20 | 88483060 | 88483079 | 180 |
| DG323 | Exon31 | TTTGCTCTGTTTCTTCCCTC | 20 | 88483056 | 88483075 | 181 |
| DG324 | Exon31 | TGTTTTGCTCTGTTTCTTCC | 20 | 88483053 | 88483072 | 182 |
| DG325 | Exon31 | CAGATGTTTTGCTCTGTTTC | 20 | 88483049 | 88483068 | 183 |
| DG326 | Exon31 | GCGCAGATGTTTTGCTCTGT | 20 | 88483046 | 88483065 | 184 |
| DG327 | Exon31 | TTTGGCGCAGATGTTTTGCT | 20 | 88483042 | 88483061 | 185 |
| DG328 | Exon31 | TTGTTTGGCGCAGATGTTTT | 20 | 88483039 | 88483058 | 186 |
| DG329 | Exon31 | TGAATTGTTTGGCGCAGATG | 20 | 88483035 | 88483054 | 187 |
| DG330 | Exon31 | GACTGAATTGTTTGGCGCAG | 20 | 88483032 | 88483051 | 188 |
| DG331 | Exon31 | TAGAGACTGAATTGTTTGGC | 20 | 88483028 | 88483047 | 189 |
| DG332 | Exon31 | TCGTAGAGACTGAATTGTTT | 20 | 88483025 | 88483044 | 190 |
| DG333 | Exon31 | GTCGTCGTAGAGACTGAATT | 20 | 88483021 | 88483040 | 191 |
| DG334 | Exon31 | ACTGTCGTCGTAGAGACTGA | 20 | 88483018 | 88483037 | 192 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG335 | Exon31 | CTAAACTGTCGTCGTAGAGA | 20 | 88483014 | 88483033 | 193 |
| DG336 | Exon31 | CCACTAAACTGTCGTCGTAG | 20 | 88483011 | 88483030 | 194 |
| DG337 | Exon31 | AGCTCCACTAAACTGTCGTC | 20 | 88483007 | 88483026 | 195 |
| DG338 | Exon31 | TAAAGCTCCACTAAACTGTC | 20 | 88483004 | 88483023 | 196 |
| DG339 | Exon31 | AGGGTAAAGCTCCACTAAAC | 20 | 88483000 | 88483019 | 197 |
| DG340 | Exon31 | CCAAGGGTAAAGCTCCACTA | 20 | 88482997 | 88483016 | 198 |
| DG341 | Exon31 | TGTGCCAAGGGTAAAGCTCC | 20 | 88482993 | 88483012 | 199 |
| DG342 | Exon31 | TGTTGTGCCAAGGGTAAAGC | 20 | 88482990 | 88483009 | 200 |
| DG343 | Exon31 | TTCCTGTTGTGCCAAGGGTA | 20 | 88482986 | 88483005 | 201 |
| DG344 | Exon31 | CTTTTCCTGTTGTGCCAAGG | 20 | 88482983 | 88483002 | 202 |
| DG345 | Exon31 | AGAACTTTTCCTGTTGTGCC | 20 | 88482979 | 88482998 | 203 |
| DG346 | Exon31 | TGGAGAACTTTTCCTGTTGT | 20 | 88482976 | 88482995 | 204 |
| DG347 | Exon31 | GTTTTGGAGAACTTTTCCTG | 20 | 88482972 | 88482991 | 205 |
| DG348 | Exon31 | ATTGTTTTGGAGAACTTTTC | 20 | 88482969 | 88482988 | 206 |
| DG349 | Exon31 | AATCATTGTTTTGGAGAACT | 20 | 88482965 | 88482984 | 207 |
| DG350 | Exon31 | TTGAATCATTGTTTTGGAGA | 20 | 88482962 | 88482981 | 208 |
| DG351 | Exon31 | GTAGTTGAATCATTGTTTTG | 20 | 88482958 | 88482977 | 209 |
| DG352 | Exon31 | TTTGTAGTTGAATCATTGTT | 20 | 88482955 | 88482974 | 210 |
| DG353 | Exon31 | TCATTTTGTAGTTGAATCAT | 20 | 88482951 | 88482970 | 211 |
| DG354 | Exon31 | TTGTCATTTTGTAGTTGAAT | 20 | 88482948 | 88482967 | 212 |
| DG355 | Exon31 | AAGTTTGTCATTTTGTAGTT | 20 | 88482944 | 88482963 | 213 |
| DG356 | Exon31 | CTTAAGTTTGTCATTTTGTA | 20 | 88482941 | 88482960 | 214 |
| DG357 | Exon31 | TTATCTTAAGTTTGTCATTT | 20 | 88482937 | 88482956 | 215 |
| DG358 | Exon31 | GCATTATCTTAAGTTTGTCA | 20 | 88482934 | 88482953 | 216 |
| DG359 | Exon31 | TCTTGCATTATCTTAAGTTT | 20 | 88482930 | 88482949 | 217 |
| DG360 | Exon31 | ATTTCTTGCATTATCTTAAG | 20 | 88482927 | 88482946 | 218 |
| DG361 | Exon31 | TTTCATTTCTTGCATTATCT | 20 | 88482923 | 88482942 | 219 |
| DG362 | Exon31 | ATTTTCATTTCTTGCATTA | 20 | 88482920 | 88482939 | 220 |
| DG363 | Exon31 | GAGAATTTTTCATTTCTTGC | 20 | 88482916 | 88482935 | 221 |
| DG364 | Exon31 | GTTGAGAATTTTTCATTTCT | 20 | 88482913 | 88482932 | 222 |
| DG365 | Exon31 | TCTTGTTGAGAATTTTTCAT | 20 | 88482909 | 88482928 | 223 |
| DG366 | Exon31 | TGTTCTTGTTGAGAATTTTT | 20 | 88482906 | 88482925 | 224 |
| DG367 | Exon31 | TCTATGTTCTTGTTGAGAAT | 20 | 88482902 | 88482921 | 225 |
| DG368 | Exon31 | ATTTCTATGTTCTTGTTGAG | 20 | 88482899 | 88482918 | 226 |
| DG369 | Exon31 | CCATATTTCTATGTTCTTGT | 20 | 88482895 | 88482914 | 227 |
| DG370 | Exon31 | TCTCCATATTTCTATGTTCT | 20 | 88482892 | 88482911 | 228 |
| DG371 | Exon31 | TTGTTCTCCATATTTCTATG | 20 | 88482888 | 88482907 | 229 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG372 | Exon31 | GTTTTGTTCTCCATATTTCT | 20 | 88482885 | 88482904 | 230 |
| DG373 | Exon31 | CAATGTTTTGTTCTCCATAT | 20 | 88482881 | 88482900 | 231 |
| DG374 | Exon31 | CTCCAATGTTTTGTTCTCCA | 20 | 88482878 | 88482897 | 232 |
| DG375 | Exon31 | CCATCTCCAATGTTTTGTTC | 20 | 88482874 | 88482893 | 233 |
| DG376 | Exon31 | ATTCCATCTCCAATGTTTTG | 20 | 88482871 | 88482890 | 234 |
| DG377 | Exon31 | TTTAATTCCATCTCCAATGT | 20 | 88482867 | 88482886 | 235 |
| DG378 | Exon31 | AATTTAATTCCATCTCCAA | 20 | 88482864 | 88482883 | 236 |
| DG379 | Exon31 | CTTTAATTTAATTCCATCT | 20 | 88482860 | 88482879 | 237 |
| DG380 | Exon31 | GCCCTTTAATTTTAATTCCA | 20 | 88482857 | 88482876 | 238 |
| DG381 | Exon31 | CCAGGCCCTTTAATTTTAAT | 20 | 88482853 | 88482872 | 239 |
| DG382 | Exon31 | CTTCCAGGCCCTTTAATTTT | 20 | 88482850 | 88482869 | 240 |
| DG383 | Exon31 | AACTCTTCCAGGCCCTTTAA | 20 | 88482846 | 88482865 | 241 |
| DG384 | Exon31 | ATTAACTCTTCCAGGCCCTT | 20 | 88482843 | 88482862 | 242 |
| DG385 | Exon31 | GCTTATTAACTCTTCCAGGC | 20 | 88482839 | 88482858 | 243 |
| DG386 | Exon31 | AGTGCTTATTAACTCTTCCA | 20 | 88482836 | 88482855 | 244 |
| DG387 | Exon31 | TTAAAGTGCTTATTAACTCT | 20 | 88482832 | 88482851 | 245 |
| DG388 | Exon31 | CCTTTAAAGTGCTTATTAAC | 20 | 88482829 | 88482848 | 246 |
| DG389 | Exon31 | GTATCCTTTAAAGTGCTTAT | 20 | 88482825 | 88482844 | 247 |
| DG390 | Exon31 | TTGGTATCCTTTAAAGTGCT | 20 | 88482822 | 88482841 | 248 |
| DG391 | Exon31 | TCCTTTGGTATCCTTTAAAG | 20 | 88482818 | 88482837 | 249 |
| DG392 | Exon31 | GGCTCCTTTGGTATCCTTTA | 20 | 88482815 | 88482834 | 250 |
| DG393 | Exon31 | TTTGGGCTCCTTTGGTATCC | 20 | 88482811 | 88482830 | 251 |
| DG394 | Exon31 | CCTTTTGGGCTCCTTTGGTA | 20 | 88482808 | 88482827 | 252 |
| DG395 | Exon31 | TTTACCTTTTGGGCTCCTTT | 20 | 88482804 | 88482823 | 253 |
| DG396 | Exon31 | ATGTTTACCTTTTGGGCTCC | 20 | 88482801 | 88482820 | 254 |
| DG397 | Exon31 | TTAAATGTTTACCTTTTGGG | 20 | 88482797 | 88482816 | 255 |
| DG398 | Exon31 | AGTTTAAATGTTTACCTTTT | 20 | 88482794 | 88482813 | 256 |
| DG399 | Exon31 | ATCAAGTTTAAATGTTTACC | 20 | 88482790 | 88482809 | 257 |
| DG400 | Exon31 | AAAATCAAGTTTAAATGTTT | 20 | 88482787 | 88482806 | 258 |
| DG401 | Exon31 | AAAAAAATCAAGTTTAAAT | 20 | 88482783 | 88482802 | 259 |
| DG402 | Exon31 | AAAAAAAAAATCAAGTTTA | 20 | 88482780 | 88482799 | 260 |
| DG403 | Exon31 | TCTTAAAAAAAAAATCAAG | 20 | 88482776 | 88482795 | 261 |
| DG404 | Exon31 | GTCTCTTAAAAAAAAAATC | 20 | 88482773 | 88482792 | 262 |
| DG405 | Exon31 | TACTGTCTCTTAAAAAAAAA | 20 | 88482769 | 88482788 | 263 |
| DG406 | Exon31 | AGATACTGTCTCTTAAAAAA | 20 | 88482766 | 88482785 | 264 |
| DG407 | Exon31 | ATCAAGATACTGTCTCTTAA | 20 | 88482762 | 88482781 | 265 |
| DG408 | Exon31 | CAGATCAAGATACTGTCTCT | 20 | 88482759 | 88482778 | 266 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG409 | Exon31 | GAAACAGATCAAGATACTGT | 20 | 88482755 | 88482774 | 267 |
| DG410 | Exon31 | TGGGAAACAGATCAAGATAC | 20 | 88482752 | 88482771 | 268 |
| DG411 | Exon31 | GCCTGGGAAACAGATCAAGA | 20 | 88482749 | 88482768 | 269 |
| DG412 | Exon7 | AATTCAGCAGTAATTTTTTT | 20 | 88525036 | 88525055 | 270 |
| DG413 | Exon7 | ATAAAATTCAGCAGTAATTT | 20 | 88525032 | 88525051 | 271 |
| DG414 | Exon7 | GAAGATAAAATTCAGCAGTA | 20 | 88525028 | 88525047 | 272 |
| DG415 | Exon7 | AGAAGAAGATAAAATTCAGC | 20 | 88525024 | 88525043 | 273 |
| DG416 | Exon7 | AATAAGAAGAAGATAAAATT | 20 | 88525020 | 88525039 | 274 |
| DG417 | Exon7 | AATAAATAAGAAGAAGATAA | 20 | 88525016 | 88525035 | 275 |
| DG418 | Exon7 | AAAAAATAAATAAGAAGAAG | 20 | 88525012 | 88525031 | 276 |
| DG419 | Exon7 | AAAAAAAAAATAAATAAGAA | 20 | 88525008 | 88525027 | 277 |
| DG420 | Exon7 | GTAAAAAAAAAAAATAAATA | 20 | 88525004 | 88525023 | 278 |
| DG421 | Exon7 | AATAGTAAAAAAAAAAAATA | 20 | 88525000 | 88525019 | 279 |
| DG422 | Exon7 | CTAAAATAGTAAAAAAAAAA | 20 | 88524996 | 88525015 | 280 |
| DG423 | Exon7 | CCAACTAAAATAGTAAAAAA | 20 | 88524992 | 88525011 | 281 |
| DG424 | Exon7 | AGAGCCAACTAAAATAGTAA | 20 | 88524988 | 88525007 | 282 |
| DG425 | Exon7 | TCGAAGAGCCAACTAAAATA | 20 | 88524984 | 88525003 | 283 |
| DG426 | Exon7 | CATTTCGAAGAGCCAACTAA | 20 | 88524980 | 88524999 | 284 |
| DG427 | Exon7 | TCCTCATTTCGAAGAGCCAA | 20 | 88524976 | 88524995 | 285 |
| DG428 | Exon7 | TGCCTCCTCATTTCGAAGAG | 20 | 88524972 | 88524991 | 286 |
| DG429 | Exon7 | TTTCTGCCTCCTCATTTCGA | 20 | 88524968 | 88524987 | 287 |
| DG430 | Exon7 | TCATTTCTGCCTCCTCATT | 20 | 88524964 | 88524983 | 288 |
| DG431 | Exon7 | GTTTTCATTTCTGCCTCCT | 20 | 88524960 | 88524979 | 289 |
| DG432 | Exon7 | GCTGTTTTCATTTCTGCCT | 20 | 88524957 | 88524976 | 290 |
| DG433 | Exon7 | ATTTGCTGTTTTCATTTCT | 20 | 88524953 | 88524972 | 291 |
| DG434 | Exon7 | CTTAATTTGCTGTTTTCATT | 20 | 88524949 | 88524968 | 292 |
| DG435 | Exon7 | TCTTCTTAATTTGCTGTTTT | 20 | 88524945 | 88524964 | 293 |
| DG436 | Exon7 | CCTCTCTTCTTAATTTGCTG | 20 | 88524941 | 88524960 | 294 |
| DG437 | Exon7 | TTTACCTCTCTTCTTAATTT | 20 | 88524937 | 88524956 | 295 |
| DG438 | Exon7 | ATTTTTTACCTCTCTTCTTA | 20 | 88524933 | 88524952 | 296 |
| DG439 | Exon7 | TAAAATTTTTTACCTCTCTT | 20 | 88524929 | 88524948 | 297 |
| DG440 | Exon7 | CTACTAAAATTTTTTACCTC | 20 | 88524925 | 88524944 | 298 |
| DG441 | Exon7 | ACAACTACTAAAATTTTTTA | 20 | 88524921 | 88524940 | 299 |
| DG442 | Exon7 | CACCACAACTACTAAAATTT | 20 | 88524917 | 88524936 | 300 |
| DG443 | Exon7 | GAACCACCACAACTACTAAA | 20 | 88524913 | 88524932 | 301 |
| DG444 | Exon7 | TGTTGAACCACCACAACTAC | 20 | 88524909 | 88524928 | 302 |
| DG445 | Exon7 | CCTTTGTTGAACCACCACAA | 20 | 88524905 | 88524924 | 303 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG446 | Exon7 | AGTACCTTTGTTGAACCACC | 20 | 88524901 | 88524920 | 304 |
| DG447 | Exon7 | AATAAGTACCTTTGTTGAAC | 20 | 88524897 | 88524916 | 305 |
| DG448 | Exon7 | TTTTAATAAGTACCTTTGTT | 20 | 88524893 | 88524912 | 306 |
| DG449 | Exon7 | CTTATTTTAATAAGTACCTT | 20 | 88524889 | 88524908 | 307 |
| DG450 | Exon7 | GGTACTTATTTTAATAAGTA | 20 | 88524885 | 88524904 | 308 |
| DG451 | Exon7 | TTAGGTACTTATTTTAATAA | 20 | 88524882 | 88524901 | 309 |
| DG733 | Exon41 | TCAGGGGTTTGCCCTA | 16 | 88471109 | 88471124 | 310 |
| DG735 | Exon41 | CTGTCAGGGGTTTGCC | 16 | 88471106 | 88471121 | 311 |
| DG736 | Exon41 | TCAGGGGTTTGCCCTAA | 17 | 88471109 | 88471125 | 312 |
| DG737 | Exon41 | GTCAGGGGTTTGCCCTA | 17 | 88471108 | 88471124 | 313 |
| DG738 | Exon41 | TGTCAGGGGTTTGCCCT | 17 | 88471107 | 88471123 | 314 |
| DG739 | Exon41 | CTGTCAGGGGTTTGCCC | 17 | 88471106 | 88471122 | 315 |
| DG740 | Exon41 | TCTGTCAGGGGTTTGCC | 17 | 88471105 | 88471121 | 316 |
| DG741 | Exon41 | GTCAGGGGTTTGCCCTAA | 18 | 88471108 | 88471125 | 317 |
| DG742 | Exon41 | TGTCAGGGGTTTGCCCTA | 18 | 88471107 | 88471124 | 318 |
| DG743 | Exon41 | CTGTCAGGGGTTTGCCCT | 18 | 88471106 | 88471123 | 319 |
| DG744 | Exon41 | TCTGTCAGGGGTTTGCCC | 18 | 88471105 | 88471122 | 320 |
| DG745 | Exon41 | ATCTGTCAGGGGTTTGCC | 18 | 88471104 | 88471121 | 321 |
| DG746 | Exon41 | GTCAGGGGTTTGCCCTAAA | 19 | 88471108 | 88471126 | 322 |
| DG747 | Exon41 | TGTCAGGGGTTTGCCCTAA | 19 | 88471107 | 88471125 | 323 |
| DG748 | Exon41 | CTGTCAGGGGTTTGCCCTA | 19 | 88471106 | 88471124 | 324 |
| DG749 | Exon41 | TCTGTCAGGGGTTTGCCCT | 19 | 88471105 | 88471123 | 325 |
| DG750 | Exon41 | ATCTGTCAGGGGTTTGCCC | 19 | 88471104 | 88471122 | 326 |
| DG751 | Exon41 | TGTCAGGGGTTTGCCCTAAA | 20 | 88471107 | 88471126 | 327 |
| DG752 | Exon41 | CTGTCAGGGGTTTGCCCTAA | 20 | 88471106 | 88471125 | 328 |
| DG754 | Exon41 | ATCTGTCAGGGGTTTGCCCT | 20 | 88471104 | 88471123 | 329 |
| DG755 | Exon41 | TATCTGTCAGGGGTTTGCCC | 20 | 88471103 | 88471122 | 330 |
| DG756 | Exon41 | AGTTCTTCAATTAGAC | 16 | 88471078 | 88471093 | 331 |
| DG757 | Exon41 | GTTCTTCAATTAGACTT | 17 | 88471079 | 88471095 | 332 |
| DG758 | Exon41 | GAGTTCTTCAATTAGAC | 17 | 88471077 | 88471093 | 333 |
| DG759 | Exon41 | TGGAGTTCTTCAATTAG | 17 | 88471075 | 88471091 | 334 |
| DG760 | Exon41 | TTCCTTTGGAGTTCTTC | 17 | 88471069 | 88471085 | 335 |
| DG761 | Exon41 | AGTTCTTCAATTAGACTT | 18 | 88471078 | 88471095 | 336 |
| DG762 | Exon41 | GAGTTCTTCAATTAGACT | 18 | 88471077 | 88471094 | 337 |
| DG764 | Exon41 | TGGAGTTCTTCAATTAGA | 18 | 88471075 | 88471092 | 338 |
| DG765 | Exon41 | TTGGAGTTCTTCAATTAG | 18 | 88471074 | 88471091 | 339 |
| DG766 | Exon41 | TCCTTTGGAGTTCTTCAA | 18 | 88471070 | 88471087 | 340 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG767 | Exon41 | TTCCTTTGGAGTTCTTCA | 18 | 88471069 | 88471086 | 341 |
| DG769 | Exon41 | ACTTTCCTTTGGAGTTCT | 18 | 88471066 | 88471083 | 342 |
| DG770 | Exon41 | AGTTCTTCAATTAGACTTT | 19 | 88471078 | 88471096 | 343 |
| DG771 | Exon41 | GAGTTCTTCAATTAGACTT | 19 | 88471077 | 88471095 | 344 |
| DG772 | Exon41 | GGAGTTCTTCAATTAGACT | 19 | 88471076 | 88471094 | 345 |
| DG773 | Exon41 | TGGAGTTCTTCAATTAGAC | 19 | 88471075 | 88471093 | 346 |
| DG774 | Exon41 | TTGGAGTTCTTCAATTAGA | 19 | 88471074 | 88471092 | 347 |
| DG775 | Exon41 | TTTGGAGTTCTTCAATTAG | 19 | 88471073 | 88471091 | 348 |
| DG776 | Exon41 | CCTTTGGAGTTCTTCAATT | 19 | 88471071 | 88471089 | 349 |
| DG777 | Exon41 | TCCTTTGGAGTTCTTCAAT | 19 | 88471070 | 88471088 | 350 |
| DG778 | Exon41 | TTTCCTTTGGAGTTCTTCA | 19 | 88471068 | 88471086 | 351 |
| DG779 | Exon41 | CTTTCCTTTGGAGTTCTTC | 19 | 88471067 | 88471085 | 352 |
| DG780 | Exon41 | ACTTTCCTTTGGAGTTCTT | 19 | 88471066 | 88471084 | 353 |
| DG781 | Exon41 | GAGTTCTTCAATTAGACTTT | 20 | 88471077 | 88471096 | 354 |
| DG782 | Exon41 | GGAGTTCTTCAATTAGACTT | 20 | 88471076 | 88471095 | 355 |
| DG783 | Exon41 | TGGAGTTCTTCAATTAGACT | 20 | 88471075 | 88471094 | 356 |
| DG784 | Exon41 | TTGGAGTTCTTCAATTAGAC | 20 | 88471074 | 88471093 | 357 |
| DG785 | Exon41 | TTTGGAGTTCTTCAATTAGA | 20 | 88471073 | 88471092 | 358 |
| DG786 | Exon41 | CCTTTGGAGTTCTTCAATTA | 20 | 88471071 | 88471090 | 359 |
| DG787 | Exon41 | TCCTTTGGAGTTCTTCAATT | 20 | 88471070 | 88471089 | 360 |
| DG788 | Exon41 | TTCCTTTGGAGTTCTTCAAT | 20 | 88471069 | 88471088 | 361 |
| DG789 | Exon41 | CTTTCCTTTGGAGTTCTTCA | 20 | 88471067 | 88471086 | 362 |
| DG790 | Exon41 | ACTTTCCTTTGGAGTTCTTC | 20 | 88471066 | 88471085 | 363 |
| DG791 | Exon41 | GGTCTACTTCCTCCAC | 16 | 88471019 | 88471034 | 364 |
| DG792 | Exon41 | TCTACTTCCTCCACCTT | 17 | 88471021 | 88471037 | 365 |
| DG793 | Exon41 | AGGTCTACTTCCTCCAC | 17 | 88471018 | 88471034 | 366 |
| DG794 | Exon41 | TTTAGGTCTACTTCCTC | 17 | 88471015 | 88471031 | 367 |
| DG795 | Exon41 | TCTACTTCCTCCACCTTT | 18 | 88471021 | 88471038 | 368 |
| DG796 | Exon41 | GTCTACTTCCTCCACCTT | 18 | 88471020 | 88471037 | 369 |
| DG798 | Exon41 | AGGTCTACTTCCTCCACC | 18 | 88471018 | 88471035 | 370 |
| DG799 | Exon41 | TAGGTCTACTTCCTCCAC | 18 | 88471017 | 88471034 | 371 |
| DG800 | Exon41 | TTTAGGTCTACTTCCTCC | 18 | 88471015 | 88471032 | 372 |
| DG801 | Exon41 | TTTTAGGTCTACTTCCTC | 18 | 88471014 | 88471031 | 373 |
| DG802 | Exon41 | GTTTTAGGTCTACTTCCT | 18 | 88471013 | 88471030 | 374 |
| DG803 | Exon41 | TCTACTTCCTCCACCTTTC | 19 | 88471021 | 88471039 | 375 |
| DG804 | Exon41 | GTCTACTTCCTCCACCTTT | 19 | 88471020 | 88471038 | 376 |
| DG805 | Exon41 | GGTCTACTTCCTCCACCTT | 19 | 88471019 | 88471037 | 377 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG806 | Exon41 | TAGGTCTACTTCCTCCACC | 19 | 88471017 | 88471035 | 378 |
| DG807 | Exon41 | TTAGGTCTACTTCCTCCAC | 19 | 88471016 | 88471034 | 379 |
| DG808 | Exon41 | TTTAGGTCTACTTCCTCCA | 19 | 88471015 | 88471033 | 380 |
| DG809 | Exon41 | TTTTAGGTCTACTTCCTCC | 19 | 88471014 | 88471032 | 381 |
| DG810 | Exon41 | GTTTTAGGTCTACTTCCTC | 19 | 88471013 | 88471031 | 382 |
| DG811 | Exon41 | GTCTACTTCCTCCACCTTTC | 20 | 88471020 | 88471039 | 383 |
| DG812 | Exon41 | GGTCTACTTCCTCCACCTTT | 20 | 88471019 | 88471038 | 384 |
| DG813 | Exon41 | AGGTCTACTTCCTCCACCTT | 20 | 88471018 | 88471037 | 385 |
| DG814 | Exon41 | TAGGTCTACTTCCTCCACCT | 20 | 88471017 | 88471036 | 386 |
| DG815 | Exon41 | TTAGGTCTACTTCCTCCACC | 20 | 88471016 | 88471035 | 387 |
| DG816 | Exon41 | TTTAGGTCTACTTCCTCCAC | 20 | 88471015 | 88471034 | 388 |
| DG818 | Exon41 | GTTTTAGGTCTACTTCCTCC | 20 | 88471013 | 88471032 | 389 |
| DG819 | Exon41 | GGTTTTAGGTCTACTTCCTC | 20 | 88471012 | 88471031 | 390 |
| DG925 | Exon41 | TTTCATAGGTTTTAGGTCTACTTCC | 25 | 88471005 | 88471029 | 391 |
| DG926 | Exon41 | AACTTTCCTTTGGAGTTCTTCAATT | 25 | 88471065 | 88471089 | 392 |
| DG927 | Exon41 | GGTTTTAGGTCTACTTCCTCCACCT | 25 | 88471012 | 88471036 | 393 |
| DG993 | Exon41 | TGTTTCTTCACATACCTTTTCTTTC | 25 | 88470984 | 88471008 | 394 |
| DG1489 | Exon46 | TTTCCGCTGAACTTCT | 16 | 88456487 | 88456502 | 395 |
| DG1490 | Exon46 | TTCCGCTGAACTTCTG | 16 | 88456488 | 88456503 | 396 |
| DG1492 | Exon46 | CCGCTGAACTTCTGCT | 16 | 88456490 | 88456505 | 397 |
| DG1493 | Exon46 | CGCTGAACTTCTGCTT | 16 | 88456491 | 88456506 | 398 |
| DG1494 | Exon46 | GCTGAACTTCTGCTTT | 16 | 88456492 | 88456507 | 399 |
| DG1495 | Exon46 | CTGAACTTCTGCTTTT | 16 | 88456493 | 88456508 | 400 |
| DG1496 | Exon46 | TGAACTTCTGCTTTTT | 16 | 88456494 | 88456509 | 401 |
| DG1497 | Exon46 | GAACTTCTGCTTTTTC | 16 | 88456495 | 88456510 | 402 |
| DG1498 | Exon46 | TCTGACTTGATTCTGA | 16 | 88456544 | 88456559 | 403 |
| DG1499 | Exon46 | CTGACTTGATTCTGAA | 16 | 88456545 | 88456560 | 404 |
| DG1500 | Exon46 | TTGATTCTGAAAGATA | 16 | 88456550 | 88456565 | 405 |
| DG1501 | Exon46 | TGATTCTGAAAGATAA | 16 | 88456551 | 88456566 | 406 |
| DG1502 | Exon46 | GATTCTGAAAGATAAC | 16 | 88456552 | 88456567 | 407 |
| DG1503 | Exon46 | AAGTTTCCGCTGAACTT | 17 | 88456484 | 88456500 | 408 |
| DG1504 | Exon46 | AGTTTCCGCTGAACTTC | 17 | 88456485 | 88456501 | 409 |
| DG1505 | Exon46 | GTTTCCGCTGAACTTCT | 17 | 88456486 | 88456502 | 410 |
| DG1506 | Exon46 | TTTCCGCTGAACTTCTG | 17 | 88456487 | 88456503 | 411 |
| DG1507 | Exon46 | TTCCGCTGAACTTCTGC | 17 | 88456488 | 88456504 | 412 |
| DG1508 | Exon46 | TCCGCTGAACTTCTGCT | 17 | 88456489 | 88456505 | 413 |
| DG1509 | Exon46 | CCGCTGAACTTCTGCTT | 17 | 88456490 | 88456506 | 414 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG1510 | Exon46 | CGCTGAACTTCTGCTTT | 17 | 88456491 | 88456507 | 415 |
| DG1511 | Exon46 | GCTGAACTTCTGCTTTT | 17 | 88456492 | 88456508 | 416 |
| DG1512 | Exon46 | CTGAACTTCTGCTTTTT | 17 | 88456493 | 88456509 | 417 |
| DG1513 | Exon46 | TGAACTTCTGCTTTTTC | 17 | 88456494 | 88456510 | 418 |
| DG1514 | Exon46 | TCTGACTTGATTCTGAA | 17 | 88456544 | 88456560 | 419 |
| DG1515 | Exon46 | CTGACTTGATTCTGAAA | 17 | 88456545 | 88456561 | 420 |
| DG1516 | Exon46 | TGACTTGATTCTGAAAG | 17 | 88456546 | 88456562 | 421 |
| DG1517 | Exon46 | GACTTGATTCTGAAAGA | 17 | 88456547 | 88456563 | 422 |
| DG1518 | Exon46 | ACTTGATTCTGAAAGAT | 17 | 88456548 | 88456564 | 423 |
| DG1519 | Exon46 | CTTGATTCTGAAAGATA | 17 | 88456549 | 88456565 | 424 |
| DG1520 | Exon46 | TTGATTCTGAAAGATAA | 17 | 88456550 | 88456566 | 425 |
| DG1521 | Exon46 | TGATTCTGAAAGATAAC | 17 | 88456551 | 88456567 | 426 |
| DG1522 | Exon46 | AAGTTTCCGCTGAACTTC | 18 | 88456484 | 88456501 | 427 |
| DG1523 | Exon46 | AGTTTCCGCTGAACTTCT | 18 | 88456485 | 88456502 | 428 |
| DG1524 | Exon46 | GTTTCCGCTGAACTTCTG | 18 | 88456486 | 88456503 | 429 |
| DG1525 | Exon46 | TTTCCGCTGAACTTCTGC | 18 | 88456487 | 88456504 | 430 |
| DG1526 | Exon46 | TTCCGCTGAACTTCTGCT | 18 | 88456488 | 88456505 | 431 |
| DG1528 | Exon46 | CCGCTGAACTTCTGCTTT | 18 | 88456490 | 88456507 | 432 |
| DG1529 | Exon46 | CGCTGAACTTCTGCTTTT | 18 | 88456491 | 88456508 | 433 |
| DG1530 | Exon46 | GCTGAACTTCTGCTTTTT | 18 | 88456492 | 88456509 | 434 |
| DG1531 | Exon46 | CTGAACTTCTGCTTTTTC | 18 | 88456493 | 88456510 | 435 |
| DG1532 | Exon46 | TCTGACTTGATTCTGAAA | 18 | 88456544 | 88456561 | 436 |
| DG1533 | Exon46 | CTGACTTGATTCTGAAAG | 18 | 88456545 | 88456562 | 437 |
| DG1534 | Exon46 | TGACTTGATTCTGAAAGA | 18 | 88456546 | 88456563 | 438 |
| DG1535 | Exon46 | GACTTGATTCTGAAAGAT | 18 | 88456547 | 88456564 | 439 |
| DG1536 | Exon46 | ACTTGATTCTGAAAGATA | 18 | 88456548 | 88456565 | 440 |
| DG1537 | Exon46 | CTTGATTCTGAAAGATAA | 18 | 88456549 | 88456566 | 441 |
| DG1538 | Exon46 | TTGATTCTGAAAGATAAC | 18 | 88456550 | 88456567 | 442 |
| DG1539 | Exon46 | AAGTTTCCGCTGAACTTCT | 19 | 88456484 | 88456502 | 443 |
| DG1540 | Exon46 | AGTTTCCGCTGAACTTCTG | 19 | 88456485 | 88456503 | 444 |
| DG1541 | Exon46 | GTTTCCGCTGAACTTCTGC | 19 | 88456486 | 88456504 | 445 |
| DG1542 | Exon46 | TTTCCGCTGAACTTCTGCT | 19 | 88456487 | 88456505 | 446 |
| DG1543 | Exon46 | TTCCGCTGAACTTCTGCTT | 19 | 88456488 | 88456506 | 447 |
| DG1544 | Exon46 | TCCGCTGAACTTCTGCTTT | 19 | 88456489 | 88456507 | 448 |
| DG1545 | Exon46 | CCGCTGAACTTCTGCTTTT | 19 | 88456490 | 88456508 | 449 |
| DG1546 | Exon46 | CGCTGAACTTCTGCTTTTT | 19 | 88456491 | 88456509 | 450 |
| DG1547 | Exon46 | GCTGAACTTCTGCTTTTTC | 19 | 88456492 | 88456510 | 451 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG1548 | Exon46 | TCTGACTTGATTCTGAAAG | 19 | 88456544 | 88456562 | 452 |
| DG1549 | Exon46 | CTGACTTGATTCTGAAAGA | 19 | 88456545 | 88456563 | 453 |
| DG1550 | Exon46 | TGACTTGATTCTGAAAGAT | 19 | 88456546 | 88456564 | 454 |
| DG1551 | Exon46 | GACTTGATTCTGAAAGATA | 19 | 88456547 | 88456565 | 455 |
| DG1552 | Exon46 | ACTTGATTCTGAAAGATAA | 19 | 88456548 | 88456566 | 456 |
| DG1553 | Exon46 | CTTGATTCTGAAAGATAAC | 19 | 88456549 | 88456567 | 457 |
| DG1554 | Exon46 | AAGTTTCCGCTGAACTTCTG | 20 | 88456484 | 88456503 | 458 |
| DG1555 | Exon46 | AGTTTCCGCTGAACTTCTGC | 20 | 88456485 | 88456504 | 459 |
| DG1556 | Exon46 | GTTTCCGCTGAACTTCTGCT | 20 | 88456486 | 88456505 | 460 |
| DG2010 | Exon36 | TAAAACAAATTCACATTTTG | 20 | 88477772 | 88477791 | 461 |
| DG2011 | Exon36 | TGATTAAAACAAATTCACAT | 20 | 88477768 | 88477787 | 462 |
| DG2012 | Exon36 | ATTGTGATTAAAACAAATTC | 20 | 88477764 | 88477783 | 463 |
| DG2013 | Exon36 | TAAATTGTGATTAAAACAAA | 20 | 88477761 | 88477780 | 464 |
| DG2014 | Exon36 | ATCTTAAATTGTGATTAAAA | 20 | 88477757 | 88477776 | 465 |
| DG2015 | Exon36 | TATATCTTAAATTGTGATTA | 20 | 88477754 | 88477773 | 466 |
| DG2016 | Exon36 | AAACTATATCTTAAATTGTG | 20 | 88477750 | 88477769 | 467 |
| DG2017 | Exon36 | TCGAAACTATATCTTAAATT | 20 | 88477747 | 88477766 | 468 |
| DG2018 | Exon36 | AAAATCGAAACTATATCTTA | 20 | 88477743 | 88477762 | 469 |
| DG2019 | Exon36 | CAGAAAATCGAAACTATATC | 20 | 88477740 | 88477759 | 470 |
| DG2020 | Exon36 | TTTACAGAAAATCGAAACTA | 20 | 88477736 | 88477755 | 471 |
| DG2021 | Exon36 | TGTTTTACAGAAAATCGAAA | 20 | 88477733 | 88477752 | 472 |
| DG2022 | Exon36 | CTCCTGTTTTACAGAAAATC | 20 | 88477729 | 88477748 | 473 |
| DG2023 | Exon36 | TTGCTCCTGTTTTACAGAAA | 20 | 88477726 | 88477745 | 474 |
| DG2024 | Exon36 | CTCTTTGCTCCTGTTTTACA | 20 | 88477722 | 88477741 | 475 |
| DG2025 | Exon36 | TTTCTCTTTGCTCCTGTTTT | 20 | 88477719 | 88477738 | 476 |
| DG2026 | Exon36 | ACAATTTCTCTTTGCTCCTG | 20 | 88477715 | 88477734 | 477 |
| DG2027 | Exon36 | TTCACAATTTCTCTTTGCTC | 20 | 88477712 | 88477731 | 478 |
| DG2028 | Exon36 | TTTCTTCACAATTTCTCTTT | 20 | 88477708 | 88477727 | 479 |
| DG2029 | Exon36 | ATGTTTCTTCACAATTTCTC | 20 | 88477705 | 88477724 | 480 |
| DG2030 | Exon36 | CCTCATGTTTCTTCACAATT | 20 | 88477701 | 88477720 | 481 |
| DG2031 | Exon36 | TCTTCCTCATGTTTCTTCAC | 20 | 88477697 | 88477716 | 482 |
| DG2032 | Exon36 | AGGTCTTCCTCATGTTTCTT | 20 | 88477694 | 88477713 | 483 |
| DG2033 | Exon36 | ATGAAGGTCTTCCTCATGTT | 20 | 88477690 | 88477709 | 484 |
| DG2034 | Exon36 | AATATGAAGGTCTTCCTCAT | 20 | 88477687 | 88477706 | 485 |
| DG2035 | Exon36 | GAAGAATATGAAGGTCTTCC | 20 | 88477683 | 88477702 | 486 |
| DG2036 | Exon36 | GATGAAGAATATGAAGGTCT | 20 | 88477680 | 88477699 | 487 |
| DG2037 | Exon36 | CTGTGATGAAGAATATGAAG | 20 | 88477676 | 88477695 | 488 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG2038 | Exon36 | AATCTGTGATGAAGAATATG | 20 | 88477673 | 88477692 | 489 |
| DG2039 | Exon36 | TTCTAATCTGTGATGAAGAA | 20 | 88477669 | 88477688 | 490 |
| DG2040 | Exon36 | TAGTTCTAATCTGTGATGAA | 20 | 88477666 | 88477685 | 491 |
| DG2041 | Exon36 | CCTGTAGTTCTAATCTGTGA | 20 | 88477662 | 88477681 | 492 |
| DG2042 | Exon36 | CAGCCTGTAGTTCTAATCTG | 20 | 88477659 | 88477678 | 493 |
| DG2043 | Exon36 | CTATCAGCCTGTAGTTCTAA | 20 | 88477655 | 88477674 | 494 |
| DG2044 | Exon36 | GAACTATCAGCCTGTAGTTC | 20 | 88477652 | 88477671 | 495 |
| DG2045 | Exon36 | TAGTGAACTATCAGCCTGTA | 20 | 88477648 | 88477667 | 496 |
| DG2046 | Exon36 | ATTTAGTGAACTATCAGCCT | 20 | 88477645 | 88477664 | 497 |
| DG2047 | Exon36 | ATTTATTTAGTGAACTATCA | 20 | 88477641 | 88477660 | 498 |
| DG2048 | Exon36 | TGAATTTATTTAGTGAACTA | 20 | 88477638 | 88477657 | 499 |
| DG2049 | Exon36 | TGTTTGAATTTATTTAGTGA | 20 | 88477634 | 88477653 | 500 |
| DG2050 | Exon36 | CGTTTGTTTGAATTTATTTA | 20 | 88477630 | 88477649 | 501 |
| DG2051 | Exon36 | AGCCGTTTGTTTGAATTTAT | 20 | 88477627 | 88477646 | 502 |
| DG2052 | Exon36 | CCCAAGCCGTTTGTTTGAAT | 20 | 88477623 | 88477642 | 503 |
| DG2053 | Exon36 | TTACCCAAGCCGTTTGTTTG | 20 | 88477620 | 88477639 | 504 |
| DG2054 | Exon36 | AATCTTACCCAAGCCGTTTG | 20 | 88477616 | 88477635 | 505 |
| DG2055 | Exon36 | TAGAATCTTACCCAAGCCGT | 20 | 88477613 | 88477632 | 506 |
| DG2056 | Exon36 | TTCTTAGAATCTTACCCAAG | 20 | 88477609 | 88477628 | 507 |
| DG2057 | Exon36 | AAGTTCTTAGAATCTTACCC | 20 | 88477606 | 88477625 | 508 |
| DG2058 | Exon36 | AACAAAGTTCTTAGAATCTT | 20 | 88477602 | 88477621 | 509 |
| DG2059 | Exon36 | TGGAACAAAGTTCTTAGAAT | 20 | 88477599 | 88477618 | 510 |
| DG2060 | Exon36 | AGAATGGAACAAAGTTCTTA | 20 | 88477595 | 88477614 | 511 |
| DG2061 | Exon36 | TAAAGAATGGAACAAAGTTC | 20 | 88477592 | 88477611 | 512 |
| DG2062 | Exon36 | TCAATAAAGAATGGAACAAA | 20 | 88477588 | 88477607 | 513 |
| DG2063 | Exon36 | AAATCAATAAAGAATGGAAC | 20 | 88477585 | 88477604 | 514 |
| DG2064 | Exon36 | ACAAAAATCAATAAAGAATG | 20 | 88477581 | 88477600 | 515 |
| DG2065 | Exon36 | GTCACAAAAATCAATAAAGA | 20 | 88477578 | 88477597 | 516 |
| DG2066 | Exon36 | CATGGTCACAAAAATCAATA | 20 | 88477574 | 88477593 | 517 |
| DG2067 | Exon36 | TTACATGGTCACAAAAATCA | 20 | 88477571 | 88477590 | 518 |
| DG2068 | Exon36 | TAATTTACATGGTCACAAAA | 20 | 88477567 | 88477586 | 519 |
| DG2069 | Exon36 | TTTTAATTTACATGGTCACA | 20 | 88477564 | 88477583 | 520 |
| DG2070 | Exon36 | CATGTTTCTTCACAATTTCT | 20 | 88477704 | 88477723 | 521 |
| DG2071 | Exon36 | GGTCTTCCTCATGTTTCTTC | 20 | 88477695 | 88477714 | 522 |
| DG2072 | Exon36 | CTTCCTCATGTTTCTTCACA | 20 | 88477698 | 88477717 | 523 |
| DG2073 | Exon36 | GAAGGTCTTCCTCATGTTTC | 20 | 88477692 | 88477711 | 524 |
| DG2074 | Exon36 | TTCTTCACAATTTCTCTTTG | 20 | 88477709 | 88477728 | 525 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG2075 | Exon36 | GTCTTCCTCATGTTTCTTCA | 20 | 88477696 | 88477715 | 526 |
| DG2076 | Exon36 | TCCTCATGTTTCTTCACAAT | 20 | 88477700 | 88477719 | 527 |
| DG2077 | Exon36 | TTCCTCATGTTTCTTCACAA | 20 | 88477699 | 88477718 | 528 |
| DG2078 | Exon36 | AAGGTCTTCCTCATGTTTCT | 20 | 88477693 | 88477712 | 529 |
| DG2079 | Exon36 | GTTTCTTCACAATTTCTCTT | 20 | 88477707 | 88477726 | 530 |
| DG2080 | Exon36 | TGAAGAATATGAAGGTCTTC | 20 | 88477682 | 88477701 | 531 |
| DG2081 | Exon36 | TCATGTTTCTTCACAATTTC | 20 | 88477703 | 88477722 | 532 |
| DG2082 | Exon36 | TGTTTCTTCACAATTTCTCT | 20 | 88477706 | 88477725 | 533 |
| DG2083 | Exon36 | TGAAGGTCTTCCTCATGTTT | 20 | 88477691 | 88477710 | 534 |
| DG2084 | Exon36 | CTCATGTTTCTTCACAATTT | 20 | 88477702 | 88477721 | 535 |
| DG2085 | Exon36 | AGAATATGAAGGTCTTCCTC | 20 | 88477685 | 88477704 | 536 |
| DG2086 | Exon36 | CACAATTTCTCTTTGCTCCT | 20 | 88477714 | 88477733 | 537 |
| DG2087 | Exon36 | GAATATGAAGGTCTTCCTCA | 20 | 88477686 | 88477705 | 538 |
| DG2088 | Exon36 | TCTTCACAATTTCTCTTTGC | 20 | 88477710 | 88477729 | 539 |
| DG2089 | Exon36 | AAGAATATGAAGGTCTTCCT | 20 | 88477684 | 88477703 | 540 |
| DG2974 | Exon41 | TCAGGGGTTTGCCCTAAAAA | 20 | 88471109 | 88471128 | 541 |
| DG2975 | Exon41 | GTCAGGGGTTTGCCCTAAAA | 20 | 88471108 | 88471127 | 542 |
| DG2976 | Exon41 | TTATCTGTCAGGGGTTTGCC | 20 | 88471102 | 88471121 | 543 |
| DG2977 | Exon41 | ATTATCTGTCAGGGGTTTGC | 20 | 88471101 | 88471120 | 544 |
| DG2978 | Exon41 | TATTATCTGTCAGGGGTTTG | 20 | 88471100 | 88471119 | 545 |
| DG2979 | Exon41 | TTATTATCTGTCAGGGGTTT | 20 | 88471099 | 88471118 | 546 |
| DG2980 | Exon41 | TTTATTATCTGTCAGGGGTT | 20 | 88471098 | 88471117 | 547 |
| DG2981 | Exon41 | GTTTATTATCTGTCAGGGGT | 20 | 88471097 | 88471116 | 548 |
| DG2982 | Exon41 | TGTTTATTATCTGTCAGGGG | 20 | 88471096 | 88471115 | 549 |
| DG2983 | Exon41 | TTGTTTATTATCTGTCAGGG | 20 | 88471095 | 88471114 | 550 |
| DG2984 | Exon41 | TTTGTTTATTATCTGTCAGG | 20 | 88471094 | 88471113 | 551 |
| DG2985 | Exon41 | CTTTGTTTATTATCTGTCAG | 20 | 88471093 | 88471112 | 552 |
| DG2986 | Exon41 | ACTTTGTTTATTATCTGTCA | 20 | 88471092 | 88471111 | 553 |
| DG2987 | Exon41 | GACTTTGTTTATTATCTGTC | 20 | 88471091 | 88471110 | 554 |
| DG2988 | Exon41 | AGACTTTGTTTATTATCTGT | 20 | 88471090 | 88471109 | 555 |
| DG2989 | Exon41 | TAGACTTTGTTTATTATCTG | 20 | 88471089 | 88471108 | 556 |
| DG2990 | Exon41 | TTAGACTTTGTTTATTATCT | 20 | 88471088 | 88471107 | 557 |
| DG2991 | Exon41 | ATTAGACTTTGTTTATTATC | 20 | 88471087 | 88471106 | 558 |
| DG2992 | Exon41 | AATTAGACTTTGTTTATTAT | 20 | 88471086 | 88471105 | 559 |
| DG2993 | Exon41 | CAATTAGACTTTGTTTATTA | 20 | 88471085 | 88471104 | 560 |
| DG2994 | Exon41 | TCAATTAGACTTTGTTTATT | 20 | 88471084 | 88471103 | 561 |
| DG2995 | Exon41 | TTCAATTAGACTTTGTTTAT | 20 | 88471083 | 88471102 | 562 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG2996 | Exon41 | CTTCAATTAGACTTTGTTTA | 20 | 88471082 | 88471101 | 563 |
| DG2997 | Exon41 | TCTTCAATTAGACTTTGTTT | 20 | 88471081 | 88471100 | 564 |
| DG2998 | Exon41 | TTCTTCAATTAGACTTTGTT | 20 | 88471080 | 88471099 | 565 |
| DG2999 | Exon41 | GTTCTTCAATTAGACTTTGT | 20 | 88471079 | 88471098 | 566 |
| DG3000 | Exon41 | AGTTCTTCAATTAGACTTTG | 20 | 88471078 | 88471097 | 567 |
| DG3001 | Exon41 | CTTTGGAGTTCTTCAATTAG | 20 | 88471072 | 88471091 | 568 |
| DG3002 | Exon41 | TTTCCTTTGGAGTTCTTCAA | 20 | 88471068 | 88471087 | 569 |
| DG3003 | Exon41 | AACTTTCCTTTGGAGTTCTT | 20 | 88471065 | 88471084 | 570 |
| DG3004 | Exon41 | TAACTTTCCTTTGGAGTTCT | 20 | 88471064 | 88471083 | 571 |
| DG3005 | Exon41 | TTAACTTTCCTTTGGAGTTC | 20 | 88471063 | 88471082 | 572 |
| DG3006 | Exon41 | TTTAACTTTCCTTTGGAGTT | 20 | 88471062 | 88471081 | 573 |
| DG3007 | Exon41 | TTTTAACTTTCCTTTGGAGT | 20 | 88471061 | 88471080 | 574 |
| DG3008 | Exon41 | TTTTTAACTTTCCTTTGGAG | 20 | 88471060 | 88471079 | 575 |
| DG3009 | Exon41 | TTTTTTAACTTTCCTTTGGA | 20 | 88471059 | 88471078 | 576 |
| DG3010 | Exon41 | GTTTTTTAACTTTCCTTTGG | 20 | 88471058 | 88471077 | 577 |
| DG3011 | Exon41 | AGTTTTTTAACTTTCCTTTG | 20 | 88471057 | 88471076 | 578 |
| DG3012 | Exon41 | TAGTTTTTTAACTTTCCTTT | 20 | 88471056 | 88471075 | 579 |
| DG3013 | Exon41 | CTAGTTTTTTAACTTTCCTT | 20 | 88471055 | 88471074 | 580 |
| DG3014 | Exon41 | TCTAGTTTTTTAACTTTCCT | 20 | 88471054 | 88471073 | 581 |
| DG3015 | Exon41 | CTCTAGTTTTTTAACTTTCC | 20 | 88471053 | 88471072 | 582 |
| DG3016 | Exon41 | TCTCTAGTTTTTTAACTTTC | 20 | 88471052 | 88471071 | 583 |
| DG3017 | Exon41 | TTCTCTAGTTTTTTAACTTT | 20 | 88471051 | 88471070 | 584 |
| DG3018 | Exon41 | GTTCTCTAGTTTTTTAACTT | 20 | 88471050 | 88471069 | 585 |
| DG3019 | Exon41 | GGTTCTCTAGTTTTTTAACT | 20 | 88471049 | 88471068 | 586 |
| DG3020 | Exon41 | TGGTTCTCTAGTTTTTTAAC | 20 | 88471048 | 88471067 | 587 |
| DG3021 | Exon41 | TTGGTTCTCTAGTTTTTTAA | 20 | 88471047 | 88471066 | 588 |
| DG3022 | Exon41 | ATTGGTTCTCTAGTTTTTTA | 20 | 88471046 | 88471065 | 589 |
| DG3023 | Exon41 | AATTGGTTCTCTAGTTTTTT | 20 | 88471045 | 88471064 | 590 |
| DG3024 | Exon41 | TAATTGGTTCTCTAGTTTTT | 20 | 88471044 | 88471063 | 591 |
| DG3025 | Exon41 | CTAATTGGTTCTCTAGTTTT | 20 | 88471043 | 88471062 | 592 |
| DG3026 | Exon41 | TCTAATTGGTTCTCTAGTTT | 20 | 88471042 | 88471061 | 593 |
| DG3027 | Exon41 | CTCTAATTGGTTCTCTAGTT | 20 | 88471041 | 88471060 | 594 |
| DG3028 | Exon41 | CCTCTAATTGGTTCTCTAGT | 20 | 88471040 | 88471059 | 595 |
| DG3029 | Exon41 | CCCTCTAATTGGTTCTCTAG | 20 | 88471039 | 88471058 | 596 |
| DG3030 | Exon41 | TCCCTCTAATTGGTTCTCTA | 20 | 88471038 | 88471057 | 597 |
| DG3031 | Exon41 | TTCCCTCTAATTGGTTCTCT | 20 | 88471037 | 88471056 | 598 |
| DG3032 | Exon41 | TTTCCCTCTAATTGGTTCTC | 20 | 88471036 | 88471055 | 599 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG3033 | Exon41 | CTTTCCCTCTAATTGGTTCT | 20 | 88471035 | 88471054 | 600 |
| DG3034 | Exon41 | CCTTTCCCTCTAATTGGTTC | 20 | 88471034 | 88471053 | 601 |
| DG3035 | Exon41 | ACCTTTCCCTCTAATTGGTT | 20 | 88471033 | 88471052 | 602 |
| DG3036 | Exon41 | CACCTTTCCCTCTAATTGGT | 20 | 88471032 | 88471051 | 603 |
| DG3037 | Exon41 | CCACCTTTCCCTCTAATTGG | 20 | 88471031 | 88471050 | 604 |
| DG3038 | Exon41 | TCCACCTTTCCCTCTAATTG | 20 | 88471030 | 88471049 | 605 |
| DG3039 | Exon41 | CTCCACCTTTCCCTCTAATT | 20 | 88471029 | 88471048 | 606 |
| DG3040 | Exon41 | CCTCCACCTTTCCCTCTAAT | 20 | 88471028 | 88471047 | 607 |
| DG3041 | Exon41 | TCCTCCACCTTTCCCTCTAA | 20 | 88471027 | 88471046 | 608 |
| DG3042 | Exon41 | TTCCTCCACCTTTCCCTCTA | 20 | 88471026 | 88471045 | 609 |
| DG3043 | Exon41 | CTTCCTCCACCTTTCCCTCT | 20 | 88471025 | 88471044 | 610 |
| DG3044 | Exon41 | ACTTCCTCCACCTTTCCCTC | 20 | 88471024 | 88471043 | 611 |
| DG3045 | Exon41 | TACTTCCTCCACCTTTCCCT | 20 | 88471023 | 88471042 | 612 |
| DG3046 | Exon41 | CTACTTCCTCCACCTTTCCC | 20 | 88471022 | 88471041 | 613 |
| DG3047 | Exon41 | TCTACTTCCTCCACCTTTCC | 20 | 88471021 | 88471040 | 614 |
| DG3048 | Exon41 | AGGTTTTAGGTCTACTTCCT | 20 | 88471011 | 88471030 | 615 |
| DG3049 | Exon41 | TAGGTTTTAGGTCTACTTCC | 20 | 88471010 | 88471029 | 616 |
| DG3050 | Exon41 | ATAGGTTTTAGGTCTACTTC | 20 | 88471009 | 88471028 | 617 |
| DG3051 | Exon41 | CATAGGTTTTAGGTCTACTT | 20 | 88471008 | 88471027 | 618 |
| DG3052 | Exon41 | TCATAGGTTTTAGGTCTACT | 20 | 88471007 | 88471026 | 619 |
| DG3053 | Exon41 | TTCATAGGTTTTAGGTCTAC | 20 | 88471006 | 88471025 | 620 |
| DG3054 | Exon41 | TTTCATAGGTTTTAGGTCTA | 20 | 88471005 | 88471024 | 621 |
| DG3055 | Exon41 | CTTTCATAGGTTTTAGGTCT | 20 | 88471004 | 88471023 | 622 |
| DG3056 | Exon41 | TCTTTCATAGGTTTTAGGTC | 20 | 88471003 | 88471022 | 623 |
| DG3057 | Exon41 | TTCTTTCATAGGTTTTAGGT | 20 | 88471002 | 88471021 | 624 |
| DG3058 | Exon41 | TTTCTTTCATAGGTTTTAGG | 20 | 88471001 | 88471020 | 625 |
| DG3059 | Exon41 | TTTTCTTTCATAGGTTTTAG | 20 | 88471000 | 88471019 | 626 |
| DG3060 | Exon41 | CTTTTCTTTCATAGGTTTTA | 20 | 88470999 | 88471018 | 627 |
| DG3061 | Exon41 | CCTTTTCTTTCATAGGTTTT | 20 | 88470998 | 88471017 | 628 |
| DG3062 | Exon41 | ACCTTTTCTTTCATAGGTTT | 20 | 88470997 | 88471016 | 629 |
| DG3063 | Exon41 | TACCTTTTCTTTCATAGGTT | 20 | 88470996 | 88471015 | 630 |
| DG3064 | Exon41 | CATACCTTTTCTTTCATAGG | 20 | 88470994 | 88471013 | 631 |
| DG3065 | Exon41 | ACATACCTTTTCTTTCATAG | 20 | 88470993 | 88471012 | 632 |
| DG3066 | Exon41 | CACATACCTTTTCTTTCATA | 20 | 88470992 | 88471011 | 633 |
| DG4388 | Exon41 | CCACCTTTCCCTCTAA | 16 | 88471031 | 88471046 | 634 |
| DG4389 | Exon41 | CACCTTTCCCTCTAAT | 16 | 88471032 | 88471047 | 635 |
| DG4390 | Exon41 | ACCTTTCCCTCTAATT | 16 | 88471033 | 88471048 | 636 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4391 | Exon41 | CCTTTCCCTCTAATTG | 16 | 88471034 | 88471049 | 637 |
| DG4392 | Exon41 | CTTTCCCTCTAATTGG | 16 | 88471035 | 88471050 | 638 |
| DG4393 | Exon41 | TTTCCCTCTAATTGGT | 16 | 88471036 | 88471051 | 639 |
| DG4394 | Exon41 | TTCCCTCTAATTGGTT | 16 | 88471037 | 88471052 | 640 |
| DG4395 | Exon41 | TCCCTCTAATTGGTTC | 16 | 88471038 | 88471053 | 641 |
| DG4396 | Exon41 | CCCTCTAATTGGTTCT | 16 | 88471039 | 88471054 | 642 |
| DG4397 | Exon41 | CCTCTAATTGGTTCTC | 16 | 88471040 | 88471055 | 643 |
| DG4398 | Exon41 | CTCTAATTGGTTCTCT | 16 | 88471041 | 88471056 | 644 |
| DG4399 | Exon41 | TCTAATTGGTTCTCTA | 16 | 88471042 | 88471057 | 645 |
| DG4400 | Exon41 | CTAATTGGTTCTCTAG | 16 | 88471043 | 88471058 | 646 |
| DG4401 | Exon41 | TAATTGGTTCTCTAGT | 16 | 88471044 | 88471059 | 647 |
| DG4402 | Exon41 | AATTGGTTCTCTAGTT | 16 | 88471045 | 88471060 | 648 |
| DG4403 | Exon41 | CCACCTTTCCCTCTAAT | 17 | 88471031 | 88471047 | 649 |
| DG4405 | Exon41 | ACCTTTCCCTCTAATTG | 17 | 88471033 | 88471049 | 650 |
| DG4406 | Exon41 | CCTTTCCCTCTAATTGG | 17 | 88471034 | 88471050 | 651 |
| DG4407 | Exon41 | CTTTCCCTCTAATTGGT | 17 | 88471035 | 88471051 | 652 |
| DG4408 | Exon41 | TTTCCCTCTAATTGGTT | 17 | 88471036 | 88471052 | 653 |
| DG4409 | Exon41 | TTCCCTCTAATTGGTTC | 17 | 88471037 | 88471053 | 654 |
| DG4410 | Exon41 | TCCCTCTAATTGGTTCT | 17 | 88471038 | 88471054 | 655 |
| DG4411 | Exon41 | CCCTCTAATTGGTTCTC | 17 | 88471039 | 88471055 | 656 |
| DG4412 | Exon41 | CCTCTAATTGGTTCTCT | 17 | 88471040 | 88471056 | 657 |
| DG4413 | Exon41 | CTCTAATTGGTTCTCTA | 17 | 88471041 | 88471057 | 658 |
| DG4414 | Exon41 | TCTAATTGGTTCTCTAG | 17 | 88471042 | 88471058 | 659 |
| DG4415 | Exon41 | CTAATTGGTTCTCTAGT | 17 | 88471043 | 88471059 | 660 |
| DG4416 | Exon41 | TAATTGGTTCTCTAGTT | 17 | 88471044 | 88471060 | 661 |
| DG4417 | Exon41 | CCACCTTTCCCTCTAATT | 18 | 88471031 | 88471048 | 662 |
| DG4419 | Exon41 | ACCTTTCCCTCTAATTGG | 18 | 88471033 | 88471050 | 663 |
| DG4420 | Exon41 | CCTTTCCCTCTAATTGGT | 18 | 88471034 | 88471051 | 664 |
| DG4421 | Exon41 | CTTTCCCTCTAATTGGTT | 18 | 88471035 | 88471052 | 665 |
| DG4422 | Exon41 | TTTCCCTCTAATTGGTTC | 18 | 88471036 | 88471053 | 666 |
| DG4423 | Exon41 | TTCCCTCTAATTGGTTCT | 18 | 88471037 | 88471054 | 667 |
| DG4424 | Exon41 | TCCCTCTAATTGGTTCTC | 18 | 88471038 | 88471055 | 668 |
| DG4425 | Exon41 | CCTCTAATTGGTTCTCTA | 18 | 88471040 | 88471057 | 669 |
| DG4426 | Exon41 | CTCTAATTGGTTCTCTAG | 18 | 88471041 | 88471058 | 670 |
| DG4427 | Exon41 | TCTAATTGGTTCTCTAGT | 18 | 88471042 | 88471059 | 671 |
| DG4428 | Exon41 | CTAATTGGTTCTCTAGTT | 18 | 88471043 | 88471060 | 672 |
| DG4429 | Exon41 | CCACCTTTCCCTCTAATTG | 19 | 88471031 | 88471049 | 673 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4430 | Exon41 | CACCTTTCCCTCTAATTGG | 19 | 88471032 | 88471050 | 674 |
| DG4431 | Exon41 | ACCTTTCCCTCTAATTGGT | 19 | 88471033 | 88471051 | 675 |
| DG4432 | Exon41 | CCTTTCCCTCTAATTGGTT | 19 | 88471034 | 88471052 | 676 |
| DG4433 | Exon41 | CTTTCCCTCTAATTGGTTC | 19 | 88471035 | 88471053 | 677 |
| DG4434 | Exon41 | TTTCCCTCTAATTGGTTCT | 19 | 88471036 | 88471054 | 678 |
| DG4435 | Exon41 | TTCCCTCTAATTGGTTCTC | 19 | 88471037 | 88471055 | 679 |
| DG4436 | Exon41 | TCCCTCTAATTGGTTCTCT | 19 | 88471038 | 88471056 | 680 |
| DG4437 | Exon41 | CCCTCTAATTGGTTCTCTA | 19 | 88471039 | 88471057 | 681 |
| DG4438 | Exon41 | CCTCTAATTGGTTCTCTAG | 19 | 88471040 | 88471058 | 682 |
| DG4439 | Exon41 | CTCTAATTGGTTCTCTAGT | 19 | 88471041 | 88471059 | 683 |
| DG4440 | Exon41 | TCTAATTGGTTCTCTAGTT | 19 | 88471042 | 88471060 | 684 |
| DG4441 | Exon46 | CATTTCTGGCTTATCACTGC | 20 | 88456412 | 88456431 | 685 |
| DG4442 | Exon46 | TGGCTTATCACTGCTGAAAC | 20 | 88456418 | 88456437 | 686 |
| DG4443 | Exon46 | ATCACTGCTGAAACCAAAAC | 20 | 88456424 | 88456443 | 687 |
| DG4444 | Exon46 | GCTGAAACCAAAACAAATGT | 20 | 88456430 | 88456449 | 688 |
| DG4446 | Exon46 | ACAAATGTATGGTAAATTCT | 20 | 88456442 | 88456461 | 689 |
| DG4447 | Exon46 | GTATGGTAAATTCTCACATA | 20 | 88456448 | 88456467 | 690 |
| DG4448 | Exon46 | TAAATTCTCACATACCCCTC | 20 | 88456454 | 88456473 | 691 |
| DG4449 | Exon46 | TACCCCTCTAACATGGCCAA | 20 | 88456466 | 88456485 | 692 |
| DG4450 | Exon46 | TGCTTTTTCTTTCTTAAGAA | 20 | 88456502 | 88456521 | 693 |
| DG4451 | Exon46 | TTCTTTCTTAAGAAATTCAC | 20 | 88456508 | 88456527 | 694 |
| DG4452 | Exon46 | CTTAAGAAATTCACACATTT | 20 | 88456514 | 88456533 | 695 |
| DG4453 | Exon46 | AAATTCACACATTTCCTTCA | 20 | 88456520 | 88456539 | 696 |
| DG4454 | Exon46 | ACACATTTCCTTCAAATCTC | 20 | 88456526 | 88456545 | 697 |
| DG4455 | Exon46 | CTGAAAGATAACAAGCAAAC | 20 | 88456556 | 88456575 | 698 |
| DG4456 | Exon46 | AAGCAAACATGTAATAATTT | 20 | 88456568 | 88456587 | 699 |
| DG4457 | Exon46 | ACATGTAATAATTTAACATA | 20 | 88456574 | 88456593 | 700 |
| DG4458 | Exon46 | AATAATTTAACATAGCTACA | 20 | 88456580 | 88456599 | 701 |
| DG4459 | Exon46 | TAGCTACAGCCATTGAAAAG | 20 | 88456592 | 88456611 | 702 |
| DG4724 | Exon36 | CAGCCTGTAGTTCTAA | 16 | 88477659 | 88477674 | 703 |
| DG4727 | Exon36 | CCTGTAGTTCTAATCT | 16 | 88477662 | 88477677 | 704 |
| DG4728 | Exon36 | CTGTAGTTCTAATCTG | 16 | 88477663 | 88477678 | 705 |
| DG4729 | Exon36 | TGTAGTTCTAATCTGT | 16 | 88477664 | 88477679 | 706 |
| DG4730 | Exon36 | GTAGTTCTAATCTGTG | 16 | 88477665 | 88477680 | 707 |
| DG4732 | Exon36 | AGTTCTAATCTGTGAT | 16 | 88477667 | 88477682 | 708 |
| DG4733 | Exon36 | GTTCTAATCTGTGATG | 16 | 88477668 | 88477683 | 709 |
| DG4734 | Exon36 | TTCTAATCTGTGATGA | 16 | 88477669 | 88477684 | 710 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4735 | Exon36 | TCTAATCTGTGATGAA | 16 | 88477670 | 88477685 | 711 |
| DG4737 | Exon36 | AGCCTGTAGTTCTAATC | 17 | 88477660 | 88477676 | 712 |
| DG4738 | Exon36 | GCCTGTAGTTCTAATCT | 17 | 88477661 | 88477677 | 713 |
| DG4739 | Exon36 | CCTGTAGTTCTAATCTG | 17 | 88477662 | 88477678 | 714 |
| DG4740 | Exon36 | CTGTAGTTCTAATCTGT | 17 | 88477663 | 88477679 | 715 |
| DG4741 | Exon36 | TGTAGTTCTAATCTGTG | 17 | 88477664 | 88477680 | 716 |
| DG4742 | Exon36 | GTAGTTCTAATCTGTGA | 17 | 88477665 | 88477681 | 717 |
| DG4743 | Exon36 | TAGTTCTAATCTGTGAT | 17 | 88477666 | 88477682 | 718 |
| DG4744 | Exon36 | AGTTCTAATCTGTGATG | 17 | 88477667 | 88477683 | 719 |
| DG4745 | Exon36 | GTTCTAATCTGTGATGA | 17 | 88477668 | 88477684 | 720 |
| DG4746 | Exon36 | TTCTAATCTGTGATGAA | 17 | 88477669 | 88477685 | 721 |
| DG4747 | Exon36 | CAGCCTGTAGTTCTAATC | 18 | 88477659 | 88477676 | 722 |
| DG4748 | Exon36 | AGCCTGTAGTTCTAATCT | 18 | 88477660 | 88477677 | 723 |
| DG4749 | Exon36 | GCCTGTAGTTCTAATCTG | 18 | 88477661 | 88477678 | 724 |
| DG4750 | Exon36 | CCTGTAGTTCTAATCTGT | 18 | 88477662 | 88477679 | 725 |
| DG4751 | Exon36 | CTGTAGTTCTAATCTGTG | 18 | 88477663 | 88477680 | 726 |
| DG4752 | Exon36 | TGTAGTTCTAATCTGTGA | 18 | 88477664 | 88477681 | 727 |
| DG4753 | Exon36 | GTAGTTCTAATCTGTGAT | 18 | 88477665 | 88477682 | 728 |
| DG4754 | Exon36 | TAGTTCTAATCTGTGATG | 18 | 88477666 | 88477683 | 729 |
| DG4755 | Exon36 | AGTTCTAATCTGTGATGA | 18 | 88477667 | 88477684 | 730 |
| DG4756 | Exon36 | GTTCTAATCTGTGATGAA | 18 | 88477668 | 88477685 | 731 |
| DG4757 | Exon36 | CAGCCTGTAGTTCTAATCT | 19 | 88477659 | 88477677 | 732 |
| DG4758 | Exon36 | AGCCTGTAGTTCTAATCTG | 19 | 88477660 | 88477678 | 733 |
| DG4759 | Exon36 | GCCTGTAGTTCTAATCTGT | 19 | 88477661 | 88477679 | 734 |
| DG4760 | Exon36 | CCTGTAGTTCTAATCTGTG | 19 | 88477662 | 88477680 | 735 |
| DG4761 | Exon36 | CTGTAGTTCTAATCTGTGA | 19 | 88477663 | 88477681 | 736 |
| DG4762 | Exon36 | TGTAGTTCTAATCTGTGAT | 19 | 88477664 | 88477682 | 737 |
| DG4763 | Exon36 | GTAGTTCTAATCTGTGATG | 19 | 88477665 | 88477683 | 738 |
| DG4764 | Exon36 | TAGTTCTAATCTGTGATGA | 19 | 88477666 | 88477684 | 739 |
| DG4765 | Exon36 | AGTTCTAATCTGTGATGAA | 19 | 88477667 | 88477685 | 740 |
| DG4766 | Exon36 | AGCCTGTAGTTCTAATCTGT | 20 | 88477660 | 88477679 | 741 |
| DG4767 | Exon36 | GCCTGTAGTTCTAATCTGTG | 20 | 88477661 | 88477680 | 742 |
| DG4768 | Exon36 | CTGTAGTTCTAATCTGTGAT | 20 | 88477663 | 88477682 | 743 |
| DG4769 | Exon36 | TGTAGTTCTAATCTGTGATG | 20 | 88477664 | 88477683 | 744 |
| DG4770 | Exon36 | GTAGTTCTAATCTGTGATGA | 20 | 88477665 | 88477684 | 745 |
| DG4771 | Exon36 | GATGAAGAATATGAAG | 16 | 88477680 | 88477695 | 746 |
| DG4772 | Exon36 | ATGAAGAATATGAAGG | 16 | 88477681 | 88477696 | 747 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4773 | Exon36 | TGAAGAATATGAAGGT | 16 | 88477682 | 88477697 | 748 |
| DG4774 | Exon36 | GAAGAATATGAAGGTC | 16 | 88477683 | 88477698 | 749 |
| DG4775 | Exon36 | AAGAATATGAAGGTCT | 16 | 88477684 | 88477699 | 750 |
| DG4776 | Exon36 | AGAATATGAAGGTCTT | 16 | 88477685 | 88477700 | 751 |
| DG4777 | Exon36 | GAATATGAAGGTCTTC | 16 | 88477686 | 88477701 | 752 |
| DG4778 | Exon36 | AATATGAAGGTCTTCC | 16 | 88477687 | 88477702 | 753 |
| DG4779 | Exon36 | ATATGAAGGTCTTCCT | 16 | 88477688 | 88477703 | 754 |
| DG4780 | Exon36 | TATGAAGGTCTTCCTC | 16 | 88477689 | 88477704 | 755 |
| DG4781 | Exon36 | ATGAAGGTCTTCCTCA | 16 | 88477690 | 88477705 | 756 |
| DG4782 | Exon36 | TGAAGGTCTTCCTCAT | 16 | 88477691 | 88477706 | 757 |
| DG4783 | Exon36 | GAAGGTCTTCCTCATG | 16 | 88477692 | 88477707 | 758 |
| DG4784 | Exon36 | AAGGTCTTCCTCATGT | 16 | 88477693 | 88477708 | 759 |
| DG4785 | Exon36 | AGGTCTTCCTCATGTT | 16 | 88477694 | 88477709 | 760 |
| DG4786 | Exon36 | GGTCTTCCTCATGTTT | 16 | 88477695 | 88477710 | 761 |
| DG4787 | Exon36 | GTCTTCCTCATGTTTC | 16 | 88477696 | 88477711 | 762 |
| DG4788 | Exon36 | TCTTCCTCATGTTTCT | 16 | 88477697 | 88477712 | 763 |
| DG4789 | Exon36 | CTTCCTCATGTTTCTT | 16 | 88477698 | 88477713 | 764 |
| DG4790 | Exon36 | TTCCTCATGTTTCTTC | 16 | 88477699 | 88477714 | 765 |
| DG4791 | Exon36 | TCCTCATGTTTCTTCA | 16 | 88477700 | 88477715 | 766 |
| DG4792 | Exon36 | CCTCATGTTTCTTCAC | 16 | 88477701 | 88477716 | 767 |
| DG4793 | Exon36 | CTCATGTTTCTTCACA | 16 | 88477702 | 88477717 | 768 |
| DG4794 | Exon36 | TCATGTTTCTTCACAA | 16 | 88477703 | 88477718 | 769 |
| DG4795 | Exon36 | CATGTTTCTTCACAAT | 16 | 88477704 | 88477719 | 770 |
| DG4796 | Exon36 | ATGTTTCTTCACAATT | 16 | 88477705 | 88477720 | 771 |
| DG4797 | Exon36 | TGTTTCTTCACAATTT | 16 | 88477706 | 88477721 | 772 |
| DG4798 | Exon36 | GATGAAGAATATGAAGG | 17 | 88477680 | 88477696 | 773 |
| DG4799 | Exon36 | ATGAAGAATATGAAGGT | 17 | 88477681 | 88477697 | 774 |
| DG4800 | Exon36 | TGAAGAATATGAAGGTC | 17 | 88477682 | 88477698 | 775 |
| DG4801 | Exon36 | GAAGAATATGAAGGTCT | 17 | 88477683 | 88477699 | 776 |
| DG4802 | Exon36 | AAGAATATGAAGGTCTT | 17 | 88477684 | 88477700 | 777 |
| DG4803 | Exon36 | AGAATATGAAGGTCTTC | 17 | 88477685 | 88477701 | 778 |
| DG4820 | Exon36 | CTCATGTTTCTTCACAA | 17 | 88477702 | 88477718 | 779 |
| DG4821 | Exon36 | TCATGTTTCTTCACAAT | 17 | 88477703 | 88477719 | 780 |
| DG4822 | Exon36 | CATGTTTCTTCACAATT | 17 | 88477704 | 88477720 | 781 |
| DG4823 | Exon36 | ATGTTTCTTCACAATTT | 17 | 88477705 | 88477721 | 782 |
| DG4828 | Exon36 | AAGAATATGAAGGTCTTC | 18 | 88477684 | 88477701 | 783 |
| DG4829 | Exon36 | AGAATATGAAGGTCTTCC | 18 | 88477685 | 88477702 | 784 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4830 | Exon36 | GAATATGAAGGTCTTCCT | 18 | 88477686 | 88477703 | 785 |
| DG4831 | Exon36 | AATATGAAGGTCTTCCTC | 18 | 88477687 | 88477704 | 786 |
| DG4832 | Exon36 | ATATGAAGGTCTTCCTCA | 18 | 88477688 | 88477705 | 787 |
| DG4836 | Exon36 | GAAGGTCTTCCTCATGTT | 18 | 88477692 | 88477709 | 788 |
| DG4837 | Exon36 | AAGGTCTTCCTCATGTTT | 18 | 88477693 | 88477710 | 789 |
| DG4838 | Exon36 | AGGTCTTCCTCATGTTTC | 18 | 88477694 | 88477711 | 790 |
| DG4839 | Exon36 | GGTCTTCCTCATGTTTCT | 18 | 88477695 | 88477712 | 791 |
| DG4840 | Exon36 | GTCTTCCTCATGTTTCTT | 18 | 88477696 | 88477713 | 792 |
| DG4841 | Exon36 | TCTTCCTCATGTTTCTTC | 18 | 88477697 | 88477714 | 793 |
| DG4842 | Exon36 | CTTCCTCATGTTTCTTCA | 18 | 88477698 | 88477715 | 794 |
| DG4844 | Exon36 | TCCTCATGTTTCTTCACA | 18 | 88477700 | 88477717 | 795 |
| DG4845 | Exon36 | CCTCATGTTTCTTCACAA | 18 | 88477701 | 88477718 | 796 |
| DG4846 | Exon36 | CTCATGTTTCTTCACAAT | 18 | 88477702 | 88477719 | 797 |
| DG4847 | Exon36 | TCATGTTTCTTCACAATT | 18 | 88477703 | 88477720 | 798 |
| DG4848 | Exon36 | CATGTTTCTTCACAATTT | 18 | 88477704 | 88477721 | 799 |
| DG4849 | Exon36 | GATGAAGAATATGAAGGTC | 19 | 88477680 | 88477698 | 800 |
| DG4850 | Exon36 | ATGAAGAATATGAAGGTCT | 19 | 88477681 | 88477699 | 801 |
| DG4852 | Exon36 | GAAGAATATGAAGGTCTTC | 19 | 88477683 | 88477701 | 802 |
| DG4853 | Exon36 | AAGAATATGAAGGTCTTCC | 19 | 88477684 | 88477702 | 803 |
| DG4854 | Exon36 | AGAATATGAAGGTCTTCCT | 19 | 88477685 | 88477703 | 804 |
| DG4855 | Exon36 | GAATATGAAGGTCTTCCTC | 19 | 88477686 | 88477704 | 805 |
| DG4856 | Exon36 | AATATGAAGGTCTTCCTCA | 19 | 88477687 | 88477705 | 806 |
| DG4857 | Exon36 | ATATGAAGGTCTTCCTCAT | 19 | 88477688 | 88477706 | 807 |
| DG4858 | Exon36 | TATGAAGGTCTTCCTCATG | 19 | 88477689 | 88477707 | 808 |
| DG4860 | Exon36 | TGAAGGTCTTCCTCATGTT | 19 | 88477691 | 88477709 | 809 |
| DG4861 | Exon36 | GAAGGTCTTCCTCATGTTT | 19 | 88477692 | 88477710 | 810 |
| DG4862 | Exon36 | AAGGTCTTCCTCATGTTTC | 19 | 88477693 | 88477711 | 811 |
| DG4863 | Exon36 | AGGTCTTCCTCATGTTTCT | 19 | 88477694 | 88477712 | 812 |
| DG4864 | Exon36 | GGTCTTCCTCATGTTTCTT | 19 | 88477695 | 88477713 | 813 |
| DG4865 | Exon36 | GTCTTCCTCATGTTTCTTC | 19 | 88477696 | 88477714 | 814 |
| DG4866 | Exon36 | TCTTCCTCATGTTTCTTCA | 19 | 88477697 | 88477715 | 815 |
| DG4867 | Exon36 | CTTCCTCATGTTTCTTCAC | 19 | 88477698 | 88477716 | 816 |
| DG4868 | Exon36 | TTCCTCATGTTTCTTCACA | 19 | 88477699 | 88477717 | 817 |
| DG4869 | Exon36 | TCCTCATGTTTCTTCACAA | 19 | 88477700 | 88477718 | 818 |
| DG4870 | Exon36 | CCTCATGTTTCTTCACAAT | 19 | 88477701 | 88477719 | 819 |
| DG4871 | Exon36 | CTCATGTTTCTTCACAATT | 19 | 88477702 | 88477720 | 820 |
| DG4872 | Exon36 | TCATGTTTCTTCACAATTT | 19 | 88477703 | 88477721 | 821 |

TABLE 1-continued

Synthetic polynucleotides with SEQ ID NO: 1-SEQ ID NO: 824 tested to induce skipping of exons 7, 31, 34, 36, 41 or 46 of the CEP290 mRNA

| SP_ID | Target | SP sequence (5' -> 3') | SP Length | Start | End | SEQ ID NO |
|---|---|---|---|---|---|---|
| DG4873 | Exon36 | ATGAAGAATATGAAGGTCTT | 20 | 88477681 | 88477700 | 822 |
| DG4874 | Exon36 | ATATGAAGGTCTTCCTCATG | 20 | 88477688 | 88477707 | 823 |
| DG4875 | Exon36 | TATGAAGGTCTTCCTCATGT | 20 | 88477689 | 88477708 | 824 |

TABLE 2 shows primers that can be used in combination with the methods and compositions of the present disclosure.

TABLE 2

Forward (SEQ ID NO: 825-SEQ ID NO: 831) and reverse (SEQ ID NO: 832-SEQ ID NO: 838) primers Forward primer

| Target | Name | Sequence (5'>3') | SEQ ID NO |
|---|---|---|---|
| Exon 7 | P105 | TGCAGGTGGACGAGATACTC | 825 |
| Exon 31 | P117 | AGTCCCTCAGAATGCAACTG | 826 |
| Exon 34 | P131 | AGAAAGACAAATGGCCTGGG | 827 |
| Exon 36 | P291 | TGCTTGTTGGTAGGAACTGG | 828 |
| Exon 41 (1) | P3 | TCGTCGGCAGCGTCACTGCAAAAGAAACAAAAAGCCT | 829 |
| Exon 41 (2) | P133 | CGTTGATCGACATACTAGAGAGC | 830 |
| Exon 46 | P139 | GAGAACAGGAGCTTCAGAAGG | 831 |

Reverse primer

| Target | Name | Sequence (5'>3') | PCR product size (bp) Normal | Exon-skipped | SEQ ID NO |
|---|---|---|---|---|---|
| Exon 7 | P107 | TCGGTAGTCACTGTCTTCCC | 304 | 250 | 832 |
| Exon 31 | P119 | CAAGACTGCTGATTGTACGTTC | 627 | 171 | 833 |
| Exon 34 | P132 | GTGGCAGGCAATCGAAGC | 133 | 198 | 834 |
| Exon 36 | P1845 | CTCATAGCTGAGCTAGGCAG | 305 | 197 | 835 |
| Exon 41 (1) | P4 | GTCTCGTGGGCTCGGTGGCTTGCCACTTTTTACCT | 316 | 193 | 836 |
| Exon 41 (2) | P134 | ACCTGATCAACAGTCATGCC | 585 | 462 | 837 |
| Exon 46 | P140 | CCAGTTCTGGGATTGTCTTTCC | 222 | 135 | 838 |

Synthetic Polynucleotides

The present disclosure provides synthetic polynucleotides (also described herein as "synthetic polynucleotides" or "SPs" or "oligomers" or "antisense oligomer (ASO)"), or vectors and constructs encoding the same, which target a region of the CEP290 pre-mRNA or gene. In some instances, the synthetic polynucleotides of the present disclosure comprise one or more chemical modifications, such as a nucleotide analogue instead of a canonical nucleotide or a non-phosphodiester backbone. A chemical modification can be located on one or more nucleoside(s) or the backbone of the nucleic acid molecule. In some instances, the synthetic polynucleotide comprises a modified internucleoside linkage, such as a phosphorothioate internucleoside linkage, a phosphoroamidate internuceloside linkage, or a phosphorodiamidate internucleoside linkage. In some instances, the synthetic polynucleotide comprises a modified sugar moiety, such as 2'-O-methyl or 2'-O-methoxyethyl (MOE) modifications, a locked nucleic acid (LNA), a peptide nucleic acid (PNA). In some cases, the synthetic polynucleotides as described herein can be nuclease-resistant.

In various aspects, the synthetic polynucleotides can be substantially uncharged, and are optionally suitable as a substrate for active or facilitated transport across the cell membrane. In some cases, all of the internucleoside linkages are uncharged. The ability of a synthetic polynucleotide to form a stable duplex with the target pre-mRNA may also relate to other features of the synthetic polynucleotide, including the length and degree of complementarity of the synthetic polynucleotide with respect to the target, the ratio of G:C to A:T base matches, and the positions of any mismatched bases. The ability of the synthetic polynucleotide to resist cellular nucleases may promote survival and ultimate delivery of the agent to the cell cytoplasm.

In various aspects of the present disclosure, the synthetic polynucleotides can have at least one internucleoside linkage that is positively charged or cationic at physiological pH. In further cases, the synthetic polynucleotide can have at least one internucleoside linkage that exhibits a pKa between about 5.5 and about 12. In some aspects, the synthetic polynucleotide contains about, at least about, or no more than about 1, 2, 3, 4, 5, 6, 7, 8, 9, or 10 internucleoside linkages that exhibit a pKa between about 4.5 and about 12. In some cases, the synthetic polynucleotide contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. In some cases, the synthetic polynucleotide can have at least one internucleoside linkage with both a basic nitrogen and an alkyl, aryl, or aralkyl group. In other cases, the cationic internucleoside linkage or linkages can comprise a 4-aminopiperdin-1-yl (APN) group, or a derivative thereof. In some cases, the synthetic polynucleotides can comprise a morpholine ring. While not being bound by any theory, it is believed that the presence of a cationic linkage or linkages (e.g., APN group or APN derivative) in the oligonucleotide can facilitate binding to the negatively charged phosphates in the target nucleotide. Thus, the formation of a heteroduplex between mutant RNA and the cationic linkage-containing oligomer may be held together by both an ionic attractive force and hydrogen bonding (e.g., Watson-Crick base pairing). In various cases, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In other cases, an oligomer of about 19-20 monomer subunits can have 2-10 (e.g., 4-8) cationic linkages, and the remainder uncharged linkages. In some aspects, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

A synthetic polynucleotide can have the same or a mixture of different nucleotide analogues or chemical modifications. The nucleotide analogues can have structural changes that are naturally or not naturally occurring in messenger RNA. A mixture of various analogues or modified nucleotides can be used. For example, one or more analogues within a polynucleotide can have natural modifications, while another part has modifications that are not naturally found in mRNA. Additionally, some analogues or modified ribonucleotides can have a base modification, while other modified ribonucleotides have a sugar modification. In the same way, it is possible that all modifications are base modifications, or all modifications are sugar modifications or any suitable combination thereof.

In some cases, the synthetic polynucleotides of the present disclosure can comprise phosphoroamidate containing oligomers, phosphorodiamidate containing oligomers, phosphorothioate containing oligomers, morpholino containing oligomers optionally substituted with a phosphoramidate internucleoside linkage or a phosphorodiamidate internucleoside linkage, 2'-O-methyl containing oligomers can optionally be substituted with a phosphorothioate internucleoside linkage, Locked nucleic acid (LNA) containing oligomers can optionally be substituted with a phosphorothioate internucleoside linkage, and 2'-O-methoxyethyl (MOE) containing oligomers can optionally be substituted with a phosphorothioate internucleoside linkage. In some cases, 2'-fluoro-containing oligomers can optionally be substituted with a phosphorothioate internucleoside linkage, and 2'-O, 4'-C-ethylene-bridged nucleic acids (ENAs) containing oligomers can optionally be substituted with a phosphorothioate internucleoside linkage. In some cases, tricyclo-DNA (tc-DNA) containing oligomers can be substituted with a phosphorothioate internucleoside linkage, Moreover, 2'-O-[2-(N-methyl-carbamoyl)ethyl] containing oligomers can optionally be substituted with a phosphorothioate internucleoside linkage, morpholino containing oligomers can further comprise a phosphorodiamidate internucleoside linkage wherein the phosphorous atom of the phosphorodiamidate can be covalently bonded to the nitrogen atom of a morpholine ring, and can be covalently bonded to a (1,4-piperazin)-1-yl moiety or to a substituted (1,4-piperazin)-1-yl (PMOplus) moiety, morpholino containing oligomers further can comprise a phosphorodiamidate internucleoside linkage wherein the phosphorus atom of the phosphorodiamidate can be covalently bonded to the nitrogen atom of a morpholine ring and can be covalently bonded to a 4-aminopiperdin-1-yl moiety (i.e., APN) or a substituted 4-aminopiperidin-1-yl (PMO-X) moiety, ribose sugar containing oligomers can further comprise a phosphorothioate internucleoside linkage or a phosphoramidate internucleoside linkage deoxyribose sugar containing oligomers further comprising a phosphorothioate internucleoside linkage oligomer or a phosphoramidate internucleoside linkage, peptide-conjugated phosphorodiamidate morpholino containing oligomers (PPMO) which are further optionally substituted, peptide nucleic acid (PNA) oligomers which can further be substituted including further substitutions and combinations of any of the foregoing.

In certain aspects, the phosphorous atom of a phosphorodiamidate linkage can be further substituted with a (1,4-piperazin)-1-yl moiety, a substituted (1,4-piperazin)-1-yl moiety, a 4-aminopiperidin-1-yl moiety, or a substituted 4-aminopiperidin-1-yl moiety. In some cases, PNA and LNA chemistries can utilize shorter targeting sequences because of their relatively high target binding strength relative to PMO and 2'-O-Me oligomers. Phosphorothioate and 2'-O-Me chemistries can be combined to generate a 2'-O-Me-phosphorothioate analog. (See, e.g., PCT Publication Nos. WO/2013/112053 and WO/2009/008725, which are hereby incorporated by reference in their entireties). In some instances, synthetic polynucleotides, such as phosphorodiamidate morpholino oligomers (PMO), can be covalently linked to cell penetrating peptides (CPPs) to facilitate intracellular delivery. Peptide-conjugated PMOs are called PPMOs and in certain instances include those described in PCT Publication No. WO/2012/150960, which is hereby incorporated by reference in its entirety. In some cases, an arginine-rich peptide sequence covalently bonded, for example, to the 3' terminal end of an synthetic polynucleotide as described herein may be used.

Phosphorothioates.

Phosphorothioates (or S-oligos) are a variant of native DNA or RNA in which one of the nonbridging oxygens of the phosphodiester internucleoside linkages is replaced by sulfur. A non-limiting example of a phosphorothioate DNA, comprising deoxyribose subunits and phosphorothioate internucleoside linkages is depicted below, wherein the base can be any nucleobase or modified derivative thereof:

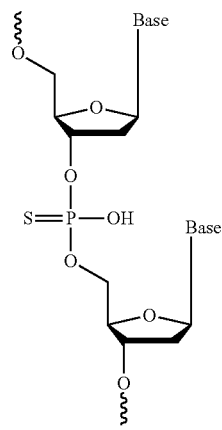

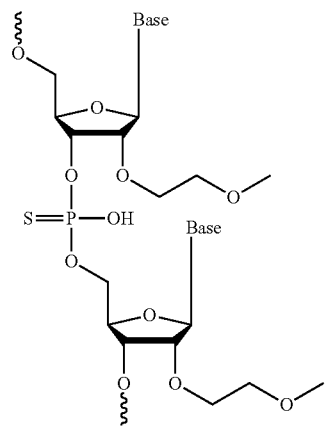

The sulfurization of the internucleoside bond reduces the action of endo- and exonucleases including 5' to 3' and 3' to 5' DNA POL 1 exonuclease, nucleases Si and P1, RNases, serum nucleases and snake venom phosphodiesterase. Phosphorothioates may be made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD). The latter methods avoid the problem of elemental sulfur's insolubility in most organic solvents and the toxicity of carbon disulfide. The TETD and BDTD methods also yield higher purity phosphorothioates.

2-O-Methyl, 2'-O-MOE, and 2'-F Synthetic Polynucleotides.

2'-O-Me synthetic polynucleotide molecules can comprise subunits that carry a methyl group at the 2'-OH residue of the ribose molecule. 2'-O-Me-RNAs can show the same (or similar) behavior as DNA, but are protected against nuclease degradation. 2'-O-Me-RNAs can also be combined with phosphorothioate oligomers (PTOs) for further stabilization. 2'-O-Me oligomers (wherein the 2'-O-Me subunits are connected by phosphodiester or phosphorothioate internucleoside linkages) can be synthesized according to routine techniques in the art. In some cases, 2'-O-Me oligomers may also comprise a phosphorothioate linkage (2'-O-Me phosphorothioate oligomers). In some cases, 2'-O-methoxyethyl oligomers (2'-O-MOE), like 2'-O-Me oligomers, can comprise subunits that carry a methoxyethyl group at the 2'-OH residue of the ribose molecule. In contrast to the preceding alkylated 2'-OH ribose derivatives, 2'-fluoro oligomers can comprise subunits that have a fluoro substituent at the 2'-position in place of the 2'-OH. Non-limiting examples of a 2'-O-Me polynucleotide (left), a 2'-O-MOE polynucleotide (middle), and a 2'-F polynucleotide (right) are depicted below, wherein the base can be any nucleobase or modified derivative thereof:

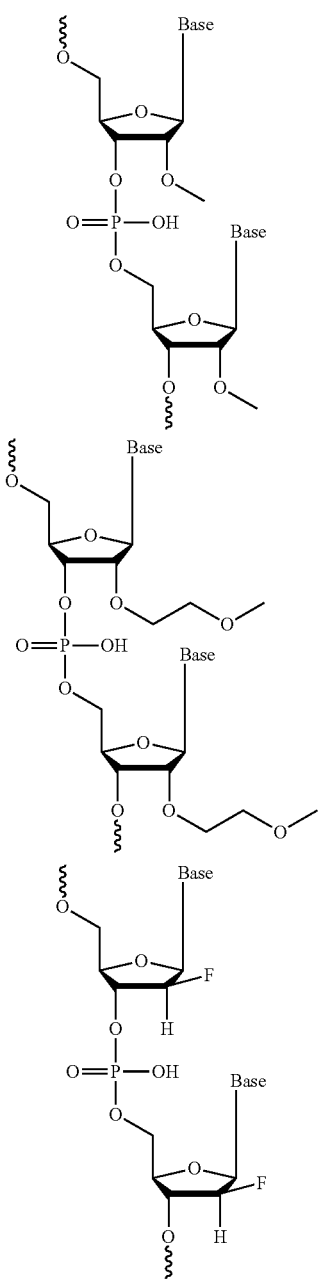

Morpholino-Based Synthetic Polynucleotides.

In some instances of the present disclosure, morpholino-based synthetic polynucleotides can refer to an oligomer comprising morpholino subunits supporting a nucleobase and, instead of a ribose, can contain a morpholine ring. Exemplary internucleoside linkages include phosphoramidate or phosphorodiamidate internucleoside linkages joining the morpholine ring nitrogen of one morpholino subunit to the 4' exocyclic carbon of an adjacent morpholino subunit. In some cases, each morpholino subunit can comprise a purine or pyrimidine nucleobase effective to bind, by base-specific hydrogen bonding, to a base in an oligonucleotide. Morpholino-based synthetic polynucleotides are further detailed, for example, in U.S. Pat. Nos. 5,698,685; 5,217,866; 5,142,047; 5,034,506; 5,166,315; 5,185,444; 5,521,063; 5,506,337; and PCT Publication No. WO/2009/064471 and WO/2012/043730, which are hereby incorporated by reference in their entirety. In some cases, a synthetic polynucleotide of the present disclosure comprising morpholino-based nucleotide analogues can have the following general structure, wherein the base can be any nucleobase or modified derivative thereof:

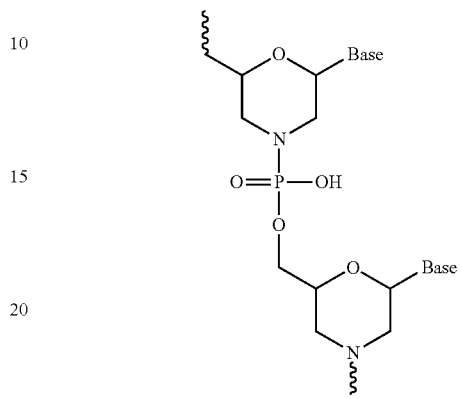

Within the synthetic polynucleotide structure, the phosphate groups can be commonly referred to as forming the "internucleoside linkages" or the "phosphodiester backbone" of the oligomer. The naturally occurring internucleoside linkage of RNA and DNA is a 3' to 5'phosphodiester linkage. In some cases, a "phosphoramidate" group can comprise a phosphorus atom having three attached oxygen atoms and one attached nitrogen atom, while a "phosphorodiamidate" group can comprise phosphorus having two attached oxygen atoms and two attached nitrogen atoms. In some cases, the uncharged or the cationic internucleoside linkages of the morpholino-based oligomers as described herein can comprise one nitrogen atom that is always pendant to the linkage chain. In some cases, the second nitrogen, in a phosphorodiamidate linkage, is typically the ring nitrogen in a morpholine ring structure. "PMO-X" refers to phosphorodiamidate morpholino-based oligomers having a phosphorus atom with (i) a covalent bond to the nitrogen atom of a morpholine ring and (ii) a second covalent bond to the ring nitrogen of, for example, a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-APN" or "APN," which refers to a PMO-X oligomer which can comprise at least one internucleoside linkage where a phosphorus atom is linked to a morpholino group and to the ring nitrogen of a 4-aminopiperdin-1-yl (i.e., APN). In some cases, a synthetic polynucleotide can comprise at least one APN-containing linkage or APN derivative-containing linkage. In various cases, a synthetic polynucleotide can comprise morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) can be uncharged linkages, e.g., about or at derivative-containing linkages.

Morpholino monomer subunits, the modified internucleoside linkages, and the synthetic polynucleotides comprising the same can be prepared as described, for example, in U.S.

Pat. Nos. 5,185,444, and 7,943,762, which are hereby incorporated by reference in their entirety.

Cell-Penetrating Peptides.

The synthetic polynucleotides of the present disclosure may be covalently linked to a peptide also referred to herein as a cell penetrating peptide (CPP). In certain aspects, the peptide is an arginine-rich peptide transport moiety effective to enhance transport of the compound into cells. The transport moiety is attached to a terminus of the oligomer. The peptides have the capability of inducing cell penetration within about 30%, 40%, 50%, 60%, 70%, 80%, 90% or 100% of cells of a given cell population, including all integers in between, and allow macromolecular translocation within multiple tissues upon administration (e.g., systemic, intrathecal, or intravitreal administration). In some cases, the cell-penetrating peptide may comprise an arginine-rich peptide transporter. In other cases, the cell-penetrating peptide may be Penetratin or the Tat peptide. See e.g., in US Publication No. 2010-0016215, which is hereby incorporated by reference in its entirety. One approach to conjugation of peptides to synthetic polynucleotides of the present disclosure can be found in PCT publication WO2012/150960, which is hereby incorporated by reference in its entirety. In some instances, a peptide-conjugated synthetic polynucleotides of the present disclosure can utilize glycine as a linker between the CPP and the synthetic polynucleotide. For example, a peptide-conjugated phosphorodiamidate morpholino containing oligomers (PMOs) of the present disclosure can comprise $R_6$-G-PMO. The transport moieties as described above have been shown to greatly enhance cell entry of attached oligomers, relative to uptake of the oligomer in the absence of the attached transport moiety. In some cases, cellular uptake of the synthetic polynucleotide can be enhanced by using a CPP of at least 10-fold, at least 20-fold, at least 50-fold, or at least 100-fold, relative to the unconjugated synthetic polynucleotide alone.

A nucleoside analogue or chemical modification can be selected from the group comprising pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, or a morpholino.

In some cases, 100% of the synthetic polynucleotide comprises a modified sugar moiety. In other instances, at least about 10%, 15%, 20%, 25%, 30%, 35%, 40%, 45%, 50%, 55%, 60%, 65%, 70%, 75%, 80%, 85%, 90%, 95% of the synthetic polynucleotide(s) or vector(s) encoding the same include non-naturally occurring uracil, adenine, guanine, or cytosine. In some cases, at most about 99%, 95%, 90%, 85%, 80%, 75%, 70%, 65%, 60%, 55%, 50%, 45%, 40%, 35%, 30%, 25%, 20%, 15%, 10%, 5%, 1%, of the synthetic polynucleotide(s) or vector encoding the same includes non-naturally occurring uracil, adenine, guanine, or cytosine. In some cases, at least the three terminal residues in either the 3' end, the 5' end, or both ends of the synthetic polynucleotide comprise the modified sugar moiety.

In some cases, 100% of the synthetic polynucleotide comprises a modified phosphate backbone. In other instances, at least about 10%, 15%, 20%, 25%, 30%, 35%, 40%, 45%, 50%, 55%, 60%, 65%, 70%, 75%, 80%, 85%, 90%, 95% of the synthetic polynucleotide(s) or vector encoding the same includes a modified phosphate backbone. In some cases, at least the three terminal residues in either the 3' end, the 5' end, or both ends of the synthetic polynucleotide comprise the modified sugar moiety.

In some cases, the synthetic polynucleotides of the present disclosure can comprise from about 5 to 200 nucleotides. In some cases, the synthetic polynucleotides of the present disclosure can comprise from about 15 to 200 nucleotides. In some cases, the synthetic polynucleotides of the present disclosure can comprise from about 10 to 50 nucleotides. In some cases, the synthetic polynucleotides of the present disclosure can comprise from about 15 to 25 nucleotides. In some cases, the synthetic polynucleotides of the present disclosure can comprise from about 20 to 75 nucleotides. In some cases, the synthetic polynucleotides of the present disclosure can comprise from about 50 to 200 nucleotides.

Methods of Treatment and Administration

Pharmaceutical compositions containing a synthetic polynucleotide, described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition.

The treatment may comprise treating a subject (e.g., a patient with a disease and/or a lab animal with a condition). In some cases, the subject is afflicted with a Mendelian disorder. In some cases, the Mendelian disorder is any one of Leber Congenital Amaurosis, Senior-Locken Syndrome, Joubert syndrome, or Meckel Syndrome. In some cases, the condition is broadly associated with defects in one or more proteins that function within cell structures understood as cilia or centrosomes. In some cases, the subject is a human. In some instances, the composition is used for the treatment of retinal dystrophy, retinitis pigmentosa, renal disease, retinal dystrophy, coloboma, kidney nephronophthisis, ataxia, mental retardation.

Treatment may be provided to the subject before clinical onset of disease. Treatment may be provided to the subject after clinical onset of disease. Treatment may be provided to the subject on or after 1 minute, 5 minutes, 10 minutes, 30 minutes, 1 hour, 2 hours, 3 hours, 4 hours, 5 hours, 6 hours, 12 hours, 1 day, 1 week, 6 months, 12 months, or 2 years after clinical onset of the disease. Treatment may be provided to the subject for a time period that is greater than or equal to 1 minute, 10 minutes, 30 minutes, 1 hour, 2 hours, 3 hours, 4 hours, 5 hours, 6 hours, 12 hours, 1 day, 1 week, 1 month, 6 months, 12 months, 2 years, 10 years, 20 years, or more after clinical onset of the disease. In some cases, treatment may be provided to a subject for the duration of the subject's life. Treatment may be provided to the subject for a time period that is less than or equal to 2 years, 12 months, 6 months, 1 month, 1 week, 1 day, 12 hours, 6 hours, 5 hours, 4 hours, 3 hours, 2 hours, 1 hour, 30 minutes, 10 minutes, or 1 minute after clinical onset of the disease. Treatment may also include treating a human in a clinical trial.

In some cases, the dosage and/or dosing schedule of the synthetic polynucleotides is adjusted according to the measurement, for example, to increase the dosage to ensure a therapeutic amount is present in a subject. A select time may include an amount of time after administration of a synthetic polynucleotide as described herein, to allow time for the construct to be absorbed into the bloodstream and/or metabolized by the liver and other metabolic processes. In some cases, a select time may be about 1, 2, 3, 4, 5, 6, 7, 8, 9, 10, 11, 12, 15, 18, 20, 22, or 24 hours after administration (e.g., systemic, intrathecal, or intravitreal administration) of a synthetic polynucleotide. In some cases, a select time may be about 12, 18 or 24 hours after administration of a synthetic polynucleotide. In other instances, a select time may be about 1, 2, 3, 4, 5, 6 or 7 days after administration of a synthetic polynucleotide. In some cases, a select time may be about 1, 2, 3, 4, 5, 6 or 7 weeks after administration of a synthetic polynucleotide. In some cases, a select time may be about 1, 2, 3, 4, 5, 6 or 7 months after administration of a synthetic polynucleotide.

In some cases, treatment using the methods and compositions of the present disclosure may be monitored, e.g., by general indicators of disease. The efficacy of an in vivo administered synthetic polynucleotide may be determined from biological samples (tissue, blood, urine etc.) taken from a subject before, during, and/or subsequent to administration of the synthetic polynucleotide. Assays of such samples can include, for example, monitoring the presence or absence of heteroduplex formation with target and non-target sequences, e.g., using an electrophoretic gel mobility assay.

In various aspects of the present disclosure, the synthetic polynucleotide can be administered in an amount and manner effective, if administered systemically, to result in a peak blood concentration of at least 200-400 nM. Typically, and in various instances, one or more doses of synthetic polynucleotide can be administered, for example at regular intervals, e.g. for a period of about one to two weeks. In some cases, doses for administration can range from about 1-1000 mg oligomer per 70 kg of body mass. In some cases, doses of greater than 1000 mg oligomer/patient may be advantageous. In some cases, doses for systemic, intrathecal or intravitreal administrations can range from about 0.5 mg to 1000 mg oligomer per 70 kg. In some instances, the synthetic polynucleotide of the present disclosure may be administered at regular intervals for a short time period, e.g., daily for two weeks or less. However, in some cases the oligomer can be administered intermittently over a longer period of time. In some cases, administration of the synthetic polynucleotide may be followed by, or concurrent with, administration of other therapeutic treatments (e.g., antibiotics). In some cases, the treatment regimen may be adjusted (e.g., the dose, frequency, route, etc.) as indicated, based on the results of immunoassays, other biochemical tests and physiological examination of the subject under treatment. An effective in vivo treatment regimen using the synthetic polynucleotide of the present disclosure may vary according to the duration, dose, frequency and route of administration, as well as the condition of the subject under treatment (e.g., prophylactic administration versus therapeutic administration). Accordingly, such in vivo therapy can require monitoring by tests appropriate to the particular type of disorder under treatment, and corresponding adjustments in the dose or treatment regimen may be advantageous in order to achieve an optimal prophylactic or therapeutic outcome.

In practicing the methods of treatment or use provided herein, therapeutically-effective amounts of the synthetic polynucleotides described herein are administered in pharmaceutical compositions to a subject having a disease or condition to be treated. In some cases, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures. In some instances, the therapeutically-effective amount may range from about 5 µg to about 2 mg of synthetic polynucleotide. In some instances, the therapeutically-effective amount may range from about 10 µg to about 1.8 mg. In some instances, the therapeutically-effective amount may range from about 30 µg to about 1.5 mg. In some instances, the therapeutically-effective amount may range from about 60 µg to about 1 mg. In some instances, the therapeutically-effective amount may range from about 50 µg to about 950 µg. In some instances, the therapeutically-effective amount may range from about 100 µg to about 500 µg. In some instance, the therapeutically-effective amount may range from about 5 µg to about 950 µg per eye for intravitreal administration. In some instance, the therapeutically-effective amount may range from about 10 µg to about 900 µg per eye for intravitreal administration. In some instance, the therapeutically-effective amount may range from about 60 µg to about 900 µg per eye for intravitreal administration.

In various instances, dosing of the compositions as described herein can be dependent on severity and responsiveness of the disease state to be treated, with the course of treatment lasting from several days to several months, or until a cure is effected or a diminution of the disease state is achieved. In some cases, dosing schedules can be calculated from measurements of drug accumulation in the body of the patient. Various approaches may be used to determine optimum dosages, dosing methodologies and repetition rates. In some cases, optimum dosages may vary depending on the relative potency of individual synthetic polynucleotides, and can generally be estimated based on $EC_{50}$ values found to be effective in in vitro and in vivo animal models. In some cases, dosages can range from about 0.05 µg per kg to about 50 µg per kg of body weight (assuming an average body weight of 70 kg). In some cases, dosages can range from about 0.1 µg per kg to about 30 µg per kg of body weight. In some cases, dosages can range from about 0.5 µg per kg to about 20 µg per kg of body weight. In some cases, dosages can range from about 1 µg per kg to about 20 µg per kg of body weight. In some cases, the compositions of the present disclosure may be given once or more daily, weekly, monthly or yearly, or even once every 2 to 20 years. Generally, it is within the scope of a skilled artisan to estimate repetition rates for dosing based on measured residence times and concentrations of the drug in bodily fluids, tissues, and/or cells. Following successful treatment, it may be desirable to have the patient undergo maintenance therapy to prevent the recurrence of the disease state, where the synthetic polynucleotide can be administered in maintenance doses, ranging from about 1 µg to about 2 mg of synthetic polynucleotide per 70 kg of body weight for oral administration, or about 5 µg to about 2 mg oligomer per 70 kg of body weight for parenteral (e.g., intravitreal) administration, once or more daily, to about once every 20 years.

As described above, the compositions of the present disclosure containing the synthetic polynucleotides described herein can be administered for prophylactic and/or therapeutic treatments. In therapeutic applications, the synthetic polynucleotides, or constructs/vectors encoding the same, can be administered to a subject already suffering from a disease, such as Leber Congenital Amaurosis (LCA), Senior-Locken Syndrome (SLS), Joubert syndrome (JS), Meckel Syndrome (MS), or another condition affecting the cilia or centrosome of a cell, in the amount sufficient to provide the amount of the encoded polypeptide that cures or at least improves the symptoms of the disease. In some cases, the compositions of the present disclosure containing the synthetic polynucleotides described herein can be administered for prophylactic and/or therapeutic treatment of diseases that affect or are located in the central nervous system (CNS). Synthetic polynucleotides, nucleic acid constructs, vectors, engineered polynucleotides, or compositions can also be administered to lessen a likelihood of developing, contracting, or worsening a disease. Amounts effective for this use can vary based on the severity and course of the disease or condition, the efficiency of transfection of a nucleic acid construct(s), vector(s), engineered polynucleotide(s), or composition(s), the affinity of an encoded polypeptide to a target molecule, preceding therapy, the subject's health status, weight, response to the drugs, and the judgment of the treating physician.

A composition of the disclosure can be a combination of any synthetic polyribonucleotide described herein with other chemical components, such as carriers, stabilizers, diluents, dispersing agents, suspending agents, thickening agents, and/or excipients. The composition facilitates administration of the compound to an organism. Compositions can be administered in therapeutically-effective amounts as pharmaceutical compositions by various forms and routes including, for example, intravitreal, intrathecal, aerosol, parenteral, and any form of viable ophthalmic administration. In some cases, a combination of any synthetic polyribonucleotide described herein can be administered intrathecally. In some cases, a combination of any synthetic polyribonucleotide described herein can be administered systemically.

The compounds of the disclosure may also be admixed, encapsulated, covalently bonded to, or otherwise associated with other molecules, molecule structures or mixtures of compounds, as for example, liposomes, receptor-targeted molecules, oral, rectal, topical or other formulations, for assisting in uptake, distribution and/or absorption.

In certain aspects, the synthetic polynucleotides of the disclosure can be delivered by transdermal methods (e.g., via incorporation of the synthetic polynucleotide into, e.g., emulsions, with such synthetic polynucleotides optionally packaged into liposomes). Such transdermal and emulsion/liposome-mediated methods of delivery are described for delivery of the synthetic polynucleotides in the art, e.g., in U.S. Pat. No. 6,965,025, which are hereby incorporated by reference in their entirety.

As described above, a pharmaceutical composition as disclosed herein can be administered in a local or systemic manner, for example, via injection of the compound directly into the eye (e.g., intravitreal) or another suitable location in the body, such as the spinal canal (e.g., intrathecal), or, optionally in a depot or another suitable formulation.

Parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, granulating, dragee-making, levigating, emulsifying, encapsulating, entrapping, or compression processes.

The pharmaceutical compositions can include at least one pharmaceutical acceptable carrier, diluent, or excipient and compounds described herein as free-base or pharmaceutically-acceptable salt form. The methods and pharmaceutical compositions described herein include the use crystalline forms (i.e., polymorphs), and active metabolites of these compounds having the same type of activity. Moreover, the methods and pharmaceutical compositions described herein include prodrugs and other bioequivalents. The term "prodrug" indicates a therapeutic agent that is prepared in an inactive form that is converted to an active form (i.e., drug) within the body or cells thereof by the action of endogenous enzymes or other chemicals and/or conditions. For example, prodrug versions of the synthetic oligonucleotides of the present disclosure can be prepared as SATE [(S-acetyl-2-thioethyl) phosphate] derivatives according to the methods disclosed in PCT Publication No. WO 1993/24510 which is hereby incorporated by reference in their entirety. Prodrugs include, for example, compounds of this disclosure where hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the synthetic polynucleotides of the disclosure. Further, in the case of a carboxylic acid (—COOH), esters may be employed, such as methyl esters, ethyl esters, and the like.

The pharmaceutical formulations of the present disclosure, which may conveniently be presented in unit dosage form, may be prepared according to conventional techniques used in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then shaping the product.

Methods for the preparation of compositions comprising the synthetic polynucleotides described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid before use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

In some cases, formulations of the present disclosure can include liposomal formulations. As used in the present disclosure, the term "liposome" can indicate a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells. Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic oligomers, such as a polyethylene glycol (PEG) moiety. Liposomes and their uses are further described in U.S. Pat. No. 6,287,860, which is hereby incorporated by reference in its entirety.

In some cases, the methods and compositions of the present disclosure can be used in combination with various penetration enhancers (e.g., above described cell penetrating peptides) to enable the efficient cellular delivery of nucleic acids, particularly oligomers. In addition to aiding the diffusion of non-lipophilic drugs across cell membranes, penetration enhancers can also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is hereby incorporated by reference in its entirety. One of ordinary skill will recognize that formulations are routinely designed according to their intended use, e.g. route of administration. For instance, formulations for topical administration can include those in which the oligomers of the disclosure are in admixture with a topical delivery agent such as lipids, liposomes, fatty acids, fatty acid esters, steroids, chelating agents and surfactants. Lipids and liposomes include neutral (e.g., dioleoylphosphatidyl ethanolamine (DOPE), dimyristoylphosphatidyl choline (DMPC), distearolyphosphatidyl choline), negative (e.g., dimyristoylphosphatidyl glycerol (DMPG)), and cationic (e.g., dioleoyltetramethyl-aminopropyl (DOTAP) and dioleoylphosphatidyl ethanolamine (DOTMA)). For topical or other administration routes, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is hereby incorporated by reference in its entirety. Topical formulations are described in detail in U.S. patent application Ser. No. 09/315,298 filed on May 20, 1999, which is hereby incorporated by reference in its entirety.

In some cases, intracellular delivery of the therapeutic compositions of the present disclosure may be enhanced by attaching a ligand to a synthetic polynucleotide that facilitates and/or enhances intracellular uptake and/or increases cell-specific delivery of the synthetic polynucleotide through binding to a specific cell surface receptor. In some cases, for example, a N-acetylgalactosamine (GalNAc)-based ligand may be conjugated to the synthetic polynucleotide to enhance intracellular delivery and/or increases cell-specific delivery. Without being bound to any theory, these oligonucleotide-ligand conjugates may show an improved and more specific intracellular uptake compared to the synthetic oligonucleotides alone. Receptor-mediated update may further increase the number of functional and intact synthetic polynucleotides inside the cell by, for example, circumventing the endosome.

The synthetic polynucleotides of the present disclosure may generally be utilized as the free acid or free base. Alternatively, the compounds of this disclosure may be used in the form of acid or base addition salts. Acid addition salts of the free amino compounds of the present disclosure may be prepared by various methods, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like).

In some cases, the synthetic polynucleotides described herein may also be delivered via an implantable device. Design of such a device is an art-recognized process, with, e.g., synthetic implant design described in, e.g., U.S. Pat. No. 6,969,400, which are hereby incorporated by reference in their entirety. Synthetic polynucleotides can be introduced into cells using art-recognized techniques (e.g., transfection, electroporation, fusion, liposomes, colloidal polymeric particles and viral and non-viral vectors among others). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like. Synthetic polynucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, or various non-invasive non-endocytic methods of delivery.

Various aspects of the present disclosure relate to methods of decreasing expression of a misfolded and/or non-functional disease-related protein in a cell, tissue, and/or subject using the synthetic polynucleotides as described herein. In some instances, the expression of a misfolded and/or non-functional, disease-related protein is decreased or reduced by about or at least about 5%, 6%, 8%, 10%, 12%, 15%, 20%, 22%, 25%, 30%, 35%, 40%, 45%, 50%, 55%, 60%, 65%, 70%, 75%, 80%, 85%, 90%, 92%, 95%, or 100% relative to a control, for example, a correctly folded and functional control protein, a control cell/subject, a control composition without the synthetic polynucleotide, the absence of treatment, and/or an earlier time-point.

In some cases, the methods and compositions of the present disclosure can increase the production or expression of a CEP290 protein by about or at least about 5%, 6%, 8%, 10%, 12%, 15%, 20%, 22%, 25%, 30%, 35%, 40%, 45%, 50%, 55%, 60%, 65%, 70%, 75%, 80%, 85%, 90%, 92%, 95%, or 100% relative to a control, for example, an incorrectly folded and/or non-functional, disease-related control protein, a control cell/subject, a control composition without the synthetic polynucleotide, the absence of treatment, and/or an earlier time-point.

In various aspects, the methods and compositions of the present disclosure relate to inhibiting the progression of a Mendelian or related disorder in a subject using the synthetic polynucleotides as described herein. Moreover, various aspects relate to methods of reducing, or improving, as appropriate, one or more symptoms of a Mendelian and related disorders in a subject.

EMBODIMENTS

Embodiment 1

In some embodiments, the disclosure provides a composition comprising a therapeutically effective amount of a synthetic polynucleotide between 10 nucleotides to 200 nucleotides in length that is at least 60% complementary to a region of a pre-mRNA molecule, which pre-mRNA encodes a centrosomal protein 290.

Embodiment 2

The composition of embodiment 1, wherein the region of the pre-mRNA molecule corresponds to an intron of the pre-mRNA molecule.

Embodiment 3

The composition of any one of embodiments 1 and 2, wherein at least 90% of the region of the pre-mRNA molecule comprises an intron of the pre-mRNA molecule.

Embodiment 4

The composition of any one of embodiments 1-3, wherein at least 90% of the region of the pre-mRNA molecule corresponds to an exon of the pre-mRNA molecule.

Embodiment 5

The composition of any one of embodiments 1-4, wherein the region of the pre-mRNA molecule comprises a junction between an intron and an exon of the pre-mRNA molecule.

Embodiment 6

The composition of any one of embodiments 1-5, wherein the region of the pre-mRNA molecule is within 500 bases from an exon of the pre-mRNA molecule.

Embodiment 7

The composition of any one of embodiments 1-6, wherein the region of the pre-mRNA molecule comprises exon 7 of the centrosomal protein 290.

Embodiment 8

The composition of any one of embodiments 1-6, wherein the synthetic polynucleotide is any one of SEQ ID NO: 270-SEQ ID NO: 309.

Embodiment 9

The composition of any one of embodiments 1-6, wherein the region of the pre-mRNA molecule comprises exon 31 of the centrosomal protein 290.

Embodiment 10

The composition of any one of embodiments 1-6, wherein the synthetic polynucleotide is any one of SEQ ID NO: 110-SEQ ID NO: 269.

Embodiment 11

The composition of any one of embodiments 1-6, wherein the region of the pre-mRNA molecule comprises exon 34 of the centrosomal protein 290.

Embodiment 12

The composition of any one of embodiments 1-6, wherein the synthetic polynucleotide is any one of SEQ ID NO: 70-SEQ ID NO: 109.

Embodiment 13

The composition of any one of embodiments 1-6, wherein the region of the pre-mRNA molecule comprises exon 36 of the centrosomal protein 290.

Embodiment 14

The composition of any one of embodiments 1-6, wherein the synthetic polynucleotide is any one of SEQ ID NO: 461-SEQ ID NO: 540, or SEQ ID NO: 703-SEQ ID NO: 824.

Embodiment 15

The composition of any one of embodiments 1-6, wherein the synthetic polynucleotide is SEQ ID NO: 486.

Embodiment 16

The composition of any one of embodiments 1-6, wherein the synthetic polynucleotide is SEQ ID NO: 487.

Embodiment 17

The composition of any one of embodiments 1-6, wherein the synthetic polynucleotide is SEQ ID NO: 492.

Embodiment 18

The composition of any one of embodiments 1-6, wherein the synthetic polynucleotide is SEQ ID NO: 503.

Embodiment 19

The composition of any one of embodiments 1-6, wherein the synthetic polynucleotide is SEQ ID NO: 531.

Embodiment 20

The composition of any one of embodiments 1-6, wherein the synthetic polynucleotide is SEQ ID NO: 535.

Embodiment 21

The composition of any one of embodiments 1-6, wherein the region of the pre-mRNA molecule comprises exon 41 of the centrosomal protein 290.

Embodiment 22

The composition of any one of embodiments 1-6, wherein the synthetic polynucleotide is any one of SEQ ID NO: 1-SEQ ID NO: 19, or SEQ ID NO: 310-SEQ ID NO: 394, or SEQ ID NO: 541-SEQ ID NO: 684.

Embodiment 23

The composition of any one of embodiments 1-6, wherein the synthetic polynucleotide is SEQ ID NO: 19.

Embodiment 24

The composition of any one of embodiments 1-6, wherein the synthetic polynucleotide is SEQ ID NO: 316.

Embodiment 25

The composition of any one of embodiments 1-6, wherein the synthetic polynucleotide is SEQ ID NO: 331.

Embodiment 26

The composition of any one of embodiments 1-6, wherein the synthetic polynucleotide is SEQ ID NO: 333.

Embodiment 27

The composition of any one of embodiments 1-6, wherein the synthetic polynucleotide is SEQ ID NO: 335.

Embodiment 28

The composition of any one of embodiments 1-6, wherein the synthetic polynucleotide is SEQ ID NO: 336.

Embodiment 29

The composition of any one of embodiments 1-6, wherein the synthetic polynucleotide is SEQ ID NO: 337.

Embodiment 30

The composition of any one of embodiments 1-6, wherein the synthetic polynucleotide is SEQ ID NO: 340.

Embodiment 31

The composition of any one of embodiments 1-6, wherein the synthetic polynucleotide is SEQ ID NO: 341.

Embodiment 32

The composition of any one of embodiments 1-6, wherein the synthetic polynucleotide is SEQ ID NO: 343.

Embodiment 33

The composition of any one of embodiments 1-6, wherein the synthetic polynucleotide is SEQ ID NO: 345.

Embodiment 34

The composition of any one of embodiments 1-6, wherein the synthetic polynucleotide is SEQ ID NO: 362.

Embodiment 35

The composition of any one of embodiments 1-6, wherein the synthetic polynucleotide is SEQ ID NO: 563.

Embodiment 36

The composition of any one of embodiments 1-6, wherein the synthetic polynucleotide is SEQ ID NO: 568.

Embodiment 37

The composition of any one of embodiments 1-6, wherein the synthetic polynucleotide is SEQ ID NO: 569.

Embodiment 38

The composition of any one of embodiments 1-6, wherein the synthetic polynucleotide is SEQ ID NO: 570.

Embodiment 39

The composition of any one of embodiments 1-6, wherein the synthetic polynucleotide is SEQ ID NO: 571.

Embodiment 40

The composition of any one of embodiments 1-6, wherein the synthetic polynucleotide is SEQ ID NO: 572.

Embodiment 41

The composition of any one of embodiments 1-6, wherein the synthetic polynucleotide is SEQ ID NO: 573.

Embodiment 42

The composition of any one of embodiments 1-6, wherein the synthetic polynucleotide is SEQ ID NO: 596.

Embodiment 43

The composition of any one of embodiments 1-6, wherein the synthetic polynucleotide is SEQ ID NO: 597.

Embodiment 44

The composition of any one of embodiments 1-6, wherein the synthetic polynucleotide is SEQ ID NO: 599.

Embodiment 45

The composition of any one of embodiments 1-6, wherein the synthetic polynucleotide is SEQ ID NO: 601.

Embodiment 46

The composition of any one of embodiments 1-6, wherein the synthetic polynucleotide is SEQ ID NO: 604.

Embodiment 47

The composition of any one of embodiments 1-6, wherein the region of the pre-mRNA molecule comprises exon 46 of the centrosomal protein 290.

Embodiment 48

The composition of any one of embodiments 1-6, wherein the synthetic polynucleotide is any one of SEQ ID NO: 20-SEQ ID NO: 69, SEQ ID NO: 395-SEQ ID NO: 460, or SEQ ID NO: 685-SEQ ID NO: 702.

Embodiment 49

The composition of any one of embodiments 1-6, wherein the synthetic polynucleotide comprises a modified internucleoside linkage.

Embodiment 50

The composition of embodiment 49, wherein the modified internucleoside linkage is selected from the group consisting of a phosphorothioate internucleoside linkage, a phosphoroamidate internuceloside linkage, and a phosphorodiamidate internucleoside linkage.

Embodiment 51

The composition of embodiment 49, wherein the modified internucleoside linkage is a phosphorodiamidate Morpholino oligomer.

Embodiment 52

The composition of embodiment 49, wherein 100% of the synthetic polynucleotide comprises a modified internucleoside linkage.

Embodiment 53

The composition of embodiment 49, wherein at least the three terminal residues in either the 3' end, the 5' end, or both ends of the synthetic polynucleotide comprises the modified internucleoside linkage.

Embodiment 54

The composition of any one of embodiments 1-53, wherein the synthetic polynucleotide comprises a modified sugar moiety.

Embodiment 55

The composition of embodiment 54, wherein the modified sugar moiety is selected from the group consisting of a 2' O-methyl modification, a locked nucleic acid (LNA), and a peptide nucleic acid (PNA).

Embodiment 56

The composition of embodiment 54, wherein 100% of the synthetic polynucleotide comprises the modified sugar moiety.

Embodiment 57

The composition of embodiment 54, wherein the modified sugar moiety is 2'-O-methoxyethyl (MOE).

Embodiment 58

The composition of embodiment 54, wherein at least the three terminal residues in either the 3' end, the 5' end, or both ends of the synthetic polynucleotide comprise the modified sugar moiety.

Embodiment 59

The composition of any one of embodiments 1-58, wherein the composition is formulated for administration to a subject.

Embodiment 60

The composition of embodiment 59, wherein the composition is formulated for intravitreal administration to the subject.

Embodiment 61

The composition of embodiment 59, wherein the composition is formulated for systemic administration to the subject.

Embodiment 62

The composition of any one of embodiments 1-61, wherein the subject is afflicted with any one of Leber Congenital Amaurosis, Senior-Locken Syndrome, Joubert syndrome, or Meckel Syndrome.

Embodiment 63

The composition of any one of embodiments 1-62, wherein the subject is a human.

Embodiment 64

The composition of any one of embodiments 1-63, wherein the composition is used for the treatment of a retinal condition.

Embodiment 65

The composition of embodiment 64, wherein the composition is used for the retinal condition is retinal degeneration, retinal dystrophy, or retinitis pigmentosa.

Embodiment 66

The composition of any one of embodiments 1-65, wherein the composition is used for the treatment of renal disease, retinal dystrophy, coloboma, kidney nephronophthisis, ataxia, mental retardation.

Embodiment 67

The composition of embodiment 1, wherein the therapeutically effective amount is from 50 µg to 950 µg.

Embodiment 68

A method of treating a subject afflicted with a condition comprising administering to the subject a therapeutically effective amount of a composition comprising a synthetic polynucleotide between 15 nucleotides to 200 nucleotides in length that is at least 60% complementary to a region of a pre-mRNA molecule, which pre-mRNA molecule encodes a centrosomal protein 290.

Embodiment 69

The method of embodiment 68, wherein the synthetic polynucleotide induces exon-skipping of one or more exons in the pre-mRNA molecule when the synthetic polynucleotide is administered to the subject.

Embodiment 70

The method of any one of embodiments 68 and 69, wherein the condition is an ocular condition.

Embodiment 71

The method of any one of embodiments 68-70, wherein the ocular condition is any one of retinal dystrophy, retinitis pigmentosa, or coloboma.

Embodiment 72

The method of any one of embodiments 68-70, wherein the condition is a renal condition.

Embodiment 73

The method of embodiment 72, wherein the renal condition is a kidney nephronophthisis.

Embodiment 74

The method of any one of embodiments 68-71, wherein the condition is a neurological condition.

Embodiment 75

The method of embodiment 74, wherein the neurological condition is a ataxia or mental retardation.

Embodiment 76

The method of any one of embodiments 68-75, wherein the region of the pre-mRNA molecule corresponds to an intron of the pre-mRNA molecule.

Embodiment 77

The method of any one of embodiments 68-76, wherein at least 90% of the region of the pre-mRNA molecule comprises an intron of the pre-mRNA molecule.

Embodiment 78

The method of any one of embodiments 68-76, wherein at least 90% of the region of the pre-mRNA molecule corresponds to an exon of the pre-mRNA molecule.

Embodiment 79

The method of any one of embodiments 68-78, wherein the region of the pre-mRNA molecule comprises a junction between an intron and an exon of the pre-mRNA molecule.

Embodiment 80

The method of any one of embodiments 68-79, wherein the region of the pre-mRNA molecule is within 500 bases from an exon of the pre-mRNA molecule.

Embodiment 81

The method of any one of embodiments 68-80, wherein the region of the pre-mRNA molecule comprises exon 7 of the centrosomal protein 290.

Embodiment 82

The method of any one of embodiments 68-80, wherein the synthetic polynucleotide is any one of SEQ ID NO: 270-SEQ ID NO: 309.

Embodiment 83

The method of any one of embodiments 68-80, wherein the region of the pre-mRNA molecule comprises exon 31 of the centrosomal protein 290.

Embodiment 84

The method of any one of embodiments 68-80, wherein the synthetic polynucleotide is any one of SEQ ID NO: 110-SEQ ID NO: 269.

Embodiment 85

The method of any one of embodiments 68-80, wherein the region of the pre-mRNA molecule comprises exon 34 of the centrosomal protein 290.

Embodiment 86

The method of any one of embodiments 68-80, wherein the synthetic polynucleotide is any one of SEQ ID NO: 70-SEQ ID NO: 109.

Embodiment 86

The method of any one of embodiments 68-80, wherein the region of the pre-mRNA molecule comprises exon 36 of the centrosomal protein 290.

Embodiment 87

The method of any one of embodiments 68-80, wherein the synthetic polynucleotide is any one of SEQ ID NO: 461-SEQ ID NO: 540, or SEQ ID NO: 703-SEQ ID NO: 824.

Embodiment 88

The method of any one of embodiments 68-80, wherein the synthetic polynucleotide is SEQ ID NO: 486.

Embodiment 89

The method of any one of embodiments 68-80, wherein the synthetic polynucleotide is SEQ ID NO: 487.

Embodiment 90

The method of any one of embodiments 68-80, wherein the synthetic polynucleotide is SEQ ID NO: 492.

Embodiment 91

The method of any one of embodiments 68-80, wherein the synthetic polynucleotide is SEQ ID NO: 503.

Embodiment 92

The method of any one of embodiments 68-80, wherein the synthetic polynucleotide is SEQ ID NO: 531.

Embodiment 93

The method of any one of embodiments 68-80, wherein the synthetic polynucleotide is SEQ ID NO: 535.

Embodiment 94

The method of any one of embodiments 68-80, wherein the region of the pre-mRNA molecule comprises exon 41 of the centrosomal protein 290.

Embodiment 95

The method of any one of embodiments 68-80, wherein the synthetic polynucleotide is any one of SEQ ID NO: 1-SEQ ID NO: 19 or SEQ ID NO: 310-SEQ ID NO: 394, or SEQ ID NO: 541-SEQ ID NO: 684.

Embodiment 96

The method of any one of embodiments 68-80, wherein the synthetic polynucleotide is SEQ ID NO: 19.

Embodiment 97

The method of any one of embodiments 68-80, wherein the synthetic polynucleotide is SEQ ID NO: 316.

Embodiment 98

The method of any one of embodiments 68-80, wherein the synthetic polynucleotide is SEQ ID NO: 331.

Embodiment 99

The method of any one of embodiments 68-80, wherein the synthetic polynucleotide is SEQ ID NO: 333.

Embodiment 100

The method of any one of embodiments 68-80, wherein the synthetic polynucleotide is SEQ ID NO: 335.

Embodiment 101

The method of any one of embodiments 68-80, wherein the synthetic polynucleotide is SEQ ID NO: 336.

Embodiment 102

The method of any one of embodiments 68-80, wherein the synthetic polynucleotide is SEQ ID NO: 337.

Embodiment 103

The method of any one of embodiments 68-80, wherein the synthetic polynucleotide is SEQ ID NO: 340.

Embodiment 104

The method of any one of embodiments 68-80, wherein the synthetic polynucleotide is SEQ ID NO: 341.

Embodiment 105

The method of any one of embodiments 68-80, wherein the synthetic polynucleotide is SEQ ID NO: 343.

Embodiment 106

The method of any one of embodiments 68-80, wherein the synthetic polynucleotide is SEQ ID NO: 345.

Embodiment 107

The method of any one of embodiments 68-80, wherein the synthetic polynucleotide is SEQ ID NO: 362.

Embodiment 108

The method of any one of embodiments 68-80, wherein the synthetic polynucleotide is SEQ ID NO: 563.

Embodiment 109

The method of any one of embodiments 68-80, wherein the synthetic polynucleotide is SEQ ID NO: 568.

Embodiment 110

The method of any one of embodiments 68-80, wherein the synthetic polynucleotide is SEQ ID NO: 569.

Embodiment 111

The method of any one of embodiments 68-80, wherein the synthetic polynucleotide is SEQ ID NO: 570.

Embodiment 112

The method of any one of embodiments 68-80, wherein the synthetic polynucleotide is SEQ ID NO: 571.

Embodiment 113

The method of any one of embodiments 68-80, wherein the synthetic polynucleotide is SEQ ID NO: 572.

Embodiment 114

The method of any one of embodiments 68-80, wherein the synthetic polynucleotide is SEQ ID NO: 573.

Embodiment 115

The method of any one of embodiments 68-80, wherein the synthetic polynucleotide is SEQ ID NO: 596.

Embodiment 116

The method of any one of embodiments 68-80, wherein the synthetic polynucleotide is SEQ ID NO: 597.

Embodiment 117

The method of any one of embodiments 68-80, wherein the synthetic polynucleotide is SEQ ID NO: 599.

Embodiment 118

The method of any one of embodiments 68-80, wherein the synthetic polynucleotide is SEQ ID NO: 601.

Embodiment 119

The method of any one of embodiments 68-80, wherein the synthetic polynucleotide is SEQ ID NO: 604.

Embodiment 120

The method of any one of embodiments 68-80, wherein the region of the pre-mRNA molecule comprises exon 46 of the centrosomal protein 290.

Embodiment 121

The method of any one of embodiments 68-80, wherein the synthetic polynucleotide is any one of SEQ ID NO: 20-SEQ ID NO: 69, SEQ ID NO: 395-SEQ ID NO: 460, or SEQ ID NO: 685-SEQ ID NO: 702.

Embodiment 122

The method of any one of embodiments 68-121, wherein the synthetic polynucleotide comprises a modified internucleoside linkage.

Embodiment 123

The method of embodiment 122, wherein the modified internucleoside linkage is selected from the group consisting of a phosphorothioate internucleoside linkage, a phosphoroamidate internuceloside linkage, and a phosphorodiamidate internucleoside linkage.

Embodiment 124

The method of embodiment 122, wherein the modified internucleoside linkage is a phosphorodiamidate Morpholino oligomer.

Embodiment 125

The method of embodiment 122, wherein 100% of the synthetic polynucleotide comprises a modified internucleoside linkage.

Embodiment 126

The method of embodiment 122, wherein at least the three terminal residues in either the 3' end, the 5' end, or both ends of the synthetic polynucleotide comprises the modified internucleoside linkage.

Embodiment 127

The method of any one of embodiments 68-126, wherein the synthetic polynucleotide comprises a modified sugar moiety.

Embodiment 128

The method of embodiment 68, wherein the modified sugar moiety is selected from the group consisting of a 2' O-methyl modification, a locked nucleic acid (LNA), a peptide nucleic acid (PNA), and a morpholino.

Embodiment 129

The method of embodiment 68, herein the modified sugar moiety is 2'-O-methoxyethyl (MOE).

Embodiment 130

The method of embodiment 68, wherein 100% of the synthetic polynucleotide comprises the modified sugar moiety.

Embodiment 131

The method of embodiment 68, wherein at least the three terminal residues in either the 3' end, the 5' end, or both ends of the synthetic polynucleotide comprises the modified sugar moiety.

Embodiment 132

The method of any one of embodiments 68-131, wherein the composition is formulated for intravitreal administration to the subject.

Embodiment 133

The method of any one of embodiments 68-131, wherein the composition is formulated for systemic administration to the subject.

Embodiment 134

The method of any one of embodiments 68-133, wherein the subject is afflicted with any one of Leber Congenital Amaurosis, Senior-Locken Syndrome, Joubert syndrome, or Meckel Syndrome.

Embodiment 135

The method of embodiment 134, wherein the subject is afflicted with Leber Congenital Amaurosis.

Embodiment 136

The method of embodiment 134, wherein the subject is afflicted with Senior-Locken Syndrome.

Embodiment 137

The method of embodiment 134, wherein the subject is afflicted with Joubert syndrome.

Embodiment 138

The method of embodiment 134, wherein the subject is afflicted with Meckel Syndrome.

Embodiment 139

The method of any one of embodiments 68-138, wherein the subject is a human.

Embodiment 140

The method of any one of embodiments 68-139, wherein the therapeutically effective amount is from 50 µg to 950 µg.

Embodiment 141

The method of any one of embodiments 68-140, further comprising monitoring the subject for a progression or regression of the condition.

Embodiment 142

A synthetic polynucleotide between 15 nucleotides to 200 nucleotides in length that is at least 60% complementary to a region of a pre-mRNA molecule, which pre-mRNA molecule encodes a centrosomal protein 290 for use in treating an ocular condition.

Embodiment 143

A synthetic polynucleotide between 15 nucleotides to 200 nucleotides in length that is at least 60% complementary to a region of a pre-mRNA molecule, which pre-mRNA molecule encodes a centrosomal protein 290 for use in treating a renal disease.

Embodiment 144

The synthetic polynucleotide of embodiment 142, wherein the ocular disorder is a retinal condition.

Embodiment 145

The synthetic polynucleotide of embodiment 142, wherein the retinal condition is retinal degeneration, retinal dystrophy, or retinitis pigmentosa.

Embodiment 146

The synthetic polynucleotide of embodiment 142, wherein the ocular disorder is associated with Leber Congenital Amaurosis.

Embodiment 147

The synthetic polynucleotide of embodiment 142, wherein the ocular disorder is associated with Senior-Locken Syndrome.

Embodiment 148

The synthetic polynucleotide of embodiment 142, wherein the ocular disorder is associated with Joubert syndrome.

Embodiment 149

The synthetic polynucleotide of embodiment 142, wherein the ocular disorder is associated with Meckel Syndrome.

Embodiment 150

The synthetic polynucleotide of any one of embodiments 142 and 143, wherein the synthetic polynucleotide induces exon-skipping of one or more exons in the pre-mRNA molecule when used for the treatment of the ocular condition.

Embodiment 151

The synthetic polynucleotide of any one of embodiments 142, 143, and 150, wherein the region of the pre-mRNA molecule corresponds to an intron of the pre-mRNA molecule.

Embodiment 152

The synthetic polynucleotide of any one of embodiments 142, 143, 150, and 151, wherein at least 90% of the region of the pre-mRNA molecule comprises an intron of the pre-mRNA molecule.

Embodiment 153

The synthetic polynucleotide of any one of embodiments 142, 143, and 150-152, wherein at least 90% of the region of the pre-mRNA molecule corresponds to an exon of the pre-mRNA molecule.

Embodiment 154

The synthetic polynucleotide of any one of embodiments 142, 143, and 150-153, wherein the region of the pre-mRNA molecule comprises a junction between an intron and an exon of the pre-mRNA molecule.

Embodiment 155

The synthetic polynucleotide of any one of embodiments 142, 143, and 150-154, wherein the region of the pre-mRNA molecule is within 500 bases from an exon of the pre-mRNA molecule.

Embodiment 156

The synthetic polynucleotide of any one of embodiments 142-155, wherein the region of the pre-mRNA molecule comprises exon 7 of the centrosomal protein 290.

Embodiment 157

The synthetic polynucleotide of any one of embodiments 142-155, wherein the synthetic polynucleotide is any one of SEQ ID NO: 270-SEQ ID NO: 309.

Embodiment 158

The synthetic polynucleotide of any one of embodiments 142-155, wherein the region of the pre-mRNA molecule comprises exon 31 of the centrosomal protein 290.

Embodiment 159

The synthetic polynucleotide of any one of embodiments 142-155, wherein the synthetic polynucleotide is any one of SEQ ID NO: 110-SEQ ID NO: 269.

Embodiment 160

The synthetic polynucleotide of any one of embodiments 142-155, wherein the region of the pre-mRNA molecule comprises exon 34 of the centrosomal protein 290.

Embodiment 161

The synthetic polynucleotide of any one of embodiments 142-155, wherein the synthetic polynucleotide is any one of SEQ ID NO: 70-SEQ ID NO: 109.

Embodiment 162

The synthetic polynucleotide of any one of embodiments 142-155, wherein the region of the pre-mRNA molecule comprises exon 36 of the centrosomal protein 290.

Embodiment 163

The synthetic polynucleotide of any one of embodiments 142-155, wherein the synthetic polynucleotide is any one of SEQ ID NO: 461-SEQ ID NO: 540, or SEQ ID NO: 703-SEQ ID NO: 824.

Embodiment 164

The synthetic polynucleotide of any one of embodiments 142-155, wherein the synthetic polynucleotide is SEQ ID NO: 486.

Embodiment 165

The synthetic polynucleotide of any one of embodiments 142-155, wherein the synthetic polynucleotide is SEQ ID NO: 487.

Embodiment 166

The synthetic polynucleotide of any one of embodiments 142-155, wherein the synthetic polynucleotide is SEQ ID NO: 492.

Embodiment 167

The synthetic polynucleotide of any one of embodiments 142-155, wherein the synthetic polynucleotide is SEQ ID NO: 503.

Embodiment 168

The synthetic polynucleotide of any one of embodiments 142-155, wherein the synthetic polynucleotide is SEQ ID NO: 531.

Embodiment 169

The synthetic polynucleotide of any one of embodiments 142-155, wherein the synthetic polynucleotide is SEQ ID NO: 535.

Embodiment 170

The synthetic polynucleotide of any one of claims 142 and 155, wherein the region of the pre-mRNA molecule comprises exon 41 of the centrosomal protein 290.

Embodiment 171

The synthetic polynucleotide of any one of embodiments 142-155, wherein the synthetic polynucleotide is any one of SEQ ID NO: 1-SEQ ID NO: 19 or SEQ ID NO: 310-SEQ ID NO: 394, or SEQ ID NO: 541-SEQ ID NO: 684.

Embodiment 172

The synthetic polynucleotide of any one of embodiments 142-155, wherein the synthetic polynucleotide is SEQ ID NO: 19.

Embodiment 173

The synthetic polynucleotide of any one of embodiments 142-155, wherein the synthetic polynucleotide is SEQ ID NO: 316.

Embodiment 174

The synthetic polynucleotide of any one of embodiments 142-155, wherein the synthetic polynucleotide is SEQ ID NO: 331.

Embodiment 175

The synthetic polynucleotide of any one of embodiments 142-155, wherein the synthetic polynucleotide is SEQ ID NO: 333.

Embodiment 176

The synthetic polynucleotide of any one of embodiments 142-155, wherein the synthetic polynucleotide is SEQ ID NO: 335.

Embodiment 177

The synthetic polynucleotide of any one of embodiments 142-155, wherein the synthetic polynucleotide is SEQ ID NO: 336.

Embodiment 178

The synthetic polynucleotide of any one of embodiments 142-155, wherein the synthetic polynucleotide is SEQ ID NO: 337.

Embodiment 179

The synthetic polynucleotide of any one of embodiments 142-155, wherein the synthetic polynucleotide is SEQ ID NO: 340.

Embodiment 180

The synthetic polynucleotide of any one of embodiments 142-155, wherein the synthetic polynucleotide is SEQ ID NO: 341.

Embodiment 181

The synthetic polynucleotide of any one of embodiments 142-155, wherein the synthetic polynucleotide is SEQ ID NO: 343.

Embodiment 182

The synthetic polynucleotide of any one of embodiments 142-155, wherein the synthetic polynucleotide is SEQ ID NO: 345.

Embodiment 183

The synthetic polynucleotide of any one of embodiments 142-155, wherein the synthetic polynucleotide is SEQ ID NO: 362.

Embodiment 184

The synthetic polynucleotide of any one of embodiments 142-155, wherein the synthetic polynucleotide is SEQ ID NO: 563.

Embodiment 185

The synthetic polynucleotide of any one of embodiments 142-155, wherein the synthetic polynucleotide is SEQ ID NO: 568.

Embodiment 186

The synthetic polynucleotide of any one of embodiments 142-155, wherein the synthetic polynucleotide is SEQ ID NO: 569.

Embodiment 187

The synthetic polynucleotide of any one of embodiments 142-155, wherein the synthetic polynucleotide is SEQ ID NO: 570.

Embodiment 188

The synthetic polynucleotide of any one of embodiments 142-155, wherein the synthetic polynucleotide is SEQ ID NO: 571.

Embodiment 189

The synthetic polynucleotide of any one of embodiments 142-155, wherein the synthetic polynucleotide is SEQ ID NO: 572.

Embodiment 190

The synthetic polynucleotide of any one of embodiments 142-155, wherein the synthetic polynucleotide is SEQ ID NO: 573.

Embodiment 191

The synthetic polynucleotide of any one of embodiments 142-155, wherein the synthetic polynucleotide is SEQ ID NO: 596.

Embodiment 192

The synthetic polynucleotide of any one of embodiments 142-155, wherein the synthetic polynucleotide is SEQ ID NO: 597.

Embodiment 193

The synthetic polynucleotide of any one of embodiments 142-155, wherein the synthetic polynucleotide is SEQ ID NO: 599.

Embodiment 194

The synthetic polynucleotide of any one of embodiments 142-155, wherein the synthetic polynucleotide is SEQ ID NO: 601.

Embodiment 195

The synthetic polynucleotide of any one of embodiments 142-155, wherein the synthetic polynucleotide is SEQ ID NO: 604

Embodiment 196

The synthetic polynucleotide of any one of embodiments 142-155, wherein the region of the pre-mRNA molecule comprises exon 46 of the centrosomal protein 290.

Embodiment 197

The synthetic polynucleotide of any one of embodiments 142-155, wherein the synthetic polynucleotide is any one of SEQ ID NO: 20-SEQ ID NO: 69, SEQ ID NO: 395-SEQ ID NO: 460, or SEQ ID NO: 685-SEQ ID NO: 702.

Embodiment 198

The synthetic polynucleotide of any one of embodiments 142-197, wherein the synthetic polynucleotide comprises a modified internucleoside linkage.

Embodiment 199

The synthetic polynucleotide of any one of embodiments 142-197, wherein the modified internucleoside linkage is selected from the group consisting of a phosphorothioate internucleoside linkage, a phosphoroamidate internucleoside linkage, and a phosphorodiamidate internucleoside linkage.

Embodiment 200

The synthetic polynucleotide of any one of embodiments 142-197, wherein the modified internucleoside linkage is a phosphorodiamidate Morpholino oligomer.

Embodiment 201

The synthetic polynucleotide of any one of embodiments 142-197, wherein 100% of the synthetic polynucleotide comprises a modified internucleoside linkage.

Embodiment 202

The synthetic polynucleotide of any one of embodiments 142-197, wherein at least the three terminal residues in either the 3' end, the 5' end, or both ends of the synthetic polynucleotide comprises the modified internucleoside linkage.

Embodiment 203

The synthetic polynucleotide of any one of embodiments 142-197, wherein the synthetic polynucleotide comprises a modified sugar moiety.

Embodiment 204

The synthetic polynucleotide of any one of embodiments 142-197, wherein the modified sugar moiety is selected from the group consisting of a 2' O-methyl modification, a locked nucleic acid (LNA), a peptide nucleic acid (PNA), and a morpholino.

Embodiment 205

The synthetic polynucleotide of any one of embodiments 142-197, wherein the modified sugar moiety is 2'-O-methoxyethyl (MOE).

Embodiment 206

The synthetic polynucleotide of any one of embodiments 142-197, wherein 100% of the synthetic polynucleotide comprises the modified sugar moiety.

Embodiment 207

The synthetic polynucleotide of any one of embodiments 142-197, wherein at least the three terminal residues in either the 3' end, the 5' end, or both ends of the synthetic polynucleotide comprises the modified sugar moiety.

Embodiment 208

The use of a synthetic polynucleotide between 15 nucleotides to 200 nucleotides in length that is at least 60% complementary to a region of a pre-mRNA molecule encoding a centrosomal protein 290 for use in a method of treating or diagnosing an ocular condition.

Embodiment 209

The use of a synthetic polynucleotide between 15 nucleotides to 200 nucleotides in length that is at least 60% complementary to a region of a pre-mRNA molecule encoding a centrosomal protein 290 for use in a method of treating or diagnosing a renal condition.

EXAMPLES

The following examples are included to further describe certain aspects of the present disclosure, and do not be used to limit the scope of the disclosure.

Example 1

Synthetic Polynucleotides

The synthetic polynucleotides (SPs) as disclosed herein (see e.g., TABLE 1) were designed to be complementary to exon 7, 31, 34, 36, 41 or 46 of the CEP290 mRNA sequence, as well as neighboring intronic sequence (reference sequence: NM_025114). Lyophilized SPs were obtained from both Microsynth AG (Switzerland) and Integrated DNA Technologies Inc. (USA). All bases in the SPs were 2'-O-methoxyethyl-modified (MOE) and had a full phosphorothioate backbone. SP stock solutions were made by resuspension of the oligonucleotides in Tris-EDTA buffer, pH 8.0, at a concentration of 100 µM.

Example 2

Testing of Synthetic Polynucleotides in Cell Cultures

HEK293T cells were grown in Iscove's Modified Dulbecco's Medium (Gibco) supplemented with 10% (v/v) Cosmic Calf Serum (HyClone), 2 mM L-Glutamine (Gibco) and 1% antibiotics (100-U/ml penicillin G and 100-ug/ml streptomycin, Gibco) in a humidified incubator at 37° C. with 5% $CO_2$. Upon reaching confluency, typically after 3-4 days, the cells were passaged by washing with Phosphate-Buffered Saline followed by Trypsin (Gibco) dissociation and plated in 10 to 20-fold dilution.

Transfection of Oligonucleotides in 12-Well Format.

Cells grown in 12-well format were transfected with SPs using polyethylenimine (PEI) MAX 40K (Polysciences Inc.). Briefly, one day before transfection 300,000 HEK293T cells were seeded in 12-well tissue culture plates. On the day of transfection, growth media was replaced with transfection medium (Iscove's Modified Dulbecco's Medium, 5% (v/v) Cosmic Calf Serum, 1 mM L-Glutamine and 0.5% antibiotics) and cells were incubated for an additional two hours in a humidified incubator at 37° C. with 5% CO2. PEI MAX transfection reagent (1 mg/ml, pH 7.0) was prepared according to manufacturer's recommendation. SP-PEI Transfection mixes were prepared as following. First, 3 µl (300 pmol) aliquotes of the SP stock solutions were diluted with 47 µl 150 mM NaCl to total volume of 50 µl. In separate tubes, PEI was diluted in 150 mM NaCl to an amount of 4 µg PEI per µg SP in a volume of 50 µl. Next, the SP and PEI solutions were combined, mixed by vortexing for 5 seconds and incubated at room temperature for 15 to 20 minutes. Finally, the 100 ul SP-PEI mixes were added to the cells in a dropwise fashion, followed by brief swirling of the tissue culture plates. After 24 hours, the transfection media was removed by aspiration and replaced with 2,000 µl complete media. For analysis, 48 hours after transfection RNA was extracted from the cells.

Reverse Transfections of SPs in 96-Well Format.

SP stock solutions were diluted to 10 µM working solutions in Opti-MEM reduced serum medium (Gibco) and subsequently further diluted in Opti-MEM to 1.25 and 5 µM for transfections of absolute amounts of 12.5 and 50 pmol of SP respectively. SPs were reverse transfected into HEK293T cells using Lipofectamine RNAiMAX (Invitrogen) according to manufacturer's instructions with minor modifications. Briefly, 10-µl aliquots of finally diluted SPs were transferred into the wells of a 96-well tissue culture plate and 10 µl diluted transfection reagent containing 9.7 µl Opti-MEM and 0.3 µl Lipofectamine RNAiMAX was added to the wells. SP-lipid complexes in the mixture were formed by gentle mixing by tapping the plate and incubation for 20 minutes at room temperature. Finally, for reverse transfection, a solution with 50,000 HEK293T cells in complete media without antibiotics was added to the SP-lipid complexes and incubated for 24 hours at 37° C. and 5% CO2. After 24 hours, the media was removed by aspiration and replaced with 200 µl complete media. After a total of 48 hours after transfection cells were lysed.

RNA Preparation from 12-Well Plates.

For cells grown in 12-well plates, total RNA was isolated using the GENEzol TriRNA Pure Kit (Geneaid) according to manufacturer's instructions. During the isolation, 350 µl GENEzol reagent was used and in the next step RNA was eluted in 40 µl water. RNA was stored at −80° C. until subsequent experiments.

RNA Preparation from 96-Well Plates.

For cells grown and transfected in 96-well plates, RNA was prepared by lysis using a SingleShot Cell Lysis kit (Bio-Rad) according to manufacturer's recommendations. Briefly, cells were washed with Phosphate-Buffered Saline and lysed by incubation with 50 µl SingleShot Cell Lysis buffer containing Proteinase K and DNase I for 10 min at room temperature. Next, lysates were transferred to a 96-well PCR plate and incubated in a PCR machine for 5 min at 37° C., followed by 5 min at 75° C. RNA lysates were stored at −80° C. until subsequent experiments.

RT-PCR Analysis.

Synthesis of first-strand cDNA was performed with the ImProm-II Reverse Transcription System (Promega) according to manufacturer's recommendations with minor modifications. Briefly, 5 µl aliquots of the RNA samples or the RNA lysates were incubated in a 96-well PCR plate with 1 µl Oligo-dT-VN primer (100 µM, 5'-TTTTTTTTTTTTTTTTTT VN-3' (SEQ ID NO: 839)) for 5 min at 70° C., followed by rapid cooling for 5 min at 4° C. Next, a 14.5-µl Reverse Transcriptase mixture, containing 20 Units ImProm-II Reverse Transcriptase, reaction buffer, 4 mM MgCl2, 0.5 mM dNTPs (FroggaBio) and 40 Units RNAse Inhibitor (Bioshop) was added to the RNA-Oligo-dT-VN samples and incubated for 5 min at 25° C., 60 min at 42° C. and finally cooled to 0° C.

Target-specific splicing fragments were amplified by PCR. PCR primers and PCR fragment lengths for each target exon are listed in TABLE 2. PCR samples contained 5 µl first-strand cDNA product, 0.4 µM forward primer, 0.4 µM reverse primer, 300 µM of each dNTP, 25 mM Tricine, 7.0% Glycerol (m/v), 1.6% DMSO (m/v), 2 mM MgCl2, 85 mM NH4-acetate (pH 8.7), and 1 unit Taq DNA polymerase (FroggaBio) in a total volume of 25 µl. Fragments were amplified by a touchdown PCR program (95° C. for 120 sec; 10 cycles of 95° C. for 20 sec, 68° C. for 30 sec with a decrement of 1° C. per cycle, and 72° C. for 60 sec; followed by 20 cycles of 95° C. for 20 sec, 58° C. for 30 sec, and 72° C. for 60 sec; 72° C. for 180 sec. PCR samples were analyzed by both standard 2% agarose gel electrophoresis followed by image analysis using an Amersham Imager 600 and analysis on LabChip GX II Touch HT using the HT DNA 1K reagent Kit on a HT DNA Extended Range LabChip.

Example 3

Functional Rescue of CEP290 by Synthetic Polynucleotides in Cell Cultures

Cell Culture

HEK293T cells were grown in Iscove's Modified Dulbecco's Medium (Gibco) supplemented with 10% (v/v) Cosmic Calf Serum (HyClone), 2 mM L-Glutamine (Gibco) and 1% antibiotics (100-U/ml penicillin G and 100-µg/ml streptomycin, Gibco). HepG2 cells were grown in Dulbecco's Modified Eagle's Medium (Gibco) supplemented with 10% heat inactivated fetal bovine serum (Gibco). The cells were cultured in a 5% CO2 humidified atmosphere at 37° C.

Molecular Cloning and CRISPR Editing

CRISPR guide sequences were cloned as DNA oligonucleotides carrying appropriate overhangs downstream of the U6 promoter in a CRISPR plasmid containing the Cas9 gene.

To generate HEK293T CEP290 CRISPR mutants, wild-type HEK293T cells were transiently transfected with CRISPR plasmids to co-express CRISPR guide RNAs and Cas9 protein. The CEP290 exon 36 CRISPR mutant clone was generated with the guide RNA: ATCTGTGAT-GAAGAATATGA (SEQ ID NO: 840). The CEP290 exon 41 CRISPR mutant clone was generated with the guide RNA: CTAGTTTTTTAACTTTCCTT (SEQ ID NO: 841). Individual clones were obtained from single cells and were characterized by PCR of the genomic CRISPR target region followed by Sanger sequencing. Primers to amplify the exon 36 genomic CRISPR target regions: forward—5' GCTTGT-CAACTTGAACATTGTCTGAG 3' (SEQ ID NO: 842); reverse—5' CAACAAAAAGGGTAACTTCCATTCC 3' (SEQ ID NO: 843). Primers to amplify the exon 41 genomic CRISPR target regions: forward—5' TGCAGAAGCAGC-TACCAGAT 3' (SEQ ID NO: 844); reverse—5' TCCTA-CAGAACAGAAACTTAGACTT 3' (SEQ ID NO: 845). The CRISPR clones were also analyzed by western blotting.

Ciliation Assay

Wild-type and CEP290 CRISPR HEK293T mutant cells were seeded in 12-well plates on poly-L-lysine-coated coverslips (400 k cells/well) and transfected with a non-targeting ASO or exon 36 or 41 skipping ASOs (300 pmol) using Lipofectamine RNAiMAX transfection reagent. 48 h post transfection the cells were serum-starved (IMDM media without FBS) to induce the formation of primary cilia. 72 h post-serum starvation the cells were fixed and processed for immunofluorescence microscopy.

Immunofluorescence Microscopy

For immunofluorescence, the cells were fixed with cold methanol (10 min at −20° C.), blocked with 0.2% Fish Skin Gelatin (Sigma-Aldrich) in 1×PBS (20 min), incubated with the primary antibodies in blocking solution (1 h), washed with blocking solution and incubated with fluorophore-conjugated secondary antibodies (Molecular Probes) and Hoechst dye in blocking solution (1 h). After a final wash in blocking solution the coverslips were mounted on glass slides by inverting them onto mounting solution (ProLong Gold antifade, Molecular Probes). The cells were imaged on a DeltaVision (Applied Precision) imaging system equipped with an IX71 microscope (Olympus), CCD camera (Cool-SNAP HQ2 1024×1024, Roper Scientific) and a ×40 or ×60 objective (Olympus). Z stacks were collected, deconvolved using softWoRx (v5.0, Applied Precision) and are shown as maximum intensity projections.

Primary antibodies: anti-ARL13B (rabbit: Proteintech 17711-1; mouse: Santa Cruz sc-515784); anti-gamma tubulin (Sigma-Aldrich T6557); anti-PCNT (Abcam ab28144); anti-CEP290 (Abcam ab84870).

Western Blotting

For western blotting, the cells were harvested, washed with 1×PBS and lysed in an appropriate volume of ice cold RIPA buffer (SIGMA) with 1×HALT protease inhibitor (Pierce Biotechnology). The lysate was placed on ice for 10 minutes and then centrifuged at 15000 rcf at 4° C. The supernatant was collected into a fresh tube and the pellet was discarded. Using a protein quantification kit (Pierce) the protein concentrations were determined. Twenty to thirty µg of lysate protein was heated at 95° C. with Nupage buffer (Novex) and loaded onto a 10% Bis-Tris gel (Invitrogen). The gel was run for ~40 minutes at 200V in 1×MOPS buffer (Novex). The gel was removed and transferred to a PVDF membrane (GE) on ice for 90 minutes at 350 mA constant current. After transfer, the membrane was blocked in TBST-5% milk for 90 minutes at room temperature. After blocking, primary antibodies for CEP290 (Abcam ab84870) and γ-tubulin (Sigma T6557) were added in TBSB-1% milk and refrigerated at 4° C. overnight. The membrane was then rinsed with TBST for 5 minutes 5 times. Secondary antibodies conjugated with horseradish peroxidase (Cell Signalling technology) were added to the solution for 60 minutes at room temperature. The membrane was then rinsed with TBST for 5 minutes 5 times. The images were recorded with a GE AI600RGB device.

Example 4

Identification and Optimization of SPs Inducing Skipping of CEP290 Exon 7

This example demonstrates the identification and optimization of SPs to induce skipping of CEP290 exon 7.

Figure 4A:
FIG. 4A shows the schematic representation of the synthetic polynucleotides that were designed to modulate splicing of CEP290 exon 7 mRNA (SEQ ID NO: 270-SEQ ID NO: 309).
Figure 4B:
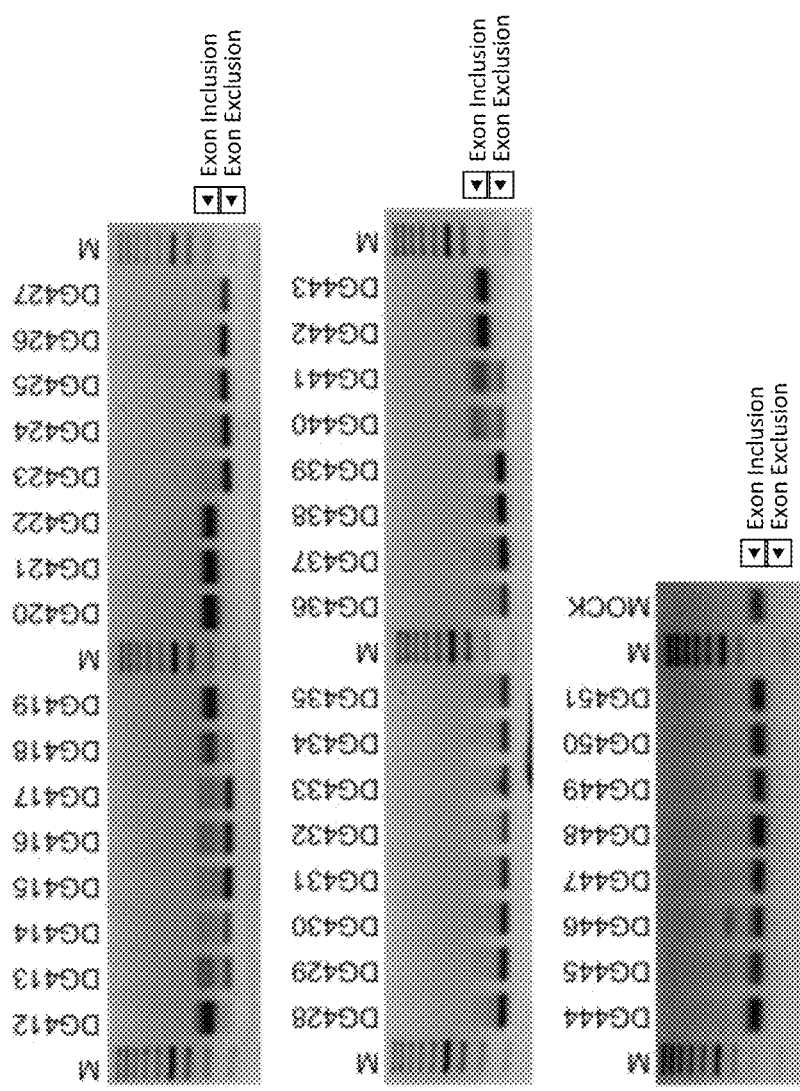
FIG. 4B shows the RT-PCR analysis of HEK293T cells transfected with the synthetic polynucleotides for CEP290 exon 7. PCR products were analyzed by agarose gel electrophoresis. M indicates the 100 bp DNA ladder.
Figure 4C:
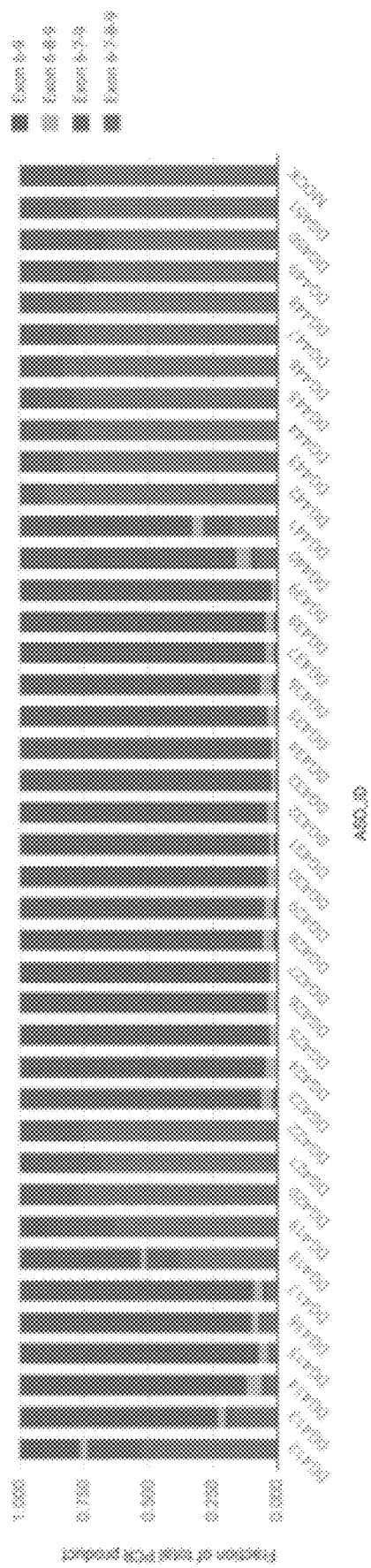
FIG. 4C shows the quantitative labchip analysis of RT-PCR fragments as shown in FIG. 4B. Fractions of total RT-PCR product were determined for each fragment containing either full or skipped exons 7 and 8. Splice forms were resolved from PCR fragment sizes.

In order to identify SPs that cause skipping of exon 7 of the CEP290 mRNA, a set of 40 synthetic oligonucleotides (SEQ ID NO: 270-309) was designed to target parts of intron 6, exon 7 and intron 7 of the CEP290 pre-mRNA sequence, corresponding to chromosomal interval chr12:88524882-88525055. All synthetic oligonucleotides that were tested are 20 nucleotides in length and are tiling the pre-mRNA target sequence with an overlapping resolution of 4 bp (SEQ ID NO: 270-309, see e.g., TABLE 1, FIG. 4A). The potential of these synthetic oligonucleotides to cause exon-skipping was determined in HEK293T cells (FIG. 4B, FIG. 4C).

Under normal conditions (mock transfection), natural skipping of exon 7 was not detected in HEK293T cells, whereas natural skipping of a combination of both exon 7 and 8 was detected at a low rate of approximately 2.5%. In contrast, natural skipping of exon 8 was detected at a higher rate of approximately 25% (FIG. 4C, TABLE 3). Upon transfection, out of the 40 synthetic oligonucleotides screened, 21 synthetic oligonucleotides (SEQ ID NO: 272-SEQ ID NO: 275 and SEQ ID NO: 281-SEQ ID NO: 297) showed strong exon-skipping activity (>90%), which was clustered around two target regions in the CEP290 pre-mRNA. The first (7-I) region is located in intron 6 and is targeted by four SPs (DG414 to DGDG417; SEQ ID NO: 272-SEQ ID NO: 275). The second region (7-II) is the complete exon 7 including the flanking splicing sites and is targeted efficiently by 17 different SPs (DG423 to DG439; SEQ ID NO: 281-SEQ ID NO: 297). The active SPs caused a modest rate of skipping of exon 7 alone, with a maximum rate of 5.8% observed for SP DG414 (SEQ ID NO: 272). In contrast, most of the active SPs (19/21) caused a high rate (>90%) of double skipping of both exon 7 and exon 8, while abolishing the skipping of exon 8 alone completely. Taken together, these results demonstrate that CEP290 exon 7 can be skipped efficiently in conjunction with exon 8.

TABLE 3

TABLE 3. Exon-skipping efficiencies for exons 7, 8, and exons 7 and 8 in conjunction using SPs with SEQ ID NO: 270-SEQ ID NO: 309

| SP_ID | SEQ ID NO | Exon-Skipping (%) | | | |
|---|---|---|---|---|---|
| | | None | Exon 7 | Exon 8 | Exon 7 + 8 |
| DG412 | 270 | 53.4 | 2.3 | 20.5 | 23.8 |
| DG413 | 271 | 16.9 | 2.8 | 3.4 | 77 |
| DG414 | 272 | 4.8 | 5.8 | 1.3 | 88.1 |
| DG415 | 273 | 2.5 | 4.1 | 0.7 | 92.7 |
| DG416 | 274 | 5.3 | 2.3 | 2 | 90.3 |
| DG417 | 275 | 4 | 3.5 | 1.8 | 90.7 |
| DG418 | 276 | 38.3 | 2.3 | 12.7 | 46.6 |
| DG419 | 277 | 63.6 | 0 | 23.8 | 12.6 |
| DG420 | 278 | 77.1 | 0 | 21.7 | 1.2 |
| DG421 | 279 | 68.9 | 0 | 27.5 | 3.6 |
| DG422 | 280 | 74.6 | 0 | 22.8 | 2.6 |
| DG423 | 281 | 1.4 | 4.2 | 0.7 | 93.8 |
| DG424 | 282 | 0.4 | 4 | 0 | 95.6 |
| DG425 | 283 | 0 | 3.1 | 0 | 96.9 |
| DG426 | 284 | 0 | 3.7 | 0 | 96.3 |
| DG427 | 285 | 0.4 | 2.8 | 0 | 96.9 |
| DG428 | 286 | 0.8 | 4.3 | 0.5 | 94.4 |
| DG429 | 287 | 0.6 | 3.9 | 0.4 | 95.1 |
| DG430 | 288 | 0.3 | 3.5 | 0 | 96.2 |
| DG431 | 289 | 0.7 | 1.6 | 0.7 | 97.1 |
| DG432 | 290 | 0.5 | 3.3 | 0.3 | 95.8 |
| DG433 | 291 | 0.6 | 1.6 | 0.2 | 97.5 |
| DG434 | 292 | 0.3 | 1.9 | 0 | 97.8 |
| DG435 | 293 | 0.6 | 3.1 | 0.3 | 96 |
| DG436 | 294 | 1.2 | 5 | 0.5 | 93.3 |
| DG437 | 295 | 0.9 | 3.2 | 0.4 | 95.6 |
| DG438 | 296 | 0.9 | 3 | 0.4 | 95.7 |
| DG439 | 297 | 0.3 | 2.1 | 0 | 97.6 |
| DG440 | 298 | 7.2 | 5.5 | 3.2 | 84.1 |
| DG441 | 299 | 17.7 | 4.4 | 11.2 | 66.7 |
| DG442 | 300 | 90.8 | 0 | 9.2 | 0 |
| DG443 | 301 | 83.5 | 0 | 13.5 | 3 |
| DG444 | 302 | 77.2 | 0 | 20.8 | 2 |
| DG445 | 303 | 78.8 | 0 | 14.5 | 6.6 |
| DG446 | 304 | 83.6 | 0 | 16.4 | 0 |
| DG447 | 305 | 78 | 0 | 20.4 | 1.6 |
| DG448 | 306 | 75.7 | 0 | 24.3 | 0 |
| DG449 | 307 | 71.1 | 0 | 27.6 | 1.3 |
| DG450 | 308 | 67 | 0 | 30.9 | 2.1 |
| DG451 | 309 | 76.4 | 0 | 22.1 | 1.5 |
| MOCK | n/a | 74.2 | 0 | 23.5 | 2.4 |

Example 5

Identification and Optimization of SPs Inducing Skipping of CEP290 Exon 31

This example demonstrates the identification and optimization of SPs to induce skipping of CEP290 exon 31.

Figure 5A:
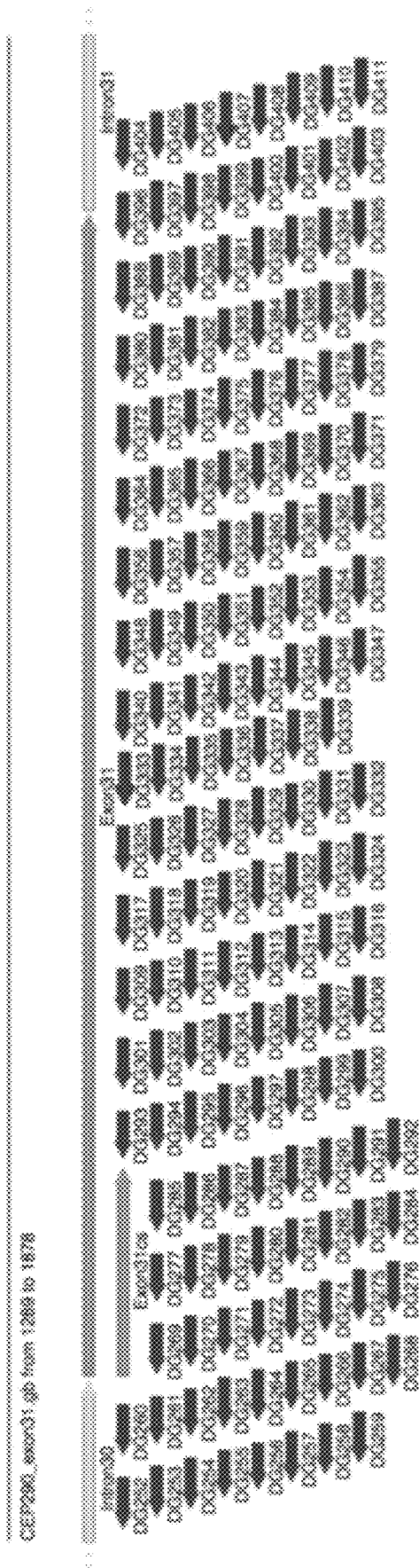
FIG. 5A shows the schematic representation of the set of synthetic polynucleotides that were designed to modulate splicing of CEP290 exon 31 (SEQ ID NO: 110-SEQ ID NO: 269).
Figure 5B:
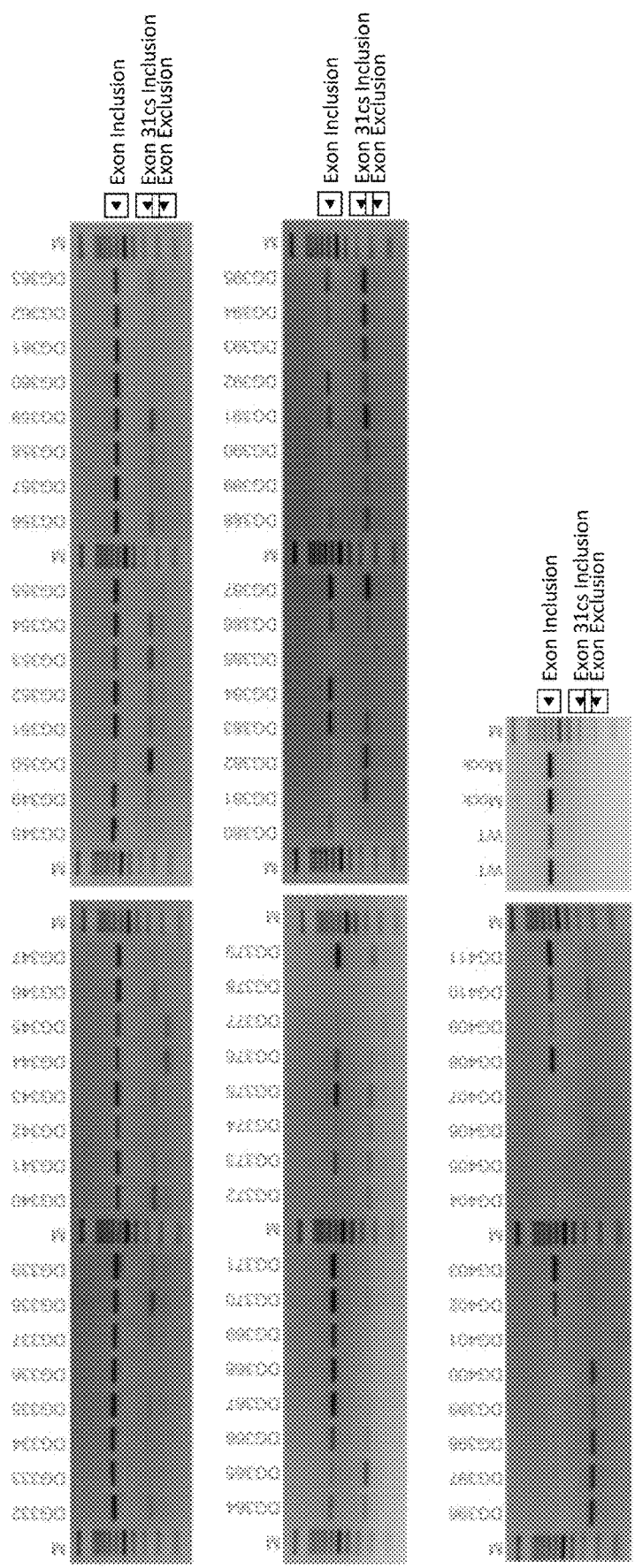
FIG. 5B shows the RT-PCR analysis of HEK293T cells transfected with the splicing modulating synthetic polynucleotides for CEP290 exon 31. PCR products were analyzed by agarose gel electrophoresis analysis. The sequence of the cryptic spliced exon 31 was determined by DNA sanger sequencing. WT indicates wildtype cells, and Mock the control transfection. M indicates the 100 bp DNA ladder.
Figure 5C:
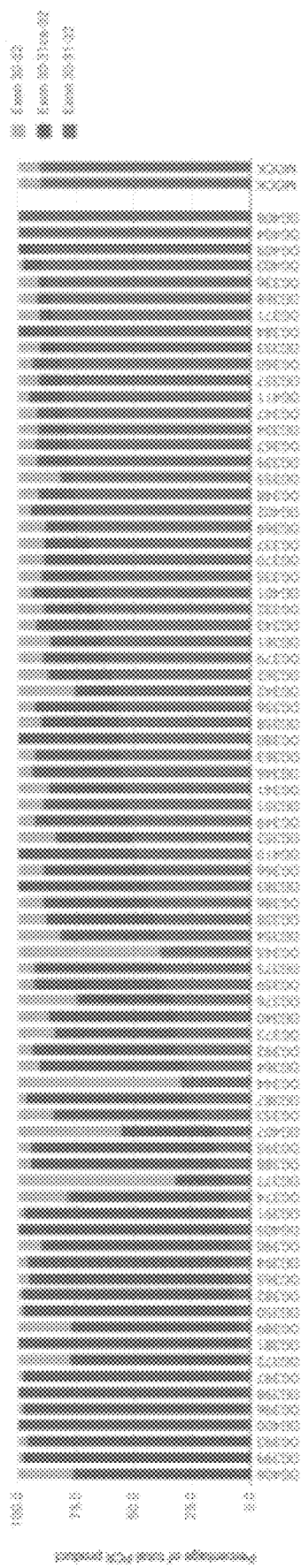
FIG. 5C shows the quantitative labchip analysis of RT-PCR fragments. Relative amounts of full inclusion (Exon 30-31-32), exon-skipping (Exon 30-32) and cryptic splicing (Exon 30-31cs-32) were determined for each synthetic polynucleotide. Synthetic polynucleotide results were sorted by full inclusion values.

In order to identify SPs that cause skipping of exon 31 a set of 160 SPs (DG252 to DG411; SEQ ID NO: 110-SEQ ID NO: 269) was designed for targeting exon 31 and its flanking regions in intron 30 and 31 of the CEP290 pre-mRNA sequence, corresponding to chromosomal positions chr12: 88482749-88483324 (TABLE 1, FIG. 5A). All SPs in this set were 20 nucleotides in length and tiled the target region with an average resolution of 3.5 bp. Of this set, 78 SPs (DG 332 to DG411; SEQ ID NO: 190-SEQ ID NO: 269) were screened for exon-skipping activity in HEK293T cells, as measured by RT-PCR and labchip analysis (FIG. 5B, FIG. 5C, TABLE 4).

Under control transfection (mock) conditions approximately 90% inclusion and 10% skipping of the exon 31 mRNA sequence was observed. Three SPs (DG404, DG408, DG409; SEQ ID NO: 262, SEQ ID NO: 266, SEQ ID NO: 267) increased this amount of exon 31 inclusion up to 100%. As expected, the majority of SPs tested (74/78) reduced exon 31 inclusion with an average of 45% and reaching down to 0% (e.g. DG406, DG399; SEQ ID NO: 264, SEQ ID NO: 257). However, in contrast to full skipping of exon 31, for most of these SPs, the bulk of the inclusion decrease was caused by alternative splicing of exon 31, using a cryptic splice site within the exon. Usage of this cryptic splice site results in partial inclusion of exon 31, which is causing a frame-shift in the coding region and subsequently encodes a truncated protein. The SPs that did cause a high frequency of full exon 31 skipping are DG345, DG377 and DG344 (SEQ ID NO: 203, SEQ ID NO: 235, and SEQ ID NO: 202), with exclusion rate of 62%, 68% and 71% respectively.

TABLE 4

TABLE 4. Skipping efficiency of exon 31 using SPs with SEQ ID NO: 190-SEQ ID NO: 269

| SP_ID | SEQ ID NO | Exon 30-31-32 | Exon 30-31cs-32 | Exon 30-32 |
|---|---|---|---|---|
| DG332 | 190 | 66.8 | 22 | 11.3 |
| DG333 | 191 | 82.3 | 8.3 | 9.5 |
| DG334 | 192 | 79.2 | 12.1 | 8.8 |
| DG335 | 193 | 67.8 | 21.7 | 10.5 |
| DG336 | 194 | 87.5 | 3.9 | 8.7 |
| DG337 | 195 | 68.4 | 20 | 11.5 |
| DG338 | 196 | 41.2 | 46.8 | 12.1 |
| DG339 | 197 | 77.7 | 13.8 | 8.5 |
| DG340 | 198 | 31.5 | 55.1 | 13.4 |
| DG341 | 199 | 54.5 | 32 | 13.5 |
| DG342 | 200 | 57.2 | 18.3 | 24.4 |
| DG343 | 201 | 63.6 | 28.6 | 7.7 |
| DG344 | 202 | 27.7 | 1.5 | 70.8 |
| DG345 | 203 | 38.5 | 0 | 61.5 |
| DG346 | 204 | 55.4 | 38.2 | 6.5 |
| DG347 | 205 | 79.8 | 12 | 8.2 |
| DG348 | 206 | 75.3 | 15.9 | 8.8 |
| DG349 | 207 | 51.3 | 41.5 | 7.2 |
| DG350 | 208 | 5.6 | 92.4 | 2 |
| DG351 | 209 | 53.6 | 35.8 | 10.6 |
| DG352 | 210 | 50.5 | 32.9 | 16.6 |
| DG353 | 211 | 22.3 | 62.3 | 15.4 |
| DG354 | 212 | 39.8 | 41.8 | 18.4 |
| DG355 | 213 | 76.4 | 5.2 | 18.4 |
| DG356 | 214 | 56.9 | 35.9 | 7.1 |
| DG357 | 215 | 81.2 | 10 | 8.8 |

TABLE 4-continued

TABLE 4. Skipping efficiency of exon 31 using SPs with SEQ ID NO: 190-SEQ ID NO: 269

| SP_ID | SEQ ID NO | Exon 30-31-32 | Exon 30-31cs-32 | Exon 30-32 |
|---|---|---|---|---|
| DG358 | 216 | 56.7 | 33.7 | 9.6 |
| DG359 | 217 | 36.8 | 56.4 | 6.8 |
| DG360 | 218 | 81.5 | 12.1 | 6.4 |
| DG361 | 219 | 63.3 | 22.6 | 14.1 |
| DG362 | 220 | 59.6 | 27.7 | 12.7 |
| DG363 | 221 | 55.5 | 37.4 | 7.1 |
| DG364 | 222 | 27.8 | 63 | 9.2 |
| DG365 | 223 | 7.5 | 87.6 | 4.9 |
| DG366 | 224 | 44.9 | 43.8 | 11.3 |
| DG367 | 225 | 78.3 | 13.7 | 8 |
| DG368 | 226 | 85.9 | 6 | 8 |
| DG369 | 227 | 74.2 | 13.8 | 12 |
| DG370 | 228 | 67.9 | 21 | 11.1 |
| DG371 | 229 | 84.7 | 5.8 | 9.5 |
| DG372 | 230 | 3.9 | 73.6 | 22.6 |
| DG373 | 231 | 31.5 | 52.5 | 15.9 |
| DG374 | 232 | 11.1 | 67.6 | 21.2 |
| DG375 | 233 | 38.1 | 54.9 | 7.1 |
| DG376 | 234 | 32.9 | 41.8 | 25.3 |
| DG377 | 235 | 11.4 | 20.7 | 67.9 |
| DG378 | 236 | NA | NA | NA |
| DG379 | 237 | 60.7 | 28.6 | 10.7 |
| DG380 | 238 | 55.9 | 44.1 | 0 |
| DG381 | 239 | 3.9 | 96.1 | 0 |
| DG382 | 240 | 7.4 | 91 | 1.6 |
| DG383 | 241 | 43.9 | 56.1 | 0 |
| DG384 | 242 | 82.3 | 17.7 | 0 |
| DG385 | 243 | NA | NA | NA |
| DG386 | 244 | 43.4 | 45.7 | 10.9 |
| DG387 | 245 | 27 | 69.3 | 3.7 |
| DG388 | 246 | 13.1 | 81.2 | 5.7 |
| DG389 | 247 | 4.7 | 72.2 | 23.1 |
| DG390 | 248 | 8.9 | 81 | 10.1 |
| DG391 | 249 | 10.5 | 86.6 | 2.9 |
| DG392 | 250 | 31.2 | 62.5 | 6.3 |
| DG393 | 251 | 0.9 | 95 | 4.1 |
| DG394 | 252 | 8.3 | 87.5 | 4.2 |
| DG395 | 253 | 14.6 | 79.6 | 5.8 |
| DG396 | 254 | 2.3 | 95.5 | 2.2 |
| DG397 | 255 | 3.6 | 94.3 | 2.1 |
| DG398 | 256 | 2.5 | 97.5 | 0 |
| DG399 | 257 | 0 | 97.8 | 2.2 |
| DG400 | 258 | 1.8 | 98.2 | 0 |
| DG401 | 259 | 66.9 | 26.9 | 6.2 |
| DG402 | 260 | 74.5 | 19.7 | 5.8 |
| DG403 | 261 | 90.2 | 7.7 | 2.1 |
| DG404 | 262 | 100 | 0 | 0 |
| DG405 | 263 | 9.2 | 90.8 | 0 |
| DG406 | 264 | 0 | 75.8 | 24.2 |
| DG407 | 265 | 15.2 | 39.8 | 45 |
| DG408 | 266 | 100 | 0 | 0 |
| DG409 | 267 | 94.9 | 5.1 | 0 |
| DG410 | 268 | 48.6 | 51.4 | 0 |
| DG411 | 269 | 80.1 | 15.4 | 4.5 |
| MOCK | n/a | 90.9 | 0 | 9.1 |
| MOCK | n/a | 90.1 | 0 | 9.9 |

Example 6

Identification and Optimization of SPs Inducing Skipping of CEP290 Exon 34

This example demonstrates the identification and optimization of SPs to induce skipping of CEP290 exon 34.

Figure 6A:
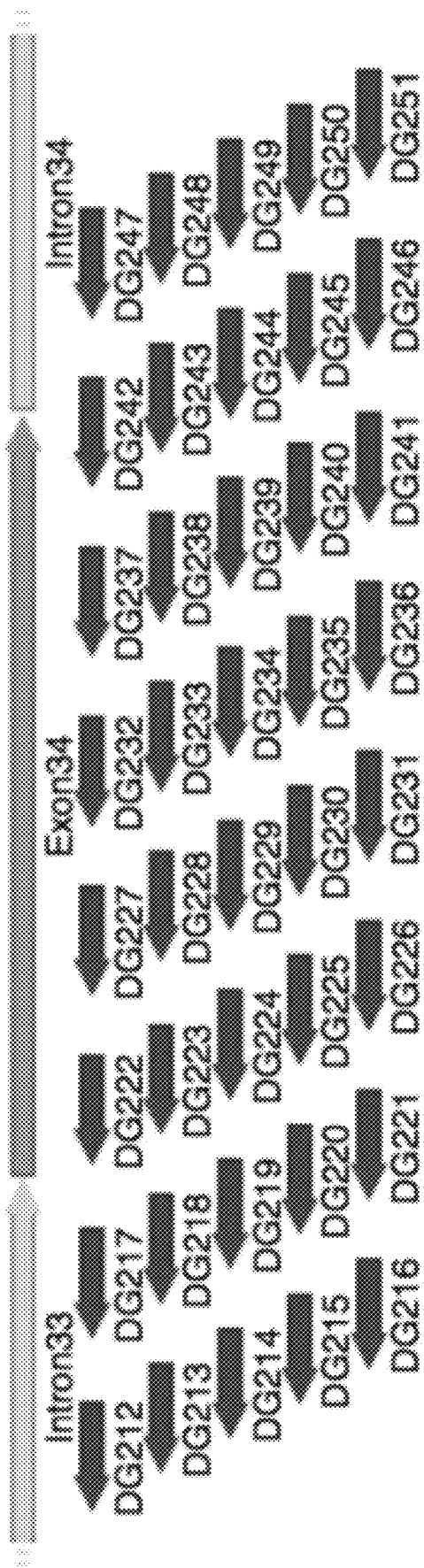
FIG. 6A shows the schematic representation of the set of synthetic polynucleotides that were designed to modulate splicing of CEP290 exon 34 (SEQ ID NO: 70-SEQ ID NO: 109).
Figure 6B:
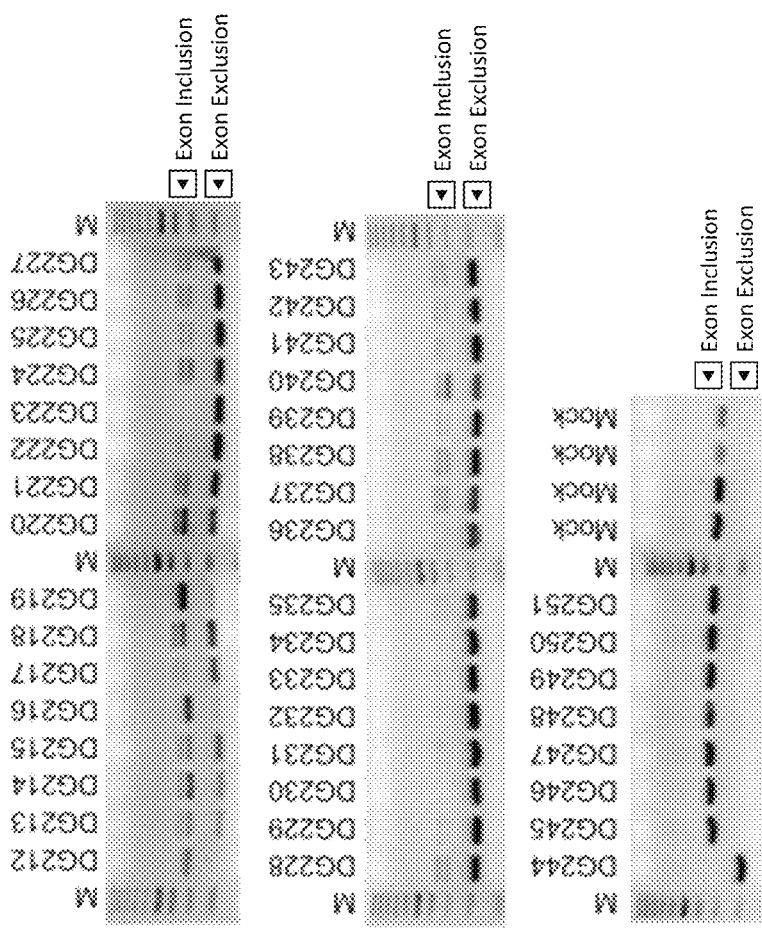
FIG. 6B shows the RT-PCR analysis of HEK293T cells transfected with the initial set splicing modulating synthetic polynucleotides for CEP290 exon 34. PCR products were analyzed by agarose gel electrophoresis analysis. M indicates the 100 bp DNA ladder.
Figure 6C:
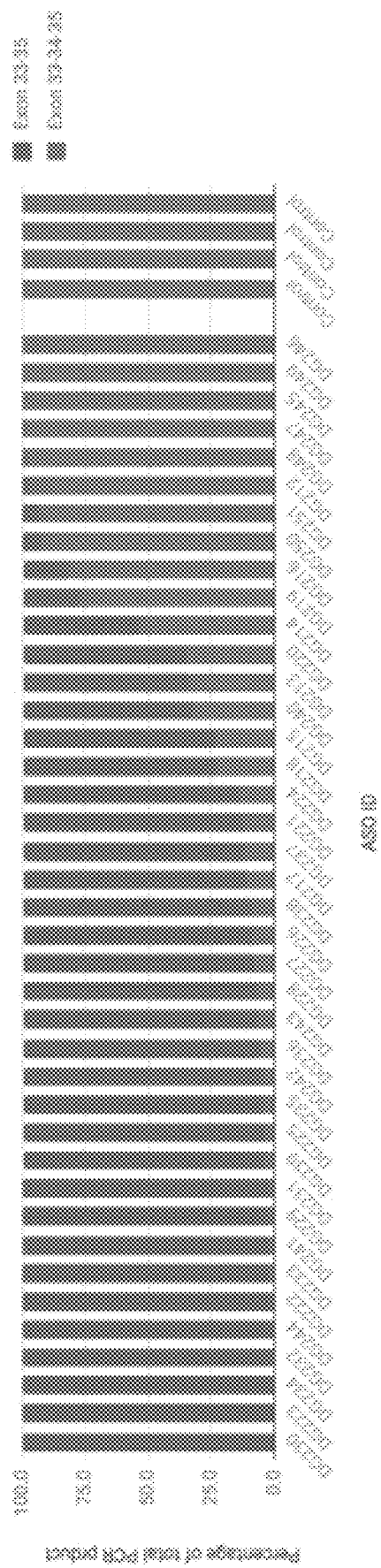
FIG. 6C shows the quantitative labchip analysis of RT-PCR fragments. Percentages were determined for each fragment containing either full or skipped exon 34. NT and Mock transfection controls are shown on the right of the diagram.

In order to identify SPs that cause skipping of exon 34 a set of 40 SPs (SEQ ID NO: 70-SEQ ID NO: 109) was designed and screened for targeting exon 34 and flanking regions of intron 33 and 34 of the CEP290 pre-mRNA sequence, corresponding to chromosomal positions chr12: 88479756-88480010. All SPs in this set were 20 nucleotides in length and tiled the target region with a 6 bp resolution (TABLE 1, FIG. 6A). SPs were screened for exon-skipping activity in HEK293T cells, as measured by RT-PCR and labchip analysis (FIG. 6B, FIG. 6C, TABLE 5). Out of the 40 SPs screened, 29 SPs (SEQ ID NO: 71, SEQ ID NO: 73, SEQ ID NO: 75, SEQ ID NO: 78-SEQ ID NO: 102) showed more than modest (>50%) exon-skipping activity. Of these active SPs, 20 SPs (SEQ ID NO: 76, SEQ ID NO: 80, SEQ ID NO: 83, SEQ ID NO: 94, SEQ ID NO: 96, SEQ ID NO: 97, SEQ ID NO: 99-SEQ ID NO: 102) with >90% exon-skipping activity were all targeted at exon 34 itself. Of these, 13 had over 95% skipping activity. The most effective SPs in this region, with over 99% activity, were DG230, DG223, DG234, DG232 and DG244 (SEQ ID NO: 81, SEQ ID NO: 88, SEQ ID NO: 90, SEQ ID NO: 92, and SEQ ID NO: 102).

TABLE 5

TABLE 5. Skipping efficiency of exon 34 using SPs with SEQ ID NO: 70 - SEQ ID NO: 109.

| SP ID | SEQ ID NO | Skipping Exon 34 (%) |
|---|---|---|
| DG212 | 70 | 3.2 |
| DG213 | 71 | 65.2 |
| DG214 | 72 | 45.6 |
| DG215 | 73 | 75.6 |
| DG216 | 74 | 17.9 |
| DG217 | 75 | 88.7 |
| DG218 | 76 | 76.3 |
| DG219 | 77 | 22.6 |
| DG220 | 78 | 64.5 |
| DG221 | 79 | 86.9 |
| DG222 | 80 | 98.6 |
| DG223 | 81 | 99.6 |
| DG224 | 82 | 85.6 |
| DG225 | 83 | 95.9 |
| DG226 | 84 | 91 |
| DG227 | 85 | 91.2 |
| DG228 | 86 | 92.4 |
| DG229 | 87 | 97.7 |
| DG230 | 88 | 100 |
| DG231 | 89 | 97.6 |
| DG232 | 90 | 99.4 |
| DG233 | 91 | 98.2 |
| DG234 | 92 | 99.5 |
| DG235 | 93 | 95.6 |
| DG236 | 94 | 94.5 |
| DG237 | 95 | 87.8 |
| DG238 | 96 | 90.9 |
| DG239 | 97 | 96.2 |
| DG240 | 98 | 67.2 |
| DG241 | 99 | 98 |
| DG242 | 100 | 94.9 |
| DG243 | 101 | 93.3 |
| DG244 | 102 | 99.3 |
| DG245 | 103 | 0.8 |
| DG246 | 104 | 0.4 |
| DG247 | 105 | 1 |
| DG248 | 106 | 1.9 |
| DG249 | 107 | 0.8 |
| DG250 | 108 | 7.4 |
| DG251 | 109 | 6.5 |
| NT | n/a | 0 |
| NT | n/a | 0 |
| NT | n/a | 0 |
| NT | n/a | 0 |

Example 7

Identification and Optimization of SPs Inducing Skipping of CEP290 Exon 36

This example demonstrates the identification and optimization of SPs to induce skipping of CEP290 exon 36.

Figure 3A:
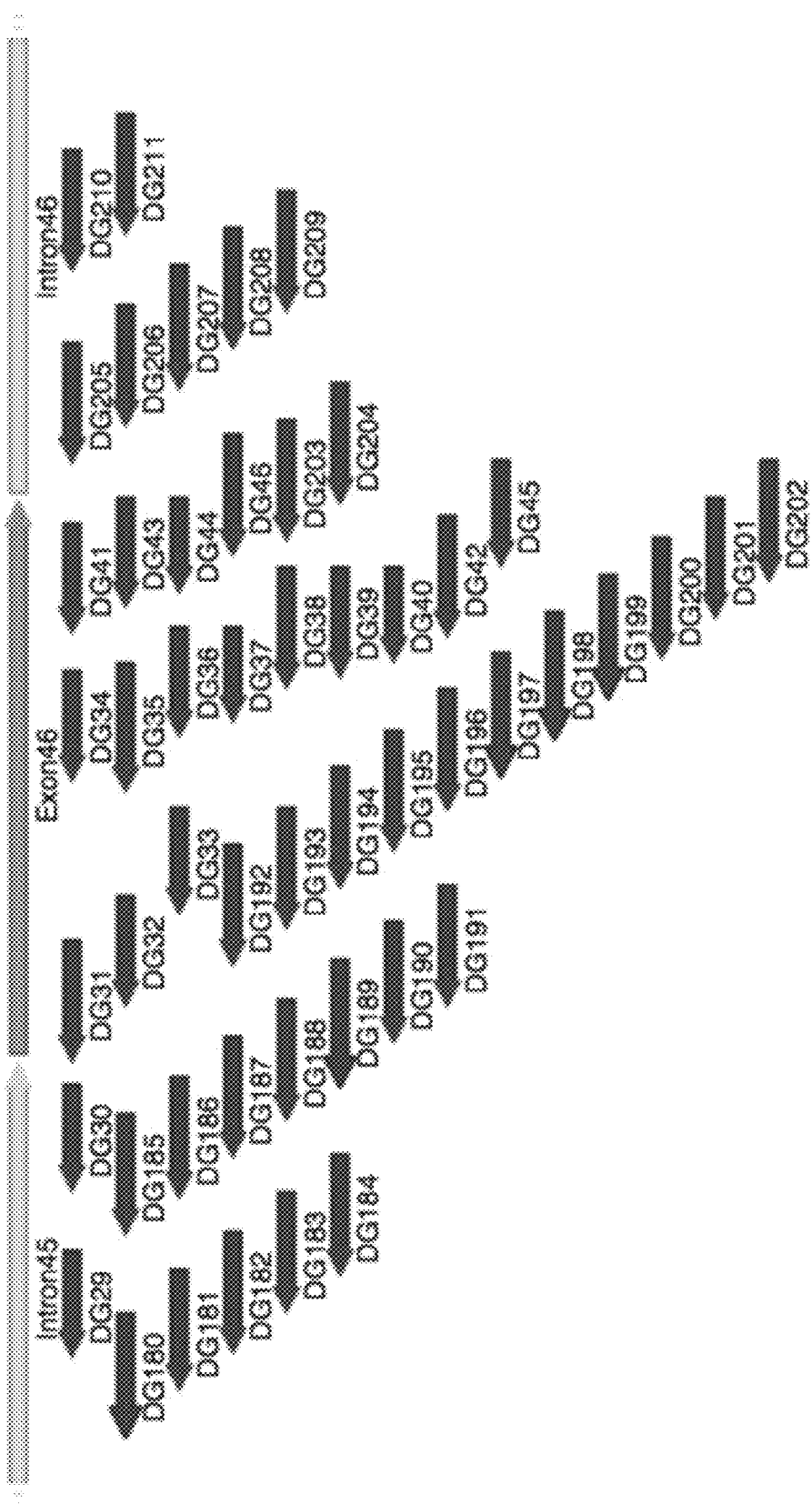
FIG. 3A shows the schematic representation of the initial set of synthetic polynucleotides that were designed to modulate splicing of CEP290 exon 46 (SEQ ID NO: 20-SEQ ID NO: 69).
Figure 7A:
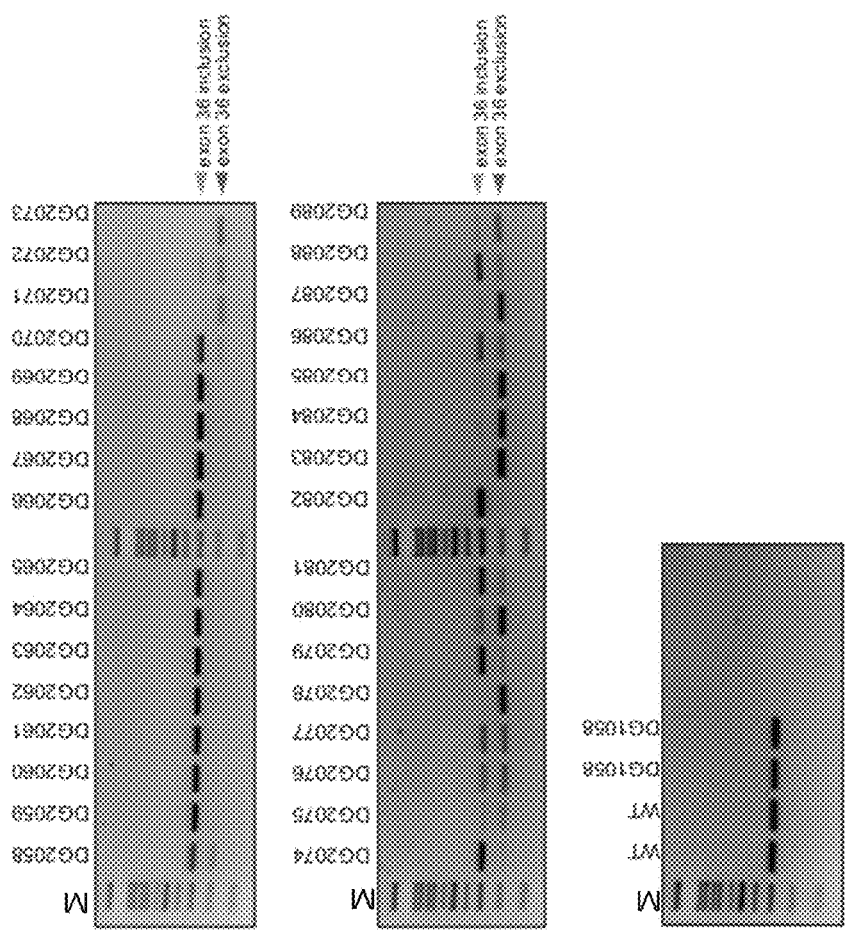
FIG. 7A shows the RT-PCR analysis of HEK293T cells transfected with the initial set splicing modulating synthetic polynucleotides for CEP290 exon 36. PCR products were analyzed by agarose gel electrophoresis analysis. M indicates the 100 bp DNA ladder.
Figure 7A:
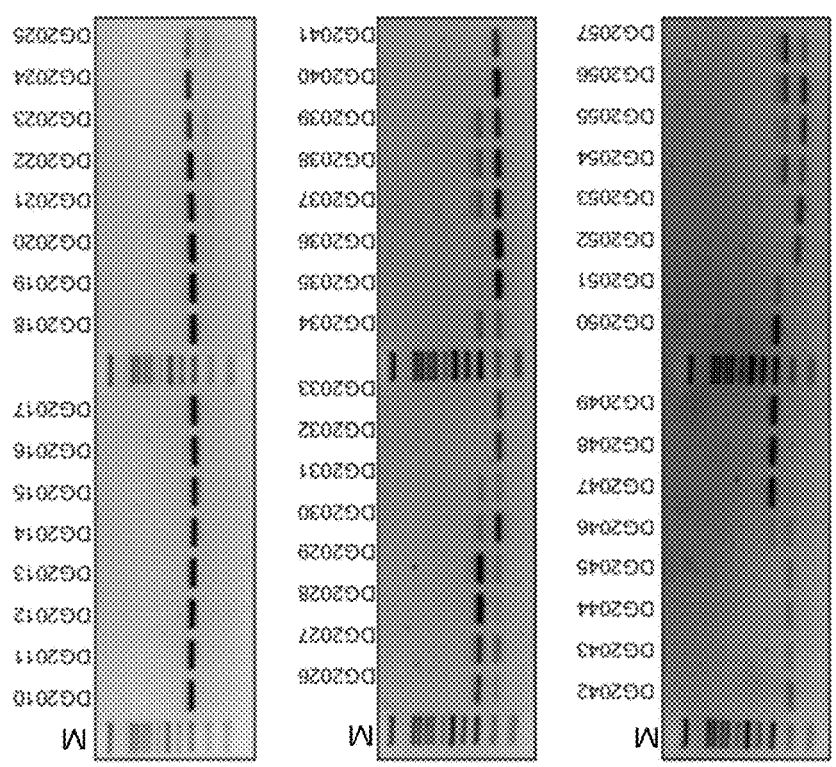
Figure 7B:
FIG. 7B shows the quantitative labchip analysis of RT-PCR fragments. Percentages were determined for each fragment containing either full or skipped exon 36.

In order to obtain SPs that cause skipping of the exon 36 of the CEP290 mRNA, SPs were designed against CEP90 pre-mRNA corresponding to the chromosomal interval chr12: 88477564-88477791. The sequences of various synthetic polynucleotides as described herein are listed in TABLE 1. These SPs with SEQ ID NO: 461-SEQ ID NO: 540, or SEQ ID NO: 703-SEQ ID NO: 824 varied in length from 16 to 20 nucleotides and targeted intron 35, exon 36 and intron 37 of the CEP290 gene (FIG. 3A). To assay their exon-skipping potential in cell culture systems, 50,000 HEK293T cells were reverse transfected in a 96-well format with an absolute doses of 50.0 pmol, respectively, and the effect on exon-skipping (measured as the difference in PSI) for exon 36 was determined by RT-PCR (FIG. 7A, FIG. 7B). In the target region for exon 36, four hotspot regions were identified that show strong exon-skipping. The first hotspot region (36-I) corresponding to the chromosomal interval chr12: 88477602-88477646 contains SPs DG2051-2058 (SEQ ID NOs: 502-509), with the strongest effect observed for DG2052 (SEQ ID NO: 503, ~99% exon-skipping). The second hotspot region (36-II) corresponding to the chromosomal interval chr12: 88477641-88477688 contains SPs DG2047, DG2046, DG2045, DG2044, DG2043, DG2042, DG4724, DG4747, DG4757, DG4737, DG4748, DG4758, DG4766, DG4738, DG4749, DG4759, DG4767, DG2041, DG4727, DG4739, DG4750, DG4760, DG4728, DG4740, DG4751, DG4761, DG4768, DG4729, DG4741, DG4752, DG4762, DG4769, DG4730, DG4742, DG4753, DG4763, DG4770, DG2040, DG4743, DG4754, DG4764, DG4732, DG4744, DG4755, DG4765, DG4733, DG4745, DG4756, and DG2039 (SEQ ID NOs: 498, 497, 496, 495, 494, 493, 703, 722, 732, 712, 723, 733, 741, 713, 724, 734, 742, 492, 704, 714, 725, 735, 705, 715, 726, 736, 743, 706, 716, 727, 737, 744, 707, 717, 728, 738, 745, 491, 718, 729, 739, 708, 719, 730, 740, 709, 720, 731, and 490), with the strongest effect observed for DG2045, DG2042, and DG4767 (~100% exon-skipping, SEQ ID NOs: 496, 493, and 742). The third hotspot region (36-III) corresponding to the chromosomal interval chr12: 88477673-88477721 contains SPs DG2038, DG2037, DG2036, DG4771, DG4798, DG4849, DG4772, DG4799, DG4850, DG4873, DG2080, DG4773, DG4800, DG2035, DG4774, DG4801, DG4852, DG2089, DG4775, DG4802, DG4828, DG4853, DG2085, DG4776, DG4803, DG4829, DG4854, DG2087, DG4777, DG4830, DG4855, DG2034, DG4778, DG4831, DG4856, DG4779, DG4832, DG4857, DG4874, DG4780, DG4858, DG4875, DG2033, DG4781, DG2083, DG4782, DG4860, DG2073, DG4783, DG4836, DG4861, DG2078, DG4784, DG4837, DG4862, DG2032, DG4785, DG4838, DG4863, DG2071, DG4786, DG4839, DG4864, DG2075, DG4787, DG4840, DG4865, DG2031, DG4788, DG4841, DG4866, DG2072, DG4789, DG4842, DG4867, DG2077, DG4790, DG4868, DG2076, DG4791, DG4844, DG4869, DG2030, DG4792, DG4845, DG4870, DG2084, DG4793, DG4820, DG4846, and DG4871 (SEQ ID NOs: 489, 488, 487, 746, 773, 800, 747, 774, 801, 822, 531, 748, 775, 486, 749, 776, 802, 540, 750, 777, 783, 803, 536, 751, 778, 784, 804, 538, 752, 785, 805, 485, 753, 786, 806, 754, 787, 807, 823, 755, 808, 824, 484, 756, 534, 757, 809, 524, 758, 788, 810, 529, 759, 789, 811, 483, 760, 790, 812, 522, 761, 791, 813, 526, 762, 792, 814, 482, 763, 793, 815, 523, 764, 794, 816, 528, 765, 817, 527, 766, 795, 818, 481, 767, 796, 819, 535, 768, 779, 797, and 820), with the strongest effect observed for DG2083, DG4860, DG2078, and DG4864 (SEQ ID NO: 534, 809, 529, and 813, ~100% exon-skipping). The second hotspot region (36-IV) corresponding to the chromosomal interval chr12: 88477710-88477759 contains SPs DG2088, DG2027, DG2086, DG2026, DG2025, DG2024, DG2023, DG2022, DG2021, DG2020, and DG2019 (SEQ ID NOs: 539, 478, 537, 477, 476, 475, 474, 473, 472, 471, and 470), with the strongest effect observed for DG2086 (~55% exon-skipping, SEQ ID NO: 537).

TABLE 6 shows the exon 36 skipping efficiency of synthetic polynucleotides with SEQ ID NO: 461-SEQ ID NO: 540, or SEQ ID NO: 703-SEQ ID NO: 824: 62 using 50 pmol of synthetic polynucleotide.

TABLE 6

TABLE 6. Exon 36 skipping efficiency of various SPs with SEQ ID NO: 470-SEQ ID NO: 549, or SEQ ID NO: 712-SEQ ID NO: 833.

| Hotspot | SP ID | SEQ ID NO | Exon 36 skipping at 50 pmol (%) | Start | End |
|---|---|---|---|---|---|
| | DG2069 | 520 | 0.0 | 88477564 | 88477583 |
| | DG2068 | 519 | 0.0 | 88477567 | 88477586 |
| | DG2067 | 518 | 0.0 | 88477571 | 88477590 |
| | DG2066 | 517 | 0.0 | 88477574 | 88477593 |
| | DG2065 | 516 | 0.0 | 88477578 | 88477597 |
| | DG2064 | 515 | 0.0 | 88477581 | 88477600 |
| | DG2063 | 514 | 0.0 | 88477585 | 88477604 |
| | DG2062 | 513 | 0.0 | 88477588 | 88477607 |
| | DG2061 | 512 | 0.0 | 88477592 | 88477611 |
| | DG2060 | 511 | 0.0 | 88477595 | 88477614 |
| | DG2059 | 510 | 0.0 | 88477599 | 88477618 |
| 36-I | DG2058 | 509 | 34.0 | 88477602 | 88477621 |
| 36-I | DG2057 | 508 | 44.0 | 88477606 | 88477625 |
| 36-I | DG2056 | 507 | 72.5 | 88477609 | 88477628 |
| 36-I | DG2055 | 506 | 81.8 | 88477613 | 88477632 |
| 36-I | DG2054 | 505 | 56.9 | 88477616 | 88477635 |
| 36-I | DG2053 | 504 | 97.5 | 88477620 | 88477639 |
| 36-I | DG2052 | 503 | 98.8 | 88477623 | 88477642 |
| 36-I | DG2051 | 502 | 33.1 | 88477627 | 88477646 |
| | DG2050 | 501 | 0.0 | 88477630 | 88477649 |
| | DG2049 | 500 | 0.2 | 88477634 | 88477653 |
| | DG2048 | 499 | 0.4 | 88477638 | 88477657 |
| 36-II | DG2047 | 498 | 6.3 | 88477641 | 88477660 |
| 36-II | DG2046 | 497 | 72.4 | 88477645 | 88477664 |
| 36-II | DG2045 | 496 | 100.0 | 88477648 | 88477667 |
| 36-II | DG2044 | 495 | 98.2 | 88477652 | 88477671 |
| 36-II | DG2043 | 494 | 97.5 | 88477655 | 88477674 |
| 36-II | DG2042 | 493 | 100.0 | 88477659 | 88477678 |
| 36-II | DG4724 | 703 | 78.5 | 88477659 | 88477674 |
| 36-II | DG4747 | 722 | 94.5 | 88477659 | 88477676 |
| 36-II | DG4757 | 732 | 95.0 | 88477659 | 88477677 |
| 36-II | DG4737 | 712 | 0.0 | 88477660 | 88477676 |
| 36-II | DG4748 | 723 | 9.3 | 88477660 | 88477677 |
| 36-II | DG4758 | 733 | 93.4 | 88477660 | 88477678 |
| 36-II | DG4766 | 741 | 95.7 | 88477660 | 88477679 |
| 36-II | DG4738 | 713 | 77.8 | 88477661 | 88477677 |
| 36-II | DG4749 | 724 | 2.2 | 88477661 | 88477678 |
| 36-II | DG4759 | 734 | 94.7 | 88477661 | 88477679 |
| 36-II | DG4767 | 742 | 100.0 | 88477661 | 88477680 |
| 36-II | DG2041 | 492 | 99.7 | 88477662 | 88477681 |
| 36-II | DG4727 | 704 | 10.4 | 88477662 | 88477677 |
| 36-II | DG4739 | 714 | 44.8 | 88477662 | 88477678 |
| 36-II | DG4750 | 725 | 35.1 | 88477662 | 88477679 |
| 36-II | DG4760 | 735 | 98.7 | 88477662 | 88477680 |
| 36-II | DG4728 | 705 | 5.0 | 88477663 | 88477678 |
| 36-II | DG4740 | 715 | 9.3 | 88477663 | 88477679 |
| 36-II | DG4751 | 726 | 76.2 | 88477663 | 88477680 |
| 36-II | DG4761 | 736 | 34.0 | 88477663 | 88477681 |
| 36-II | DG4768 | 743 | 98.5 | 88477663 | 88477682 |
| 36-II | DG4729 | 706 | 0.0 | 88477664 | 88477679 |
| 36-II | DG4741 | 716 | 0.0 | 88477664 | 88477680 |
| 36-II | DG4752 | 727 | 37.5 | 88477664 | 88477681 |
| 36-II | DG4762 | 737 | 80.4 | 88477664 | 88477682 |
| 36-II | DG4769 | 744 | 15.5 | 88477664 | 88477683 |
| 36-II | DG4730 | 707 | 7.2 | 88477665 | 88477680 |
| 36-II | DG4742 | 717 | 41.7 | 88477665 | 88477681 |
| 36-II | DG4753 | 728 | 5.4 | 88477665 | 88477682 |
| 36-II | DG4763 | 738 | 78.2 | 88477665 | 88477683 |
| 36-II | DG4770 | 745 | 91.1 | 88477665 | 88477684 |
| 36-II | DG2040 | 491 | 98.6 | 88477666 | 88477685 |
| 36-II | DG4743 | 718 | 78.7 | 88477666 | 88477682 |
| 36-II | DG4754 | 729 | 7.4 | 88477666 | 88477683 |
| 36-II | DG4764 | 739 | 87.7 | 88477666 | 88477684 |

TABLE 6-continued

TABLE 6. Exon 36 skipping efficiency of various SPs with SEQ ID NO: 470-SEQ ID NO: 549, or SEQ ID NO: 712-SEQ ID NO: 833.

| Hotspot | SP ID | SEQ ID NO | Exon 36 skipping at 50 pmol (%) | Start | End |
|---|---|---|---|---|---|
| 36-II | DG4732 | 708 | 5.2 | 88477667 | 88477682 |
| 36-II | DG4744 | 719 | 31.9 | 88477667 | 88477683 |
| 36-II | DG4755 | 730 | 95.2 | 88477667 | 88477684 |
| 36-II | DG4765 | 740 | 56.7 | 88477667 | 88477685 |
| 36-II | DG4733 | 709 | 3.9 | 88477668 | 88477683 |
| 36-II | DG4745 | 720 | 4.3 | 88477668 | 88477684 |
| 36-II | DG4756 | 731 | 22.3 | 88477668 | 88477685 |
| 36-II | DG2039 | 490 | 79.7 | 88477669 | 88477688 |
|  | DG4734 | 710 | 1.9 | 88477669 | 88477684 |
|  | DG4746 | 721 | 6.5 | 88477669 | 88477685 |
|  | DG4735 | 711 | 3.2 | 88477670 | 88477685 |
| 36-III | DG2038 | 489 | 82.9 | 88477673 | 88477692 |
| 36-III | DG2037 | 488 | 85.3 | 88477676 | 88477695 |
| 36-III | DG2036 | 487 | 96.4 | 88477680 | 88477699 |
| 36-III | DG4771 | 746 | 2.4 | 88477680 | 88477695 |
| 36-III | DG4798 | 773 | 9.8 | 88477680 | 88477696 |
| 36-III | DG4849 | 800 | 41.9 | 88477680 | 88477698 |
| 36-III | DG4772 | 747 | 5.3 | 88477681 | 88477696 |
| 36-III | DG4799 | 774 | 17.9 | 88477681 | 88477697 |
| 36-III | DG4850 | 801 | 46.6 | 88477681 | 88477699 |
| 36-III | DG4873 | 822 | 56.4 | 88477681 | 88477700 |
| 36-III | DG2080 | 531 | 88.9 | 88477682 | 88477699 |
| 36-III | DG4773 | 748 | 5.5 | 88477682 | 88477697 |
| 36-III | DG4800 | 775 | 18.9 | 88477682 | 88477698 |
| 36-III | DG2035 | 486 | 96.3 | 88477683 | 88477702 |
| 36-III | DG4774 | 749 | 12.6 | 88477683 | 88477698 |
| 36-III | DG4801 | 776 | 15.2 | 88477683 | 88477699 |
| 36-III | DG4852 | 802 | 64.0 | 88477683 | 88477701 |
| 36-III | DG2089 | 540 | 85.5 | 88477684 | 88477703 |
| 36-III | DG4775 | 750 | 2.3 | 88477684 | 88477699 |
| 36-III | DG4802 | 777 | 8.5 | 88477684 | 88477700 |
| 36-III | DG4828 | 783 | 50.7 | 88477684 | 88477701 |
| 36-III | DG4853 | 803 | 66.9 | 88477684 | 88477702 |
| 36-III | DG2085 | 536 | 96.7 | 88477685 | 88477704 |
| 36-III | DG4776 | 751 | 6.4 | 88477685 | 88477700 |
| 36-III | DG4803 | 778 | 41.7 | 88477685 | 88477701 |
| 36-III | DG4829 | 784 | 59.8 | 88477685 | 88477702 |
| 36-III | DG4854 | 804 | 78.4 | 88477685 | 88477703 |
| 36-III | DG2087 | 538 | 94.6 | 88477686 | 88477705 |
| 36-III | DG4777 | 752 | 9.2 | 88477686 | 88477701 |
| 36-III | DG4830 | 785 | 66.7 | 88477686 | 88477703 |
| 36-III | DG4855 | 805 | 77.6 | 88477686 | 88477704 |
| 36-III | DG2034 | 485 | 59.7 | 88477687 | 88477706 |
| 36-III | DG4778 | 753 | 28.3 | 88477687 | 88477702 |
| 36-III | DG4831 | 786 | 39.2 | 88477687 | 88477704 |
| 36-III | DG4856 | 806 | 70.0 | 88477687 | 88477705 |
| 36-III | DG4779 | 754 | 21.0 | 88477688 | 88477703 |
| 36-III | DG4832 | 787 | 63.9 | 88477688 | 88477705 |
| 36-III | DG4857 | 807 | 62.2 | 88477688 | 88477706 |
| 36-III | DG4874 | 823 | 88.5 | 88477688 | 88477707 |
| 36-III | DG4780 | 755 | 17.6 | 88477689 | 88477704 |
| 36-III | DG4858 | 808 | 91.5 | 88477689 | 88477707 |
| 36-III | DG4875 | 824 | 85.4 | 88477689 | 88477708 |
| 36-III | DG2033 | 484 | 96.5 | 88477690 | 88477709 |
| 36-III | DG4781 | 756 | 9.5 | 88477690 | 88477705 |
| 36-III | DG2083 | 534 | 100.0 | 88477691 | 88477710 |
| 36-III | DG4782 | 757 | 6.7 | 88477691 | 88477706 |
| 36-III | DG4860 | 809 | 100.0 | 88477691 | 88477709 |
| 36-III | DG2073 | 524 | 97.6 | 88477692 | 88477711 |
| 36-III | DG4783 | 758 | 17.9 | 88477692 | 88477707 |
| 36-III | DG4836 | 788 | 94.5 | 88477692 | 88477709 |
| 36-III | DG4861 | 810 | 98.9 | 88477692 | 88477710 |
| 36-III | DG2078 | 529 | 100.0 | 88477693 | 88477712 |
| 36-III | DG4784 | 759 | 65.3 | 88477693 | 88477708 |
| 36-III | DG4837 | 789 | 94.8 | 88477693 | 88477710 |
| 36-III | DG4862 | 811 | 98.9 | 88477693 | 88477711 |
| 36-III | DG2032 | 483 | 99.8 | 88477694 | 88477713 |
| 36-III | DG4785 | 760 | 3.7 | 88477694 | 88477709 |
| 36-III | DG4838 | 790 | 95.8 | 88477694 | 88477711 |
| 36-III | DG4863 | 812 | 96.7 | 88477694 | 88477712 |
| 36-III | DG2071 | 522 | 97.7 | 88477695 | 88477714 |
| 36-III | DG4786 | 761 | 57.9 | 88477695 | 88477710 |
| 36-III | DG4839 | 791 | 84.1 | 88477695 | 88477712 |
| 36-III | DG4864 | 813 | 100.0 | 88477695 | 88477713 |
| 36-III | DG2075 | 526 | 77.4 | 88477696 | 88477715 |
| 36-III | DG4787 | 762 | 10.4 | 88477696 | 88477711 |
| 36-III | DG4840 | 792 | 50.4 | 88477696 | 88477713 |
| 36-III | DG4865 | 814 | 32.2 | 88477696 | 88477714 |
| 36-III | DG2031 | 482 | 65.5 | 88477697 | 88477716 |
| 36-III | DG4788 | 763 | 6.3 | 88477697 | 88477712 |
| 36-III | DG4841 | 793 | 8.4 | 88477697 | 88477714 |
| 36-III | DG4866 | 815 | 24.2 | 88477697 | 88477715 |
| 36-III | DG2072 | 523 | 78.5 | 88477698 | 88477717 |
| 36-III | DG4789 | 764 | 1.8 | 88477698 | 88477713 |
| 36-III | DG4842 | 794 | 17.7 | 88477698 | 88477715 |
| 36-III | DG4867 | 816 | 19.8 | 88477698 | 88477716 |
| 36-III | DG2077 | 528 | 63.4 | 88477699 | 88477718 |
| 36-III | DG4790 | 765 | 8.5 | 88477699 | 88477714 |
| 36-III | DG4868 | 817 | 17.7 | 88477699 | 88477717 |
| 36-III | DG2076 | 527 | 68.3 | 88477700 | 88477719 |
| 36-III | DG4791 | 766 | 6.3 | 88477700 | 88477715 |
| 36-III | DG4844 | 795 | 22.3 | 88477700 | 88477717 |
| 36-III | DG4869 | 818 | 19.0 | 88477700 | 88477718 |
| 36-III | DG2030 | 481 | 86.6 | 88477701 | 88477720 |
| 36-III | DG4792 | 767 | 19.9 | 88477701 | 88477716 |
| 36-III | DG4845 | 796 | 33.0 | 88477701 | 88477718 |
| 36-III | DG4870 | 819 | 47.2 | 88477701 | 88477719 |
| 36-III | DG2084 | 535 | 96.2 | 88477702 | 88477721 |
| 36-III | DG4793 | 768 | 4.1 | 88477702 | 88477717 |
| 36-III | DG4820 | 779 | 10.5 | 88477702 | 88477718 |
| 36-III | DG4846 | 797 | 18.2 | 88477702 | 88477719 |
| 36-III | DG4871 | 820 | 21.3 | 88477702 | 88477720 |
|  | DG2081 | 532 | 34.9 | 88477703 | 88477722 |
|  | DG4794 | 769 | 3.5 | 88477703 | 88477718 |
|  | DG4821 | 780 | 4.6 | 88477703 | 88477719 |
|  | DG4847 | 798 | 5.6 | 88477703 | 88477720 |
|  | DG4872 | 821 | 11.9 | 88477703 | 88477721 |
|  | DG2070 | 521 | 21.8 | 88477704 | 88477723 |
|  | DG4795 | 770 | 0.7 | 88477704 | 88477719 |
|  | DG4822 | 781 | 1.3 | 88477704 | 88477720 |
|  | DG4848 | 799 | 1.7 | 88477704 | 88477721 |
|  | DG2029 | 480 | 22.2 | 88477705 | 88477724 |
|  | DG4796 | 771 | 1.0 | 88477705 | 88477720 |
|  | DG4823 | 782 | 0.0 | 88477705 | 88477721 |
|  | DG2082 | 533 | 4.3 | 88477706 | 88477725 |
|  | DG4797 | 772 | 0.0 | 88477706 | 88477721 |
|  | DG2079 | 530 | 24.5 | 88477707 | 88477726 |
|  | DG2028 | 479 | 8.8 | 88477708 | 88477727 |
|  | DG2074 | 525 | 9.3 | 88477709 | 88477728 |
| 36-IV | DG2088 | 539 | 37.9 | 88477710 | 88477729 |
| 36-IV | DG2027 | 478 | 48.1 | 88477712 | 88477731 |
| 36-IV | DG2086 | 537 | 54.6 | 88477714 | 88477733 |
| 36-IV | DG2026 | 477 | 30.5 | 88477715 | 88477734 |
| 36-IV | DG2025 | 476 | 40.1 | 88477719 | 88477738 |
| 36-IV | DG2024 | 475 | 0.0 | 88477722 | 88477741 |
| 36-IV | DG2023 | 474 | 25.2 | 88477726 | 88477745 |
| 36-IV | DG2022 | 473 | 20.7 | 88477729 | 88477748 |
| 36-IV | DG2021 | 472 | 15.5 | 88477733 | 88477752 |
| 36-IV | DG2020 | 471 | 4.9 | 88477736 | 88477755 |
| 36-IV | DG2019 | 470 | 1.3 | 88477740 | 88477759 |
|  | DG2018 | 469 | 0.0 | 88477743 | 88477762 |
|  | DG2017 | 468 | 0.0 | 88477747 | 88477766 |
|  | DG2016 | 467 | 0.0 | 88477750 | 88477769 |
|  | DG2015 | 466 | 0.0 | 88477754 | 88477773 |
|  | DG2014 | 465 | 0.0 | 88477757 | 88477776 |
|  | DG2013 | 464 | 0.0 | 88477761 | 88477780 |
|  | DG2012 | 463 | 0.0 | 88477764 | 88477783 |
|  | DG2011 | 462 | 0.0 | 88477768 | 88477787 |
|  | DG2010 | 461 | 0.0 | 88477772 | 88477791 |

Example 8

Identification and Optimization of SPs Inducing Skipping of CEP290 Exon 41

This example demonstrates the identification and optimization of SPs to induce skipping of CEP290 exon 41.

Figure 1B:
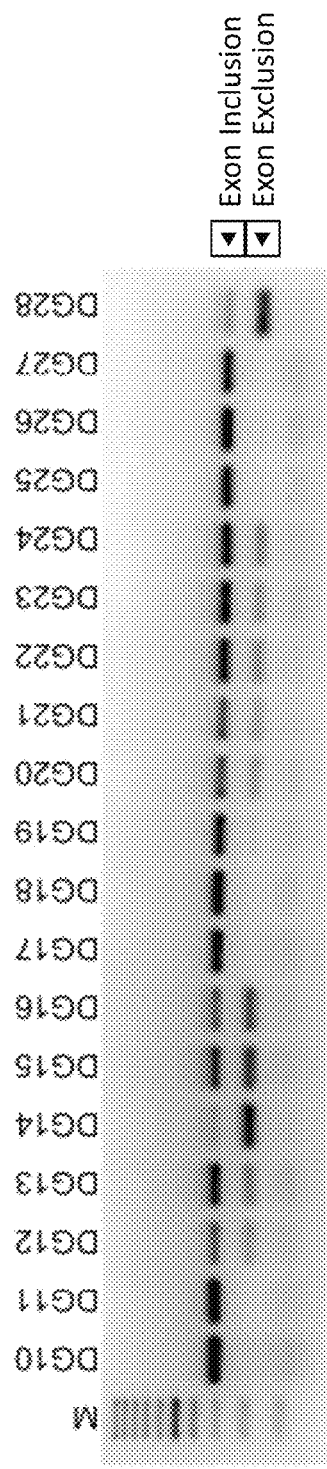
FIG. 1B shows a reverse transcription polymerase chain reaction (RT-PCR) analysis of 300,000 HEK293T cells transfected with 300 pmol of synthetic polynucleotides (SPs) against CEP290 exon 41. Polymerase chain reaction (PCR) primers were designed to amplify a CEP290 region containing exons 40, 41 and 42. PCR products were analyzed by agarose gel electrophoresis analysis. Exon inclusion (316 bp) and exclusion (192 bp) fragments are indicated by arrowheads, and heteroduplex PCR products by grey solid arrowhead. The mock treated sample solely showed the exon inclusion fragment (data not shown). M indicates the 100 bp DNA ladder.
Figure 1C:
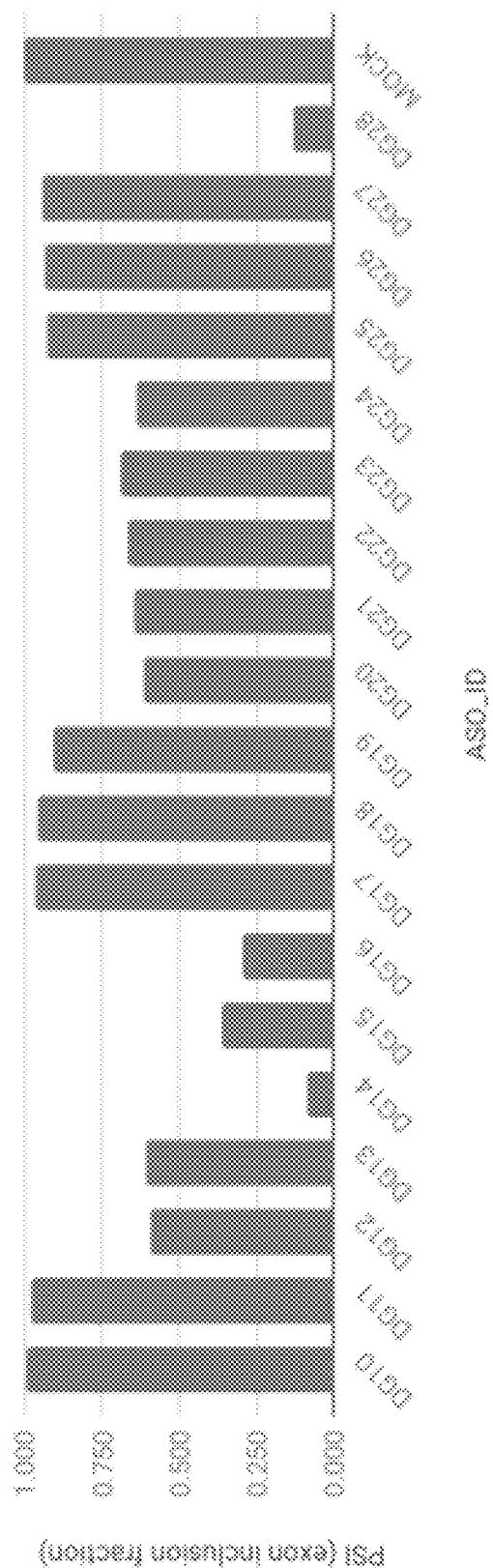
FIG. 1C shows the quantitation of the RT-PCR fragments as shown in FIG. 1B. The percent spliced (PSI) values indicates the fraction of CEP290 exon 41 inclusion within the PCR sample. PSI value calculations were corrected for heteroduplex PCR fragments.

Deletion of exon 41 of the CEP290 mRNA was predicted to have therapeutic potential in patients with disease-causing variants within exon 41. In order to identify exon-skipping SPs for exon 41, an initial set of 19 SPs (SEQ ID NO: 1-SEQ ID NO: 19) was designed against the CEP290 pre-mRNA transcript (DG10 to DG28; SEQ ID NO: 1-SEQ ID NO: 19; TABLE 1). SPs varied in length from 16 to 20 nucleotides. The target sequences for these SPs are located in intron 40, exon 41 and intron 41 (FIG. 1A) of the CEP290 pre-mRNA sequence, corresponding to the chromosomal interval chr12: 88470994-88471144 (hg19/b37). SPs were transfected into HEK293T cells and after 48 hours their potential to induce skipping of exon 41 was determined by RT-PCR analysis (FIG. 1B, FIG. 1C, TABLE 7).

Out of the 19 initial SPs, 12 SPS with SEQ ID NO: 3-SEQ ID NO: 7, SEQ ID NO: 11-SEQ ID NO: 15, and SEQ ID NO: 19 showed exon-skipping activity, which ranged from approximately 35% to over 90% and was clustered around four different regions in the pre-mRNA. These regions were denoted as hotspot regions for skipping of exon 41 (FIG. 1A). The first hotspot region, Hotspot 41-I is located at the splice acceptor site of intron 40 and exon 41 (chr12: 88471104-88471124). The two SPs targeting this area, DG12 and DG13 (SEQ ID NO: 3 and SEQ ID NO: 4), are both causing ~40% exon-skipping. The next two hotspot regions, 41-II and 41-III, are located completely within exon 41 at positions chr12: 88471066-88471093 and chr12: 88471013-88471043 respectively. Hotspot 41-II is covered by DG14, DG15 and DG16 (SEQ ID NO: 5-SEQ ID NO: 7, respectively), with DG14 causing the highest amount of exon-skipping (91%). Hotspot 41-III is targeted by SPs DG20 to DG24 (SEQ ID NO: 11-SEQ ID NO: 15), which all induced approximately 35% exon-skipping. A hotspot was found at the splice donor site of exon 41 and intron 41 (chr12:88470994-88471014). Targeting this region with SPs DG28 (SEQ ID NO: 19) resulted in 87% exon-skipping (FIG. 1C, TABLE 7).

Figure 2A:
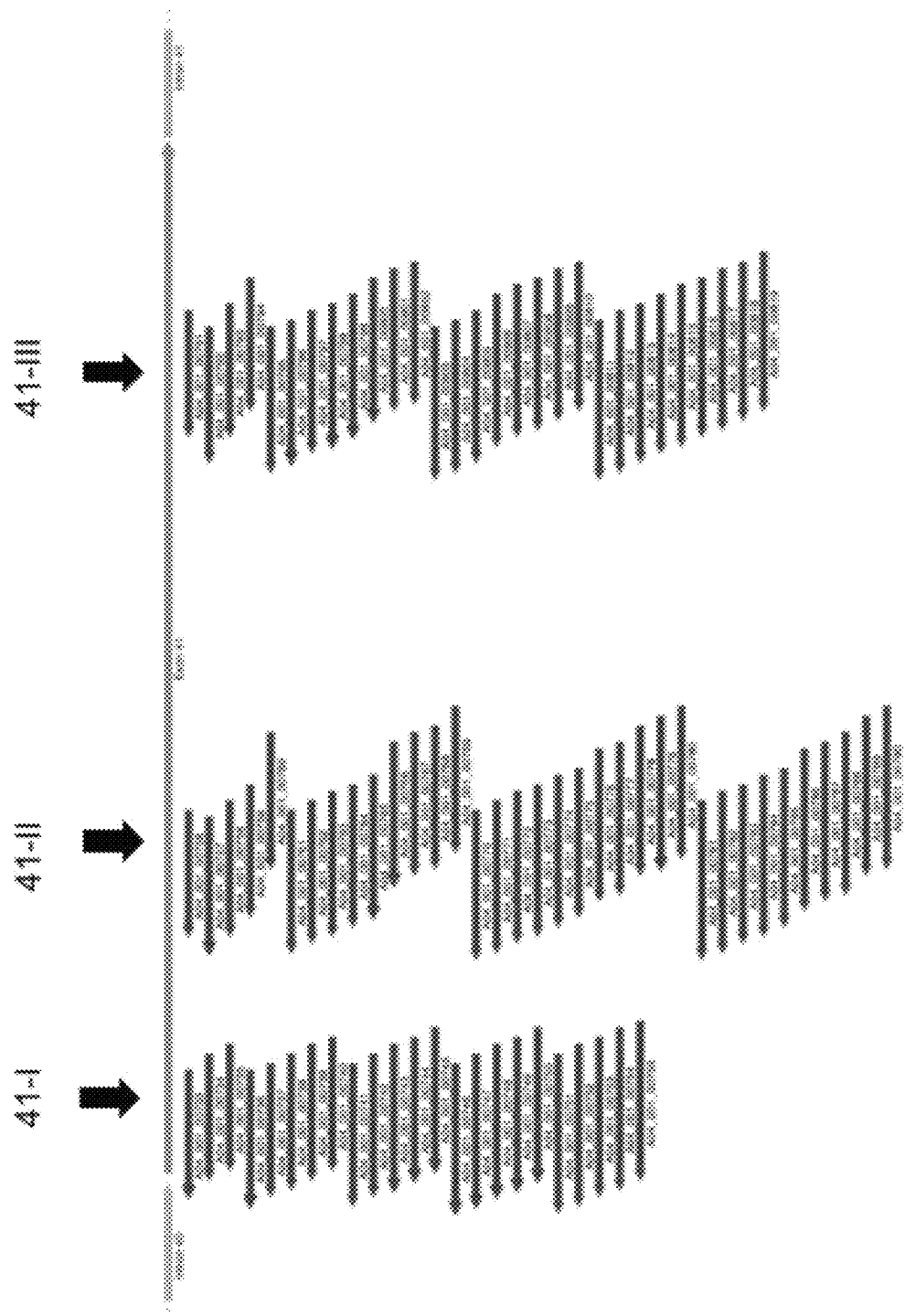
FIG. 2A shows the schematic representation of the CEP290 exon 41 hotspot regions 41-I, 41-II and 41-III, and the corresponding synthetic polynucleotides with SEQ ID NO: 310-SEQ ID NO: 330, SEQ ID NO: 331-SEQ ID NO: 363, and SEQ ID NO: 364-SEQ ID NO: 390, respectively, designed for micro-tiling.
Figure 2B:
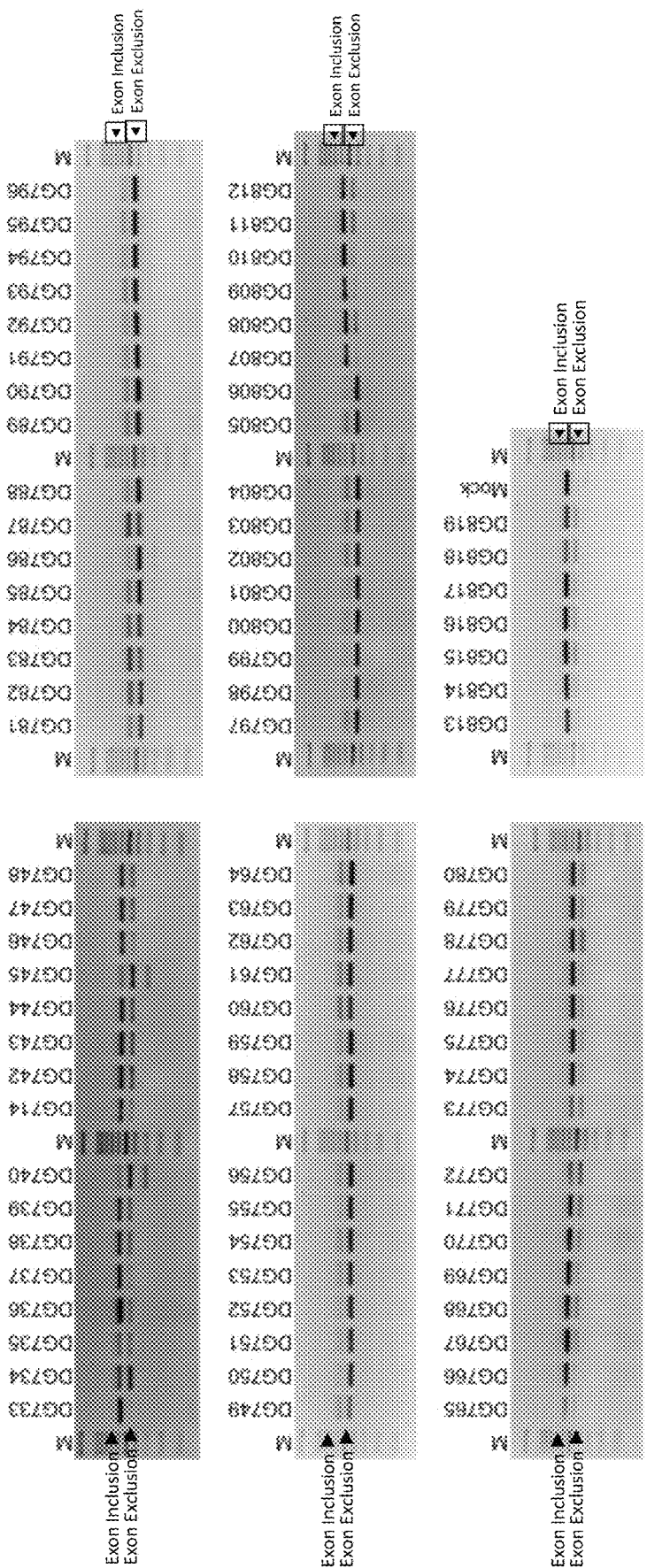
FIG. 2B shows the RT-PCR analysis of HEK293T cells transfected with the synthetic polynucleotide micro-tiling set for CEP290. PCR primers were designed to amplify a CEP290 region containing exon 39, 40, 41, 42 and 43. PCR products were analyzed by agarose gel electrophoresis analysis. Exon 41 inclusion and exclusion bands are 585 bp and 462 bp respectively. Sequence analysis of the fragment at 316 bp showed additional skipping of exon 42. M indicates the 100 bp DNA ladder.
Figure 2C:
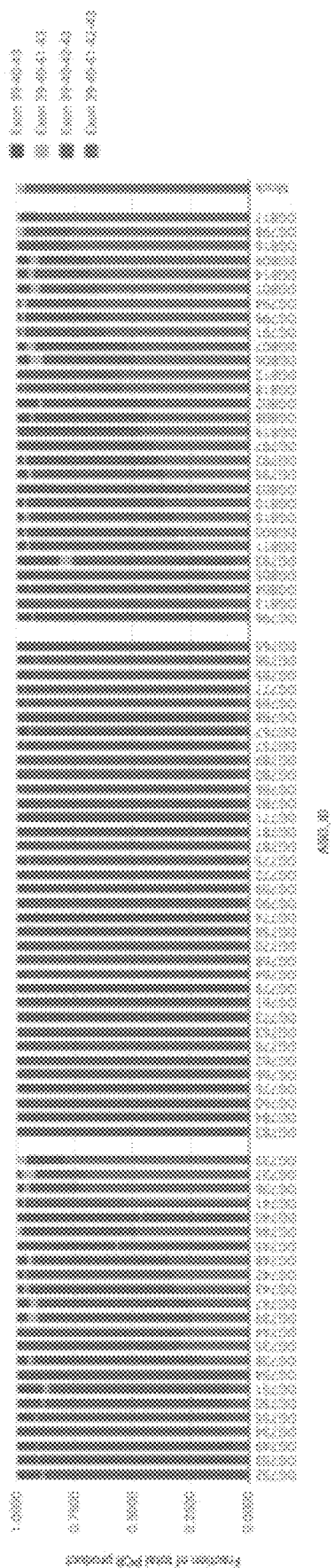
FIG. 2C shows the quantitative labchip analysis of RT-PCR fragments. Fractions were determined for each fragment containing either full or skipped exons 41 and 42. Synthetic polynucleotides were grouped by hotspot region and sorted by exon-skipping values for exon 41.

In order to identify SPs that are optimized for increased capability to cause skipping of CEP290 exon 41, three micro-tiling sets of SPs targeting the hotspots regions 41-I (SEQ ID NO: 310-SEQ ID NO: 330), 41-II (SEQ ID NO: 331-SEQ ID NO: 363) and 41-III (SEQ ID NO: 364-SEQ ID NO: 390) were designed and tested (FIG. 2A). The SPs in these sets varied in length between 16 and 20 nucleotides, tiled the hotspots regions with a 1-bp resolution and were filtered to have minimal off-target hits as determined by Blast. All these SPs were tested for activity of skipping exon 41 in HEK293T cells similarly as the primary set and their efficiency was readout by labchip analysis of RT-PCR products (FIG. 2B, FIG. 2C, TABLE 7). In total, 23 SPs against hotspot region 41-I (DG733 to DG755 (SEQ ID NO: 310-SEQ ID NO: 330), DG12 and DG13 (SEQ ID NO: 3 and SEQ ID NO: 4)) were assayed, 35 against hotspot region 41-II (DG756 to DG790 (SEQ ID NO: 331-SEQ ID NO: 363), DG14 and DG15 (SEQ ID NO: 5 and SEQ ID NO: 6)) and 31 against hotspot region 41-III (DG791 to DG819 (SEQ ID NO: 364-SEQ ID NO: 390), DG23 and DG24 (SEQ ID NO: 14 and SEQ ID NO: 15)) (TABLE 7).

For hotspot 41-I multiple SPs with a higher exon-skipping activity than the primary SPs were detected. The top SPs were DG752, DG13 and DG749 with SEQ ID NO: 328, and SEQ ID NO: 325 with 87%, and 84% exon-skipping activity, respectively. In addition, two SPs (DG740 and DG745; SEQ ID NO: 316, SEQ ID NO: 321) that enhanced endogenous skipping of exon 42 were identified, resulting in double skipping of both exon 41 and exon 42. For hotspot 41-II, all the SPs tested had similar or higher activity than the original set that was identified. The ones with the highest activity were DG783, DG784, DG760, DG776, DG766, DG762 and DG778 (SEQ ID NO: 356, SEQ ID NO: 357, SEQ ID NO: 335, SEQ ID NO: 349, SEQ ID NO: 337, and SEQ ID NO: 351) that each caused over 95% skipping of exon 41. For hotspot 41-III approximately two thirds of the SPs tested had high exon-skipping activity. The best SPs for this region were DG796, DG813 and DG804 (SEQ ID NO: 369, SEQ ID NO: 385, and SEQ ID NO: 376), with respectively 86%, 84% and 84% skipping of exon 41. Overall, micro-tiling of the hotspots resulted in the identification of SPs with enhanced capability to induce skipping of CEP290 exon 41.

TABLE 7

TABLE 7. Exon 41 skipping efficiency of various SPs with SEQ ID NO: 1-SEQ ID NO: 19, SEQ ID NO: 310-SEQ ID NO: 390.

| SP set | SP_ID | SEQ ID NO | Exon 41 skipping (%) |
| --- | --- | --- | --- |
| Initial 41 | DG10 | 1 | 1.0 |
| Initial 41 | DG11 | 2 | 1.8 |
| Initial 41 | DG12 | 3 | 40.8 |
| Initial 41 | DG13 | 4 | 39.5 |
| Initial 41 | DG14 | 5 | 91.1 |
| Initial 41 | DG15 | 6 | 64.2 |
| Initial 41 | DG16 | 7 | 70.5 |
| Initial 41 | DG17 | 8 | 3.4 |
| Initial 41 | DG18 | 9 | 4.0 |
| Initial 41 | DG19 | 10 | 9.4 |
| Initial 41 | DG20 | 11 | 38.8 |
| Initial 41 | DG21 | 12 | 35.3 |
| Initial 41 | DG22 | 13 | 33.4 |
| Initial 41 | DG23 | 14 | 30.9 |
| Initial 41 | DG24 | 15 | 36.1 |
| Initial 41 | DG25 | 16 | 7.6 |
| Initial 41 | DG26 | 17 | 6.6 |
| Initial 41 | DG27 | 18 | 5.5 |
| Initial 41 | DG28 | 19 | 87.1 |
| Hotspot 41-I | DG733 | 310 | 16.3 |
| Hotspot 41-I | DG735 | 311 | 68.5 |
| Hotspot 41-I | DG736 | 312 | 20.8 |
| Hotspot 41-I | DG737 | 313 | 20.8 |
| Hotspot 41-I | DG738 | 314 | 72.0 |
| Hotspot 41-I | DG739 | 315 | 66.7 |
| Hotspot 41-I | DG740 | 316 | 44.4 |
| Hotspot 41-I | DG741 | 317 | 42.5 |
| Hotspot 41-I | DG742 | 318 | 62.8 |
| Hotspot 41-I | DG743 | 319 | 62.9 |
| Hotspot 41-I | DG744 | 320 | 67.9 |
| Hotspot 41-I | DG745 | 321 | 52.8 |
| Hotspot 41-I | DG746 | 322 | 49.3 |
| Hotspot 41-I | DG747 | 323 | 66.1 |
| Hotspot 41-I | DG748 | 324 | 59.3 |
| Hotspot 41-I | DG749 | 325 | 83.9 |
| Hotspot 41-I | DG750 | 326 | 79.8 |
| Hotspot 41-I | DG751 | 327 | 78.0 |
| Hotspot 41-I | DG752 | 328 | 86.8 |
| Hotspot 41-I | DG754 | 329 | 77.8 |
| Hotspot 41-I | DG755 | 330 | 80.6 |
| Hotspot 41-II | DG756 | 331 | 89.8 |
| Hotspot 41-II | DG757 | 332 | 92.1 |
| Hotspot 41-II | DG758 | 333 | 94.3 |
| Hotspot 41-II | DG759 | 334 | 93.9 |
| Hotspot 41-II | DG760 | 335 | 95.8 |
| Hotspot 41-II | DG761 | 336 | 94.6 |
| Hotspot 41-II | DG762 | 337 | 95.2 |
| Hotspot 41-II | DG764 | 338 | 94.5 |
| Hotspot 41-II | DG765 | 339 | 88.4 |

TABLE 7-continued

TABLE 7. Exon 41 skipping efficiency of various SPs with SEQ ID NO: 1-SEQ ID NO: 19, SEQ ID NO: 310-SEQ ID NO: 390.

| SP set | SP_ID | SEQ ID NO | Exon 41 skipping (%) |
|---|---|---|---|
| Hotspot 41-II | DG766 | 340 | 95.4 |
| Hotspot 41-II | DG767 | 341 | 92.1 |
| Hotspot 41-II | DG769 | 342 | 91.7 |
| Hotspot 41-II | DG770 | 343 | 94.3 |
| Hotspot 41-II | DG771 | 344 | 93.1 |
| Hotspot 41-II | DG772 | 345 | 93.7 |
| Hotspot 41-II | DG773 | 346 | 94.7 |
| Hotspot 41-II | DG774 | 347 | 94.2 |
| Hotspot 41-II | DG775 | 348 | 93.2 |
| Hotspot 41-II | DG776 | 349 | 95.6 |
| Hotspot 41-II | DG777 | 350 | 91.2 |
| Hotspot 41-II | DG778 | 351 | 95.0 |
| Hotspot 41-II | DG779 | 352 | 94.6 |
| Hotspot 41-II | DG780 | 353 | 92.7 |
| Hotspot 41-II | DG781 | 354 | 93.2 |
| Hotspot 41-II | DG782 | 355 | 92.9 |
| Hotspot 41-II | DG783 | 356 | 96.2 |
| Hotspot 41-II | DG784 | 357 | 96.1 |
| Hotspot 41-II | DG785 | 358 | 91.1 |
| Hotspot 41-II | DG786 | 359 | 92.8 |
| Hotspot 41-II | DG787 | 360 | 93.2 |
| Hotspot 41-II | DG788 | 361 | 91.9 |
| Hotspot 41-II | DG789 | 362 | 92.5 |
| Hotspot 41-II | DG790 | 363 | 94.2 |
| Hotspot 41-III | DG791 | 364 | 33.6 |
| Hotspot 41-III | DG792 | 365 | 57.1 |
| Hotspot 41-III | DG793 | 366 | 70.2 |
| Hotspot 41-III | DG794 | 367 | 26.4 |
| Hotspot 41-III | DG795 | 368 | 57.9 |
| Hotspot 41-III | DG796 | 369 | 85.7 |
| Hotspot 41-III | DG798 | 370 | 18.9 |
| Hotspot 41-III | DG799 | 371 | 32.2 |
| Hotspot 41-III | DG800 | 372 | 64.3 |
| Hotspot 41-III | DG801 | 373 | 26.0 |
| Hotspot 41-III | DG802 | 374 | 49.2 |
| Hotspot 41-III | DG803 | 375 | 59.5 |
| Hotspot 41-III | DG804 | 376 | 83.6 |
| Hotspot 41-III | DG805 | 377 | 70.6 |
| Hotspot 41-III | DG806 | 378 | 39.8 |
| Hotspot 41-III | DG807 | 379 | 39.2 |
| Hotspot 41-III | DG808 | 380 | 49.2 |
| Hotspot 41-III | DG809 | 381 | 22.0 |
| Hotspot 41-III | DG810 | 382 | 59.9 |
| Hotspot 41-III | DG811 | 383 | 66.8 |
| Hotspot 41-III | DG812 | 384 | 40.8 |
| Hotspot 41-III | DG813 | 385 | 84.4 |
| Hotspot 41-III | DG814 | 386 | 24.5 |
| Hotspot 41-III | DG815 | 387 | 62.3 |
| Hotspot 41-III | DG816 | 388 | 21.6 |
| Hotspot 41-III | DG818 | 389 | 42.4 |
| Hotspot 41-III | DG819 | 390 | 51.9 |

In order to further obtain SPs that cause skipping of the exon 41 of the CEP290 mRNA, SPs were designed against CEP90 pre-mRNA corresponding to the chromosomal interval chr12: 88470992-88471128. The sequences of various synthetic polynucleotides as described herein are listed in TABLE 1. These SPs with SEQ ID NO: 541-SEQ ID NO: 684 varied in length from 16 to 20 nucleotides. In the target region for exon 41, two additional hotspot regions were identified that show strong exon-skipping. The first additional hotspot region (41-III) contains SPs DG2974-DG3011 (SEQ ID NO: 541-SEQ ID NO: 578), with the strongest effect observed for DG2976, DG2982, DG2996, DG3001, DG3002, DG3003, DG3004, DG3005, DG3006, DG3007, DG3008, DG3009, and DG3010 (SEQ ID NOs: 543, 549, 563, 568, 569, 570, 571, 572, 573, 574, 575, 576, 577, >90% exon-skipping). The second additional hotspot region (41-IV) contains SPs DG3018-DG3066 (SEQ ID NO: 585-SEQ ID NO: 633), with the strongest effect observed for DG3027, DG3028, DG3029, DG3032, DG3034, DG3037, DG3048, and DG3049 (>90% exon-skipping, SEQ ID NO: 594, 595, 596, 599, 601, 604, 615, 616).

TABLE 8 shows the exon 46 skipping efficiency of synthetic polynucleotides with SEQ ID NO: 541-SEQ ID NO: 684.

TABLE 8

TABLE 8. Exon 41 skipping efficiency of various SPs with SEQ ID NO: 541-SEQ ID NO: 684.

| SP set | SP_ID | SEQ ID NO | Exon 41 skipping (%) |
|---|---|---|---|
| Hotspot 41-IV | DG2974 | 541 | 82.2 |
| Hotspot 41-IV | DG2975 | 542 | 85.0 |
| Hotspot 41-IV | DG2976 | 543 | 99.7 |
| Hotspot 41-IV | DG2977 | 544 | 55.7 |
| Hotspot 41-IV | DG2978 | 545 | 61.8 |
| Hotspot 41-IV | DG2979 | 546 | 57.6 |
| Hotspot 41-IV | DG2980 | 547 | 75.1 |
| Hotspot 41-IV | DG2981 | 548 | 89.4 |
| Hotspot 41-IV | DG2982 | 549 | 97.9 |
| Hotspot 41-IV | DG2983 | 550 | 79.0 |
| Hotspot 41-IV | DG2984 | 551 | 81.1 |
| Hotspot 41-IV | DG2985 | 552 | 87.2 |
| Hotspot 41-IV | DG2986 | 553 | 70.1 |
| Hotspot 41-IV | DG2987 | 554 | 79.3 |
| Hotspot 41-IV | DG2988 | 555 | 87.2 |
| Hotspot 41-IV | DG2989 | 556 | 80.4 |
| Hotspot 41-IV | DG2990 | 557 | 48.8 |
| Hotspot 41-IV | DG2991 | 558 | 21.5 |
| Hotspot 41-IV | DG2992 | 559 | 23.1 |
| Hotspot 41-IV | DG2993 | 560 | 26.3 |
| Hotspot 41-IV | DG2994 | 561 | 30.1 |
| Hotspot 41-IV | DG2995 | 562 | 66.6 |
| Hotspot 41-IV | DG2996 | 563 | 91.9 |
| Hotspot 41-IV | DG2997 | 564 | 66.3 |
| Hotspot 41-IV | DG2998 | 565 | 77.6 |
| Hotspot 41-IV | DG2999 | 566 | 45.9 |
| Hotspot 41-IV | DG3000 | 567 | 54.4 |
| Hotspot 41-IV | DG3001 | 568 | 97.1 |
| Hotspot 41-IV | DG3002 | 569 | 99.5 |
| Hotspot 41-IV | DG3003 | 570 | 99.5 |
| Hotspot 41-IV | DG3004 | 571 | 98.7 |
| Hotspot 41-IV | DG3005 | 572 | 97.7 |
| Hotspot 41-IV | DG3006 | 573 | 98.4 |
| Hotspot 41-IV | DG3007 | 574 | 98.1 |
| Hotspot 41-IV | DG3008 | 575 | 99.5 |
| Hotspot 41-IV | DG3009 | 576 | 97.3 |
| Hotspot 41-IV | DG3010 | 577 | 91.9 |
| Hotspot 41-IV | DG3011 | 578 | 27.0 |
|  | DG3012 | 579 | 1.8 |
|  | DG3013 | 580 | 3.0 |
|  | DG3014 | 581 | 7.5 |
|  | DG3015 | 582 | 15.5 |
|  | DG3016 | 583 | 9.5 |
|  | DG3017 | 584 | 2.9 |
| Hotspot 41-V | DG3018 | 585 | 16.3 |
| Hotspot 41-V | DG3019 | 586 | 74.2 |
| Hotspot 41-V | DG3020 | 587 | 67.3 |
| Hotspot 41-V | DG3021 | 588 | 25.5 |
| Hotspot 41-V | DG3022 | 589 | 22.7 |
| Hotspot 41-V | DG3023 | 590 | 20.0 |
| Hotspot 41-V | DG3024 | 591 | 4.1 |
| Hotspot 41-V | DG3025 | 592 | 68.0 |
| Hotspot 41-V | DG3026 | 593 | 61.2 |
| Hotspot 41-V | DG3027 | 594 | 95.5 |
| Hotspot 41-V | DG3028 | 595 | 100.0 |
| Hotspot 41-V | DG3029 | 596 | 100.0 |
| Hotspot 41-V | DG3030 | 597 | 86.6 |
| Hotspot 41-V | DG3031 | 598 | 31.1 |
| Hotspot 41-V | DG3032 | 599 | 93.5 |
| Hotspot 41-V | DG3033 | 600 | 51.5 |
| Hotspot 41-V | DG3034 | 601 | 100.0 |
| Hotspot 41-V | DG3035 | 602 | 48.4 |
| Hotspot 41-V | DG3036 | 603 | 34.1 |
| Hotspot 41-V | DG3037 | 604 | 100.0 |
| Hotspot 41-V | DG3038 | 605 | 0.0 |
| Hotspot 41-V | DG3039 | 606 | 6.6 |

TABLE 8-continued

TABLE 8. Exon 41 skipping efficiency of various SPs with SEQ ID NO: 541-SEQ ID NO: 684.

| SP set | SP_ID | SEQ ID NO | Exon 41 skipping (%) |
|---|---|---|---|
| Hotspot 41-V | DG3040 | 607 | 0.0 |
| Hotspot 41-V | DG3041 | 608 | 39.0 |
| Hotspot 41-V | DG3042 | 609 | 27.9 |
| Hotspot 41-V | DG3043 | 610 | 0.0 |
| Hotspot 41-V | DG3044 | 611 | 0.0 |
| Hotspot 41-V | DG3045 | 612 | 31.8 |
| Hotspot 41-V | DG3046 | 613 | 9.1 |
| Hotspot 41-V | DG3047 | 614 | 20.1 |
| Hotspot 41-V | DG3048 | 615 | 95.2 |
| Hotspot 41-V | DG3049 | 616 | 90.1 |
| Hotspot 41-V | DG3050 | 617 | 12.8 |
| Hotspot 41-V | DG3051 | 618 | 24.7 |
| Hotspot 41-V | DG3052 | 619 | 50.9 |
| Hotspot 41-V | DG3053 | 620 | 36.7 |
| Hotspot 41-V | DG3054 | 621 | 53.8 |
| Hotspot 41-V | DG3055 | 622 | 0.8 |
| Hotspot 41-V | DG3056 | 623 | 1.5 |
| Hotspot 41-V | DG3057 | 624 | 45.9 |
| Hotspot 41-V | DG3058 | 625 | 19.8 |
| Hotspot 41-V | DG3059 | 626 | 21.2 |
| Hotspot 41-V | DG3060 | 627 | 28.9 |
| Hotspot 41-V | DG3061 | 628 | 25.6 |
| Hotspot 41-V | DG3062 | 629 | 21.4 |
| Hotspot 41-V | DG3063 | 630 | 8.1 |
| Hotspot 41-V | DG3064 | 631 | 2.9 |
| Hotspot 41-V | DG3065 | 632 | 1.1 |
| Hotspot 41-V | DG3066 | 633 | 1.4 |
|  | DG4388 | 634 | 0.1 |
|  | DG4389 | 635 | 0.0 |
|  | DG4390 | 636 | 0.4 |
|  | DG4391 | 637 | 0.3 |
|  | DG4392 | 638 | 0.5 |
|  | DG4393 | 639 | 0.6 |
|  | DG4394 | 640 | 1.1 |
|  | DG4395 | 641 | 1.7 |
|  | DG4396 | 642 | 6.6 |
|  | DG4397 | 643 | 1.2 |
|  | DG4398 | 644 | 2.3 |
|  | DG4399 | 645 | 0.8 |
|  | DG4400 | 646 | 2.2 |
|  | DG4401 | 647 | 1.0 |
|  | DG4402 | 648 | 2.1 |
|  | DG4403 | 649 | 0.1 |
|  | DG4405 | 650 | 0.0 |
|  | DG4406 | 651 | 0.3 |
|  | DG4407 | 652 | 0.7 |
|  | DG4408 | 653 | 0.7 |
|  | DG4409 | 654 | 0.7 |
|  | DG4410 | 655 | 1.4 |
|  | DG4411 | 656 | 1.9 |
|  | DG4412 | 657 | 1.1 |
|  | DG4413 | 658 | 3.1 |
|  | DG4414 | 659 | 0.8 |
|  | DG4415 | 660 | 7.9 |
|  | DG4416 | 661 | 1.7 |
|  | DG4417 | 662 | 0.3 |
|  | DG4419 | 663 | 0.5 |
|  | DG4420 | 664 | 1.1 |
|  | DG4421 | 665 | 1.6 |
|  | DG4422 | 666 | 1.2 |
|  | DG4423 | 667 | 2.4 |
|  | DG4424 | 668 | 1.8 |
|  | DG4425 | 669 | 0.6 |
|  | DG4426 | 670 | 1.5 |
|  | DG4427 | 671 | 2.3 |
|  | DG4428 | 672 | 15.2 |
|  | DG4429 | 673 | 0.6 |
|  | DG4430 | 674 | 1.0 |
|  | DG4431 | 675 | 1.9 |
|  | DG4432 | 676 | 1.6 |
|  | DG4433 | 677 | 1.8 |
|  | DG4434 | 678 | 2.8 |
|  | DG4435 | 679 | 1.6 |
|  | DG4436 | 680 | 1.3 |
|  | DG4437 | 681 | 1.7 |
|  | DG4438 | 682 | 0.7 |
|  | DG4439 | 683 | 2.3 |
|  | DG4440 | 684 | 2.5 |

Example 9

Identification of Exon-Skipping Synthetic Polynucleotides for CEP290 Exon 46

This example demonstrates the identification and optimization of SPs to induce skipping of CEP290 exon 46.

Figure 3B:
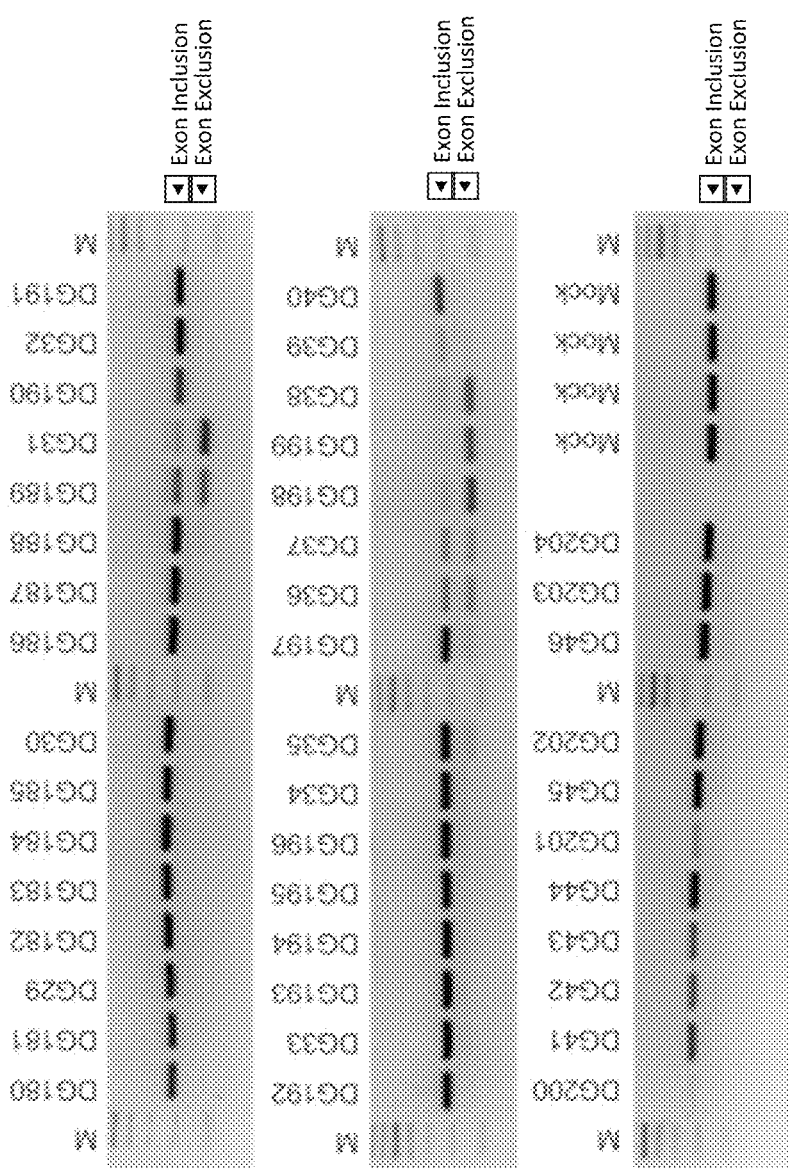
FIG. 3B shows the RT-PCR analysis of 50,000 HEK293T cells transfected with 50 pmol synthetic polynucleotides against CEP290 exon 46. PCR primers were designed to amplify a CEP290 region containing exon 45, 46 and 47. PCR products were analyzed by agarose gel electrophoresis analysis. Exon 46 inclusion and exclusion bands are 222 bp and 135 bp respectively. M indicates the 100 bp DNA ladder.
Figure 3C:
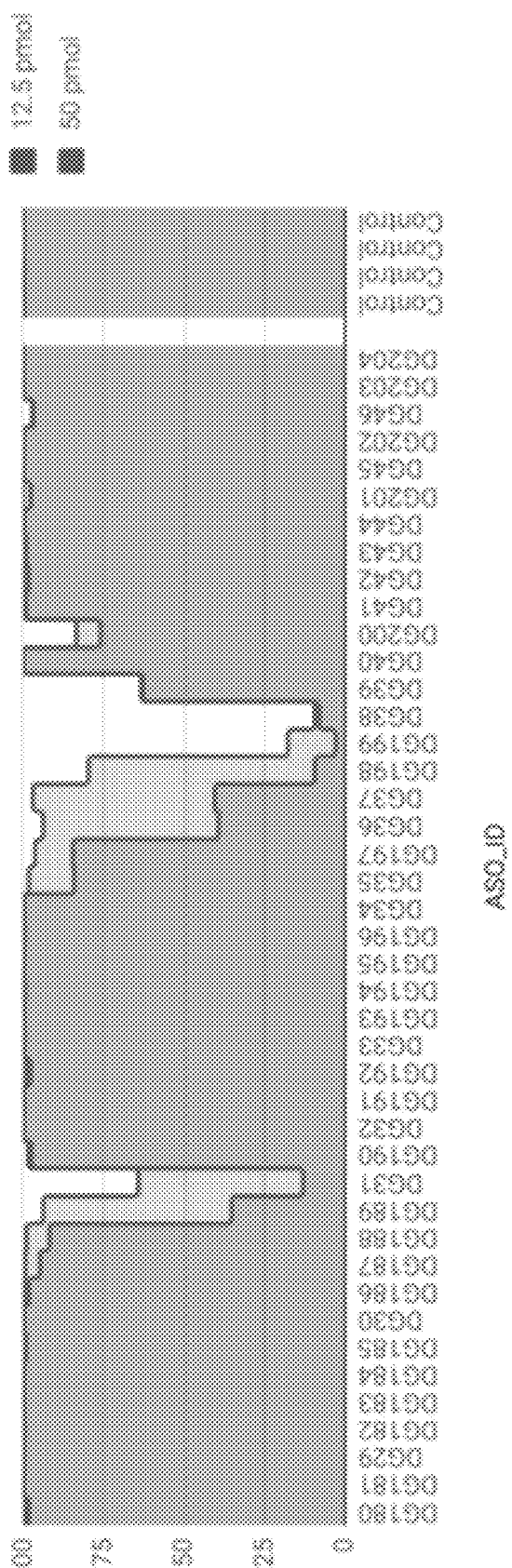
FIG. 3C shows the quantitation of the RT-PCR fragments as shown in FIG. 3B. Control samples are mock-treated for the 12.5 pmol series and non-treated for the 50 pmol series.
Figure 3D:
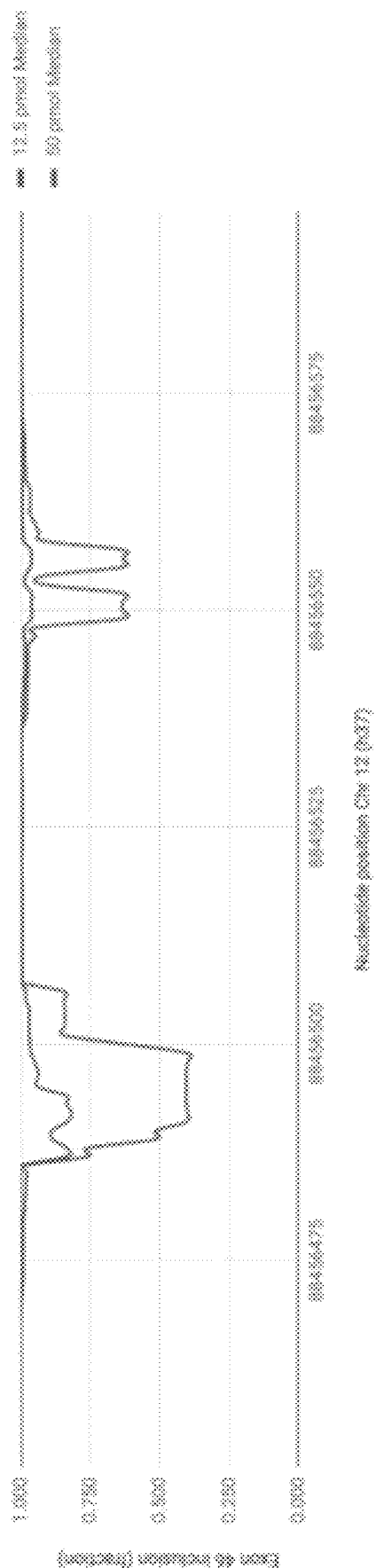
FIG. 3D shows the median exon-skipping values per nucleotide position.

In order to obtain SPs that cause skipping of the exon 46 of the CEP290 mRNA, SPs were designed against CEP90 pre-mRNA corresponding to the chromosomal interval chr12:88456409-88456596. The sequences of various synthetic polynucleotides as described herein are listed in TABLE 1. These SPs with SEQ ID NO: 20-SEQ ID NO: 69 varied in length from 16 to 20 nucleotides and targeted intron 45, exon 46 and intron 46 of the CEP290 gene (FIG. 3A). To assay their exon-skipping potential in cell culture systems, 50,000 HEK293T cells were reverse transfected in a 96-well format with two absolute doses of either 12.5 pmol or 50.0 pmol, respectively, and the effect on exon-skipping (measured as the difference in PSI) for exon 46 was determined by RT-PCR (FIG. 3B, FIG. 3C). In the target region for exon 46, two hotspot regions were identified that show strong exon-skipping. The first hotspot region (46-I) contains SPs DG31, DG188 and DG189 (SEQ ID NO: 22, SEQ ID NO: 46, and SEQ ID NO: 47), with the strongest effect observed for DG31 (SEQ ID NO: 22, ~85% exon-skipping). The second hotspot region (46-II) contains SPs DG36, DG37, DG38, DG39, DG197, DG198, DG199 and DG200 (SEQ ID NO: 27-SEQ ID NO: 30, SEQ ID NO: 55-SEQ ID NO: 58), with the strongest effect observed for DG38 (>90% exon-skipping, SEQ ID NO: 29) in the lower dose (12.5 pmol) series compared to the higher dose (50 pmol) series.

TABLE 9 shows the exon 46 skipping efficiency of synthetic polynucleotides with SEQ ID NO: 20-SEQ ID NO: 62 using 12.5 pmol and 50 pmol of synthetic polynucleotide, respectively.

TABLE 9

TABLE 9. Exon-skipping efficiencies using SPs with SEQ ID NO: 20-SEQ ID NO: 69 at 12.5 pmol and 50 pmol transfection concentrations.

| SP ID | Exon 46 skipping at 12.5 pmol (%) | Exon 46 skipping at 50 pmol (%) | SEQ ID NO |
|---|---|---|---|
| DG199 | 82.3 | 97.0 | 57 |
| DG38 | 90.6 | 92.0 | 29 |
| DG198 | 20.3 | 90.6 | 56 |
| DG31 | 35.7 | 87.0 | 22 |
| DG189 | 6.3 | 64.7 | 47 |
| DG36 | 6.2 | 60.6 | 27 |
| DG37 | 3.1 | 59.5 | 28 |
| DG39 | 36.5 | 37.4 | 30 |
| DG200 | 16.6 | 24.1 | 58 |
| DG35 | 1.8 | 15.9 | 26 |
| DG197 | 3.7 | 15.5 | 55 |
| DG188 | 1.0 | 8.2 | 46 |
| DG187 | 0.7 | 5.1 | 45 |

TABLE 9-continued

TABLE 9. Exon-skipping efficiencies using SPs with SEQ ID NO: 20-SEQ ID NO: 69 at 12.5 pmol and 50 pmol transfection concentrations.

| SP ID | Exon 46 skipping at 12.5 pmol (%) | Exon 46 skipping at 50 pmol (%) | SEQ ID NO |
|---|---|---|---|
| DG46 | 2.7 | 3.4 | 37 |
| DG190 | 1.6 | 2.7 | 48 |
| DG201 | 0.0 | 2.3 | 59 |
| DG192 | 0.8 | 2.2 | 50 |
| DG186 | 0.5 | 1.8 | 44 |
| DG180 | 0.7 | 1.7 | 38 |
| DG42 | 0.1 | 1.5 | 33 |
| DG43 | 0.0 | 1.0 | 34 |
| DG41 | 0.0 | 0.9 | 32 |
| DG185 | 0.6 | 0.9 | 43 |
| DG44 | 0.0 | 0.5 | 35 |
| DG181 | 0.3 | 0.1 | 39 |
| DG194 | 0.6 | 0.0 | 52 |
| DG196 | 0.5 | 0.0 | 54 |
| DG33 | 0.5 | 0.0 | 24 |
| DG182 | 0.5 | 0.0 | 40 |
| DG191 | 0.4 | 0.0 | 49 |
| DG184 | 0.4 | 0.0 | 42 |
| DG34 | 0.4 | 0.0 | 25 |
| DG30 | 0.3 | 0.0 | 21 |
| DG183 | 0.3 | 0.0 | 41 |
| DG193 | 0.3 | 0.0 | 51 |
| DG29 | 0.3 | 0.0 | 20 |
| DG195 | 0.2 | 0.0 | 53 |
| DG32 | 0.0 | 0.0 | 23 |
| DG40 | 0.0 | 0.0 | 31 |
| DG45 | 0.0 | 0.0 | 36 |
| DG202 | 0.0 | 0.0 | 60 |
| DG203 | 0.0 | 0.0 | 61 |
| DG204 | 0.0 | 0.0 | 62 |
| Control | 0.0 | 0.4 | n/a |
| Control | 0.0 | 0.5 | n/a |
| Control | 0.0 | 0.0 | n/a |
| Control | 0.0 | 0.0 | n/a |

In order to further obtain SPs that cause skipping of the exon 46 of the CEP290 mRNA, SPs were designed against CEP90 pre-mRNA corresponding to the chromosomal interval chr12: 88456412-88456611. The sequences of various synthetic polynucleotides as described herein are listed in TABLE 1. These SPs with SEQ ID NO: 395-SEQ ID NO: 460, or SEQ ID NO: 685-SEQ ID NO: 702 varied in length from 16 to 20 nucleotides. To assay their exon-skipping potential in cell culture systems, 50,000 HEK293T cells were reverse transfected in a 96-well format with either or two absolute doses of either 12.5 pmol or 50.0 pmol, respectively, and the effect on exon-skipping (measured as the difference in PSI) for exon 46 was determined by RT-PCR. In the target region for exon 46, two additional hotspot regions were identified that show strong exon-skipping. The first additional hotspot region (46-III) contains SPs DG1539-DG1553 (SEQ ID NO: 443-SEQ ID NO: 457), with the strongest effect observed for DG1541 (SEQ ID NO: 445, ~85% exon-skipping). The second additional hotspot region (46-IV) contains SPs DG1554-DG1556 (SEQ ID NO: 458-SEQ ID NO: 460), with the strongest effect observed for DG1154 and DG1556 (>40% exon-skipping, SEQ ID NO: 458 and SEQ ID NO: 458).

TABLE 10 shows the exon 46 skipping efficiency of synthetic polynucleotides with SEQ NO: 395-SEQ ID NO: 460, or SEQ ID NO: 685-SEQ ID NO: 702 using either 12.5 pmol and 50 pmol of synthetic polynucleotide, respectively.

TABLE 10

TABLE 10. Exon-skipping efficiencies using SPs with SEQ ID NO: 395-SEQ ID NO: 460, or SEQ ID NO: 685-SEQ ID NO: 702 at 12.5 pmol and 50 pmol transfection concentrations.

| SP ID | Exon 46 skipping at 12.5 pmol (%) | Exon 46 skipping at 50 pmol (%) | SEQ ID NO |
|---|---|---|---|
| DG1489 | 0 | n/a | 395 |
| DG1490 | 6.846 | n/a | 396 |
| DG1492 | 0.568 | n/a | 397 |
| DG1493 | 0 | n/a | 398 |
| DG1494 | 0 | n/a | 399 |
| DG1495 | 0 | n/a | 400 |
| DG1496 | 0 | n/a | 401 |
| DG1497 | 0 | n/a | 402 |
| DG1498 | 1.727 | n/a | 403 |
| DG1499 | 0.626 | n/a | 404 |
| DG1500 | 0 | n/a | 405 |
| DG1501 | 0 | n/a | 406 |
| DG1502 | 0 | n/a | 407 |
| DG1503 | 0.591 | n/a | 408 |
| DG1504 | 1.915 | n/a | 409 |
| DG1505 | 1.866 | n/a | 410 |
| DG1506 | 11.141 | n/a | 411 |
| DG1507 | 6.373 | n/a | 412 |
| DG1508 | 0 | n/a | 413 |
| DG1509 | 3.582 | n/a | 414 |
| DG1510 | 0 | n/a | 415 |
| DG1511 | 0.015 | n/a | 416 |
| DG1512 | 0 | n/a | 417 |
| DG1513 | 0 | n/a | 418 |
| DG1514 | 1.617 | n/a | 419 |
| DG1515 | 0.605 | n/a | 420 |
| DG1516 | 0.841 | n/a | 421 |
| DG1517 | 1.391 | n/a | 422 |
| DG1518 | 0.167 | n/a | 423 |
| DG1519 | 0 | n/a | 424 |
| DG1520 | 0 | n/a | 425 |
| DG1521 | 0 | n/a | 426 |
| DG1522 | 3.319 | n/a | 427 |
| DG1523 | 4.053 | n/a | 428 |
| DG1524 | 11.131 | n/a | 429 |
| DG1525 | 10.497 | n/a | 430 |
| DG1526 | 10.241 | n/a | 431 |
| DG1528 | 8.678 | n/a | 432 |
| DG1529 | 0.226 | n/a | 433 |
| DG1530 | 0 | n/a | 434 |
| DG1531 | 0 | n/a | 435 |
| DG1532 | 2.521 | n/a | 436 |
| DG1533 | 14.822 | n/a | 437 |
| DG1534 | 5.495 | n/a | 438 |
| DG1535 | 0.055 | n/a | 439 |
| DG1536 | 0 | n/a | 440 |
| DG1537 | 0 | n/a | 441 |
| DG1538 | 0 | n/a | 442 |
| DG1539 | 5.495 | n/a | 443 |
| DG1540 | 17.931 | n/a | 444 |
| DG1541 | 85.808 | n/a | 445 |
| DG1542 | 8.463 | n/a | 446 |
| DG1543 | 28.303 | n/a | 447 |
| DG1544 | 15.994 | n/a | 448 |
| DG1545 | 21.433 | n/a | 449 |
| DG1546 | 0 | n/a | 450 |
| DG1547 | 1.356 | n/a | 451 |
| DG1548 | 28.092 | n/a | 452 |
| DG1549 | 10.83 | n/a | 453 |
| DG1550 | 0.95 | n/a | 454 |
| DG1551 | 0.734 | n/a | 455 |
| DG1552 | 0 | n/a | 456 |
| DG1553 | 0.619 | n/a | 457 |
| DG1554 | 40.006 | n/a | 458 |
| DG1555 | 11.053 | n/a | 459 |
| DG1556 | 43.053 | n/a | 460 |
| DG4441 | n/a | 0 | 685 |
| DG4442 | n/a | 0.89 | 686 |
| DG4443 | n/a | 0 | 687 |
| DG4444 | n/a | 0 | 688 |
| DG4446 | n/a | 0 | 689 |
| DG4447 | n/a | 0 | 690 |
| DG4448 | n/a | 0 | 691 |

TABLE 10-continued

TABLE 10. Exon-skipping efficiencies using SPs with SEQ ID NO: 395-SEQ ID NO: 460, or SEQ ID NO: 685-SEQ ID NO: 702 at 12.5 pmol and 50 pmol transfection concentrations.

| SP ID | Exon 46 skipping at 12.5 pmol (%) | Exon 46 skipping at 50 pmol (%) | SEQ ID NO |
|---|---|---|---|
| DG4449 | n/a | 0.237 | 692 |
| DG4450 | n/a | 0.551 | 693 |
| DG4451 | n/a | 0 | 694 |
| DG4452 | n/a | 0 | 695 |
| DG4453 | n/a | 0 | 696 |
| DG4454 | n/a | 0 | 697 |
| DG4455 | n/a | 0 | 698 |
| DG4456 | n/a | 0 | 699 |
| DG4457 | n/a | 0 | 700 |
| DG4458 | n/a | 0 | 701 |
| DG4459 | n/a | 0 | 702 |

Example 10

Functional Rescue of CEP290 Exon 36 Containing LOF Mutations by Exon-Skipping Synthetic Polynucleotides This example demonstrates the identification of SPs which induce skipping of CEP290 exon 36 containing a LOF mutant resulting in restoration of the wildtype phenotype.

To generate CEP290 CRISPR exon 36 mutant, guide RNA targeting exons 36 was cloned into a CRISPR vector. These vectors were transfected into HEK293T (human embryonic kidney) cells. A CEP290 exon 36 mutant containing a LOF mutation was generated.

Figure 8A:
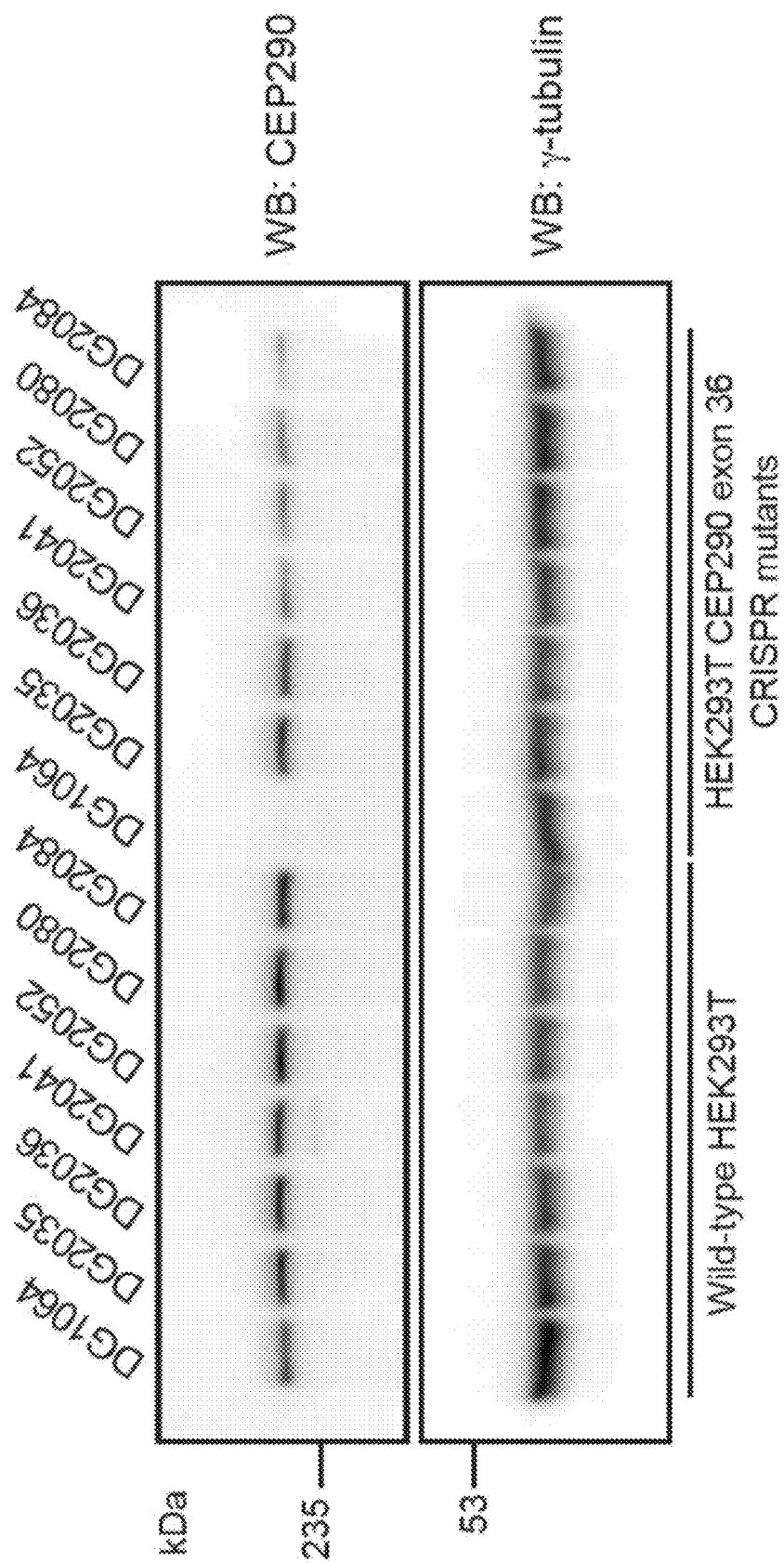
FIG. 8A shows western blot analysis HEK293T wild-type and CEP290 exon 36 CRISPR mutant cells transfected with the indicated SPs. An antibody recognizing the C-terminal region of CEP290 was used. Gamma-tubulin was used as a loading control
Figure 8B:
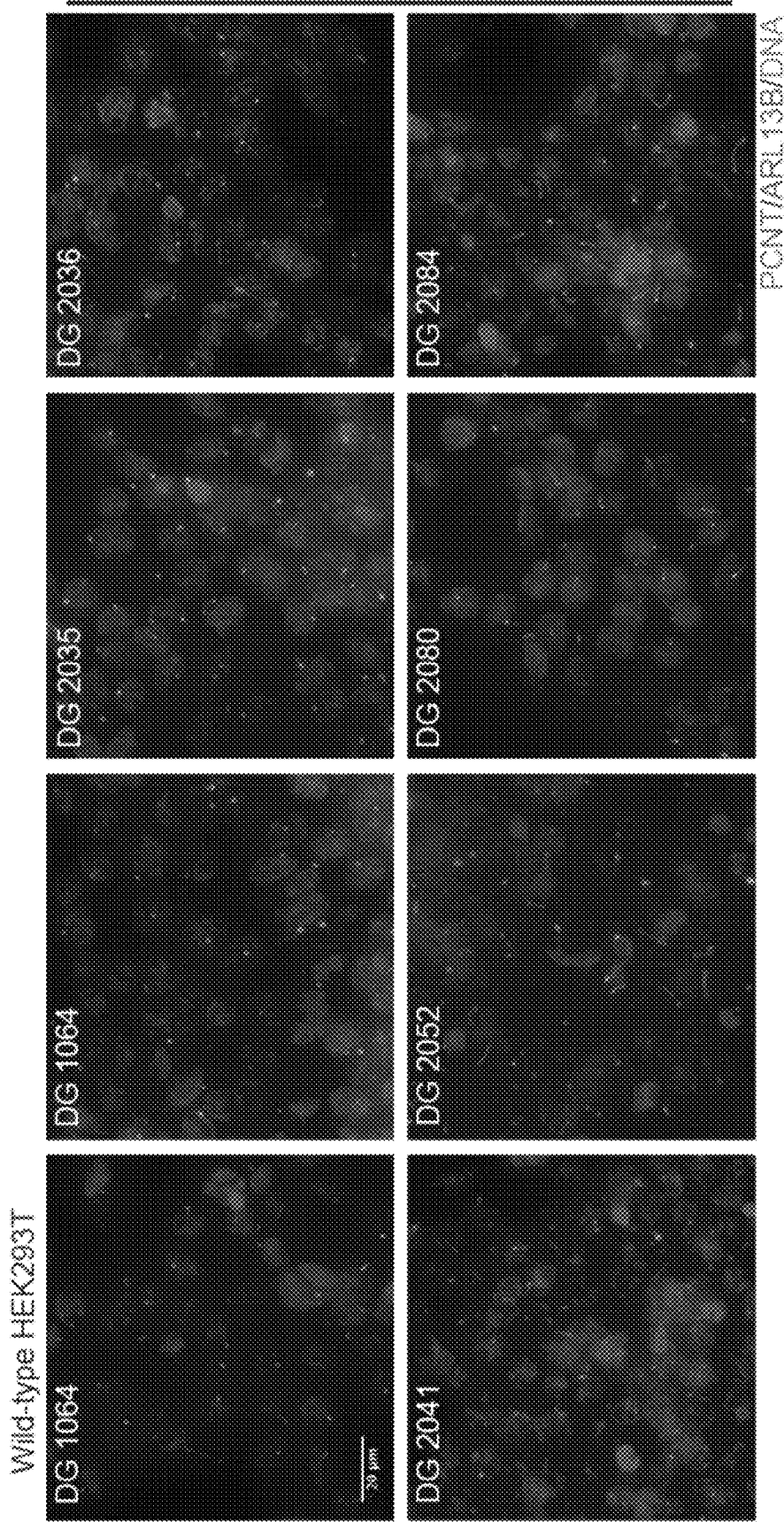
FIG. 8B shows immunohistochemistry staining of HEK293T wild-type and mutant cells (CEP290 exon 36 CRISPR mutants) transfected with the indicated SPs stained with antibodies against pericentrin (centrosome/basal body) and ARL13B (cilium marker). DNA was stained with Hoechst dye.

Upon identification of CRISPR clones carrying the above mutation of interest, and of SPs that can cause efficient skipping, the ability to restore CEP290 expression by skipping exon 36 using SPs was examined. HEK293T wild-type cells and an exon 36 mutant clone were transfected with control SPs (DG1064) and SPs previously shown to cause skipping. Western blot analysis was then performed to assess CEP290 expression levels in these cells (FIG. 8A). Observing the western blot, it is shown that the CEP290 exon 36 mutant does not produce detectable levels of CEP290 protein. Transfecting the CEP290 exon 36 mutant with known exon 36 skipping SPs (SEQ ID NOs: 486, 487, 492, 503, 531, and 535) rescues the CEP290 protein levels in the mutant.

To confirm that the skipping of exon 36 rescued protein function as well as expression a ciliation assay was performed (FIG. 8B, FIG. 8C, FIG. 8D, FIG. 8E). Ciliation was assessed by staining with antibodies against pericentrin (centrosome/basal body) and ARL13B (cilium marker). DNA was stained with Hoechst dye.

Figure 8C:
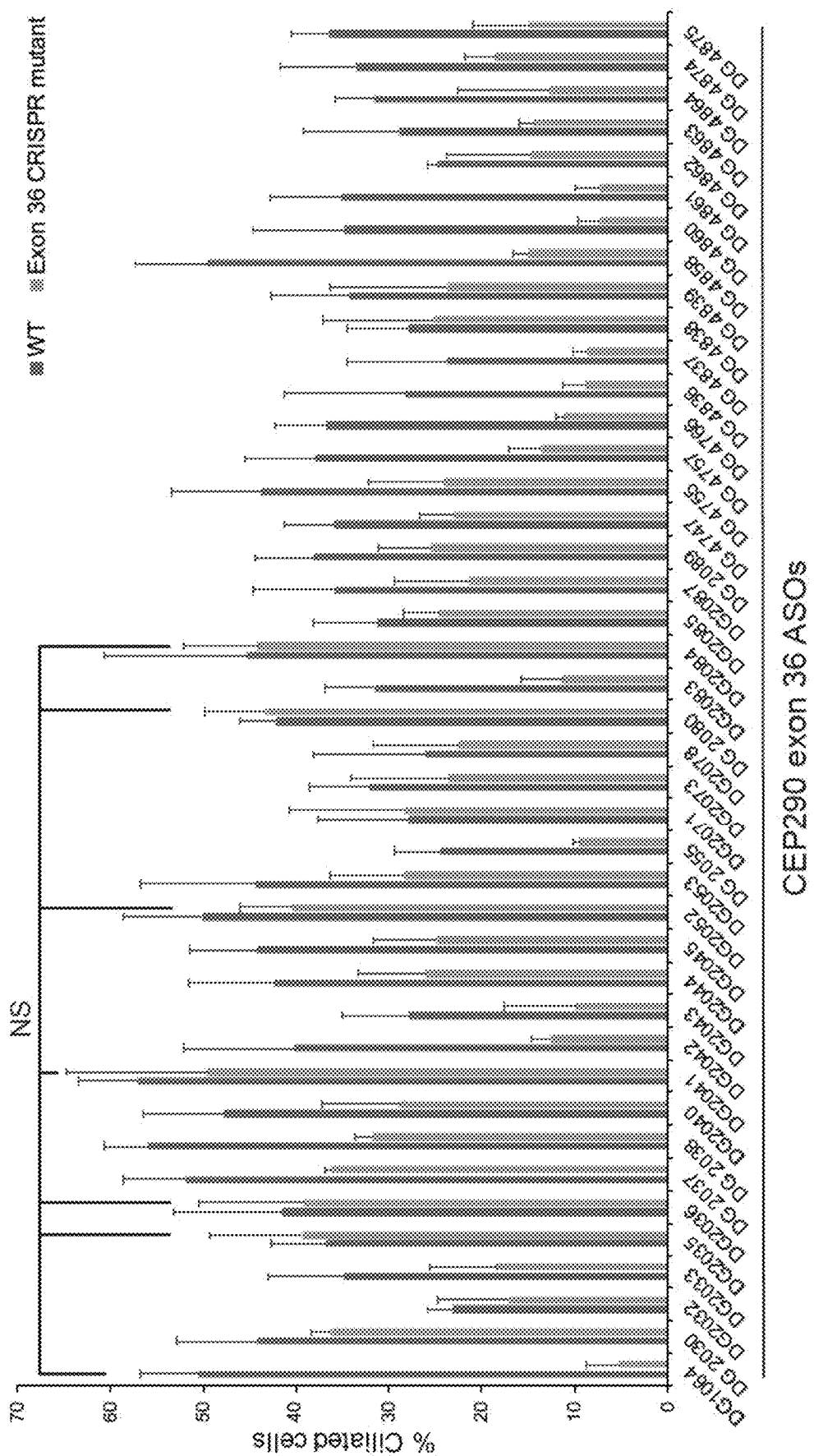
FIG. 8C shows the mean percentage of ciliated cells (n>150 cells per sample, 3 independent experiments) in wild-type and CEP290 exon 36 CRISPR mutant cells transfected with the indicated SPs. Error bars indicate SD. NS—non significant.

SP transfected wild-type and exon 36 mutant cell ciliation levels were examined (FIG. 8B) and the percentage of ciliation in each population computed (FIG. 8C). Treating with a control SP (DG1064) resulted in a decrease in ciliation levels in the exon 36 mutant CEP290 cells versus the wild-type cells. Treatment with SPs DG2035, DG2036, DG2041, DG2052, DG2080, and DG2084 (SEQ ID NOs: 486, 487, 492, 503, 531, and 535) rescued ciliation levels to wild-type levels (FIG. 8C).

Figure 8E:
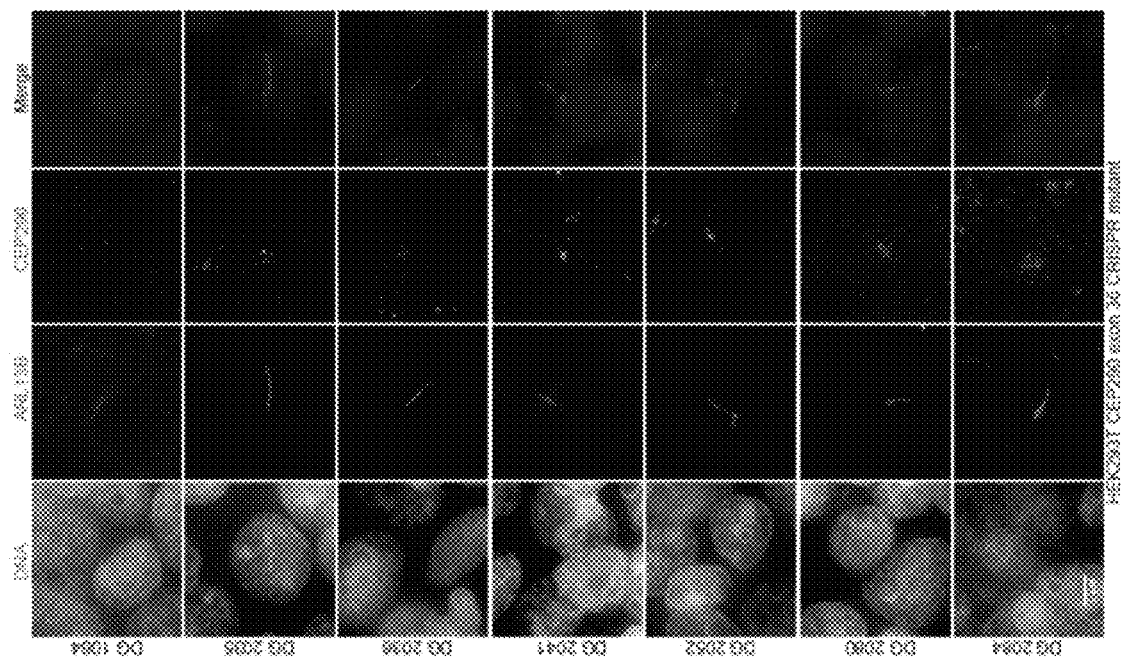
FIG. 8E shows Sub-cellular localization analysis of the rescued CEP290 protein. HEK293T CEP290 exon 36 CRISPR mutant cells were transfected with the indicated SPs and stained with antibodies against ARL13B (ciliary marker) and CEP290. DNA was stained with Hoechst dye.

CEP290 localization was also assessed by staining with antibodies against CEP290, PCM1 (centriolar satellite marker) and ARL13B. Cells transfected with the control SP (DG1064) showed no signal for CEP290 (FIG. 8D, FIG. 8E). Upon treatment with the SPs that rescue protein expression (SEQ ID NOs: 486, 487, 492, 503, 531, and 535) (FIG. 8A) a CEP290 signal is observed both at the centrosomal area and centriolar satellites (FIG. 8D), and the base of primary cilia (FIG. 8E). These results show that the amino acid residues coded by exon 36 are not required for the localization of CEP290 to the centrosome, centriolar satellites and primary cilium. Skipping of CEP290 exon 36 by SPs may thus be beneficial in the treatment of individuals with LOF mutants in exon 36.

Example 11

Functional Rescue of CEP290 Exon 41 Containing LOF Mutations by Exon-Skipping Synthetic Polynucleotides This example demonstrates the identification of SPs which induce skipping of CEP290 exon 41 containing a LOF mutant resulting in restoration of the wildtype phenotype.

To generate CEP290 CRISPR exon 41 mutant, guide RNA targeting exons 41 was cloned into a CRISPR vector. These vectors were transfected into HEK293T (human embryonic kidney) cells. A CEP290 exon 41 mutant containing LOF mutation was generated.

Figure 9A:
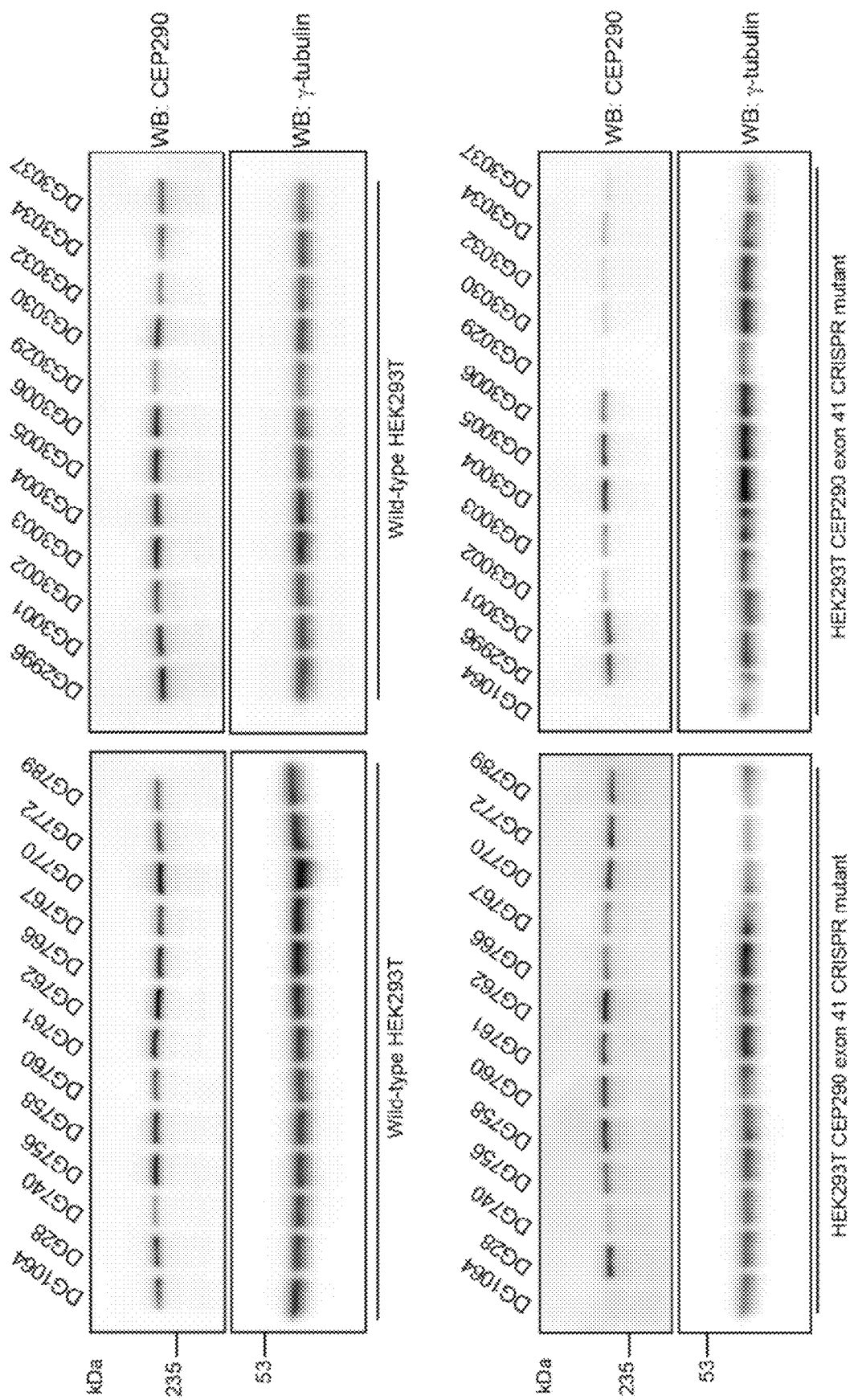
FIG. 9A shows western blot analysis HEK293T wild-type and CEP290 exon 41 CRISPR mutant cells transfected with the indicated SPs. An antibody recognizing the C-terminal region of CEP290 was used. Gamma-tubulin was used as a loading control
Figure 9B:
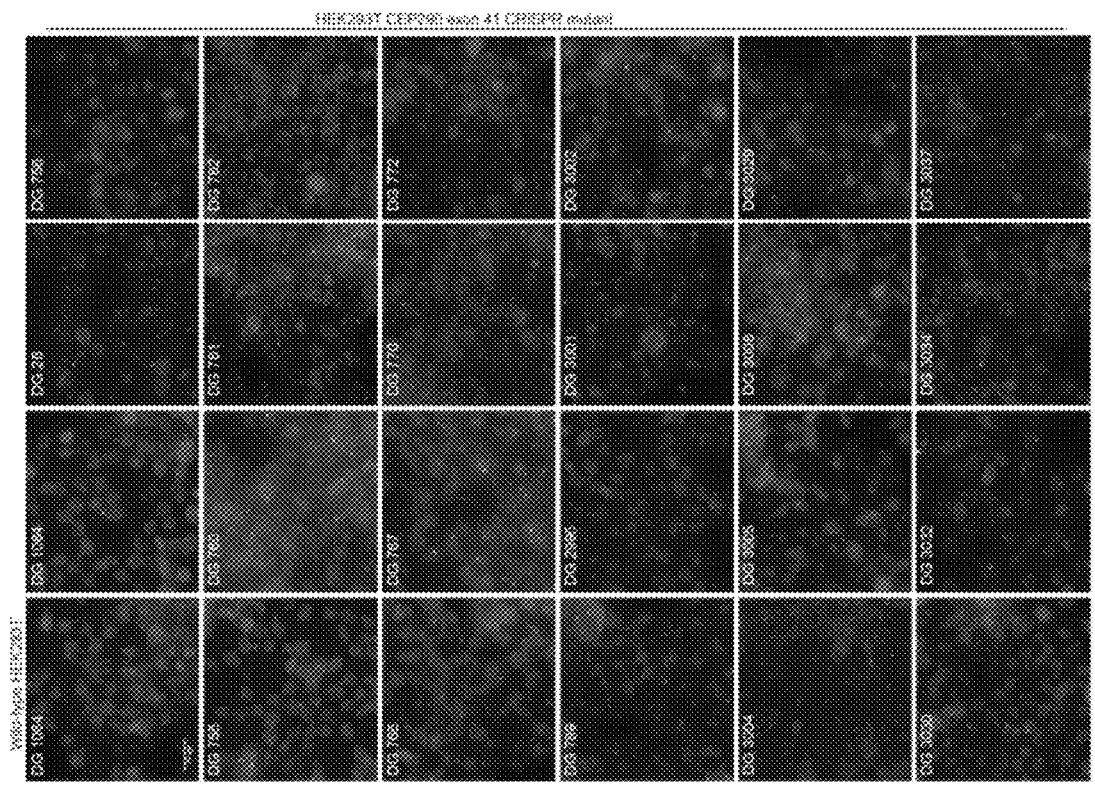
FIG. 9B shows immunohistochemistry staining of HEK293T wild-type and mutant cells (CEP290 exon 41 CRISPR mutants) transfected with the indicated SPs stained with antibodies against pericentrin (centrosome/basal body) and ARL13B (cilium marker). DNA was stained with Hoechst dye.

Upon identification of CRISPR clones carrying the above mutation of interest, and of SPs that can cause efficient skipping, the ability to restore CEP290 expression by skipping exon 41 using SPs was examined. HEK293T wild-type cells and an exon 41 mutant clone were transfected with control SPs (DG1064) and SPs previously shown to cause skipping. Western blot analysis was then performed to assess CEP290 expression levels in these cells (FIG. 9A). Observing the western blot, it is shown that the CEP290 exon 41 mutant does not produce detectable levels of CEP290 protein. Transfecting the CEP290 exon 41 mutant with known exon 41 skipping SPs (SEQ ID NOs: 19, 316, 331, 333, 335, 336, 337, 340, 341, 343, 345, 362, 563, 568, 569, 570, 571, 572, 573, 596, 597, 599, 601, and 604) rescues the CEP290 protein levels in the mutant.

To confirm that the skipping of exon 41 rescued protein function as well as expression a ciliation assay was performed (FIG. 9B, FIG. 9C, FIG. 9D, FIG. 9E). Ciliation was assessed by staining with antibodies against pericentrin (centrosome/basal body) and ARL13B (cilium marker). DNA was stained with Hoechst dye.

Figure 9C:
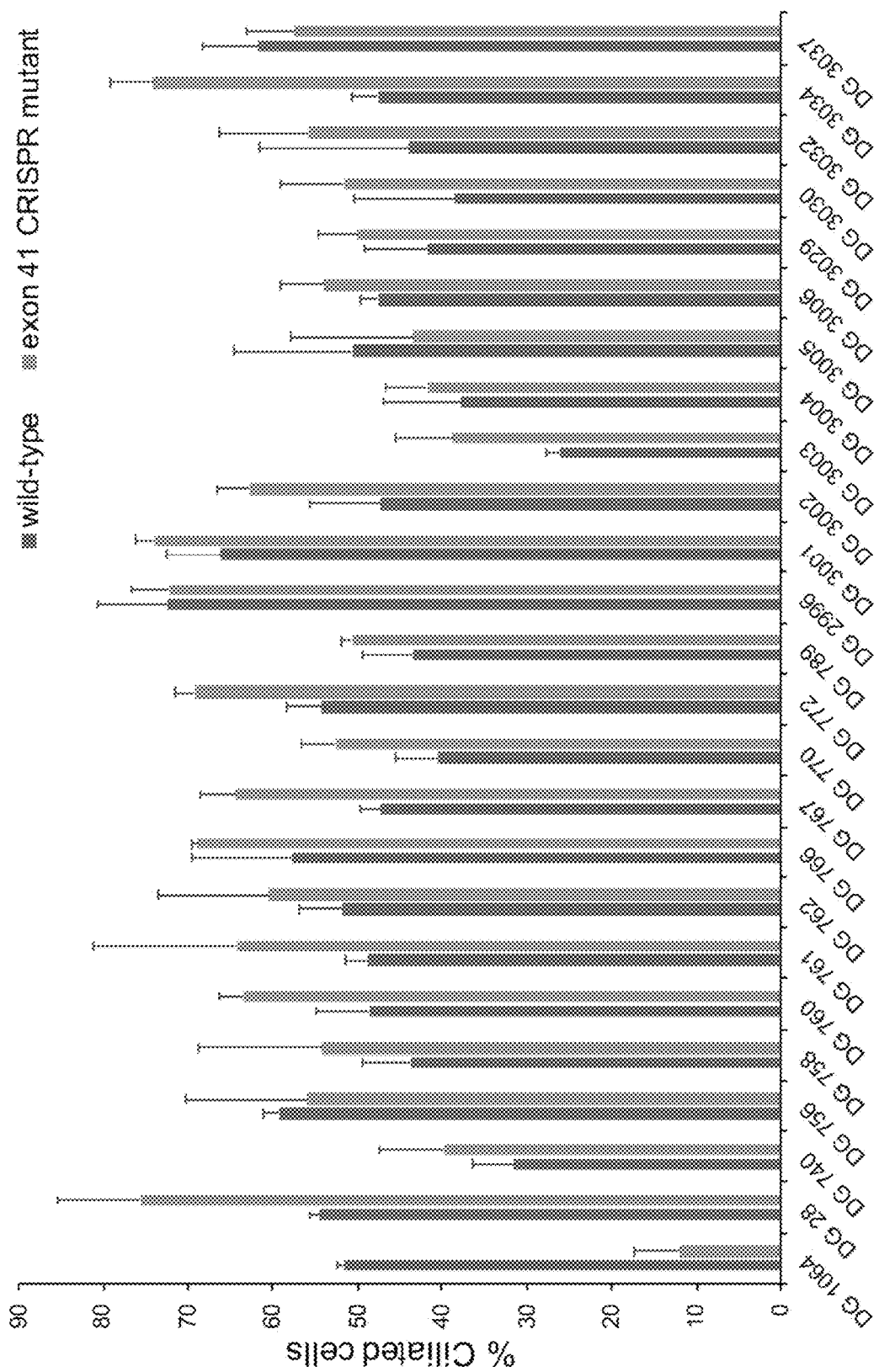
FIG. 9C shows the mean percentage of ciliated cells (n>150 cells per sample, 3 independent experiments) in wild-type and CEP290 exon 41 CRISPR mutant cells transfected with the indicated SPs. Error bars indicate SD.

SP transfected wild-type and exon 41 mutant cell ciliation levels were examined (FIG. 9B) and the percentage of ciliation in each population computed (FIG. 9C). Treating with a control SP (DG1064) resulted in a decrease in ciliation levels in the exon 41 mutant CEP290 cells versus the wild-type cells. Treatment with SPs DG28, DG740, DG756, DG758, DG760, DG761, DG762, DG766, DG767, DG770, DG772, DG789, DG2996, DG3001, DG3002, DG3003, DG3004, DG3005, DG3006, DG3029, DG3030, DG3032, DG3034, and DG3037 (SEQ ID NOs: 19, 316, 331, 333, 335, 336, 337, 340, 341, 343, 345, 362, 563, 568, 569, 570, 571, 572, 573, 596, 597, 599, 601, and 604) rescued ciliation levels to at least wild-type levels (FIG. 9C).

Figure 9D:
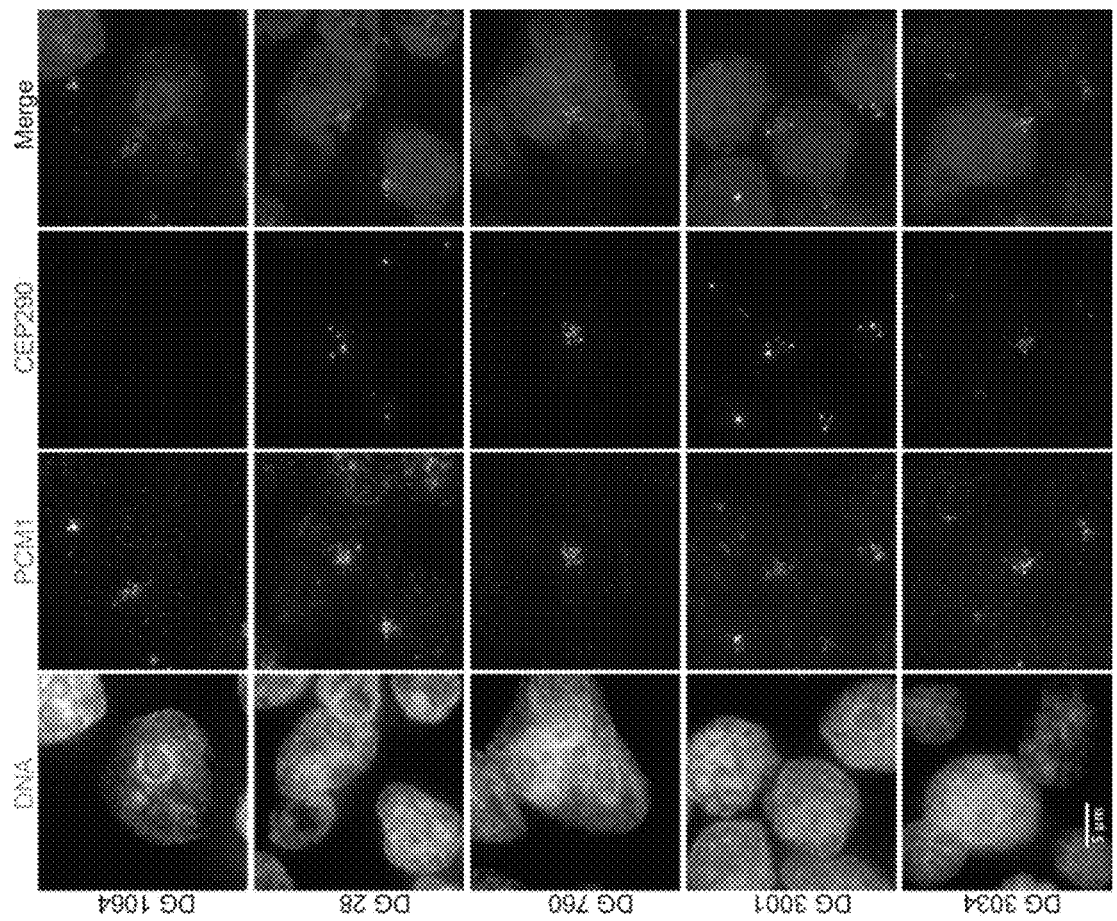
FIG. 9D shows the sub-cellular localization analysis of the rescued CEP290 protein. HEK293T CEP290 exon 41 CRISPR mutant cells were transfected with the indicated SPs and stained with antibodies against PCM1 (centriolar satellite marker) and CEP290. DNA was stained with Hoechst dye.
Figure 9E:
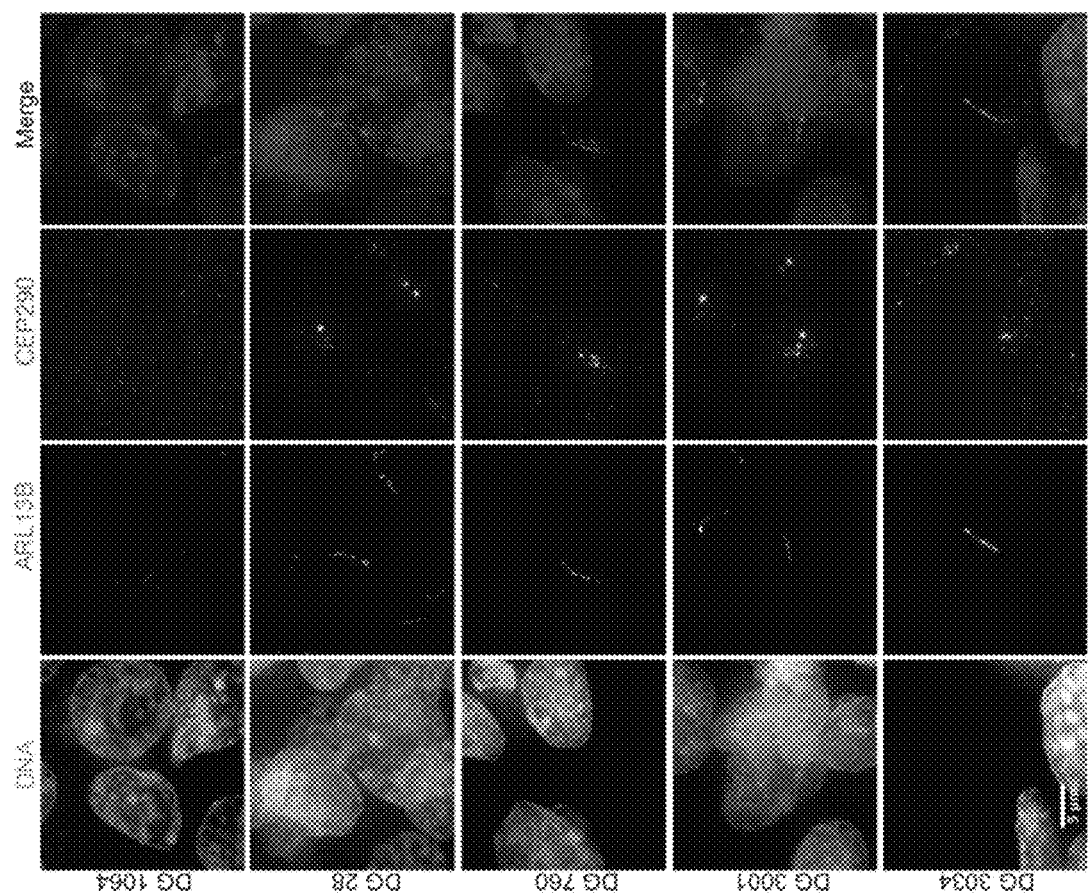
FIG. 9E shows Sub-cellular localization analysis of the rescued CEP290 protein. HEK293T CEP290 exon 41 CRISPR mutant cells were transfected with the indicated SPs and stained with antibodies against ARL13B (ciliary marker) and CEP290. DNA was stained with Hoechst dye.

CEP290 localization was also assessed by staining with antibodies against CEP290, PCM1 (centriolar satellite marker) and ARL13B. Cells transfected with the control SP (DG1064) showed no signal for CEP290 (FIG. 9D, FIG. 9E). Upon treatment with the SPs that rescue protein expression (SEQ ID NOs: 19, 333, 568, and 601) (FIG. 9A) a CEP290 signal is observed both at the centrosomal area and centriolar satellites (FIG. 9D), and the base of primary cilia (FIG. 9E). These results show that the amino acid residues coded by exon 41 are not required for the localization of CEP290 to the centrosome, centriolar satellites and primary cilium. Skipping of CEP290 exon 41 by SPs may thus be beneficial in the treatment of individuals with LOF mutants in exon 41.

While some embodiments of the present disclosure have been shown and described herein, such embodiments are provided by way of example. It is not intended that the disclosure be limited by the specific examples provided within the specification. While the disclosure has been described with reference to the aforementioned specification, the descriptions and illustrations of the embodiments herein are not meant to be construed in a limiting sense. Furthermore, it shall be understood that all aspects of the disclosure are not limited to the specific depictions, configurations or relative proportions set forth herein which depend upon a variety of conditions and variables. Various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed is:

1. A composition comprising a synthetic polynucleotide comprising:
    a) the nucleobase sequence of any one of SEQ ID NOS: 270-276, and 282-298, wherein the synthetic polynucleotide has a length from about 20 nucleotides to about 30 nucleotides; or
    b) the nucleobase sequence of any one of SEQ ID NOS: 277, 281, 299, and 303, wherein the synthetic polynucleotide has a length of 20 nucleotides,
        wherein the synthetic polynucleotide comprises a modified internucleoside linkage selected from the group consisting of a phosphorothioate internucleoside linkage, a phosphoroamidate internucleoside linkage, and a phosphorodiamidate internucleoside linkage.

2. The composition of claim 1, wherein the modified internucleoside linkage is a phosphorodiamidate morpholino internucleoside linkage.

3. The composition of claim 1, wherein 100% of internucleoside linkages of the synthetic polynucleotide comprise modified internucleoside linkages.

4. The composition of claim 1, wherein at least a terminal three residues at either a 3' end, a 5' end, or both ends of the synthetic polynucleotide comprise modified internucleoside linkages.

5. The composition of claim 1, wherein the synthetic polynucleotide comprises a modified sugar moiety.

6. The composition of claim 1, wherein the synthetic polynucleotide comprises a modification selected from the group consisting of a 2' O-methyl modification, a locked nucleic acid (LNA), and a peptide nucleic acid (PNA).

7. The composition of claim 5, wherein 100% of sugar moieties of the synthetic polynucleotide comprise the modified sugar moiety.

8. The composition of claim 5, wherein the modified sugar moiety comprises a 2'-O-methoxyethyl (MOE) modification.

9. The composition of claim 5, wherein at least a terminal three residues at either a 3' end, a 5' end, or both ends of the synthetic polynucleotide comprise the modified sugar moiety.

10. The composition of claim 1, wherein the composition is formulated for administration to a subject.

11. The composition of claim 10, wherein the composition is formulated for intravitreal administration to the subject.

12. The composition of claim 10, wherein the composition is formulated for systemic administration to the subject.

13. The composition of claim 1, wherein the synthetic polynucleotide comprising the nucleobase sequence of any one of SEQ ID NOS: 270-276 and 282-298 has the length from about 20 nucleotides to about 25 nucleotides.

14. The composition of claim 1, wherein the synthetic polynucleotide comprises any one of SEQ ID NOS: 272-275 and 282-297.

15. The composition of claim 1, wherein the synthetic polynucleotide comprises any one of SEQ ID NOS: 282-285, 287-293, and 295-297.

16. The composition of claim 1, wherein the modified internucleoside linkage is the phosphorothioate internucleoside linkage.

17. The composition of claim 1, wherein the modified internucleoside linkage is the phosphoroamidate internucleoside linkage.

18. The composition of claim 1, wherein the modified internucleoside linkage is the phosphorodiamidate internucleoside linkage.

19. The composition of claim 1, wherein the synthetic polynucleotide is conjugated to a penetration enhancer.

* * * * *

```
                          SEQUENCE LISTING

<160> NUMBER OF SEQ ID NOS: 845

<210> SEQ ID NO 1
   <211> LENGTH: 18
   <212> TYPE: DNA
   <213> ORGANISM: Artificial Sequence
   <220> FEATURE:
   <223> OTHER INFORMATION: Description of Artificial Sequence: Synthetic
         oligonucleotide

<400> SEQUENCE: 1
aaataaaatg taacttta                                                     18

<210> SEQ ID NO 2
   <211> LENGTH: 16
   <212> TYPE: DNA
   <213> ORGANISM: Artificial Sequence
   <220> FEATURE:
   <223> OTHER INFORMATION: Description of Artificial Sequence: Synthetic
         oligonucleotide

<400> SEQUENCE: 2
taaaaaataa aatgta                                                       16

<210> SEQ ID NO 3
   <211> LENGTH: 16
   <212> TYPE: DNA
   <213> ORGANISM: Artificial Sequence
   <220> FEATURE:
   <223> OTHER INFORMATION: Description of Artificial Sequence: Synthetic
         oligonucleotide

<400> SEQUENCE: 3
tgtcaggggt ttgccc                                                       16

<210> SEQ ID NO 4
   <211> LENGTH: 20
   <212> TYPE: DNA
   <213> ORGANISM: Artificial Sequence
   <220> FEATURE:
   <223> OTHER INFORMATION: Description of Artificial Sequence: Synthetic
         oligonucleotide

<400> SEQUENCE: 4
tctgtcaggg gtttgccta                                                    20

<210> SEQ ID NO 5
   <211> LENGTH: 18
   <212> TYPE: DNA
   <213> ORGANISM: Artificial Sequence
   <220> FEATURE:
   <223> OTHER INFORMATION: Description of Artificial Sequence: Synthetic
``` oligonucleotide

<400> SEQUENCE: 5
ggagttcttc aattagac                                                       18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttcctttgg agttcttc                                                       18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctttcctttg gagttcttca a                                                   21

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tagtttttta actttc                                                         16

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tctagttttt taactttc                                                       18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccctctaatt ggttctct                                                       18

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
cctccacctt tccctc                                               16

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acttcctcca cctttccc                                             18

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtctacttcc tccacc                                               16

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtctacttc ctccacct                                             18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttttaggtct acttcctcca                                           20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggttttaggt ctacttcc                                             18

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 17
ggttttaggt ctactt                                                         16

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cataggtttt aggtctac                                                       18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ataccttttc tttcataggt                                                     20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttaacatagc tacagcca                                                       18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aagataacaa gcaaacat                                                       18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caaatctctg acttgattct                                                     20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tttccttcaa atctctga                                                    18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagaaattca cacatttc                                                    18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aacttctgct ttttcttt                                                    18

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gaacttctgc tttttctttc t                                                21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tccgctgaac ttctgctt                                                    18

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tccgctgaac ttctgc                                                      16

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ggccaagttt ccgctgaact                                                    20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggccaagttt ccgctgaa                                                      18

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggccaagttt ccgctg                                                        16

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctaacatggc caagtttc                                                      18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tctaacatgg ccaagtttcc                                                    20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccctctaaca tggccaag                                                      18

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccctctaaca tggcca                                                        16
```

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
acatacccct ctaacatg                                                 18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tctcacatac ccctctaaca                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tacagccatt gaaagaaaa                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acatagctac agccattgaa                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aatttaacat agctacagcc                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgtaataatt taacatagct                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caaacatgta ataatttaac                                          20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aacaagcaaa catgtaataa                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaagataaca agcaaacatg                                          20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
attctgaaag ataacaagca                                          20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gacttgattc tgaaagataa                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atctctgact tgattctgaa                                          20

```
<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cttcaaatct ctgacttgat                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
catttccttc aaatctctga                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttcacacatt tccttcaaat                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aagaaattca cacatttcct                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttcttaaga aattcacaca                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tttttctttc ttaagaaatt                                               20

<210> SEQ ID NO 54
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttctgctttt tctttcttaa                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctgaacttct gcttttctt                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tttccgctga acttctgctt                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gccaagtttc cgctgaactt                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aacatggcca agtttccgct                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccctctaaca tggccaagtt                                              20

<210> SEQ ID NO 60
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
acatacccct ctaacatggc                                                 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
attctcacat acccctctaa                                                 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tggtaaattc tcacataccc                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aatgtatggt aaattctcac                                                 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aaaacaaatg tatggtaaat                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaaaccaaaa caaatgtatg                                                 20

<210> SEQ ID NO 66
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 66
actgctgaaa ccaaaacaaa                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cttatcactg ctgaaaccaa                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttctggctta tcactgctga                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tttcatttct ggcttatcac                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cattgagagt aactattaat                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gttgcagcat tgagagtaac                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aaagcagttg cagcattgag                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tttaaaaaag cagttgcagc                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atgtttttta aaaagcagt                                                     20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aatagtatgt tttttaaaaa                                                    20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttaagaaata gtatgttttt                                                    20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aaactattaa gaaatagtat                                                    20

<210> SEQ ID NO 78
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 78
ttcttcaaac tattaagaaa                                                    20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgtagcttct tcaaactatt                                                    20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgatcctgta gcttcttcaa                                                    20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
agggattgat cctgtagctt                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agggtcaggg attgatcctg                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
caaactaggg tcagggattg                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 84
aaggggcaaa ctagggtcag                                               20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
atttggaagg ggcaaactag                                               20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aagttgattt ggaaggggca                                               20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gatctcaagt tgatttggaa                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tagagcgatc tcaagttgat                                               20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tttccttaga gcgatctcaa                                               20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cttaattttc cttagagcga                                        20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gttctcctta attttcctta                                        20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tcgaatgttc tccttaattt                                        20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aattattcga atgttctcct                                        20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttctagaatt attcgaatgt                                        20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccgtgtttct agaattattc                                        20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 96
agttgcccgt gtttctagaa                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tttgcaagtt gcccgtgttt                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tagtgatttg caagttgccc                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ctcttctagt gatttgcaag                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aattacctct tctagtgatt                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tcttctaatt acctcttcta                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
```
gcaaattctt ctaattacct                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
caaaatgcaa attcttctaa                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
actaatcaaa atgcaaattc                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
taatacacta atcaaaatgc                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
accaaataat acactaatca                                              20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaacatacca aataatacac                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108 cccccccaaac ataccaaata                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
agaaagcccc ccaaacatac                                               20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tttttccagt gaaagttatc                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
caaatttttc cagtgaaagt                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tttcaaattt ttccagtgaa                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
taagtttcaa atttttccag                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tagtaagttt caaatttttc                                               20

```
<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tttgtagtaa gtttcaaatt                                              20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
atatttgtag taagtttcaa                                              20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atatatattt gtagtaagtt                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aaaatatata tttgtagtaa                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aaaaaaaata tatatttgta                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
attaaaaaaa atatatattt                                              20
```

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgatattaaa aaaaatatat                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gcctgatatt aaaaaaaata                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctgtgcctga tattaaaaaa                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
agactgtgcc tgatattaaa                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
catcagactg tgcctgatat                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tttcatcaga ctgtgcctga                                              20

```
<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gacttttcat cagactgtgc                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agcgactttt catcagactg                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aatgagcgac ttttcatcag                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggcaatgagc gacttttcat                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
acttggcaat gagcgacttt                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcaacttggc aatgagcgac                                              20

<210> SEQ ID NO 133
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tggtgcaact tggcaatgag                                                   20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tgttggtgca acttggcaat                                                   20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
attatgttgg tgcaacttgg                                                   20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gacattatgt tggtgcaact                                                   20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gagagacatt atgttggtgc                                                   20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaagagagac attatgttgg                                                   20

<210> SEQ ID NO 139
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
agttgaagag agacattatg                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ctcagttgaa gagagacatt                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ctcactcagt tgaagagaga                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agcctcactc agttgaagag                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
cagtagcctc actcagttga                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gagcagtagc ctcactcagt                                              20

<210> SEQ ID NO 145
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 145
ccaagagcag tagcctcact                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ttaccaagag cagtagcctc                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
caacttacca agagcagtag                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ctccaactta ccaagagcag                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ttgactccaa cttaccaaga                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
taattgactc caacttacca                                              20

<210> SEQ ID NO 151
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 151
gatgtaattg actccaactt                                                  20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ttagatgtaa ttgactccaa                                                  20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cagtttagat gtaattgact                                                  20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctgcagttta gatgtaattg                                                  20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tcttctgcag tttagatgta                                                  20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ccatcttctg cagtttagat                                                  20

<210> SEQ ID NO 157
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 157
gcctccatct tctgcagttt                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
taggcctcca tcttctgcag                                              20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gttgtaggcc tccatcttct                                              20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
caagttgtag gcctccatct                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
agcgcaagtt gtaggcctcc                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ctaagcgcaa gttgtaggcc                                              20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
tgctctaagc gcaagttgta                                          20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttctgctcta agcgcaagtt                                          20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aagtttctgc tctaagcgca                                          20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atcaagtttc tgctctaagc                                          20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tttcatcaag tttctgctct                                          20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168 cttttcatc aagtttctgc                                           20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 169
tgttcttttt catcaagttt                                          20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gcctgttctt tttcatcaag                                          20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gagagcctgt tcttttcat                                           20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
atagagagcc tgttcttttt                                          20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cataatagag agcctgttct                                          20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gagcataata gagagcctgt                                          20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aaacgagcat aatagagagc                                               20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tccaaacgag cataatagag                                               20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tccctccaaa cgagcataat                                               20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tcttccctcc aaacgagcat                                               20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tgtttcttcc ctccaaacga                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ctctgtttct tccctccaaa                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tttgctctgt ttcttccctc                                           20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgttttgctc tgtttcttcc                                           20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cagatgtttt gctctgtttc                                           20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcgcagatgt tttgctctgt                                           20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tttggcgcag atgttttgct                                           20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ttgtttggcg cagatgtttt                                           20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgaattgttt ggcgcagatg                                           20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gactgaattg tttggcgcag                                           20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tagagactga attgtttggc                                           20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tcgtagagac tgaattgttt                                           20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gtcgtcgtag agactgaatt                                           20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
actgtcgtcg tagagactga                                           20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctaaactgtc gtcgtagaga                                           20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccactaaact gtcgtcgtag                                              20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
agctccacta aactgtcgtc                                              20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
taaagctcca ctaaactgtc                                              20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
agggtaaagc tccactaaac                                              20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ccaagggtaa agctccacta                                              20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgtgccaagg gtaaagctcc                                              20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tgttgtgcca agggtaaagc                                                 20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ttcctgttgt gccaagggta                                                 20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
cttttcctgt tgtgccaagg                                                 20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203 agaactttc ctgttgtgcc                                                  20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tggagaactt ttcctgttgt                                                 20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gttttggaga acttttcctg                                                 20

```
<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
attgttttgg agaactttc                                                    20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
aatcattgtt ttggagaact                                                   20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ttgaatcatt gttttggaga                                                   20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtagttgaat cattgttttg                                                   20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tttgtagttg aatcattgtt                                                   20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tcattttgta gttgaatcat                                                   20

<210> SEQ ID NO 212
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ttgtcatttt gtagttgaat                                          20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
aagtttgtca ttttgtagtt                                          20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cttaagtttg tcattttgta                                          20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ttatcttaag tttgtcattt                                          20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gcattatctt aagtttgtca                                          20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tcttgcatta tcttaagttt                                          20

<210> SEQ ID NO 218
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
atttcttgca ttatcttaag                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tttcatttct tgcattatct                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
atttttcatt tcttgcatta                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gagaattttt catttcttgc                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gttgagaatt tttcatttct                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tcttgttgag aattttttcat                                             20

<210> SEQ ID NO 224
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 224
tgttcttgtt gagaattttt                                           20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tctatgttct tgttgagaat                                           20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
atttctatgt tcttgttgag                                           20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ccatatttct atgttcttgt                                           20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tctccatatt tctatgttct                                           20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ttgttctcca tatttctatg                                           20

<210> SEQ ID NO 230
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 230
gttttgttct ccatatttct                                                 20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
caatgttttg ttctccatat                                                 20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ctccaatgtt ttgttctcca                                                 20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ccatctccaa tgttttgttc                                                 20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
attccatctc caatgttttg                                                 20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tttaattcca tctccaatgt                                                 20

<210> SEQ ID NO 236
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 236
aattttaatt ccatctccaa                                                20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ctttaatttt aattccatct                                                20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gccctttaat tttaattcca                                                20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccaggccctt taattttaat                                                20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
cttccaggcc ctttaatttt                                                20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
aactcttcca ggccctttaa                                                20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 242
attaactctt ccaggcccctt                                              20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gcttattaac tcttccaggc                                               20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
agtgcttatt aactcttcca                                               20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ttaaagtgct tattaactct                                               20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
cctttaaagt gcttattaac                                               20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gtatccttta aagtgcttat                                               20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 248
ttggtatcct ttaaagtgct                                              20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tcctttggta tcctttaaag                                              20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggctcctttg gtatccttta                                              20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tttgggctcc tttggtatcc                                              20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cctttggggc tcctttggta                                              20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253 tttaccttttt gggctccttt                                             20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 254
atgtttacct tttgggctcc                                              20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ttaaatgttt accttttggg                                              20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
agtttaaatg tttacctttt                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
atcaagttta aatgtttacc                                              20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aaaatcaagt ttaaatgttt                                              20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aaaaaaaatc aagtttaaat                                              20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
aaaaaaaaaa atcaagttta                                              20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tcttaaaaaa aaaaatcaag                                              20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gtctcttaaa aaaaaaaatc                                              20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tactgtctct taaaaaaaaa                                              20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
agatactgtc tcttaaaaaa                                              20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
atcaagatac tgtctcttaa                                              20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cagatcaaga tactgtctct                                               20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gaaacagatc aagatactgt                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tgggaaacag atcaagatac                                               20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gcctgggaaa cagatcaaga                                               20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
aattcagcag taatttttt                                                20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ataaaattca gcagtaattt                                               20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gaagataaaa ttcagcagta                                               20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
agaagaagat aaaattcagc                                              20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
aataagaaga agataaaatt                                              20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
aataaataag aagaagataa                                              20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
aaaaaataaa taagaagaag                                              20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
aaaaaaaaaa taaataagaa                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gtaaaaaaaa aaaataaata                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
aatagtaaaa aaaaaaaata                                          20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ctaaaatagt aaaaaaaaaa                                          20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccaactaaaa tagtaaaaaa                                          20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
agagccaact aaaatagtaa                                          20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
tcgaagagcc aactaaaata                                          20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
catttcgaag agccaactaa                                          20

```
<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tcctcatttc gaagagccaa                                              20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgcctcctca tttcgaagag                                              20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tttctgcctc ctcatttcga                                              20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tcattttctg cctcctcatt                                              20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gttttcattt tctgcctcct                                              20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gctgttttca ttttctgcct                                              20

<210> SEQ ID NO 291
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
atttgctgtt ttcattttct                                               20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cttaatttgc tgttttcatt                                               20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tcttcttaat ttgctgtttt                                               20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cctctcttct taatttgctg                                               20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tttacctctc ttcttaattt                                               20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
attttttacc tctcttctta                                               20

<210> SEQ ID NO 297
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297 taaaatttt tacctctctt                                             20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ctactaaaat ttttacctc                                             20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
acaactacta aaatttttta                                            20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
caccacaact actaaaattt                                            20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gaaccaccac aactactaaa                                            20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tgttgaacca ccacaactac                                            20

<210> SEQ ID NO 303
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 303
cctttgttga accaccacaa                                                    20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
agtacctttg ttgaaccacc                                                    20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
aataagtacc tttgttgaac                                                    20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
ttttaataag tacctttgtt                                                    20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cttattttaa taagtacctt                                                    20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggtacttatt ttaataagta                                                    20

<210> SEQ ID NO 309
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 309
ttaggtactt attttaataa                                                    20

<210> SEQ ID NO 310
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tcagggrttt gcccta                                                        16

<210> SEQ ID NO 311
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
ctgtcagggg tttgcc                                                        16

<210> SEQ ID NO 312
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tcagggrttt gccctaa                                                       17

<210> SEQ ID NO 313
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gtcaggggtt tgccrta                                                       17

<210> SEQ ID NO 314
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tgtcaggggt ttgccct                                                       17

<210> SEQ ID NO 315
<211> LENGTH: 17
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 315
ctgtcagggg tttgccc                                                    17

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tctgtcaggg gtttgcc                                                    17

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gtcaggggtt tgccctaa                                                   18

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tgtcaggggt tgcccta                                                    18

<210> SEQ ID NO 319
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ctgtcagggg tttgccct                                                   18

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tctgtcaggg gtttgccc                                                   18

<210> SEQ ID NO 321
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 321
atctgtcagg ggtttgcc                                              18

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gtcaggggtt tgccctaaa                                             19

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tgtcaggggt tgccctaa                                              19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ctgtcagggg tttgcccta                                             19

<210> SEQ ID NO 325
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tctgtcaggg gtttgccct                                             19

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
atctgtcagg ggtttgccc                                             19

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 327
tgtcaggggt ttgccctaaa                                          20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ctgtcagggg tttgccctaa                                          20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
atctgtcagg ggtttgccct                                          20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tatctgtcag gggtttgccc                                          20

<210> SEQ ID NO 331
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
agttcttcaa ttagac                                              16

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gttcttcaat tagactt                                             17

<210> SEQ ID NO 333
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 333
gagttcttca attagac                                                17

<210> SEQ ID NO 334
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tggagttctt caattag                                                17

<210> SEQ ID NO 335
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
ttcctttgga gttcttc                                                17

<210> SEQ ID NO 336
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
agttcttcaa ttagactt                                               18

<210> SEQ ID NO 337
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gagttcttca attagact                                               18

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
tggagttctt caattaga                                               18

<210> SEQ ID NO 339
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
```
ttggagttct tcaattag                                                 18

<210> SEQ ID NO 340
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
tcctttggag ttcttcaa                                                 18

<210> SEQ ID NO 341
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ttcctttgga gttcttca                                                 18

<210> SEQ ID NO 342
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
actttccttt ggagttct                                                 18

<210> SEQ ID NO 343
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
agttcttcaa ttagacttt                                                19

<210> SEQ ID NO 344
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gagttcttca attagactt                                                19

<210> SEQ ID NO 345
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ggagttcttc aattagact					19

<210> SEQ ID NO 346
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tggagttctt caattagac					19

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ttggagttct tcaattaga					19

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tttggagttc ttcaattag					19

<210> SEQ ID NO 349
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
cctttggagt tcttcaatt					19

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
tcctttggag ttcttcaat					19

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tttcctttgg agttcttca					19

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ctttcctttg gagttcttc                                                   19

<210> SEQ ID NO 353
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
actttccttt ggagttctt                                                   19

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gagttcttca attagacttt                                                  20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ggagttcttc aattagactt                                                  20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tggagttctt caattagact                                                  20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
ttggagttct tcaattagac                                                  20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
tttggagttc ttcaattaga                    20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
cctttggagt tcttcaatta                    20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
tcctttggag ttcttcaatt                    20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
ttcctttgga gttcttcaat                    20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 362
ctttcctttg gagttcttca                    20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 363
actttccttt ggagttcttc                    20

```
<210> SEQ ID NO 364
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ggtctacttc ctccac                                                       16

<210> SEQ ID NO 365
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tctacttcct ccacctt                                                      17

<210> SEQ ID NO 366
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
aggtctactt cctccac                                                      17

<210> SEQ ID NO 367
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tttaggtcta cttcctc                                                      17

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
tctacttcct ccaccttt                                                     18

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gtctacttcc tccacctt                                                     18

<210> SEQ ID NO 370
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
aggtctactt cctccacc                                                 18

<210> SEQ ID NO 371
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
taggtctact tcctccac                                                 18

<210> SEQ ID NO 372
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
tttaggtcta cttcctcc                                                 18

<210> SEQ ID NO 373
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ttttaggtct acttcctc                                                 18

<210> SEQ ID NO 374
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gttttaggtc tacttcct                                                 18

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tctacttcct ccaccttte                                                19

<210> SEQ ID NO 376
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gtctacttcc tccaccttt                                                19

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggtctacttc ctccacctt                                                19

<210> SEQ ID NO 378
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
taggtctact tcctccacc                                                19

<210> SEQ ID NO 379
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ttaggtctac ttcctccac                                                19

<210> SEQ ID NO 380
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
tttaggtcta cttcctcca                                                19

<210> SEQ ID NO 381
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ttttaggtct acttcctcc                                                19

<210> SEQ ID NO 382
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 382
gttttaggtc tacttcctc                                                   19

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
gtctacttcc tccaccttc                                                   20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ggtctacttc ctccaccttt                                                  20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aggtctactt cctccacctt                                                  20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
taggtctact tcctccacct                                                  20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ttaggtctac ttcctccacc                                                  20

<210> SEQ ID NO 388
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 388
tttaggtcta cttcctccac                                                   20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gttttaggtc tacttcctcc                                                   20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
ggttttaggt ctacttcctc                                                   20

<210> SEQ ID NO 391
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
tttcataggt tttaggtcta cttcc                                             25

<210> SEQ ID NO 392
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
aactttcctt tggagttctt caatt                                             25

<210> SEQ ID NO 393
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
ggttttaggt ctacttcctc cacct                                             25

<210> SEQ ID NO 394
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 394
tgtttcttca cataccttttt ctttc                                         25

<210> SEQ ID NO 395
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
tttccgctga acttct                                                    16

<210> SEQ ID NO 396
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
ttccgctgaa cttctg                                                    16

<210> SEQ ID NO 397
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ccgctgaact tctgct                                                    16

<210> SEQ ID NO 398
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
cgctgaactt ctgctt                                                    16

<210> SEQ ID NO 399
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gctgaacttc tgcttt                                                    16

<210> SEQ ID NO 400
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 400
ctgaacttct gctttt                                                    16

<210> SEQ ID NO 401
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
tgaacttctg cttttt                                                    16

<210> SEQ ID NO 402
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gaacttctgc tttttc                                                    16

<210> SEQ ID NO 403
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tctgacttga ttctga                                                    16

<210> SEQ ID NO 404
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ctgacttgat tctgaa                                                    16

<210> SEQ ID NO 405
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ttgattctga aagata                                                    16

<210> SEQ ID NO 406
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
tgattctgaa agataa                                                        16

<210> SEQ ID NO 407
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
gattctgaaa gataac                                                        16

<210> SEQ ID NO 408
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
aagtttccgc tgaactt                                                       17

<210> SEQ ID NO 409
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
agtttccgct gaacttc                                                       17

<210> SEQ ID NO 410
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gtttccgctg aacttct                                                       17

<210> SEQ ID NO 411
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
tttccgctga acttctg                                                       17

<210> SEQ ID NO 412
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ttccgctgaa cttctgc                                                17

<210> SEQ ID NO 413
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tccgctgaac ttctgct                                                17

<210> SEQ ID NO 414
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ccgctgaact tctgctt                                                17

<210> SEQ ID NO 415
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
cgctgaactt ctgcttt                                                17

<210> SEQ ID NO 416
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gctgaacttc tgctttt                                                17

<210> SEQ ID NO 417
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ctgaacttct gctttt                                                 17

<210> SEQ ID NO 418
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tgaacttctg cttttc                                             17

<210> SEQ ID NO 419
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
tctgacttga ttctgaa                                            17

<210> SEQ ID NO 420
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
ctgacttgat tctgaaa                                            17

<210> SEQ ID NO 421
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
tgacttgatt ctgaaag                                            17

<210> SEQ ID NO 422
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
gacttgattc tgaaaga                                            17

<210> SEQ ID NO 423
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
acttgattct gaaagat                                            17

<210> SEQ ID NO 424
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
cttgattctg aaagata                                                      17

<210> SEQ ID NO 425
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
ttgattctga aagataa                                                      17

<210> SEQ ID NO 426
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
tgattctgaa agataac                                                      17

<210> SEQ ID NO 427
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
aagtttccgc tgaacttc                                                     18

<210> SEQ ID NO 428
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
agtttccgct gaacttct                                                     18

<210> SEQ ID NO 429
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
gtttccgctg aacttctg                                                     18

<210> SEQ ID NO 430
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
tttccgctga acttctgc                                                     18

<210> SEQ ID NO 431
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ttccgctgaa cttctgct                                                 18

<210> SEQ ID NO 432
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ccgctgaact tctgcttt                                                 18

<210> SEQ ID NO 433
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
cgctgaactt ctgctttt                                                 18

<210> SEQ ID NO 434
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gctgaacttc tgcttttt                                                 18

<210> SEQ ID NO 435
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ctgaacttct gcttttttc                                                18

<210> SEQ ID NO 436
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tctgacttga ttctgaaa                                                 18

<210> SEQ ID NO 437
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ctgacttgat tctgaaag                                                 18

<210> SEQ ID NO 438
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
tgacttgatt ctgaaaga                                                 18

<210> SEQ ID NO 439
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
gacttgattc tgaaagat                                                 18

<210> SEQ ID NO 440
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
acttgattct gaaagata                                                 18

<210> SEQ ID NO 441
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
cttgattctg aaagataa                                                 18

<210> SEQ ID NO 442
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ttgattctga aagataac                                                 18

```
<210> SEQ ID NO 443
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
aagtttccgc tgaacttct                                                  19

<210> SEQ ID NO 444
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
agtttccgct gaacttctg                                                  19

<210> SEQ ID NO 445
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
gtttccgctg aacttctgc                                                  19

<210> SEQ ID NO 446
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tttccgctga acttctgct                                                  19

<210> SEQ ID NO 447
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
ttccgctgaa cttctgctt                                                  19

<210> SEQ ID NO 448
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
tccgctgaac ttctgcttt                                                  19

<210> SEQ ID NO 449
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ccgctgaact tctgctttt                                               19

<210> SEQ ID NO 450
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
cgctgaactt ctgcttttt                                               19

<210> SEQ ID NO 451
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
gctgaacttc tgcttttc                                                19

<210> SEQ ID NO 452
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
tctgacttga ttctgaaag                                               19

<210> SEQ ID NO 453
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
ctgacttgat tctgaaaga                                               19

<210> SEQ ID NO 454
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
tgacttgatt ctgaaagat                                               19

<210> SEQ ID NO 455
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
gacttgattc tgaaagata                                                    19

<210> SEQ ID NO 456
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
acttgattct gaaagataa                                                    19

<210> SEQ ID NO 457
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
cttgattctg aaagataac                                                    19

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
aagtttccgc tgaacttctg                                                   20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
agtttccgct gaacttctgc                                                   20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
gtttccgctg aacttctgct                                                   20

<210> SEQ ID NO 461
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 461
taaaacaaat tcacattttg                                                    20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
tgattaaaac aaattcacat                                                    20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
attgtgatta aaacaaattc                                                    20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
taaattgtga ttaaaacaaa                                                    20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
atcttaaatt gtgattaaaa                                                    20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tatatcttaa attgtgatta                                                    20

<210> SEQ ID NO 467
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 467
aaactatatc ttaaattgtg                                                   20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tcgaaactat atcttaaatt                                                   20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
aaaatcgaaa ctatatctta                                                   20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cagaaaatcg aaactatatc                                                   20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tttacagaaa atcgaaacta                                                   20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
tgttttacag aaaatcgaaa                                                   20

<210> SEQ ID NO 473
<211> LENGTH: 20
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 473
ctcctgtttt acagaaaatc                                              20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 474
ttgctcctgt tttacagaaa                                              20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 475
ctctttgctc ctgttttaca                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 476
tttctctttg ctcctgtttt                                              20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 477
acaatttctc tttgctcctg                                              20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 478
ttcacaattt ctctttgctc                                              20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
tttcttcaca atttctcttt                                               20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
atgtttcttc acaatttctc                                               20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
cctcatgttt cttcacaatt                                               20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
tcttcctcat gtttcttcac                                               20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
aggtcttcct catgtttctt                                               20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
atgaaggtct tcctcatgtt                                               20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
aatatgaagg tcttcctcat                          20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
gaagaatatg aaggtcttcc                          20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gatgaagaat atgaaggtct                          20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
ctgtgatgaa gaatatgaag                          20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
aatctgtgat gaagaatatg                          20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
ttctaatctg tgatgaagaa                          20

<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tagttctaat ctgtgatgaa					20

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
cctgtagttc taatctgtga					20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
cagcctgtag ttctaatctg					20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
ctatcagcct gtagttctaa					20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
gaactatcag cctgtagttc					20

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
tagtgaacta tcagcctgta					20

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
atttagtgaa ctatcagcct                                          20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
atttatttag tgaactatca                                          20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
tgaatttatt tagtgaacta                                          20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
tgtttgaatt tatttagtga                                          20

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
cgtttgtttg aatttattta                                          20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
agccgtttgt ttgaatttat                                          20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
cccaagccgt ttgtttgaat                                           20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ttacccaagc cgtttgtttg                                           20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
aatcttaccc aagccgtttg                                           20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
tagaatctta cccaagccgt                                           20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ttcttagaat cttacccaag                                           20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
aagttcttag aatcttaccc                                           20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
aacaaagttc ttagaatctt                                           20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tggaacaaag ttcttagaat                                           20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
agaatggaac aaagttctta                                           20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
taaagaatgg aacaaagttc                                           20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
tcaataaaga atggaacaaa                                           20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
aaatcaataa agaatggaac                                           20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
acaaaaatca ataaagaatg                                           20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
gtcacaaaaa tcaataaaga                                                    20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
catggtcaca aaaatcaata                                                    20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
ttacatggtc acaaaaatca                                                    20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
taatttacat ggtcacaaaa                                                    20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ttttaattta catggtcaca                                                    20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
catgtttctt cacaatttct                                                    20

```
<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ggtcttcctc atgtttcttc                                                   20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
cttcctcatg tttcttcaca                                                   20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gaaggtcttc ctcatgtttc                                                   20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ttcttcacaa tttctctttg                                                   20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gtcttcctca tgtttcttca                                                   20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcctcatgtt tcttcacaat                                                   20

<210> SEQ ID NO 528
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
ttcctcatgt ttcttcacaa                                                    20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
aaggtcttcc tcatgtttct                                                    20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
gtttcttcac aatttctctt                                                    20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
tgaagaatat gaaggtcttc                                                    20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
tcatgtttct tcacaatttc                                                    20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
tgtttcttca caatttctct                                                    20

<210> SEQ ID NO 534
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
tgaaggtctt cctcatgttt                                               20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
ctcatgtttc ttcacaattt                                               20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
agaatatgaa ggtcttcctc                                               20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
cacaatttct ctttgctcct                                               20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gaatatgaag gtcttcctca                                               20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tcttcacaat ttctctttgc                                               20

<210> SEQ ID NO 540
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 540
aagaatatga aggtcttcct                                                  20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
tcagggnttt gccctaaaaa                                                  20

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
gtcaggggtt tgccctaaaa                                                  20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ttatctgtca ggggtttgcc                                                  20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
attatctgtc aggggtttgc                                                  20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
tattatctgt caggggtttg                                                  20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
ttattatctg tcaggggttt                                              20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
tttattatct gtcagggatt                                              20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gtttattatc tgtcaggggt                                              20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tgtttattat ctgtcagggg                                              20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
ttgtttatta tctgtcaggg                                              20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
tttgtttatt atctgtcagg                                              20

<210> SEQ ID NO 552
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 552
ctttgtttat tatctgtcag                                                    20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
actttgttta ttatctgtca                                                    20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
gactttgttt attatctgtc                                                    20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
agactttgtt tattatctgt                                                    20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
tagactttgt ttattatctg                                                    20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
ttagactttg tttattatct                                                    20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 558
attagacttt gtttattatc                                          20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
aattagactt tgtttattat                                          20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
caattagact ttgtttatta                                          20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
tcaattagac tttgtttatt                                          20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
ttcaattaga ctttgtttat                                          20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
cttcaattag actttgttta                                          20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
tcttcaatta gactttgttt    20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ttcttcaatt agactttgtt    20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gttcttcaat tagactttgt    20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
agttcttcaa ttagactttg    20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
ctttggagtt cttcaattag    20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
tttcctttgg agttcttcaa    20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
aactttcctt tggagttctt                                            20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
taactttcct ttggagttct                                            20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
ttaactttcc tttggagttc                                            20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
tttaactttc ctttggagtt                                            20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
ttttaacttt cctttggagt                                            20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
tttttaactt tcctttggag                                            20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576 tttttttaact ttcctttgga                                              20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577 gtttttttaac tttcctttgg                                              20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
agttttttaa ctttcctttg                                               20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
tagtttttta actttccttt                                               20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ctagtttttt aactttcctt                                               20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
tctagttttt taactttcct                                               20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
ctctagtttt ttaactttcc                                              20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tctctagttt tttaactttc                                              20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
ttctctagtt ttttaacttt                                              20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
gttctctagt tttttaactt                                              20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ggttctctag ttttttaact                                              20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
tggttctcta gttttttaac                                              20

<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
ttggttctct agttttttaa                                              20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
attggttctc tagtttttta                                                   20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
aattggttct ctagttttt                                                    20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
taattggttc tctagttttt                                                   20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
ctaattggtt ctctagtttt                                                   20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tctaattggt tctctagttt                                                   20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
ctctaattgg ttctctagtt                                                   20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
cctctaattg gttctctagt                                                  20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
ccctctaatt ggttctctag                                                  20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
tccctctaat tggttctcta                                                  20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ttccctctaa ttggttctct                                                  20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tttccctcta attggttctc                                                  20

<210> SEQ ID NO 600
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
ctttccctct aattggttct                                                  20

```
<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
cctttccctc taattggttc                                                20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
acctttccct ctaattggtt                                                20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cacctttccc tctaattggt                                                20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ccacctttcc ctctaattgg                                                20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
tccacctttc cctctaattg                                                20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ctccaccttt ccctctaatt                                                20

<210> SEQ ID NO 607
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
cctccacctt tccctctaat                                              20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tcctccacct ttccctctaa                                              20

<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
ttcctccacc tttccctcta                                              20

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
cttcctccac ctttccctct                                              20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
acttcctcca cctttccctc                                              20

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
tacttcctcc acctttccct                                              20

<210> SEQ ID NO 613
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ctacttcctc cacctttccc                                                 20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
tctacttcct ccacctttcc                                                 20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
aggttttagg tctacttcct                                                 20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
taggttttag gtctacttcc                                                 20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ataggtttta ggtctacttc                                                 20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
cataggtttt aggtctactt                                                 20

<210> SEQ ID NO 619
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 619
tcataggttt taggtctact                                                20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
ttcataggtt ttaggtctac                                                20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
tttcataggt tttaggtcta                                                20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
ctttcatagg ttttaggtct                                                20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
tctttcatag gttttaggtc                                                20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
ttctttcata ggttttaggt                                                20

<210> SEQ ID NO 625
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 625
tttctttcat aggttttagg                                           20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
ttttctttca taggttttag                                           20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
cttttctttc ataggtttta                                           20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
ccttttcttt cataggtttt                                           20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
accttttctt tcataggttt                                           20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
taccttttct ttcataggtt                                           20

<210> SEQ ID NO 631
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 631 cataccttt ctttcatagg                                                    20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
acataccttt tctttcatag                                                   20

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633 cacataccttt ttctttcata                                                  20

<210> SEQ ID NO 634
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
ccacctttcc ctctaa                                                       16

<210> SEQ ID NO 635
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
cacctttccc tctaat                                                       16

<210> SEQ ID NO 636
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
acctttccct ctaatt                                                       16

<210> SEQ ID NO 637
<211> LENGTH: 16
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 637
cctttccctc taattg                                                       16

<210> SEQ ID NO 638
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
ctttccctct aattgg                                                       16

<210> SEQ ID NO 639
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
tttccctcta attggt                                                       16

<210> SEQ ID NO 640
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
ttccctctaa ttggtt                                                       16

<210> SEQ ID NO 641
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
tccctctaat tggttc                                                       16

<210> SEQ ID NO 642
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
ccctctaatt ggttct                                                       16

<210> SEQ ID NO 643
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
cctctaattg gttctc                                                     16

<210> SEQ ID NO 644
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
ctctaattgg ttctct                                                     16

<210> SEQ ID NO 645
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
tctaattggt tctcta                                                     16

<210> SEQ ID NO 646
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
ctaattggtt ctctag                                                     16

<210> SEQ ID NO 647
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
taattggttc tctagt                                                     16

<210> SEQ ID NO 648
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
aattggttct ctagtt                                                     16

<210> SEQ ID NO 649
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
ccacctttcc ctctaat                                                    17

<210> SEQ ID NO 650
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
acctttccct ctaattg                                                    17

<210> SEQ ID NO 651
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
cctttccctc taattgg                                                    17

<210> SEQ ID NO 652
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ctttccctct aattggt                                                    17

<210> SEQ ID NO 653
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
tttccctcta attggtt                                                    17

<210> SEQ ID NO 654
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ttccctctaa ttggttc                                                    17

<210> SEQ ID NO 655
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
tccctctaat tggttct                                                  17

<210> SEQ ID NO 656
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
ccctctaatt ggttctc                                                  17

<210> SEQ ID NO 657
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
cctctaattg gttctct                                                  17

<210> SEQ ID NO 658
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ctctaattgg ttctcta                                                  17

<210> SEQ ID NO 659
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
tctaattggt tctctag                                                  17

<210> SEQ ID NO 660
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
ctaattggtt ctctagt                                                  17

<210> SEQ ID NO 661
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
taattggttc tctagtt                                                  17

<210> SEQ ID NO 662
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
ccacctttcc ctctaatt                                                 18

<210> SEQ ID NO 663
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
acctttccct ctaattgg                                                 18

<210> SEQ ID NO 664
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
cctttccctc taattggt                                                 18

<210> SEQ ID NO 665
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
ctttccctct aattggtt                                                 18

<210> SEQ ID NO 666
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
tttccctcta attggttc                                                 18

<210> SEQ ID NO 667
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
ttccctctaa ttggttct                                                 18

<210> SEQ ID NO 668
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
tccctctaat tggttctc                                                 18

<210> SEQ ID NO 669
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
cctctaattg gttctcta                                                 18

<210> SEQ ID NO 670
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
ctctaattgg ttctctag                                                 18

<210> SEQ ID NO 671
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
tctaattggt tctctagt                                                 18

<210> SEQ ID NO 672
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
ctaattggtt ctctagtt                                                 18

<210> SEQ ID NO 673
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
ccacctttcc ctctaattg                                                19

<210> SEQ ID NO 674
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
cacctttccc tctaattgg                                                   19

<210> SEQ ID NO 675
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
acctttccct ctaattggt                                                   19

<210> SEQ ID NO 676
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
cctttccctc taattggtt                                                   19

<210> SEQ ID NO 677
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
ctttccctct aattggttc                                                   19

<210> SEQ ID NO 678
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
tttccctcta attggttct                                                   19

<210> SEQ ID NO 679
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
ttccctctaa ttggttctc                                                   19

```
<210> SEQ ID NO 680
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
tccctctaat tggttctct                                                    19

<210> SEQ ID NO 681
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
ccctctaatt ggttctcta                                                    19

<210> SEQ ID NO 682
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
cctctaattg gttctctag                                                    19

<210> SEQ ID NO 683
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
ctctaattgg ttctctagt                                                    19

<210> SEQ ID NO 684
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
tctaattggt tctctagtt                                                    19

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
catttctggc ttatcactgc                                                   20

<210> SEQ ID NO 686
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
tggcttatca ctgctgaaac                                               20

<210> SEQ ID NO 687
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
atcactgctg aaaccaaaac                                               20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
gctgaaacca aacaaatgt                                                20

<210> SEQ ID NO 689
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
acaaatgtat ggtaaattct                                               20

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
gtatggtaaa ttctcacata                                               20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
taaattctca catacccctc                                               20

<210> SEQ ID NO 692
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
tacccctcta acatggccaa                                              20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
tgctttttct ttcttaagaa                                              20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
ttctttctta agaaattcac                                              20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
cttaagaaat tcacacattt                                              20

<210> SEQ ID NO 696
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
aaattcacac atttccttca                                              20

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
acacatttcc ttcaaatctc                                              20

<210> SEQ ID NO 698
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 698
ctgaaagata acaagcaaac                                            20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
aagcaaacat gtaataattt                                            20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
acatgtaata atttaacata                                            20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
aataatttaa catagctaca                                            20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
tagctacagc cattgaaaag                                            20

<210> SEQ ID NO 703
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
cagcctgtag ttctaa                                                16

<210> SEQ ID NO 704
<211> LENGTH: 16
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 704
cctgtagttc taatct                                                      16

<210> SEQ ID NO 705
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ctgtagttct aatctg                                                      16

<210> SEQ ID NO 706
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
tgtagttcta atctgt                                                      16

<210> SEQ ID NO 707
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
gtagttctaa tctgtg                                                      16

<210> SEQ ID NO 708
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
agttctaatc tgtgat                                                      16

<210> SEQ ID NO 709
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
gttctaatct gtgatg                                                      16

<210> SEQ ID NO 710
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 710
ttctaatctg tgatga                                                    16

<210> SEQ ID NO 711
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
tctaatctgt gatgaa                                                    16

<210> SEQ ID NO 712
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
agcctgtagt tctaatc                                                   17

<210> SEQ ID NO 713
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
gcctgtagtt ctaatct                                                   17

<210> SEQ ID NO 714
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
cctgtagttc taatctg                                                   17

<210> SEQ ID NO 715
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
ctgtagttct aatctgt                                                   17

<210> SEQ ID NO 716
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 716
tgtagttcta atctgtg                                               17

<210> SEQ ID NO 717
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
gtagttctaa tctgtga                                               17

<210> SEQ ID NO 718
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
tagttctaat ctgtgat                                               17

<210> SEQ ID NO 719
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
agttctaatc tgtgatg                                               17

<210> SEQ ID NO 720
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
gttctaatct gtgatga                                               17

<210> SEQ ID NO 721
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
ttctaatctg tgatgaa                                               17

<210> SEQ ID NO 722
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
cagcctgtag ttctaatc                                                   18

<210> SEQ ID NO 723
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
agcctgtagt tctaatct                                                   18

<210> SEQ ID NO 724
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
gcctgtagtt ctaatctg                                                   18

<210> SEQ ID NO 725
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
cctgtagttc taatctgt                                                   18

<210> SEQ ID NO 726
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
ctgtagttct aatctgtg                                                   18

<210> SEQ ID NO 727
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
tgtagttcta atctgtga                                                   18

<210> SEQ ID NO 728
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 728
gtagttctaa tctgtgat                                                 18

<210> SEQ ID NO 729
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
tagttctaat ctgtgatg                                                 18

<210> SEQ ID NO 730
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
agttctaatc tgtgatga                                                 18

<210> SEQ ID NO 731
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
gttctaatct gtgatgaa                                                 18

<210> SEQ ID NO 732
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
cagcctgtag ttctaatct                                                19

<210> SEQ ID NO 733
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
agcctgtagt tctaatctg                                                19

<210> SEQ ID NO 734
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
```
gcctgtagtt ctaatctgt                                                19

<210> SEQ ID NO 735
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
cctgtagttc taatctgtg                                                19

<210> SEQ ID NO 736
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
ctgtagttct aatctgtga                                                19

<210> SEQ ID NO 737
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
tgtagttcta atctgtgat                                                19

<210> SEQ ID NO 738
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
gtagttctaa tctgtgatg                                                19

<210> SEQ ID NO 739
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
tagttctaat ctgtgatga                                                19

<210> SEQ ID NO 740
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
agttctaatc tgtgatgaa                                                 19

<210> SEQ ID NO 741
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
agcctgtagt tctaatctgt                                                20

<210> SEQ ID NO 742
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
gcctgtagtt ctaatctgtg                                                20

<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
ctgtagttct aatctgtgat                                                20

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
tgtagttcta atctgtgatg                                                20

<210> SEQ ID NO 745
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
gtagttctaa tctgtgatga                                                20

<210> SEQ ID NO 746
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
gatgaagaat atgaag                                                    16

<210> SEQ ID NO 747
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
atgaagaata tgaagg                                                       16

<210> SEQ ID NO 748
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
tgaagaatat gaaggt                                                       16

<210> SEQ ID NO 749
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
gaagaatatg aaggtc                                                       16

<210> SEQ ID NO 750
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
aagaatatga aggtct                                                       16

<210> SEQ ID NO 751
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
agaatatgaa ggtctt                                                       16

<210> SEQ ID NO 752
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gaatatgaag gtcttc                                                       16

<210> SEQ ID NO 753
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
aatatgaagg tcttcc                                              16

<210> SEQ ID NO 754
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
atatgaaggt cttcct                                              16

<210> SEQ ID NO 755
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
tatgaaggtc ttcctc                                              16

<210> SEQ ID NO 756
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
atgaaggtct tcctca                                              16

<210> SEQ ID NO 757
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
tgaaggtctt cctcat                                              16

<210> SEQ ID NO 758
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
gaaggtcttc ctcatg                                              16

```
<210> SEQ ID NO 759
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
aaggtcttcc tcatgt                                                       16

<210> SEQ ID NO 760
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
aggtcttcct catgtt                                                       16

<210> SEQ ID NO 761
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
ggtcttcctc atgttt                                                       16

<210> SEQ ID NO 762
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
gtcttcctca tgtttc                                                       16

<210> SEQ ID NO 763
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
tcttcctcat gtttct                                                       16

<210> SEQ ID NO 764
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
cttcctcatg tttctt                                                       16

<210> SEQ ID NO 765
```

-continued

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
ttcctcatgt ttcttc                                                   16

<210> SEQ ID NO 766
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
tcctcatgtt tcttca                                                   16

<210> SEQ ID NO 767
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
cctcatgttt cttcac                                                   16

<210> SEQ ID NO 768
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
ctcatgtttc ttcaca                                                   16

<210> SEQ ID NO 769
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
tcatgtttct tcacaa                                                   16

<210> SEQ ID NO 770
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
catgtttctt cacaat                                                   16

<210> SEQ ID NO 771
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
atgtttcttc acaatt                                                       16

<210> SEQ ID NO 772
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
tgtttcttca caattt                                                       16

<210> SEQ ID NO 773
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
gatgaagaat atgaagg                                                      17

<210> SEQ ID NO 774
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
atgaagaata tgaaggt                                                      17

<210> SEQ ID NO 775
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
tgaagaatat gaaggtc                                                      17

<210> SEQ ID NO 776
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
gaagaatatg aaggtct                                                      17

<210> SEQ ID NO 777
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 777
aagaatatga aggtctt                                                       17

<210> SEQ ID NO 778
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
agaatatgaa ggtcttc                                                       17

<210> SEQ ID NO 779
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
ctcatgtttc ttcacaa                                                       17

<210> SEQ ID NO 780
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
tcatgtttct tcacaat                                                       17

<210> SEQ ID NO 781
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
catgtttctt cacaatt                                                       17

<210> SEQ ID NO 782
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
atgtttcttc acaattt                                                       17

<210> SEQ ID NO 783
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 783
aagaatatga aggtcttc                                                       18

<210> SEQ ID NO 784
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
agaatatgaa ggtcttcc                                                       18

<210> SEQ ID NO 785
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
gaatatgaag gtcttcct                                                       18

<210> SEQ ID NO 786
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
aatatgaagg tcttcctc                                                       18

<210> SEQ ID NO 787
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
atatgaaggt cttcctca                                                       18

<210> SEQ ID NO 788
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
gaaggtcttc ctcatgtt                                                       18

<210> SEQ ID NO 789
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 789
aaggtcttcc tcatgttt                                                      18

<210> SEQ ID NO 790
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
aggtcttcct catgtttc                                                      18

<210> SEQ ID NO 791
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
ggtcttcctc atgtttct                                                      18

<210> SEQ ID NO 792
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
gtcttcctca tgtttctt                                                      18

<210> SEQ ID NO 793
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
tcttcctcat gtttcttc                                                      18

<210> SEQ ID NO 794
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
cttcctcatg tttcttca                                                      18

<210> SEQ ID NO 795
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 795
tcctcatgtt tcttcaca                                               18

<210> SEQ ID NO 796
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
cctcatgttt cttcacaa                                               18

<210> SEQ ID NO 797
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
ctcatgtttc ttcacaat                                               18

<210> SEQ ID NO 798
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
tcatgtttct tcacaatt                                               18

<210> SEQ ID NO 799
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
catgtttctt cacaattt                                               18

<210> SEQ ID NO 800
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
gatgaagaat atgaaggtc                                              19

<210> SEQ ID NO 801
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
atgaagaata tgaaggtct                                                19

<210> SEQ ID NO 802
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
gaagaatatg aaggtcttc                                                19

<210> SEQ ID NO 803
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
aagaatatga aggtcttcc                                                19

<210> SEQ ID NO 804
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
agaatatgaa ggtcttcct                                                19

<210> SEQ ID NO 805
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
gaatatgaag gtcttcctc                                                19

<210> SEQ ID NO 806
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
aatatgaagg tcttcctca                                                19

<210> SEQ ID NO 807
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
atatgaaggt cttcctcat                                                19

<210> SEQ ID NO 808
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
tatgaaggtc ttcctcatg                                                19

<210> SEQ ID NO 809
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
tgaaggtctt cctcatgtt                                                19

<210> SEQ ID NO 810
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
gaaggtcttc ctcatgttt                                                19

<210> SEQ ID NO 811
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
aaggtcttcc tcatgtttc                                                19

<210> SEQ ID NO 812
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
aggtcttcct catgtttct                                                19

<210> SEQ ID NO 813
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
ggtcttcctc atgtttctt                                                19

<210> SEQ ID NO 814
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
gtcttcctca tgtttcttc                                                19

<210> SEQ ID NO 815
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
tcttcctcat gtttcttca                                                19

<210> SEQ ID NO 816
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
cttcctcatg tttcttcac                                                19

<210> SEQ ID NO 817
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
ttcctcatgt ttcttcaca                                                19

<210> SEQ ID NO 818
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
tcctcatgtt tcttcacaa                                                19

<210> SEQ ID NO 819
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
cctcatgttt cttcacaat                                                19

<210> SEQ ID NO 820
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
ctcatgtttc ttcacaatt                                                19

<210> SEQ ID NO 821
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
tcatgtttct tcacaattt                                                19

<210> SEQ ID NO 822
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
atgaagaata tgaaggtctt                                               20

<210> SEQ ID NO 823
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
atatgaaggt cttcctcatg                                               20

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
tatgaaggtc ttcctcatgt                                               20

<210> SEQ ID NO 825
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 825
tgcaggtgga cgagatactc                                               20

```
<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 826
agtccctcag aatgcaactg                                              20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 827
agaaagacaa atggcctggg                                              20

<210> SEQ ID NO 828
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 828
tgcttgttgg taggaactgg                                              20

<210> SEQ ID NO 829
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 829
tcgtcggcag cgtcactgca aaagaaacaa aaagcct                           37

<210> SEQ ID NO 830
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 830
cgttgatcga catactagag agc                                          23

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 831
gagaacagga gcttcagaag g                                            21
```

<210> SEQ ID NO 832
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 832
tcggtagtca ctgtcttccc                                              20

<210> SEQ ID NO 833
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 833
caagactgct gattgtacgt tc                                           22

<210> SEQ ID NO 834
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 834
gtggcaggca atcgaagc                                                18

<210> SEQ ID NO 835
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 835
ctcatagctg agctaggcag                                              20

<210> SEQ ID NO 836
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 836
gtctcgtggg ctcggtggct tgccactttt tacct                             35

<210> SEQ ID NO 837
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 837
acctgatcaa cagtcatgcc                                              20

```
<210> SEQ ID NO 838
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 838
ccagttctgg gattgtctttt cc                                              22

<210> SEQ ID NO 839
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: a, c, t, g, unknown or other

<400> SEQUENCE: 839
tttttttttt tttttttttvn                                                 20

<210> SEQ ID NO 840
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
atctgtgatg aagaatatga                                                  20

<210> SEQ ID NO 841
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ctagtttttt aactttcctt                                                  20

<210> SEQ ID NO 842
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 842
gcttgtcaac ttgaacattg tctgag                                           26

<210> SEQ ID NO 843
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 843
caacaaaaag ggtaacttcc attcc                                            25

<210> SEQ ID NO 844
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 844
tgcagaagca gctaccagat                                                  20

<210> SEQ ID NO 845
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 845
tcctacagaa cagaaactta gactt                                            25
```